(12) United States Patent
Burns et al.

(10) Patent No.: US 11,555,031 B2
(45) Date of Patent: Jan. 17, 2023

(54) COMPOUNDS AND METHODS FOR REGULATING INSULIN SECRETION

(71) Applicants: The Broad Institute, Inc., Cambridge, MA (US); The General Hospital Corporation, Boston, MA (US); Instituto Carlos Slim de la Salud, A.C., Mexico City (MX)

(72) Inventors: Sean M. Burns, Boston, MA (US); Bridget K. Wagner, Cambridge, MA (US); Amedeo Vetere, Cambridge, MA (US)

(73) Assignees: The Broad Institute, Inc., Cambridge, MA (US); The General Hospital Corporation, Boston, MA (US); Instituto Carlos Slim de la Salud, A.C., Mexico City (MX)

( * ) Notice: Subject to any disclaimer, the term of this patent is extended or adjusted under 35 U.S.C. 154(b) by 0 days.

(21) Appl. No.: 16/494,744

(22) PCT Filed: Mar. 19, 2018

(86) PCT No.: PCT/US2018/023149
§ 371 (c)(1),
(2) Date: Sep. 16, 2019

(87) PCT Pub. No.: WO2018/175324
PCT Pub. Date: Sep. 27, 2018

(65) Prior Publication Data
US 2020/0017485 A1  Jan. 16, 2020

Related U.S. Application Data

(60) Provisional application No. 62/473,811, filed on Mar. 20, 2017, provisional application No. 62/632,865, filed on Feb. 20, 2018.

(51) Int. Cl.
| | | |
|---|---|---|
| *C07D 413/12* | (2006.01) |
| *A61P 3/08* | (2006.01) |
| *C07C 235/84* | (2006.01) |
| *C07D 213/30* | (2006.01) |
| *C07D 231/12* | (2006.01) |
| *C07D 237/08* | (2006.01) |
| *C07D 261/08* | (2006.01) |
| *C07D 495/04* | (2006.01) |

(52) U.S. Cl.
CPC ............. *C07D 413/12* (2013.01); *A61P 3/08* (2018.01); *C07C 235/84* (2013.01); *C07D 213/30* (2013.01); *C07D 231/12* (2013.01); *C07D 237/08* (2013.01); *C07D 261/08* (2013.01); *C07D 495/04* (2013.01)

(58) Field of Classification Search
CPC ................................. C07D 261/08; C07D 413/12
See application file for complete search history.

(56) References Cited

U.S. PATENT DOCUMENTS

| | | |
|---|---|---|
| 8,236,824 B2 | 8/2012 | Burgdorf et al. |
| 2014/0142035 A1 | 5/2014 | Wice et al. |

FOREIGN PATENT DOCUMENTS

| | | |
|---|---|---|
| EP | 0335144 A1 | 10/1989 |
| IN | 2648MU2009 A | 11/2012 |
| WO | 1999062885 A1 | 12/1999 |
| WO | 2007002433 A1 | 1/2007 |
| WO | 2010150280 A1 | 12/2010 |
| WO | 2011132048 A1 | 10/2011 |
| WO | 2013045431 A1 | 4/2013 |
| WO | 2013070796 A2 | 5/2013 |
| WO | 2013160419 A1 | 10/2013 |

OTHER PUBLICATIONS

Banker et al. "Modern Pharmaceutics", 3rd Ed. p. 596 (1996). (Year: 1996).*
"Burger's Medicinal Chemistry", edited by Manfred E.Wolf, 5th Ed. Part 1, pp. 975-977 (1995). (Year: 1995).*
Evans in "Principles of Radiopharmacology", Colombett, L.G. editor, CRC Press, pp. 11-13 and 24 (1979).*
CA Registry No. 460329-42-4, entered into CA Registry File on Oct. 10, 2002,supplied by Ambinter Chemical Library. (Year: 2002).*
Interchim Product Guide downloaded from the Internet at https://www.interchim.com/screening-library on May 7, 2021.*
CA Registry No. 879163-97-0, entered into CA Registry File on Apr. 4, 2006, suppled by Enamine Chemical Library.*
Enamine Product Guide downloaded from the Internet at http://www.enamine.net/index.php?option=com_content&task=view&id=22 on Apr. 13, 2015.*
CA Registry No. 851911-02-9, entered into CA Registry File on Jun. 8, 2005, supplied by Enamine Chemical Library. (Year: 2005).*
CA Registry No. 796097-82-0, entered into CA Registry File on Dec. 10, 2004, supplied by Enamine Chemical Library. (Year: 2004).*

(Continued)

*Primary Examiner* — Paul V Ward
(74) *Attorney, Agent, or Firm* — Melissa Hunter-Ensor; Scott Goncher; Greenberg Traurig, LLP

(57) ABSTRACT

Disclosed herein are methods for inducing insulin secretion in a glucose-dependent manner and compounds for use in these methods. The compounds may have the structure of formula I(a):

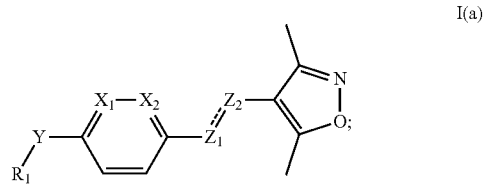

wherein the substituents are as described in the description; or a pharmaceutically acceptable form thereof.

6 Claims, 33 Drawing Sheets

(56) References Cited

OTHER PUBLICATIONS

BioAssay Record for AID 977607, 'Luminescent GLuc Reporter Gene Assay Primary HTS to Identify Small Molecule Activator of Glucose Dependent Insulin Secretion Measured In Cell-Based System Using Plate Reader-7055-01_Activator_Dose_CherryPick_Activity_Set2', U.S. (https://pubchem.ncbi.nlm.nih.gov/bioassay/977607), (1page).

Litchfield et al. 'Hyperglycemia—induced metabolic compensation inhibits metformin sensitivity in ovarian cancer', Oncotarget, Jun. 19, 2015 (Jun. 19, 2015), vol. 6, pp. 23548-23560; p. 23549.

Pubmed Compound Summary for CID 2461646, 'POTSISFIPXACCS-UHFFFAOYSA-N', U.S. National Library of Medicine, Jul. 15, 2005 (Jul. 15, 2005), p. 1-15; p. 4 (https://pubchem.ncbi.nlm.nih.gov/compund/2461646).

Pubmed Compound Summary for CID 2572928 'QLUHJWORLKMEJI-UHFFFAOYSA-N', U.S. National Library of Medicine, Jul. 16, 2005 (Jul. 16, 2005), p. 1-14; p. 4 (https://pubchem.ncbi.nlm.nih.gov/compound/2572928).

Pubmed Compound Summary for CID 26915036, 'ZGDHESDYRRWLPJ-UHFFFAOYSA-N', U.S. National Library of Medicine, May 28, 2009 (May 28, 2009), p. 1-11; p. 3 (https://pubchem.ncbi.nlm.nih.gov/compound/26915036).

Pubmed Substance Record for SID 22401812, '4-chloro-N-(4-{[(3,4-dihydro-1Hisochromen-1-ylmethyl)amino]carbonyl)phenyl)benzamide', U.S. National Library of Medicine, Mar. 5, 2007 (Mar. 5, 2007), pp. 1-8; p. 3 (https://pubchem.ncbi.nlm.nih.gov/substance/22401812).

Pubmed Substance Record for SID 24796409, 'MLS000679919', U.S. National Library of Medicine, Jul. 5, 2007 (Jul. 5, 2007), pp. 1-8; p. 3 (https://pubchem.ncbi.nlm.nih.gov/substance/24796409).

Pubmed Substance Record for SID 57257114, 'MLS002165768', U.S. National Library of Medicine, Feb. 23, 2009 (Feb. 23, 2009), pp. 1-8; p. 3 (https://pubchem.ncbi.nlm.nih.gov/substance/57257114).

International Search Report and Written Opinion for corresponding PCT Patent Application No. PCT/US18/23149, dated Jul. 24, 2018 (22 pages).

Partial Supplementary European Search Report issued in corresponding European Patent Application No. 18772200.4, dated Aug. 13, 2020 (19 pages).

Burns et al., "High-Throughput Luminescent Reporter of Insulin Secretion for Discovering Regulators of Pancreatic Beta-Cell Function," Cell Metabolism, Jan. 6, 2015, vol. 21, pp. 126-137.

Office Action dated Aug. 11, 2021 in corresponding Mexican Patent Application No. MX/a/2019/011168 (5 pages).

English translation of the Office Action dated Aug. 11, 2021 in corresponding Mexican Patent Application No. MX/a/2019/011168 (3 pages).

Office Action dated Mar. 4, 2022 in corresponding Mexican Patent Application No. MX/a/2019/011168 (4 pages).

English translation of the Office Action dated Mar. 4, 2022 in corresponding Mexican Patent Application No. MIX/a/2019/011168 (2 pages).

Frimurer et al., "Model-Based Discovery of Synthetic Agonists for the Zn2+-Sensing G-Protein-Coupled Receptor 39 (GPR39) Reveals Novel Biological Functions," Journal of Medicinal Chemistry, 2017, vol. 60, No. 3, pp. 886-898.

Examination Report dated Sep. 30, 2022 in corresponding European Patent Application No. 18772200.4 (9 pages).

* cited by examiner

(Oral Glucose Challenge)

(High throughput assay for insulin secretion)

(Pro-insulin luciferase reporter)

(Compound 8 Dose Response in INS-1E cells)

(Compound 8 on normal human islets)

(Compound 8 on type 2 diabetes human islets)

(cAMP competition assay)

(Alpha-cell secretion)

JQ1

(Effect of JQ1 on glucose-stimulated luciferase secretion)

FIG. 13A Bromodomain inhibitors for effects on INS-1E luciferase secretion (compounds tested at 10 uM)
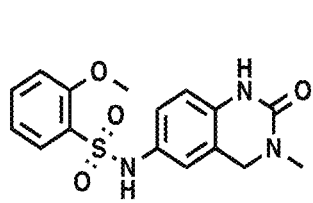
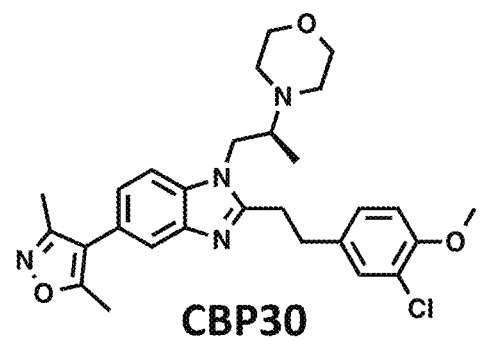
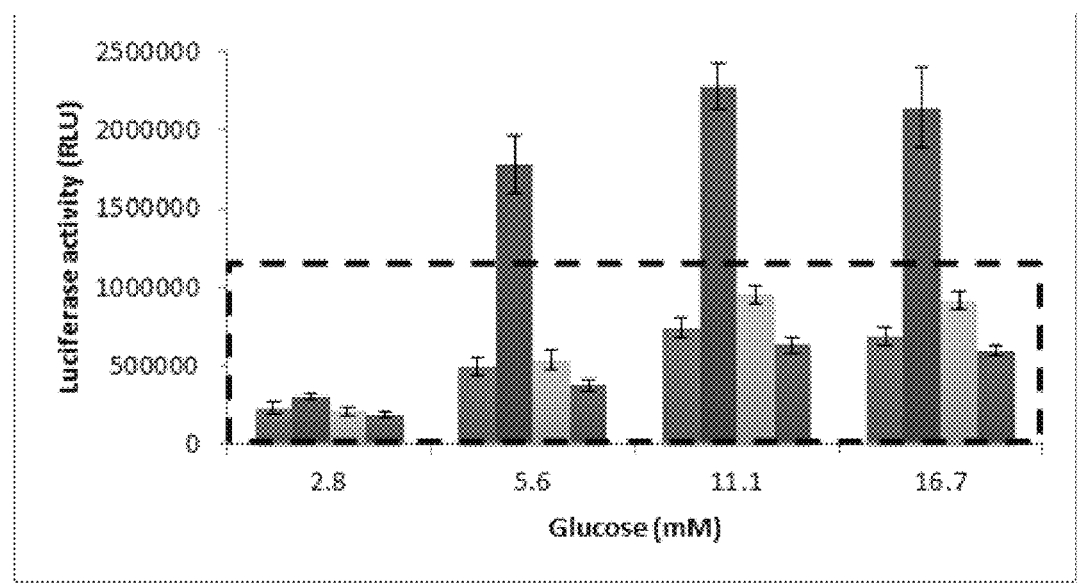

COMPOUNDS AND METHODS FOR REGULATING INSULIN SECRETION

CROSS REFERENCE TO RELATED APPLICATIONS

The present application is the U.S. national phase application, pursuant to 35 U.S.C. § 371, of PCT international application Ser. No.: PCT/US2018/023149, filed Mar. 19, 2018, designating the United States and published in English, which claims priority to U.S. Provisional Application Ser. No. 62/473,811, filed Mar. 20, 2017, and U.S. Provisional Application Ser. No. 62/632,865, filed Feb. 20, 2018, the contents of which are hereby incorporated by reference in their entirety.

STATEMENT OF RIGHTS TO INVENTIONS MADE UNDER FEDERALLY SPONSORED RESEARCH

This invention was made with government support under Grant No. 1 R03 DA035188-01 awarded by the National Institutes of Health. The government has certain rights in the invention.

BACKGROUND

Diabetes mellitus type 2 (type 2 diabetes) is a metabolic disorder that results in patients having high blood sugar level and insulin resistance. Long-term complications from high blood sugar include heart disease, strokes, diabetic retinopathy which can result in blindness, kidney failure, and poor blood flow in the limbs which may lead to amputations. Type 2 diabetes is primarily due to obesity and not enough exercise in people who are genetically predisposed. It makes up about 90% of cases of diabetes, with the other 10% due primarily to diabetes mellitus type 1 and gestational diabetes. In diabetes mellitus type 1 there is an absolute lack of insulin due to breakdown of islet cells in the pancreas. Diagnosis of diabetes is by blood tests such as fasting plasma glucose, oral glucose tolerance test, or A1C.

The number of people affected by type 2 diabetes has grown substantially over the last decades. As of 2013 there were approximately 368 million people diagnosed with the disease compared to around 30 million in 1985. Type 2 diabetes is associated with a ten-year-shorter life expectancy. Thus, numerous therapies have been developed to treat or ameliorate the symptoms of type 2 diabetes. One such therapy involves drugs that promote the ß-cells from pancreatic islet to secret insulin independent of how much glucose is circulating in the blood. For example, sulfonureas induce constant insulin secretion but in doing so, they can cause hypoglycemia and ß-islet cell burnout. GLP-1 analogs require administration by injection and can result in pancreatitis. Thus, there is a need in the art for insulin secretagogues that are glucose-dependent, such that they activate insulin secretion only when the circulating blood glucose level is physiologically high.

SUMMARY

Disclosed herein are compounds that can be used as insulin secretagogues in a glucose-dependent manner. These compounds have the advantage of working on β cells only when needed such that they are more resilient and lead to less insulin resistance. Without wishing to be bound by theory, it is believed the compounds of the invention are capable of targeting voltage gated potassium channels to prevent or slow membrane repolarization. In normal cells, membrane polarization is required for the regulation of β cell secretion of insulin. By inhibiting repolarization, more insulin may be secreted. Because, the rate of membrane repolarization occurs in a glucose dependent manner, the compounds of the invention also operate in a glucose dependent manner.

In certain embodiments, the compounds disclosed herein are used in methods of regulating circulating insulin levels in the body.

These compounds may have the structure of Formula I:

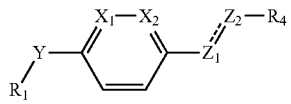

wherein the "dashed" bond is a single or double bond;
$X_1$ and $X_2$ are independently selected at each occurrence from $C(R_2)$ and N, wherein two vicinal $R_2$ groups may together form an optionally aromatic five- or six membered fused ring;
Y is selected from $-R^Q-$, $-O-$, $-C(O)-$, $-C(O)N(R_3)-$, $-C(R_4)_2N(R_3)-$, $-N(R_3)C(R_3)_2-$, $-N(R_3)C(O)-$, $-SO_2N(R_3)-$, and $-N(R_3)SO_2-$;
$Z_1$ and $Z_2$ are independently $CH_2$, O, N, $CHR_5$, $CR_5$, or $NR_5$;
$R_1$ is selected from aryl, heteroaryl, heterocyclyl, and $-(C(R_3)_2)$-heterocyclyl optionally substituted with one or more (e.g., one, two, three, four, etc.) substituents independently selected from alkyl (e.g., methyl, ethyl, propyl, isopropyl, etc.), alkenyl (e.g., ethenyl, etc.), hydroxyalkyl (e.g., hydroxymethyl, etc.), ether (e.g., methoxymethyl, etc.), acyl (e.g., $-C(O)CH_3$, etc.), and halogen (e.g., Cl, F, Br, I, etc.), and wherein any two vicinal substituents of $R_1$ may together form a five- or six-optionally aromatic membered ring;
$R_2$ is selected from hydrogen, alkyl, alkoxy, $-CN$, $-NH_2$, $-(CH_2)_{1-4}NH_2$, $-(CH_2)_{1-4}N_3$, $-(CH_2)_{1-4}NHC(O)CH_3$; and
$R_3$ is independently selected at each occurrence from hydrogen and alkyl optionally substituted with one to three groups independently selected from halogen (e.g., F, Cl, etc.), and wherein a substitutent of $R_1$ and any $R_4$ may together form a fused five- or six-membered ring optionally substituted with one two three groups Cl, F, OH, CN, N, O, or S;
$R_4$ is a five- or six-membered aromatic heterocycle optionally substituted with one or more alkyl (e.g., methyl, ethyl, propyl, isopropyl, etc.), halogen (e.g., F, Cl, etc.), alkoxy (e.g., methoxy, etc.), and wherein any two vicinal substituents may together form an optionally aromatic five- or six-membered fused ring optionally substituted with alkyl, N, O, S, or $C(=O)$; and wherein $R_3$ may together with $R_2$ of $X_1$ form a five- or six membered optionally substituted fused ring;
$R_5$ is independently at each occurrence hydrogen or alkyl (e.g., methyl, ethyl, propyl, isopropyl, etc.), and $R_5$ and $R_2$ of $X_2$ may together form a five- or six-membered fused ring; and
$R^Q$ is independently selected at each occurrence a bivalent optionally aromatic heterocycles (e.g. monocyclic heterocycle, bicyclic heterocycle, etc.);
or a pharmaceutically acceptable form (e.g., salt, prodrug, etc.) thereof.

In some embodiments, compounds may have the structure of Formula I(d):

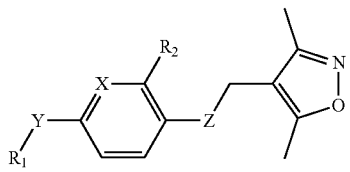

wherein X is $CR_2$ or N;
Y is selected from —C(O)—, —C(O)N($R_3$)—, —C($R_3$)$_2$NH—, —C(O) N($R_3$)—, —$NR_4$C(O)—, —$SO_2$N($R_3$)—, and —N($R_3$)$SO_2$—;
Z is O or NH;
$R_1$ is selected from aryl, heteroaryl, heterocyclyl, and —C($R_3$)$_2$-heterocyclyl, optionally substituted with one or more groups selected from alkyl, CN, Cl, F, Br, OH, $NH_2$, and/or substituted with a five- or six-membered saturated cyclyl or heterocyclyl radical;
$R_2$ is independently selected at each occurrence from hydrogen, alkyl, alkoxy, —$NH_2$, and —$(CH_2)_{1-4}NH_2$;
$R_3$ is independently selected at each occurrence from the group consisting of hydrogen and alkyl, and $R_3$ may together with substituents of $R_1$ form a five- or six-membered ring or a pharmaceutically acceptable form thereof.

In formula I (including sub formulas I(a), I(b), I(c), I(d), etc.), $R_1$ and any $R_3$ may together form a five or six membered ring fused with $R_1$. In some embodiments, the compound is not Compound 8 (i.e., $X_1$ and $X_2$ are each CH, Y is —C(O)NH—, $Z_1$ is O, $Z_2$ is CH, $R_1$ is 2,3-dimethylphenyl, and $R_4$ is 3,5-dimethylisoxazol-4-yl). In preferred embodiments, $R_4$ is 3,5-dimethylisoxazol-4-yl, dimethylpyridinyl, or dimethyldiazinyl. In some embodiments, $R_1$ may be aryl substituted with one or more substitutents selected from alkyl, cyano, or morpholinyl. In other embodiments, $R_1$ is a substituted phenyl, where one or more substituents are selected from alkyl (e.g., methyl, ethyl, propyl, isopropyl, etc.), cyano, or morpholinyl. In some embodiments, $R_1$ is heteroaryl (e.g., piperidinyl). In some embodiments, $R_1$ is a substituted piperidinyl, where one or more substituents are methyl, ethyl, propyl, isopropyl, or butyl. In other embodiments, $R_1$ is —C($R_3$)$_2$-heterocyclyl. $R_2$ may be alkyl (e.g., methyl, ethyl, propyl, isopropyl, etc.) or alkoxy (e.g., methoxy, ethoxy, propoxy, isopropoxy, etc.). In some embodiments, Y may be selected from —$NR_3$C(O)—, —C(O)$NR_3$—, or —$NR_3SO_2$—. In some embodiments the compound has the structure

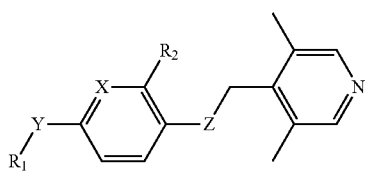

In some embodiments, the compound has the structure

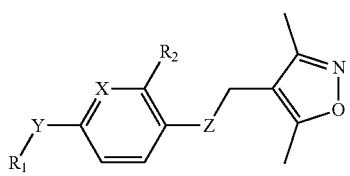

In preferred embodiments, the compound may have the structure:

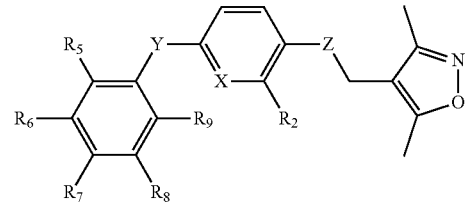

wherein $R_5$-$R_9$ are independently selected from hydrogen, alkyl, cyano, or morpholinyl. In some embodiments, at least one of $R_5$-$R_9$ is not hydrogen. In some embodiments, one of $R_5$-$R_9$ is methyl. In other embodiments, two of $R_5$-$R_9$ methyl.

Pharmaceutical compositions are disclosed herein, wherein the pharmaceutical composition comprises a compound having the structure of Formula I:

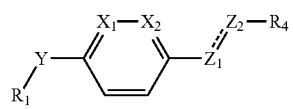

wherein the "dashed" bond is a single or double bond;
$X_1$ and $X_2$ are independently selected at each occurrence from C($R_2$) and N, wherein two vicinal $R_2$ groups may together form an optionally aromatic five- or six membered fused ring;
Y is selected from —$R^Q$—, —O—, —C(O)—, —C(O)N($R_3$)—, —C($R_4$)$_2$N($R_3$)—, —N($R_3$)C($R_3$)$_2$—, —N($R_3$)C(O)—, —$SO_2$N($R_3$)—, and —N($R_3$)$SO_2$—;
$Z_1$ and $Z_2$ are independently $CH_2$, O, N, $CHR_5$, $CR_5$, or $NR_5$;
$R_1$ is selected from aryl, heteroaryl, heterocyclyl, and —(C($R_3$)$_2$)-heterocyclyl optionally substituted with one or more (e.g., one, two, three, four, etc.) substituents independently selected from alkyl (e.g., methyl, ethyl, propyl, isopropyl, etc.), alkenyl (e.g., ethenyl, etc.), hydroxyalkyl (e.g., hydroxymethyl, etc.), ether (e.g., methoxymethyl, etc.), acyl (e.g., —C(O)$CH_3$, etc.), and halogen (e.g., Cl, F, Br, I, etc.), and wherein any two vicinal substituents of $R_1$ may together form a five- or six-optionally aromatic membered ring; $R_2$ is selected from hydrogen, alkyl, alkoxy, —CN, —$NH_2$, —$(CH_2)_{1-4}NH_2$, —$(CH_2)_{1-4}N_3$, —$(CH_2)_{1-4}NHC(O)CH_3$; and
$R_3$ is independently selected at each occurrence from hydrogen and alkyl optionally substituted with one to three groups independently selected from halogen (e.g., F, Cl, etc.), and wherein a substitutent of $R_1$ and any $R_4$ may together form a fused five- or six-membered ring optionally substituted with one two three groups Cl, F, OH, CN, N, O, or S;
$R_4$ is a five- or six-membered aromatic heterocycle optionally substituted with one or more alkyl (e.g., methyl, ethyl, propyl, isopropyl, etc.), halogen (e.g., F, Cl, etc.), alkoxy (e.g., methoxy, etc.), and wherein any two vicinal substituents may together form an optionally aromatic five- or six-membered fused ring optionally substituted with alkyl, N, O, S, or C(=O); and wherein $R_3$ may together with $R_2$ of $X_1$ form a five- or six membered optionally substituted fused ring;
$R_5$ is independently at each occurrence hydrogen or alkyl (e.g., methyl, ethyl, propyl, isopropyl, etc.), and $R_5$ and $R_2$ of $X_2$ may together form a five- or six-membered fused ring; and $R^Q$ is independently selected at each occurrence a bivalent optionally aromatic heterocycles (e.g. monocyclic heterocycle, bicyclic heterocycle, etc.);
or a pharmaceutically acceptable form (e.g., salt, prodrug, etc.) thereof.

The pharmaceutical composition may comprise a compound having the structure of formula I(d)

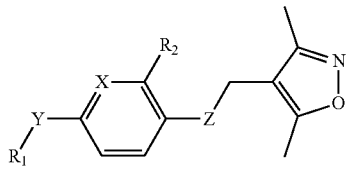

wherein X is $CR_2$ or N,
Y is selected from —C(O)—, —C(O)$NR_3$—, —C($R_3$)$_2$NH—, —$NR_3$C(O)—, —SO$_2$$NR_3$—, and —$NR_3$SO$_2$—,
Z is O or NH,
$R_1$ is selected from aryl, heteroaryl, heterocyclyl, and —C($R_3$)$_2$-heterocyclyl,
$R_2$ is independently selected at each occurrence from hydrogen, alkoxy, —$NH_2$ and —(CH$_2$)$_{1-4}$$NH_2$; and
$R_3$ is independently selected at each occurrence from the group consisting of hydrogen and alkyl, and substituents of $R_1$ and any $R_4$ may together form a five or six membered ring fused with R; or
a pharmaceutically acceptable form thereof.

Pharmaceutical compositions may also comprise an effective amount of a compound having the structure of Formula II:

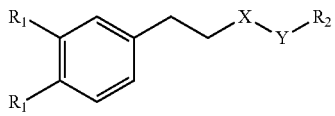

wherein
X is selected from —C(O)$NR_3$—, —$NR_3$C(O)—, —SO$_2$$NR_3$— and —$NR_3$SO$_2$—,
Y is selected from a bond, —C($R_3$)$_2$—, —C($R_3$)$_2$—C($R_3$)$_2$— and —C($R_3$)$_2$—O—,
each $R_1$ is independently selected from H, halo, and alkoxy,
$R_2$ is selected from aryl and heteroaryl, and
each $R_3$ is independently selected from H and alkyl,
or a pharmaceutically acceptable form thereof.

Pharmaceutical compositions may also comprise an effective amount of a compound having the structure of Formula III:

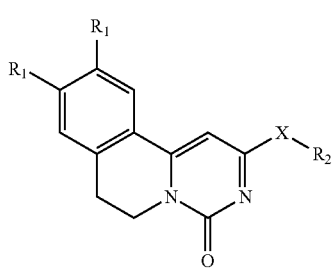

wherein X is $NR_3$ or O,
each $R_1$ is independently selected from alkoxy,
$R_2$ is selected from —C(O)-alkyl, alkyl, aryl, cycloalkyl, and —(CH$_2$)$_n$-aryl,
$R_3$ is selected from H, alkyl and aryl, and
n is 1 or 2,
or a pharmaceutically acceptable form thereof.

Pharmaceutical compositions may also comprise an effective amount of a compound having the structure of Formula IV:

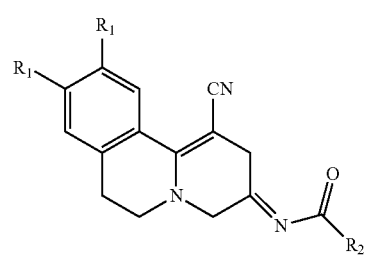

wherein
each $R_1$ is independently selected from alkoxy, and
$R_2$ is aryl or heteroaryl,
or a pharmaceutically acceptable form thereof.

Pharmaceutical compositions may also comprise an effective amount of a compound having the structure of Formula V:

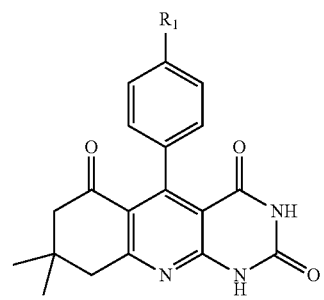

wherein $R_1$ is selected from H, halo and nitro,
or a pharmaceutically acceptable form thereof.

Pharmaceutical compositions may also comprise an effective amount of a compound having the structure of Formula VI:

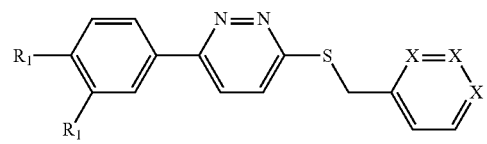

wherein each X is independently selected from CH or N, and
each $R_1$ is independently selected from H, halo, and alkoxy,
or a pharmaceutically acceptable form thereof.

The pharmaceutical compositions may be formulated for administration in solid or liquid form. For example, the pharmaceutical compositions may be formulated for oral, parenteral, topical or controlled administration.

A method of modulating insulin secretion is disclosed herein, wherein the method comprises contacting a β-cell with a compound, wherein insulin secretion from the β-cell occurs only when said blood glucose levels exceed normoglycemic conditions. In some embodiments, the blood glucose levels are greater than about 5 mM (e.g., 7 mM, 10 mM, 12 mM, etc.). The normoglycemic conditions may comprise a blood glucose concentration from about 3.5 mM to about 7 mM. In some embodiments, the method of modulating insulin secrection comprises contacting one or more cells with a compound of formula I. In other embodiments, the method of modulating insulin secretion comprises contacting one or more cells with a compound having a structure of any one of Formulas II-VI (e.g., II, III, IV, V, or VI).

Provided herein are numerous compounds, compositions comprising the same, and methods of inducing insulin secretion. Compositions and articles disclosed herein can be isolated or otherwise manufactured in connection with the examples provided below or by any methods known to a person of ordinary skill in the art. Other features and advantages of the disclosure will be apparent from the detailed description and from the claims.

BRIEF DESCRIPTION OF THE DRAWINGS

The following detailed description of exemplary embodiments can be better understood when read in conjunction with the appended drawings. It should be understood, however, that the disclosure is not limited to the precise arrangements and instrumentalities of the embodiments shown in the drawings.

FIG. 13A and FIG. 13B depict the effect of the indicated compounds, which are bromodomain inhibitors, on glucose-stimulated secretion from the INS-IE beta-cell lines using the Luciferase Insulin Secretion Assay. FIG. 13B is a magnification of the region boxed in FIG. 13A. While there may be a small effect of JQ1 on glucose-stimulated secretion, neither of the known bromodomain inhibitors (PF1 or CBP30) affect secretion to the extent of Compound 8. In each graph, each glucose concentration shows the luceriferase insulin secretion assay results for DMSO, Compound 8, PF1, and CBP30, from left to right.

DETAILED DESCRIPTION

Definitions

Figure 1:
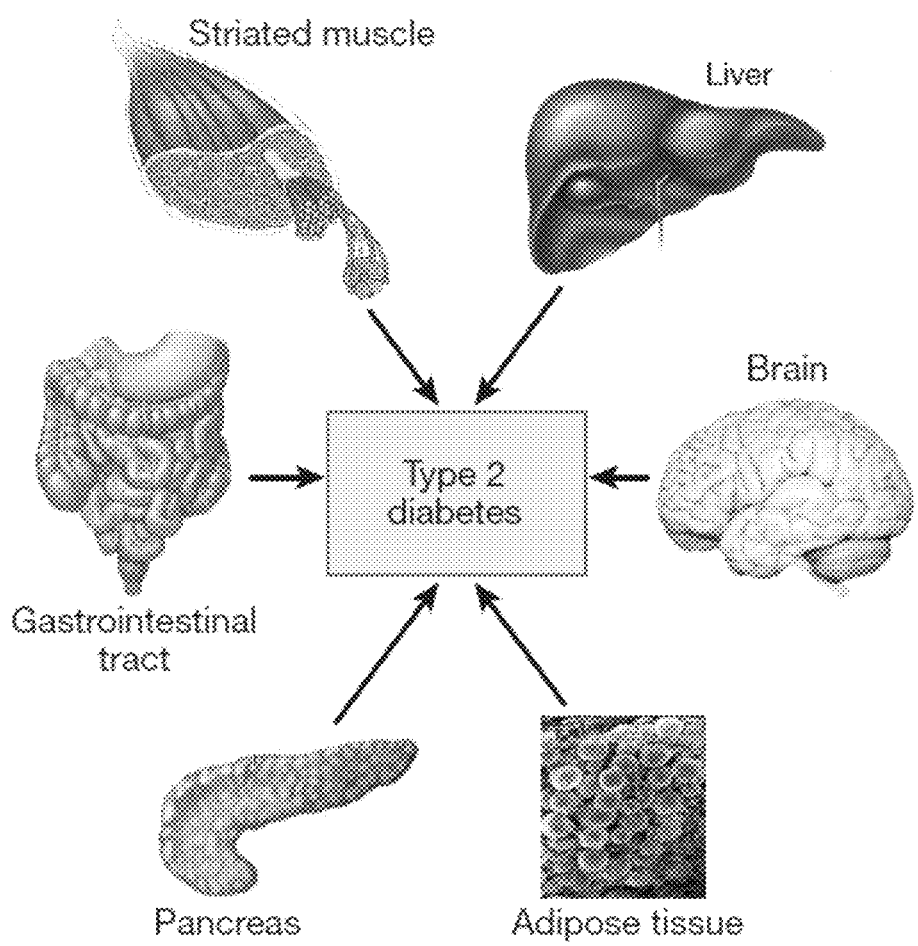
FIG. 1 depicts some exemplary organs that are affected by type 2 diabetes.

Unless defined otherwise, all technical and scientific terms used herein generally have the same meaning as commonly understood by one of ordinary skill in the art to which this disclosure belongs. The following references provide one of skill with a general definition of many of the terms used herein: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Generally, the nomenclature used herein and the laboratory procedures in medicine, organic chemistry and polymer chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, such as ±5%, such as ±1%, and such as ±0.1% from the specified value, as such variations are appropriate to perform the disclosed methods.

The term "hydrocarbon" refers to a radical or group containing carbon and hydrogen atoms. Examples of hydrocarbon radicals include, without limitation, alkyl, alkenyl, alkynyl, aryl, aryl-alkyl, alkyl-aryl, and any combination thereof (e.g., alkyl-aryl-alkyl, etc.). As used herein, unless otherwise indicated, hydrocarbons may be monovalent or multivalent (e.g., divalent, trivalent, etc) hydrocarbon radicals. A radical of the form —$(CH_2)_n$—, including a methylene radical, i.e., —$CH_2$—, is regarded as an alkyl radical if it does not have unsaturated bonds between carbon atoms. Unless otherwise specified, all hydrocarbon radicals (including substituted and unsubstituted alkyl, alkenyl, alkynyl, aryl, aryl-alkyl, alkyl-aryl, etc.) may have from 1-35 carbon atoms. In other embodiments, hydrocarbons will have from 1-20 or from 1-12 or from 1-8 or from 1-6 or from 1-3 carbon atoms, including for example, embodiments having one, two, three, four, five, six, seven, eight, nine, or ten carbon atoms. Hydrocarbons may have from about 2 to about 70 atoms or from 4 to about 40 atoms or from 4 to about 20 atoms.

A "substituted" hydrocarbon may have as a substituent one or more hydrocarbon radicals, substituted hydrocarbon radicals, or may comprise one or more heteroatoms. Any hydrocarbon substituents disclosed herein may optionally include from 1-20 (e.g., 1-10, 1-5, etc.) heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (F, Cl, Br, I, etc.), boron, silicon, etc. In some embodiments, heteroatoms will be selected from the group consisting of oxygen, nitrogen, sulfur, phosphorous, and halogen (F, Cl, Br, I, etc.). In preferred embodiments, the heteroatoms may be selected from O, N, or S. In some embodiments, a heteroatom or group may substitute a carbon. In some embodiments, a heteroatom or group may substitute a hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo").

In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

"Acyl" refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cyclohexyl, heteroaryl or heterocycloalkyl portion plus the carbonyl carbon of acyl. For example, a $C_4$-acyl has three other ring or chain atoms plus carbonyl. If the R radical is heteroaryl or heterocycloalkyl, the hetero ring or chain atoms contribute to the total number of chain or ring atoms.

As used herein, the term "alkyl", by itself or as part of another substituent means, unless otherwise stated, a branched or unbranched saturated hydrocarbon group. The term "n-alkyl" refers to an unbranched alkyl group. The term "$C_x$-$C_y$ alkyl" refers to an alkyl group having between x and y carbon atoms, inclusively, in the branched or unbranched hydrocarbon group. By way of illustration, but without limitation, the term "$C_1$-$C_8$ alkyl" refers to a straight chain or branched hydrocarbon moiety having from 1, 2, 3, 4, 5, 6, 7, or 8 carbon atoms. "$C_1$-$C_6$" refers to a straight chain or branched hydrocarbon moiety having from 1, 2, 3, 4, 5, or 6 carbon atoms. "$C_1$-$C_4$ alkyl" refers to a straight chain or branched hydrocarbon moiety having from 1, 2, 3, or 4 carbon atoms, including methyl, ethyl, n-propyl, iso-propyl, n-butyl, iso-butyl, sec-butyl, and tert-butyl. The term "$C_1$-$C_4$ n-alkyl" refers to straight chain hydrocarbon moieties that have 1, 2, 3, or 4 carbon atoms including methyl, ethyl, n-propyl, and n-butyl.

As used herein, the term "alkoxy" by itself or as part of another substituent means, unless otherwise stated, an —O-alkyl group, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. In some embodiments, an alkoxy group can have one to six carbons denoted $C_1$-$C_3$. In some embodiments, $C_{1-4}$ alkoxy is an alkoxy group which encompasses both straight and branched chain alkyls of from 1 to 4 carbon atoms. In some aspects, the alkoxy group is a ($C_1$-$C_3$)alkoxy, such as, but not limited to, ethoxy and methoxy.

"Amino" or "amine" refers to a —N($R_b$)$_2$, —N($R_b$) $R_b$—, or —$R_b$N($R_b$)$R_b$— radical group, where each $R_b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. When a —N($R_b$)$_2$ group has two $R_b$ other than hydrogen, they can be combined with the nitrogen atom to form a 3-, 4-, 5-, 6-, or 7-membered ring. For example, —N($R_b$), is meant to include, but not be limited to, 1-pyrrolidinyl and 4-morpholinyl.

"Amide" or "amido" refers to a chemical moiety with formula —C(O)N($R^b$)$_2$, —C(O)N($R^b$)—, —N$R_b$C(O)— or —N$R_b$C(O)$R_b$, where $R_b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, this radical is a $C_{1-4}$ amido or amide radical, which includes the amide carbonyl in the total number of carbons in the radical. When a —C(O)N($R^b$)$_2$ has two $R^b$ other than hydrogen, they can be combined with the nitrogen atom to form a 3-, 4-, 5-, 6-, or 7-membered ring. For example, N($R^b$)$_2$ portion of a —C(O)N($R^b$), radical is meant to include, but not be limited to, 1-pyrrolidinyl and 4-morpholinyl.

As used herein, the term "aryl" or "arene" employed alone or in combination with other terms means, unless otherwise stated, a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-10}$ aryl group. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like.

As used herein, the term "cycloalkyl" by itself or as part of another substituent means, unless otherwise stated, a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_3$-$C_{13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl radical. In some embodiments, it is a $C_3$-$C_6$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_3$-$C_{13}$ carbocyclyl groups include the aforementioned $C_{3-8}$ carbocyclyl groups as well as octahydro-1H indenyl, decahydronaphthalenyl, spiro[4.5]decanyl and the like.

"Carbonyl" refers to a —(C═O)— radical. The descriptors "C═O" or "C(O)" or "carbonyl" refers to a carbon atom that is doubly bonded to an oxygen atom. "Alkyl carbonyl" has a common formula of R—C(O)— wherein R may be $C_{1-12}$ alkyl, $C_{2-12}$ alkenyl, $C_{2-12}$ alkynyl, $C_{3-12}$ cycloalkyl, $C_{6-12}$ aryl, $C_{3-12}$ heteroaryl, or $C_{3-12}$ heterocyclyl.

As used herein, the term "δ" refers to delta (ppm).

As used herein, the term "DMSO" refers to dimethylsulfoxide.

"Ether" refers to a $R^b$—O—$R^b$— radical where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. "Each of the alkyl, alkenyl, alkynyl and alkoxy groups are as defined herein and can be optionally further substituted as defined herein.

As used herein, the term "heteroalkyl" by itself or in combination with another term means, unless otherwise stated, a stable straight or branched chain alkyl group which have one or more skeletal chain atoms selected from an atom other than carbon, e.g., oxygen, nitrogen, sulfur, phosphorus or combinations thereof. A numerical range can be given, e.g., $C_1$-$C_4$ heteroalkyl which refers to the chain length in total, which in this example is 4 atoms long. For example, a —$CH_2OCH_2CH_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. In some aspects, the heteroalkyl group has one or two heteroatoms selected from the group consisting of O, N, and S. Exemplary heteroalkyl groups include, without limitation, ethers such as methoxyethanyl (—$CH_2CH_2OCH_3$), ethoxymethanyl (—$CH_2OCH_2CH_3$), (methoxymethoxy)ethanyl (—$CH_2CH_2OCH_2OCH_3$), (methoxymethoxy)methanyl (—$CH_2OCH_2OCH_3$) and (methoxyethoxy)methanyl (—$CH_2OCH_2CH_2OCH_3$) and the like; amines such as (—$CH_2CH_2NHCH_3$, —$CH_2CH_2N(CH_3)_2$, —$CH_2NHCH_2CH_3$, —$CH_2N(CH_2CH_3)(CH_3)$) and the like. Other examples include —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$.

As used herein, the term "heterocycle" or "heterocyclyl", by itself or as part of another substituent means, unless otherwise stated, an unsubstituted or substituted, stable, mono- or multi-cyclic heterocyclic ring system that consists of carbon atoms and at least one heteroatom. A heterocycle refers to any 3- to 18-membered non-aromatic radical monocyclic or polycyclic moiety comprising at least one heteroatom selected from nitrogen, oxygen, phosphorous and sulfur. In some aspects, the heteroatom(s) are chosen from N, O, and S. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms. In general, the limits (end points) of any range recited herein are within the scope of the invention and should be understood to be disclosed embodiments. Additionally, any half integral value within that range is also contemplated. If the range requires integral numbers (e.g. number ring atoms) then only integral numbers are contemplated. For example, a range of about 0 to 4 expressly discloses 0, 0.5, 1, 1.5, 2, 2.5, 3, 3.5, 4, and any subset within that range (e.g., from about 1 to 2.5). However, a range of "3 to 6 ring atoms" refers to 3 ring atoms, 4 ring atoms, 5, ring atoms or six ring atoms.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e] [1,4]diazepinyl, 1,4,5,7-tetrahydropyrano[3,4-b]pyrrolyl, 5,6-dihydro-4H-furo[3,2-b]pyrrolyl, 6,7-dihydro-5H-furo [3,2-b]pyranyl, 5,7-dihydro-4H-thieno [2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro [3,2-c]pyridinyl, 4,5,6,7-tetrahydrothieno[3,2-b]pyridinyl, 1,2,3,4-tetrahydro-1,6-naphthyridinyl, and the like.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

As used herein, the term "heteroaryl" or "heteroaromatic", by itself or as part of another substituent means, unless otherwise stated, a 5-18 membered monocyclic or polycyclic (e.g., bicyclic or tricyclic) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms.

For example, an N-containing "heteroaryl" or "heteroaromatic" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b] [1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo [h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocyclooctа[d]pyrimidinyl, 5,6,7,8,9,10-hexahydrocyclooctа[d] pyridazinyl, 5,6,7,8,9,10 hexahydrocyclooctа[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5] thieno [2,3-d]pyrimdinyl, 6,7,8,9-tetrahydro-5H-cyclohepta[4,5]thieno [2,3-d]pyrimidinyl, 5,6,7, 8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl).

Further examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. The aforementioned listings of heterocyclyl and heteroaryl moieties are intended to be representative and not limiting.

"Nitro" refers to the —NO₂ radical.

As used herein, the term "reaction condition" refers to a physical treatment, chemical reagent, or combination thereof, which is required or optionally required to promote a reaction. Non-limiting examples of reaction conditions are electromagnetic radiation, heat, a catalyst, a chemical reagent (such as, but not limited to, an acid, base, electrophile or nucleophile), and a buffer.

"Sulfonamidyl" or "sulfonamido" refers to the following radicals: —S(=O)₂—(R$^b$)₂, —N(R$^b$)—S(=O)₂—R$^b$, —S(=O)₂—N(R$^b$)—, or —N(R$^b$)—S(=O)₂—, where each R$^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. The R$^b$ groups in —S(=O)₂—(R$^b$)₂ can be taken together with the nitrogen to which they are attached to form a 4-, 5-, 6-, or 7-membered heterocyclyl ring. In some embodiments, the term designates a $C_{1-4}$ sulfonamido, wherein each R$^b$ in the sulfonamido contains 1 carbon, 2 carbons, 3 carbons, or 4 carbons total.

As used herein, the term "substituted" means that an atom or group of atoms has replaced hydrogen as the substituent attached to another group. Unless stated otherwise, any group recited within may be substituted. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

The term "vicinal" refers to the configuration in which any two atoms or groups are, respectively, bonded to two adjacent atoms (i.e., the two atoms are directly bonded to one another). The term "geminal" describes a configuration in which any atoms or two functional groups are bonded to the same atom. As used herein, when any two groups are said to together form a ring, unless otherwise indicated, it is meant that a bond is formed between each of said two groups, with the valences of the atoms appropriately adjusted to accomadate at least a bond (e.g., a hydrogen atom may be removed from each group).

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic, such as straight.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "pharmaceutically acceptable derivative" denotes any pharmaceutically acceptable salt, ester, enol ether, or salt of such ester, of such compound, or any other adduct or derivative which, upon administration to a subject, is capable of providing (directly or indirectly) a compound as otherwise described herein, or a metabolite or residue (MW>300) thereof.

As used herein, "pharmaceutically acceptable ester" refers to esters which hydrolyze in vivo and include those that break down readily in the human body to leave the parent compound or a salt thereof. Such esters can act as a prodrug as defined herein. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfinic acids, sulfonic acids and boronic acids. Examples of esters include formates, acetates, propionates, butyrates, acrylates and ethylsuccinates. The esters can be formed with a hydroxyl or carboxylic acid group on the compound.

As used herein, "pharmaceutically acceptable enol ethers" include, but are not limited to, derivatives of formula —C=C(OR) where R can be selected from alkyl, alkenyl, alkynyl, aryl, aralkyl and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl and cycloalkyl.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchioric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a disclosed compound with a suitable base or acid, respectively. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well known methods, such as those described in Burger's Medicinal Chemistry and Drug Discovery, 172-178, 949-982 (Manfred E. Wolff ed., 5th ed., 1995), and Design of Prodrugs (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as $(C_{1-8})$alkyl, $(C_{1-12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 10 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a disclosed compound or a pharmaceutically acceptable form of the compound contains an alcohol functional group, a prodrug can be formed by the replacement of the hydrogen atom of the alcohol group with a group such as $(C_{1-6})$alkanoyloxymethyl, 1-($(C_{1-6})$alkanoyloxy)ethyl, 1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, α-amino$(C_{1-4})$alkanoyl, arylacyl, and α-aminoacyl, or α-aminoacyl-α-aminoacyl, where each α-aminoacyl group is independently selected from the naturally occurring L-amino acids, —P(O)(OH)$_2$, —P(O)(O$(C_{1-6})$alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently $(C_{1-10})$alkyl, $(C_{3-7})$cycloalkyl, benzyl, a natural α-aminoacyl or natural α-aminoacyl-natural-α-aminoacyl, —C(OH)C(O)OY$^1$ wherein Y$^1$ is H, $(C_{1-6})$ alkyl or benzyl, C(OY$^2$)Y$^3$ wherein Y$^2$ is $(C_{1-4})$alkyl and Y$^3$ is $(C_{1-6})$alkyl, carboxy$(C_{1-6})$alkyl, amino$(C_{1-4})$alkyl or mono-N— or di-N,N—$(C_{1-6})$alkylaminoalkyl, —C(Y$^4$)Y$^5$ wherein Y$^4$ is H or methyl and Y$^5$ is mono-N— or di-N,—$(C_{1-6})$alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol = which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or"trans," where"cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" or "ee" of a composition can be calculated using the equation shown below. In the example shown below, a composition contains 90% of one enantiomer, e.g., the S enantiomer, and 10% of the other enantiomer, e.g., the R enantiomer.

$$ee=(90-10)/100=80\%.$$

Thus, a composition containing 90% of one enantiomer and 10% of the other enantiomer is said to have an enantiomeric excess of 80%. Some compositions described herein contain an enantiomeric excess of at least about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein.

These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least about 95% by weight. In certain embodiments, the compound provided herein is made up of at least about 90% by weight of one enantiomer. In other embodiments, the compound is made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has a —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, Enantiomers, Racemates and Resolutions (Jacques, Ed., Wiley Interscience, New York, 1981); Wilen et al., Tetrahedron 33:2725 (1977); Stereochemistry of Carbon Compounds (E. L. Eliel, Ed., McGraw-Hill, N Y, 1962); and Tables of Resolving Agents and Optical Resolutions p. 268 (E. L. ElM, Ed., Univ. of Notre Dame Press, Notre Dame, Ind. 1972).

Optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or"proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^2H$, $^3H$, $^{13}C$ $^{14}C$, $^{15}N$, $^{18}O$, $^{17}O$ $^{31}P$, $^{32}P$, $^{35}S$ and $^{36}Cl$, respectively. Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes can allow for ease of preparation and detectability. Further, substitution with heavier isotopes such as deuterium (i.e., $^2H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure. In some embodiments, radiolabeled compounds are useful for studying metabolism and/or tissue distribution of the compounds or to alter the rate or path of metabolism or other aspects of biological functioning.

Linking moieties in chemical compounds may be represented with "-" and/or "-" on each side of a set of atomic symbols. Generally, these moieties are intended to indicate that any "R" group (e.g., R, $R_1$, $R_2$, $R_5$, etc.) is linked on the right of the moiety and chemical scaffold is linked on the left. For example, the moiety —NH—C(O)— may indicate that the C(O) group is closer to the terminal R group than the NH group and the NH group is closer to the scaffold than the C(O) group. In some embodiments, these moieties may indicate that any "R" group is linked on the left of the moiety and chemical scaffold is linked on the right.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo (e.g. F), $C_{1-12}$ straight chain or branched chain alkyl, $C_{2-12}$ alkenyl, $C_{2-12}$ alkynyl, $C_{3-12}$ cycloalkyl, $C_{6-12}$ aryl, $C_{3-12}$ heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Unless otherwise noted, all groups described herein optionally contain one or more common substituents, to the extent permitted by valency. Further, as used herein, the phrase "optionally substituted" means unsubstituted (e.g., substituted with an H) or substituted. As used herein, the term "substituted" means that a hydrogen atom is removed and replaced by a substituent (e.g., a common substituent). It is understood by one of ordinary skill in the chemistry art that substitution at a given atom is limited by valency. The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used.

Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines, and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger, and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274: 1520-1522 (1996) and U.S. Pat. No. 5,593,853). The methods above may be used to synthesize single molecular species.

"Pharmaceutically acceptable carrier" or "pharmaceutically acceptable excipient" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; nontoxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; selfemulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

As used herein, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide active compounds, such as plant or animal extracts, and the like. A skilled artisan can readily recognize that there is no limit as to the structural nature of the agents of this disclosure.

The terms "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitor" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of that target protein or polypeptide are also specifically included within this definition. Non-limiting examples of biological activity inhibited by an antagonist include those associated with the development, growth, or spread of a tumor, or an undesired immune response as manifested in autoimmune disease.

"Administration" of a disclosed compound encompasses the delivery to a subject of a compound as described herein, or a prodrug or other pharmaceutically acceptable derivative thereof, using any suitable formulation or route of administration, as discussed herein.

The term "co-administration," "administered in combination with," and their grammatical equivalents, as used herein, encompasses administration of two or more agents to the subject so that both agents and/or their metabolites are present in the subject at the same time. Co-administration includes simultaneous administration in separate compositions, administration at different times in separate compositions, or administration in a composition in which both agents are present.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes an about 10% change in expression levels, such as an about 25% change, such as an about 40% change, and further such as an about 50% or greater change in expression levels.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "detect" is meant identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ. Examples of diseases include [insert]

The term "effective amount" or "therapeutically effective amount" refers to that amount of a compound or pharmaceutical composition described herein that is sufficient to effect the intended application including, but not limited to, disease treatment, as illustrated below. In some embodiments, the amount is that effective for detectable killing or inhibition of the growth or spread of cancer cells; the size or number of tumors; or other measure of the level, stage, progression or severity of the cancer. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a given response in target cells, e.g., reduction of cell migration. The specific dose will vary depending on, for example, the compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

By "normoglycemia" is meant a fasting glucose level of about 99 mg/dl or lower.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduces" is meant a negative alteration of at least about 10%, about 25%, about 50%, about 75%, or about 100%, unless otherwise specified. When used in the context of a chemical reaction, "reduces" refers to the mechanism by which a compound "reduces" another in a reduction-oxidation reaction.

By "reference" is meant a standard or control condition.

"Subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a certain disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof. Unless specifically stated or obvious from context, as used herein, the term "or" is understood to be inclusive. Unless specifically stated or obvious from context, as used herein, the terms "a", "an", and "the" are understood to be singular or plural.

The term "in vivo" refers to an event that takes place in a subject's body. In vivo also includes events occurring in rodents, such as rats, mice, guinea pigs, and the like.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Throughout this disclosure, various aspects of the subject matter may be presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6, and so forth, as well as individual numbers within that range, for example, 1, 2, 2.7, 3, 4, 5, 5.3, and 6. This applies regardless of the breadth of the range.

Overview

In one embodiment, provided are compounds, and pharmaceutically acceptable forms, including, but not limited to, salts, hydrates, solvates, isomers, prodrugs, and isotopically labeled derivatives thereof. These compounds may be used to modulate insulin secretion. In some embodiments, the pharmaceutically acceptable form is selected from pharmaceutically acceptable salts, isomers, prodrugs and isotopically labeled derivatives of disclosed compounds.

In one embodiment, provided are methods for modulating insulin secretion. In another embodiment, provided are methods of treating and/or managing various diseases and disorders, which comprises administering to a patient a therapeutically effective amount of a compound provided herein, or a pharmaceutically acceptable form (e.g., salts, hydrates, solvates, isomers, prodrugs, and isotopically labeled derivatives) thereof. Examples of diseases and disorders are described herein.

In another embodiment, provided are methods of preventing various diseases and disorders, which comprises administering to a patient in need of such prevention a prophylactically effective amount of a compound provided herein, or a pharmaceutically acceptable form (e.g., salts, hydrates, solvates, isomers, prodrugs, and isotopically labeled derivatives) thereof. Non-limiting examples of diseases and disorders are described herein.

In other embodiments, a compound provided herein, or a pharmaceutically acceptable form (e.g., salts, hydrates, solvates, isomers, prodrugs, and isotopically labeled derivatives) thereof, is administered in combination with another drug ("second active agent") or treatment. Second active agents include small molecules and large molecules (e.g., proteins and antibodies), non-limiting examples of which are provided herein. Other methods or therapies that can be used in combination with the administration of compounds provided herein include, but are not limited to, surgery, blood transfusions, immunotherapy, biological therapy, radiation therapy, and other non-drug based therapies presently used to treat, prevent or manage various disorders described herein.

Also provided are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, prodrugs, and isotopically labeled derivatives) thereof, and optionally one or more second active agents. While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

Compounds

Some embodiments provided herein are compounds of Formula I:

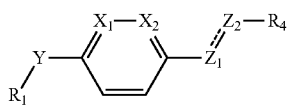

I wherein the "dashed" bond ("-----") between $Z_1$ and $Z_2$ is a single or double bond;

$X_1$ and $X_2$ are independently selected at each occurrence from $C(R_2)$ and N, wherein two vicinal $R_2$ groups may together form an optionally aromatic five- or six membered fused ring;

Y is selected from $-R^Q-$, $-O-$, $-C(O)-$, $-C(O)N(R_3)-$, $-C(R_4)_2N(R_3)-$, $-N(R_3)C(R_3)_2-$, $-N(R_3)C(O)-$, $-SO_2N(R_3)-$, and $-N(R_3)SO_2-$;

$Z_1$ and $Z_2$ are independently $CH_2$, O, N, $CHR_5$, $CR_5$, or $NR_5$;

$R_1$ is selected from aryl, heteroaryl, heterocyclyl, and $-(C(R_3)_2)$-heterocyclyl optionally substituted with one or more (e.g., one, two, three, four, etc.) substituents independently selected from alkyl (e.g., methyl, ethyl, propyl, isopropyl, $C_1$-$C_{12}$ alkyl, etc.), alkenyl (e.g., ethenyl, $C_1$-$C_{12}$ alkenyl etc.), hydroxyalkyl (e.g., hydroxymethyl, $C_1$-$C_{12}$-alkyl-OH, etc.), ether (e.g., $-C_1$-$C_{12}$ alkyl-O-$C_1$-$C_{12}$alkyl, methoxymethyl, etc.), acyl (e.g., $-C(O)-C_1$-$C_{12}$ alkyl, $-C(O)CH_3$, etc.), and halogen (e.g., Cl, F, Br, I, etc.), and wherein any two vicinal substituents of $R_1$ may together form a five- or six-optionally aromatic membered ring;

$R_2$ is selected from hydrogen, alkyl, alkoxy, $-CN$, $-NH_2$, $-(CH_2)_{1-4}NH_2$, $-(CH_2)_{1-4}N_3$, $-(CH_2)_{1-4}NHC(O)CH_3$; and $R_3$ is independently selected at each occurrence from hydrogen and alkyl optionally substituted with one to three groups independently selected from halogen (e.g., F, Cl, etc.), and wherein a substitutent of $R_1$ and any $R_4$ may together form a fused five- or six-membered ring optionally substituted with one two three groups Cl, F, OH, CN, N, O, or S;

$R_4$ is a five- or six-membered aromatic heterocycle optionally substituted with one or more alkyl (e.g., methyl, ethyl, propyl, isopropyl, $C_1$-$C_{12}$ alkyl, etc.), halogen (e.g., F, Cl, etc.), alkoxy (e.g., methoxy, etc.), and wherein any two vicinal substituents may together form an optionally aromatic five- or six-membered fused ring optionally substituted with alkyl (e.g., $C_1$-$C_{12}$ alkyl, N, O, S, or C(=O); and wherein $R_3$ may together with $R_2$ of $X_1$ form a five- or six membered fused ring optionally substituted with alkyl (e.g., $C_1$-$C_{12}$ alkyl, N, O, S, or C(=O);

$R_5$ is independently at each occurrence hydrogen or alkyl (e.g., methyl, ethyl, propyl, isopropyl, $C_1$-$C_{12}$ alkyl, etc.), and $R_5$ and $R_2$ of $X_2$ may together form a five- or six-membered fused ring; and $R^Q$ is independently selected at each occurrence a bivalent optionally aromatic heterocycles (e.g. monocyclic heterocycle, bicyclic heterocycle, etc.);

or a pharmaceutically acceptable form (e.g., salt, prodrug, etc.) thereof.

$R_4$ may be a five-membered optionally substituted heterocycle (e.g., pyrrolyl, furanyl, imidazoylyl, oxazolyl, isoxazolyl, etc.). In other embodiments, $R_4$ may be a six-membered optionally substituted heterocycle (e.g., pyridinyl, pyranyl, diazinyl, oxazinyl, etc.). In some embodiments, $R_1$ is substituted with methyl, methoxy, or chloro. In certain preferred embodiments, the compound may have the structure of formula I(a):

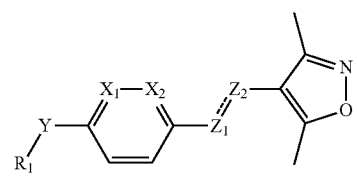

I(a)

In some embodiments, the compound may have the structure of formula I(b):

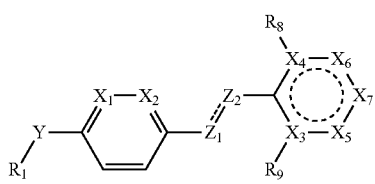

I(b)

wherein the ring with the "dashed" circle is optionally aromatic;

$R_8$ and $R_9$ are independently selected from hydrogen, alkyl (e.g., methyl, etc.), alkoxy (e.g., methoxy, etc.), and halogen (e.g., Cl, etc.);

$X_3$ and $X_4$ are independently selected from C or N;

$X_5$ and $X_6$ are independently selected from CH, N, C-alkyl, NH, N-alkyl, or O;

$X_7$ is absent (i.e., it is a bond) or selected from CH, N, C-alkyl, NH, N-alkyl, or O; and any two vicinal substituents of $X_3$-$X_7$ may together form a five or six membered ring substituted with oxo and/or halogen and/or alkyl.

For example, the compound may have the structure of

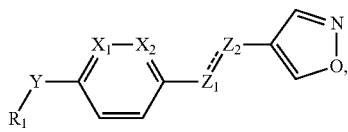

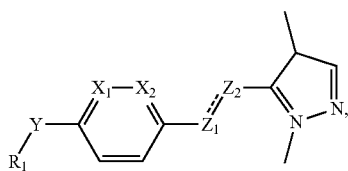

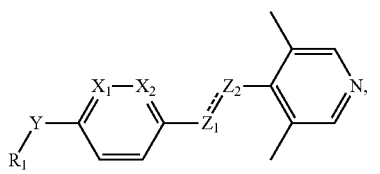

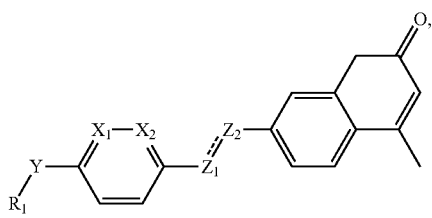

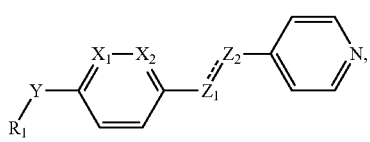

-continued

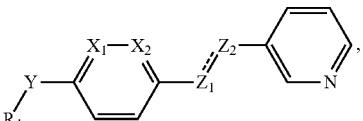

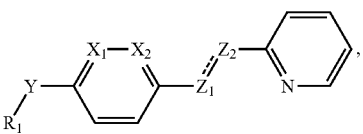

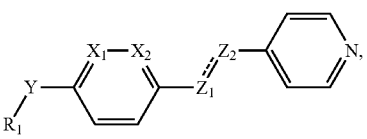

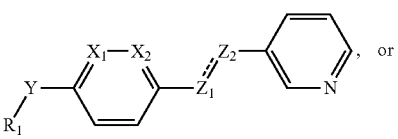

, or

.

In formula I (including sub formulas I(a), I(b), I(c), I(d), etc.) $R_1$ may be aryl, such as optionally substituted phenyl. For example, $R_1$ may be phenyl substituted with one or more alkyl groups, such as one methyl group or two methyl groups. In some embodiments, $R_1$ is 2,6 dimethyl phenyl. In some embodiments, the phenyl substituent is selected from one or more of cyano, morpholino and acetyl. In some embodiments, the phenyl substituent is not substituted with acetyl. In some embodiments $R_1$ is not unsubstituted phenyl. In some embodiments, each of the one or more phenyl substituents may be in the ortho, meta or para positions with reference to Y. For example, two methyl groups may be in the ortho and meta positions on the phenyl ring or two methyl groups may be in both ortho positions on the phenyl ring. In other embodiments, $R_1$ is optionally substituted heteroaryl, such as pyridinyl. For example, the substituted pyridinyl may be substituted with one or more alkyl groups, such as one methyl group or two methyl groups. In some embodiments, the pyridinyl substituent is selected from one or more of cyano, morpholino and acetyl. In some embodiments, each of the one or more pyridinyl substituents may be in the ortho, meta and/or para positions with reference to Y. For example, two methyl groups can be in the ortho and meta positions on the pyridinyl ring (with respect to Y) or two methyl groups may be in both ortho positions on the pyridinyl ring. In some embodiments, $R_1$ is —$(C(R_3)_2)$— heterocyclyl where the heterocyclyl group is tetrahydrofuranyl.

In formula I (including sub formulas I(a), I(b), I(c), I(d), etc.) Y is $R^Q$ and $R^Q$ may be a five-membered bivalent optionally substituted heterocyclyl. For example, $R^Q$ may be:

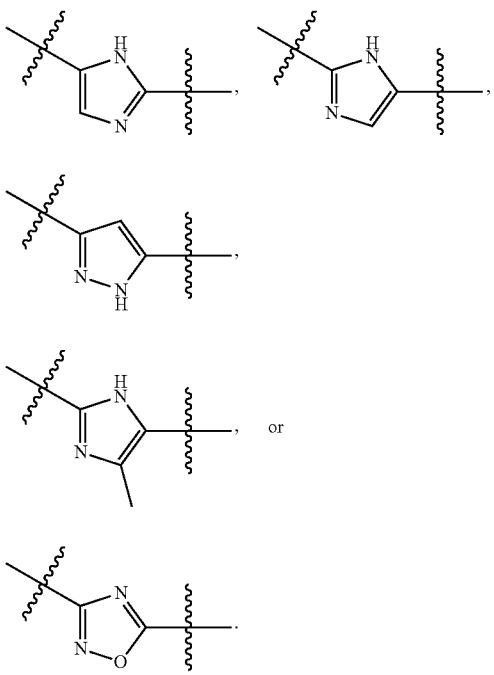

In some embodiments, $R_4$ of Y forms a fused ring with substituents of $R_1$ or $R_2$ of $X_2$. For example, the compound may have the structure:

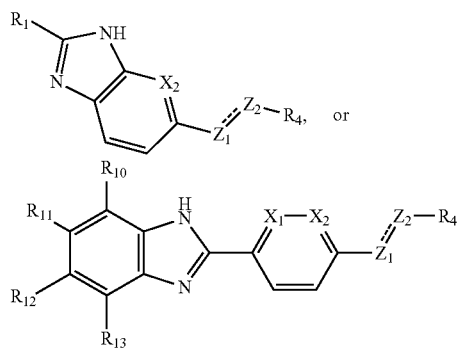

wherein $R_{10}$-$R_{13}$ are independently selected from hydrogen, alkyl (e.g., methyl, etc.), alkoxy (e.g., methoxy, etc.) halogen (e.g., Cl), hydroxy, hydroxyalkyl, ether, and cyano. In some embodiments, $X_1$ and $X_2$ are $CR_2$ wherein $R_2$ is independently selected from hydrogen, methyl, cyano, methoxy, hydroxy. In some embodiments, $R_2$ is alkoxy. In some embodiments, $R_2$ is alkyl. In some embodiments, $R_3$ is alkyl. In some embodiments, Y is —$NR_3C(O)$— (e.g., —NHC(O)—, etc.). In other embodiments, Y is —$C(O)NR_3$— (e.g., —C(O)NH—, etc.). In some embodiments, Y is —$NR_3SO_2$— (e.g., —$NHSO_2$—, etc.). Typically, $Z_1$ is O.

In some embodiments, the compound may have the structure of formula I(c):

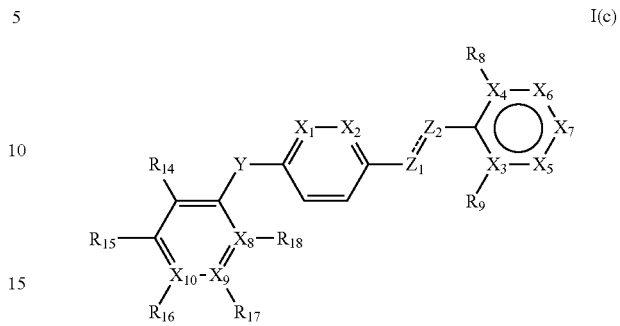

I(c)

wherein $X_8$-$X_{10}$ are independently selected at each occurrence from C or N; $R_{14}$-$R_{18}$ are independently absent or selected at each occurrence from hydrogen, alkyl (e.g., methyl, etc.), alkenyl (e.g., ethynyl, etc.), alkoxy (e.g., methoxy, etc.) halogen (e.g., Cl, etc.), hydroxy, hydroxyalkyl, ether, and cyano. In some embodiments, any two vicinal groups of $R_{14}$-$R_{18}$ may together form a five or six membered fused ring. In some embodiments, $R_{14}$ and $R_{18}$ may together form a five or six membered fused ring with $R_4$.

In certain embodiments, the compound may have the structure of formula I(d):

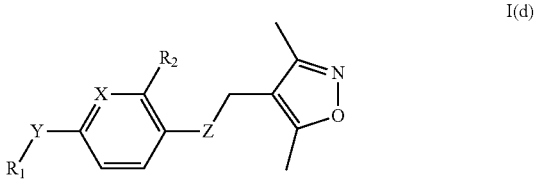

I(d)

wherein X is $CR_2$ or N;
Y is selected from —C(O)—, —C(O)$NR_3$—, —C($R_3$)$_2$NH—, —C(O) $NR_3$—, —$NR_3$C(O)—, —$SO_2NR_3$—, and —$NR_3SO_2$—;
Z is O or NH;
$R_1$ is selected from aryl, heteroaryl, heterocyclyl, and —C($R_4$)$_2$-heterocyclyl, optionally substituted with one or more groups selected from alkyl, CN, Cl, F, Br, OH, $NH_2$, and/or substituted with a five- or six-membered saturated cyclyl or heterocyclyl radical, wherein if Y is —C(O)NH— then $R_1$ is not unsubstituted phenyl;
$R_2$ is selected from hydrogen, alkyl and alkoxy;
$R_3$ is independently selected at each occurrence from the group consisting of hydrogen and alkyl; and substituents of $R_1$ and any $R_3$ may together form a five or six membered ring fused with $R_1$ or a pharmaceutically acceptable form thereof. Table 1 illustrates some measured compounds having the structure of Formula I(d).

TABLE 1

| Compound | X | Y | Z | $R_1$ | $R_2$ | X-$R_2$ | $R_3$ (ring size) |
|---|---|---|---|---|---|---|---|
| Compound 1 | CH | —C(O)NH— | O | 4-methyl-pyridin-3-yl | H | CH | |
| Compound 2 | CH | —C(O)NH— | O | 2-methyl-pyridin-3-yl | H | CH | |
| Compound 3 | CH | —C(O)NH— | O | 4-methyl-phenyl | H | CH | |

TABLE 1-continued

| Compound | X | Y | Z | R₁ | R₂ | X-R₂ | R₃ (ring size) |
|---|---|---|---|---|---|---|---|
| Compound 4 | CH | —C(O)NR₃— | O | phenyl | H | CH | ethyl (five membered ring) |
| Compound 5 | CH | —C(O)NR₃— | O | phenyl | H | CH | butyl (six membered ring) |
| Compound 6 | CH | —C(O)NH— | O | 6-methyl-pyridin-2-yl | H | CH | |
| Compound 7 | CH | —C(O)NH— | O | 3-methyl-pyridin-4-yl | H | CH | |
| Compound 8 | CH | —C(O)NH— | O | 2,3-dimethyl phenyl | H | CH | |
| Compound 9 | CH | —C(O)NH— | O | 3-methyl phenyl | H | CH | |
| Compound 10 | CH | —C(O)NR₃— | O | 3-methyl phenyl | H | CH | methyl |
| Compound 11 | CH | —C(O)NH— | O | 2-cyano-phenyl | H | CH | |
| Compound 12 | CH | —C(O)NR₃— | O | 2,3-dimethyl phenyl | H | CH | methyl |
| Compound 13 | CH | —CH₂NH— | O | 2,3-dimethyl phenyl | H | CH | |
| Compound 16 | CH | —C(O)NH— | O | 2,6-dimethyl phenyl | H | CH | |
| Compound 17 | CH | —C(O)NH— | O | 2-methyl phenyl | H | CH | |
| Compound 18 | CH | —C(O)NH— | O | 2 N-morpholino phenyl | methoxy | CH | |
| Compound 19 | CH | —SO₂NR₃— | O | phenyl | methoxy | CH | ethyl |
| Compound 23 | CH | —C(O)NH— | O | 3-methyl pyridine-2-yl | H | CH | |
| Compound 14 | CH | —C(O)NH— | O | 2,3-dimethyl phenyl | methyl | CH | |
| Compound 15 | CH | —C(O)NH— | O | 2,3-dimethyl phenyl | H | CCH₃ | |
| Compound 24 | CH | —NHC(O)— | O | 2,3-dimethyl phenyl | H | H | |
| Compound 25 | CH | —C(O)NH— | NH | 2,3-dimethyl phenyl | H | H | |

Some embodiments provided herein are compounds of Formula II:

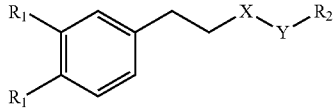

wherein
X is selected from —C(O)NR₃—, —NR₃C(O)—, —SO₂NR₃— and —NR₃SO₂—,
Y is selected from a bond, —C(R₃)₂—, —C(R₃)₂—C(R₃)₂— and —C(R₃)₂—O—,
each $R_1$ is independently selected from H, halo, and alkoxy,
$R_2$ is selected from aryl and heteroaryl, and
each $R_3$ is independently selected from H and alkyl,
or a pharmaceutically acceptable form thereof.

In some embodiments, X is —NR₃SO₂— and Y is a bond.
In some embodiments, X is —NR₃C(O)—, and Y is a bond.
In other embodiments, X is —NR₃C(O)—, and Y is —C(R₃)₂— or —C(R₃)₂—C(R₃)₂—. In some embodiments, X is —C(O)NR₃— and Y is —C(R₃)₂—C(R₃)₂—. In other embodiments, X is —NR₃C(O)— and Y is —C(R₃)₂—C(R₃)₂—.

In some embodiments, one or two $R_1$ are methoxy. In other embodiments, both $R_1$ are ethoxy. In some embodiments, one $R_1$ is halo.

In some embodiments, $R_2$ is aryl, such as substituted phenyl. For example, the phenyl substituent can be substituted with one or more alkyl groups, such as one methyl group or two methyl groups. In other embodiments, the phenyl substituent can be selected from one or more of halo, alkoxy, cyano, morpholino and acetyl. In some embodiments, $R_2$ is heteroaryl and selected from imidazolyl, benzoimidazolyl, indolyl, benzofuranyl, pyrimidinyl, tetrazolyl, quinolinyl, and isoquinolinonyl.

In some embodiments, each $R_3$ is H.
Some embodiments provided herein are compounds of Formula III:

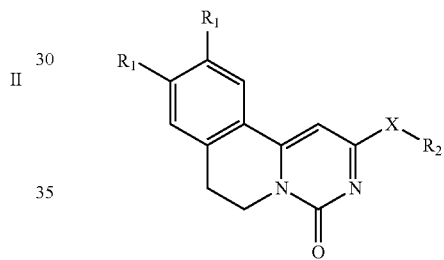

wherein
X is NR₃ or O,
each $R_1$ is independently selected from alkoxy,
$R_2$ is selected from —C(O)-alkyl, alkyl, aryl, cycloalkyl, and —(CH₂)ₙ-aryl,
$R_3$ is selected from H, alkyl and aryl, and
n is 1 or 2,
or a pharmaceutically acceptable form thereof.

In some embodiments, X is NR₃, where $R_3$ is selected from H, methyl and phenyl.

In some embodiments, each $R_1$ substituent is methoxy.

In some embodiments, $R_2$ is aryl, such as phenyl. The phenyl group can be substituted by one or more groups selected from halo; alkyl, such as methyl or trifluoromethyl; alkoxy, such as methoxy; cycloalkyl, such as cyclopropyl; and heterocyclyl, such as piperidinyl. In some embodiments, two or more phenyl substituents can be in the ortho, meta or para positions with reference to the bond to X. For example, two methyl groups can be in the ortho and meta positions.

In some embodiments, n is 1 and $R_2$ is phenyl, and in other embodiments, n is 2 and $R_2$ is phenyl.

Some embodiments provided herein are compounds of Formula IV:

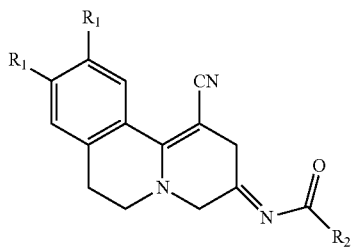

wherein
each R₁ is independently selected from alkoxy, and
R₂ is aryl or heteroaryl,
or a pharmaceutically acceptable form thereof.

In some embodiments, each R₁ is methoxy. In other embodiments, R₂ is phenyl or furanyl. The phenyl group can be substituted by one or more groups, such as halo.

Some embodiments provided herein are compounds of Formula V:

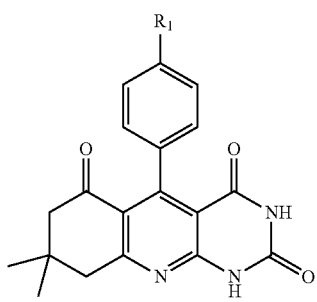

wherein
R₁ is selected from H, halo and nitro,
or a pharmaceutically acceptable form thereof.

Some embodiments provided herein are compounds of Formula VI:

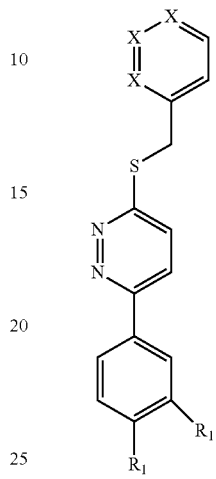

wherein
each X is independently selected from CH or N, and
each R₁ is independently selected from H, halo, and alkoxy,
or a pharmaceutically acceptable form thereof.

In some embodiments, one X is N and the other two X are each CH. In some embodiments, each R₁ is methoxy, or one R₁ is methoxy and the other R₁ is H. In some embodiments, at least one R₁ is halo.

In some embodiments the compounds may have the structure of any of the compounds shown in Table 2.

TABLE 2

| Compound Name | Structure |
|---|---|
| Compound 1 | 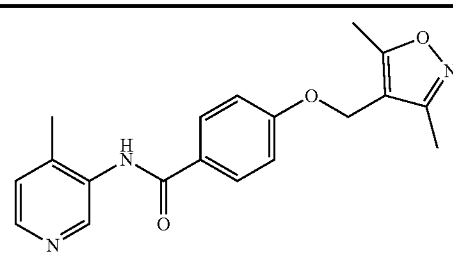 |
| Compound 2 | 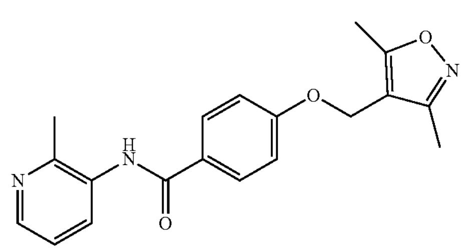 [SMILES: Cc1ncccc1NC(=O)c1ccc(OCc2c(C)noc2C)cc1] |

TABLE 2-continued

| Compound Name | Structure |
| --- | --- |
| Compound 3 | 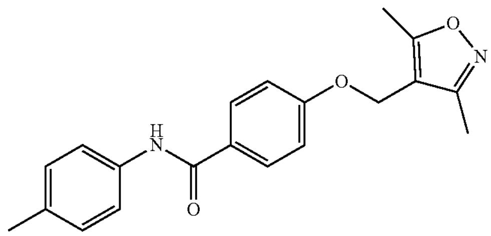 [SMILES: Cc1ccc(NC(=O)c2ccc(OCc3c(C)noc3C)cc2)cc1] |
| Compound 4 | 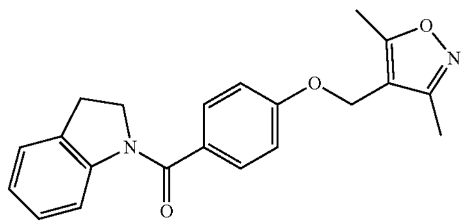 [SMILES: Cc1noc(C)c1COc1ccc(C(=O)N2CCc3ccccc32)cc1] |
| Compound 5 | 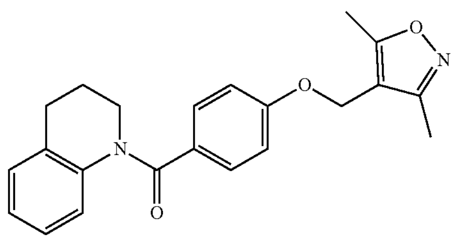 [SMILES: Cc1noc(C)c1COc1ccc(C(=O)N2CCCc3ccccc32)cc1] |
| Compound 6 | 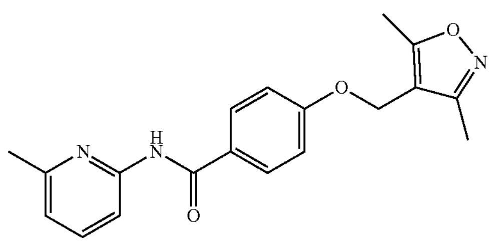 [SMILES: Cc1cccc(NC(=O)c2ccc(OCc3c(C)noc3C)cc2)n1] |
| Compound 7 | 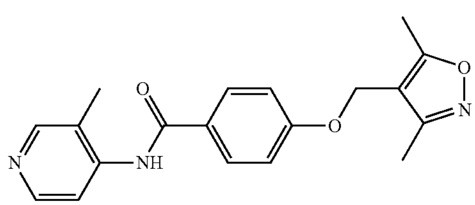 [SMILES: Cc1cnccc1NC(=O)c1ccc(OCc2c(C)noc2C)cc1] |
| Compound 8 | 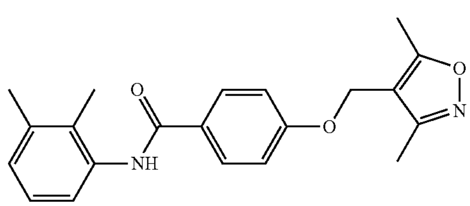 |
| Compound 9 | 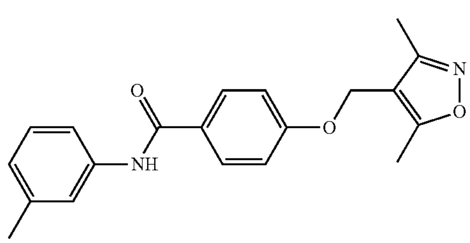 [SMILES: Cc1cccc(NC(=O)c2ccc(OCc3c(C)noc3C)cc2)c1] |

TABLE 2-continued

| Compound Name | Structure |
| --- | --- |
| Compound 10 | 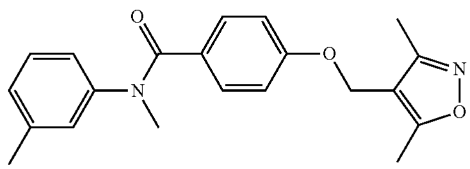 [SMILES: Cc1cccc(N(C)C(=O)c2ccc(OCc3c(C)noc3C)cc2)c1] |
| Compound 11 | 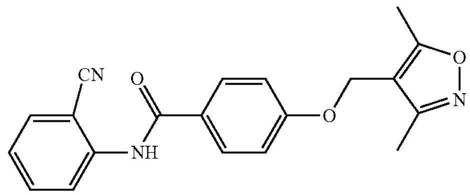 [SMILES: Cc1noc(C)c1COc1ccc(C(=O)Nc2ccccc2C#N)cc1] |
| Compound 12 | 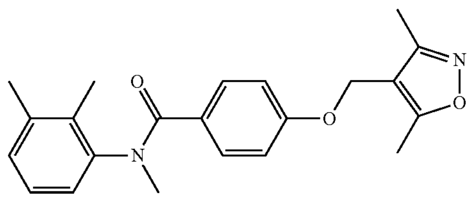 [SMILES: Cc1cccc(N(C)C(=O)c2ccc(OCc3c(C)noc3C)cc2)c1C] |
| Compound 13 | 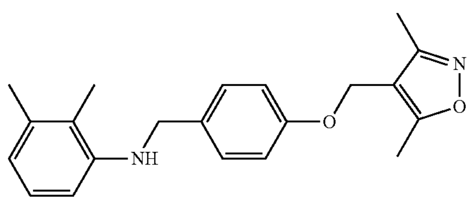 [SMILES: Cc1cccc(NCc2ccc(OCc3c(C)noc3C)cc2)c1C] |
| Compound 14 | 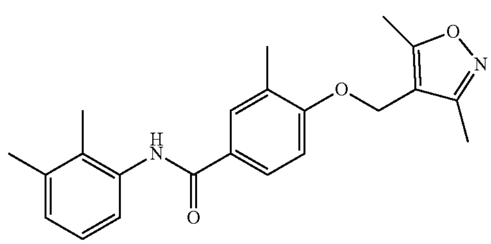 [SMILES: Cc1cc(C(=O)Nc2cccc(C)c2C)ccc1OCc1c(C)noc1C] |
| Compound 15 | 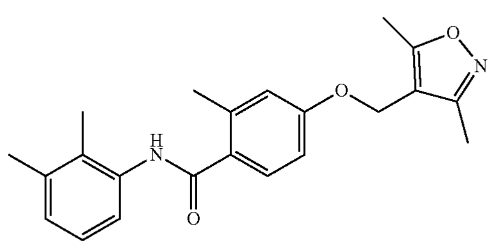 [SMILES: Cc1cc(OCc2c(C)noc2C)ccc1C(=O)Nc1cccc(C)c1C] |
| Compound 16 | 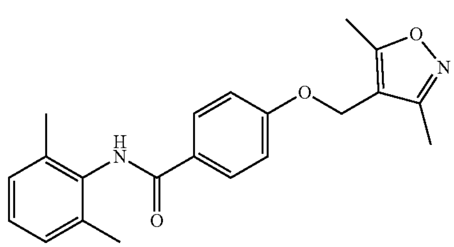 [SMILES: Cc1cccc(C)c1NC(=O)c1ccc(OCc2c(C)noc2C)cc1] |

TABLE 2-continued
| Compound Name | Structure |
| --- | --- |
| Compound 17 | 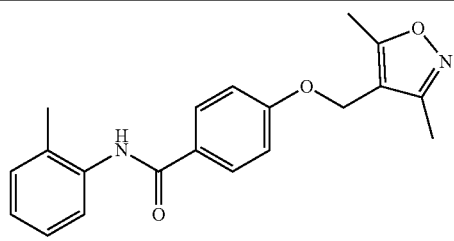 |
| Compound 18 | 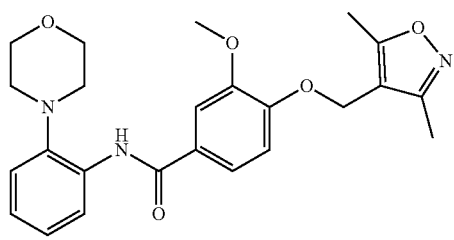 [SMILES: COc1cc(C(=O)Nc2ccccc2N2CCOCC2)ccc1OCc1c(C)noc1C] |
| Compound 19 | 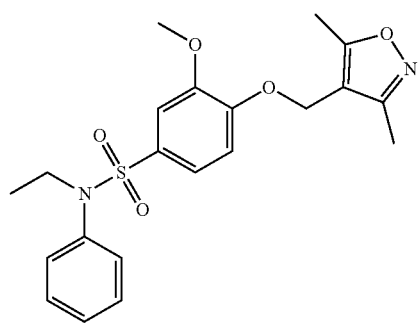 [SMILES: CCN(c1ccccc1)S(=O)(=O)c1ccc(OCc2c(C)noc2C)c(OC)c1] |
| Compound 20 | 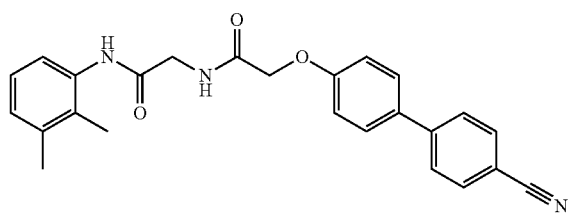 [SMILES: Cc1cccc(NC(=O)CNC(=O)COc2ccc(-c3ccc(C#N)cc3)cc2)c1C] |
| Compound 21 | 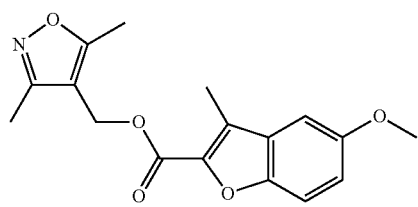 |
| Compound 22 | 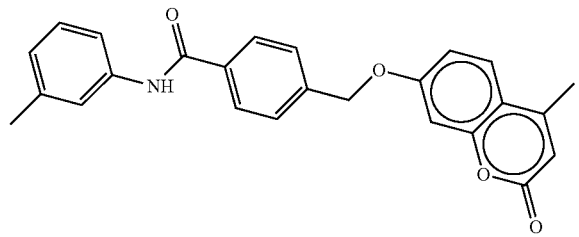 |

TABLE 2-continued
| Compound Name | Structure |
| --- | --- |
| Compound 23 | 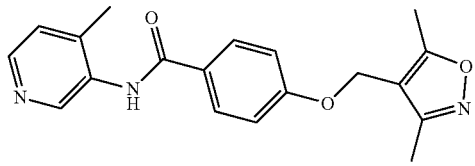 [SMILES: Cc1ccncc1NC(=O)c1ccc(OCc2c(C)noc2C)cc1] |
| Compound 24 | 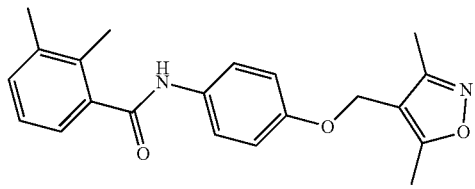 [SMILES: Cc1cccc(C(=O)Nc2ccc(OCc3c(C)noc3C)cc2)c1C] |
| Compound 25 | 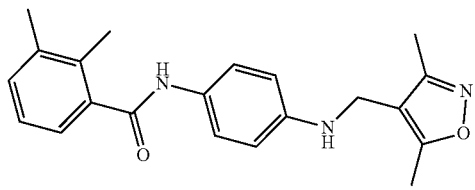 [SMILES: Cc1cccc(C(=O)Nc2ccc(NCc3c(C)noc3C)cc2)c1C] |
| Compound 26 | |
| Compound 27 | 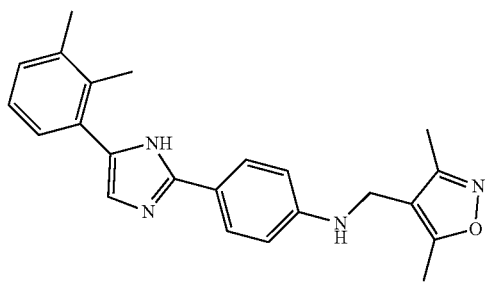 [SMILES: Cc1cccc(-c2cnc(-c3ccc(NCc4c(C)noc4C)cc3)[nH]2)c1C] |
| Compound 28 | 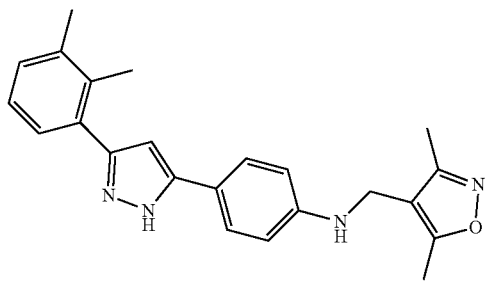 [SMILES: Cc1cccc(-c2cc(-c3ccc(NCc4c(C)noc4C)cc3)[nH]n2)c1C] |
| Compound 29 | 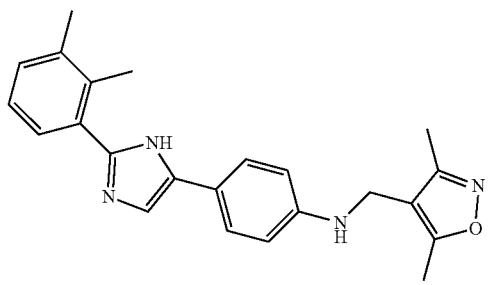 [SMILES: Cc1cccc(-c2ncc(-c3ccc(NCc4c(C)noc4C)cc3)[nH]2)c1C] |

TABLE 2-continued
| Compound Name | Structure |
| --- | --- |
| Compound 30 | 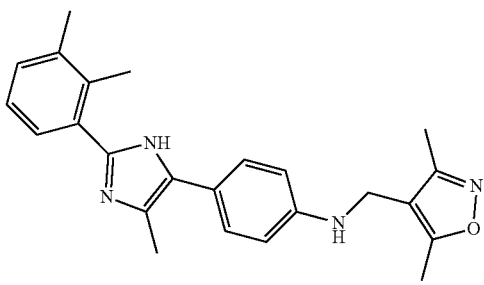 [SMILES: Cc1cccc(-c2nc(C)c(-c3ccc(NCc4c(C)noc4C)cc3)[nH]2)c1C] |
| Compound 31 | 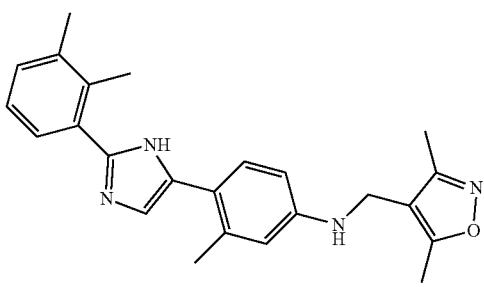 [SMILES: Cc1cc(NCc2c(C)noc2C)ccc1-c1cnc(-c2cccc(C)c2C)[nH]1] |
| Compound 32 | 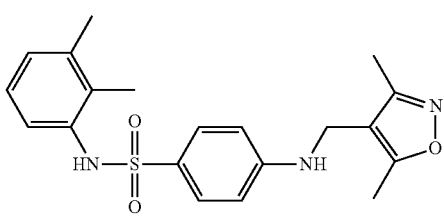 [SMILES: Cc1cccc(NS(=O)(=O)c2ccc(NCc3c(C)noc3C)cc2)c1C] |
| Compound 33 | 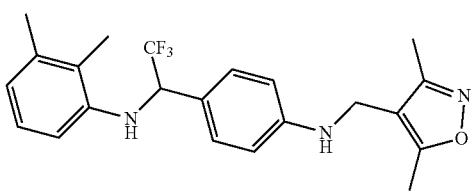 [SMILES: Cc1cccc(NC(c2ccc(NCc3c(C)noc3C)cc2)C(F)(F)F)c1C] |
| Compound 34 | 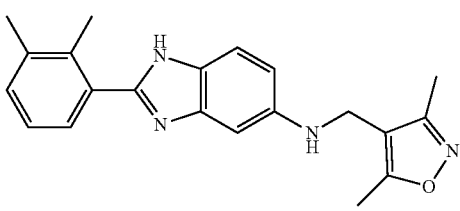 [SMILES: Cc1cccc(-c2nc3cc(NCc4c(C)noc4C)ccc3[nH]2)c1C] |
| Compound 35 | 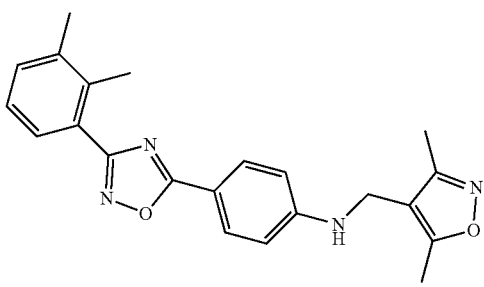 [SMILES: Cc1cccc(-c2noc(-c3ccc(NCc4c(C)noc4C)cc3)n2)c1C] |

TABLE 2-continued
| Compound Name | Structure |
| --- | --- |
| Compound 36 | 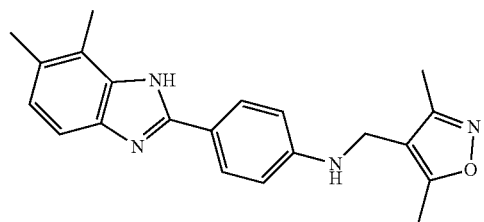 [SMILES: Cc1ccc2nc(-c3ccc(NCc4c(C)noc4C)cc3)[nH]c2c1C] |
| Compound 37 | 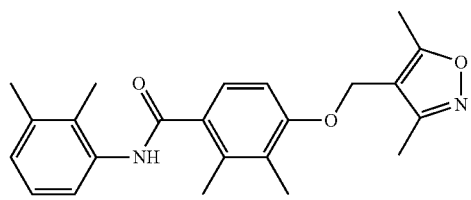 [SMILES: Cc1cccc(NC(=O)c2ccc(OCc3c(C)noc3C)c(C)c2C)c1C] |
| Compound 38 | 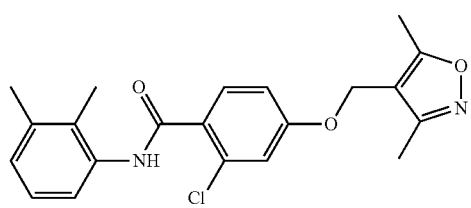 |
| Compound 39 | 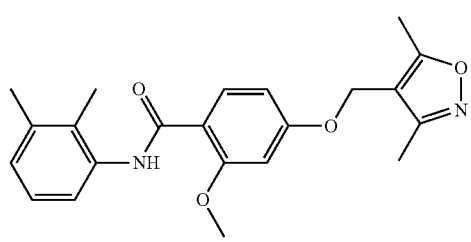 [SMILES: COc1cc(OCc2c(C)noc2C)ccc1C(=O)Nc1cccc(C)c1C] |
| Compound 40 | 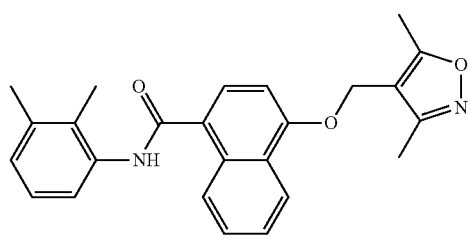 [SMILES: Cc1cccc(NC(=O)c2ccc(OCc3c(C)noc3C)c3ccccc23)c1C] |
| Compound 41 | 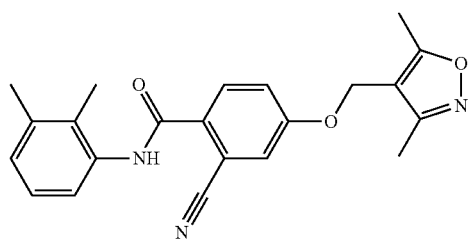 [SMILES: Cc1cccc(NC(=O)c2ccc(OCc3c(C)noc3C)cc2C#N)c1C] |
| Compound 42 | 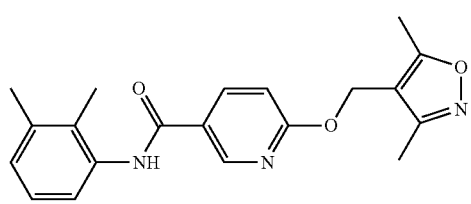 |

TABLE 2-continued
| Compound Name | Structure |
| --- | --- |
| Compound 43 | 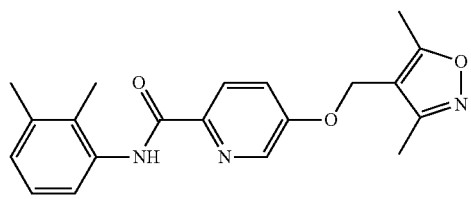 [SMILES: Cc1cccc(NC(=O)c2ccc(OCc3c(C)noc3C)cn2)c1C] |
| Compound 44 | 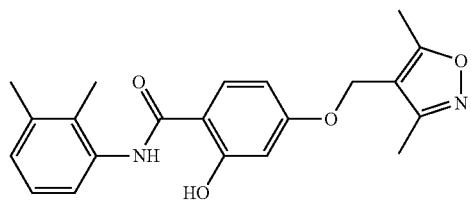 [SMILES: Cc1cccc(NC(=O)c2ccc(OCc3c(C)noc3C)cc2O)c1C] |
| Compound 45 | 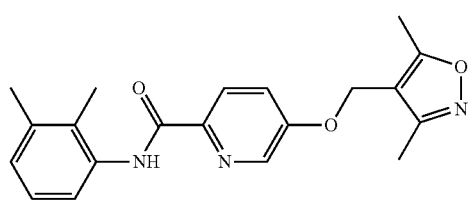 [SMILES: Cc1cccc(NC(=O)c2ccc(OCc3c(C)noc3C)cn2)c1C] |
| Compound 46 | 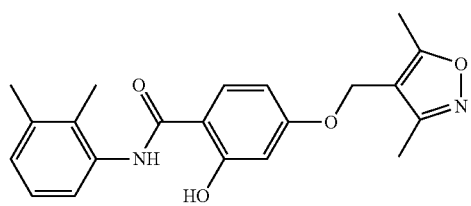 |
| Compound 47 | 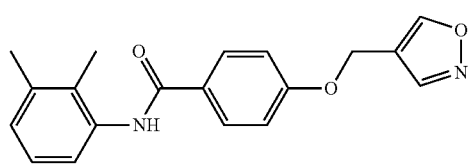 [SMILES: Cc1cccc(NC(=O)c2ccc(OCc3cnoc3)cc2)c1C] |
| Compound 48 | 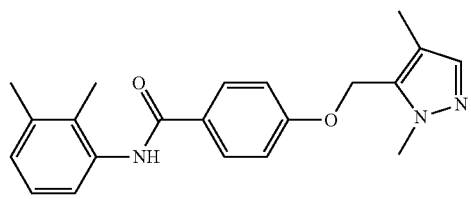 [SMILES: Cc1cccc(NC(=O)c2ccc(OCc3c(C)cnn3C)cc2)c1C] |
| Compound 49 | 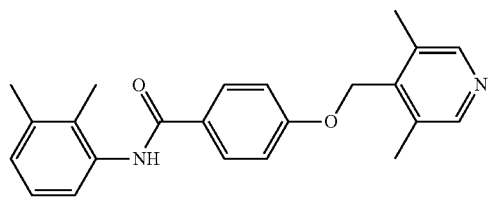 |
| Compound 50 | 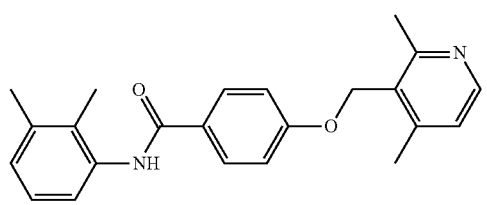 |

TABLE 2-continued
| Compound Name | Structure |
| --- | --- |
| Compound 51 | 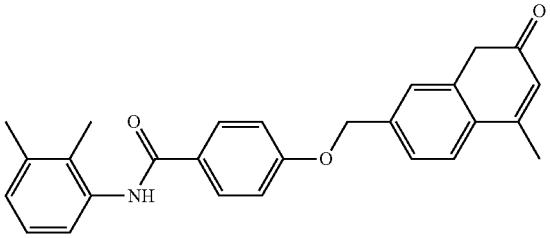 [SMILES: CC1=CC(=O)Cc2cc(COc3ccc(C(=O)Nc4cccc(C)c4C)cc3)ccc21] |
| Compound 52 | 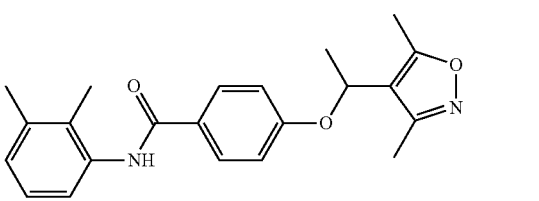 [SMILES: Cc1cccc(NC(=O)c2ccc(OC(C)c3c(C)noc3C)cc2)c1C] |
| Compound 53 | 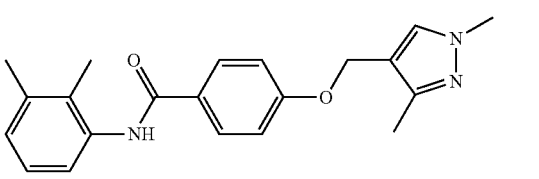 [SMILES: Cc1cccc(NC(=O)c2ccc(OCc3cn(C)nc3C)cc2)c1C] |
| Compound 54 | 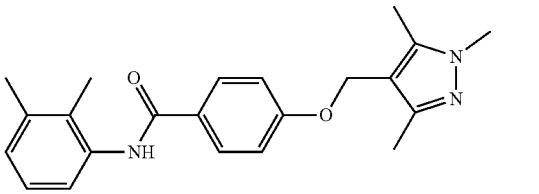 [SMILES: Cc1cccc(NC(=O)c2ccc(OCc3c(C)nn(C)c3C)cc2)c1C] |
| Compound 55 | 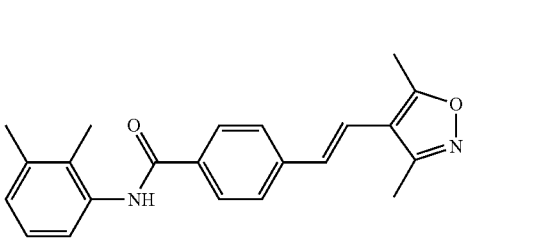 [SMILES: Cc1cccc(NC(=O)c2ccc(/C=C/c3c(C)noc3C)cc2)c1C] |
| Compound 56 | 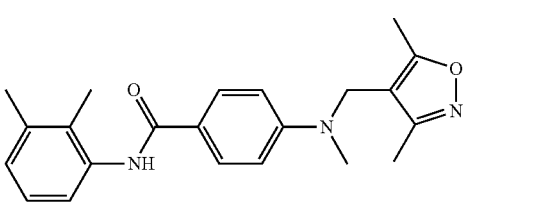 [SMILES: Cc1cccc(NC(=O)c2ccc(N(C)Cc3c(C)noc3C)cc2)c1C] |
| Compound 57 | 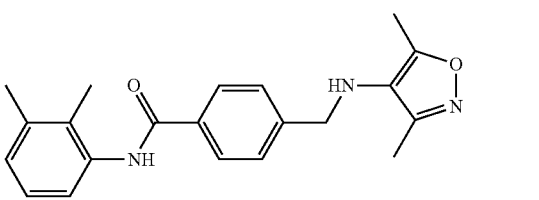 [SMILES: Cc1cccc(NC(=O)c2ccc(CNc3c(C)noc3C)cc2)c1C] |

TABLE 2-continued
| Compound Name | Structure |
| --- | --- |
| Compound 58 | 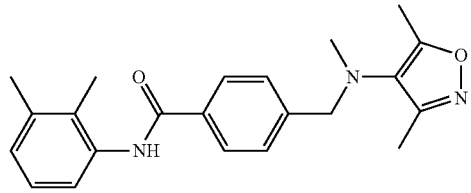 [SMILES: Cc1cccc(NC(=O)c2ccc(CN(C)c3c(C)noc3C)cc2)c1C] |
| Compound 59 | 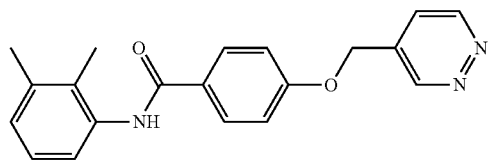 [SMILES: Cc1cccc(NC(=O)c2ccc(OCc3ccnnc3)cc2)c1C] |
| Compound 60 | 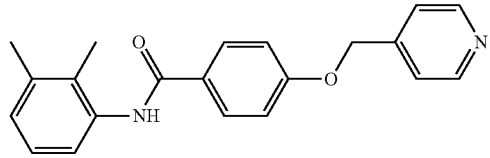 |
| Compound 61 | 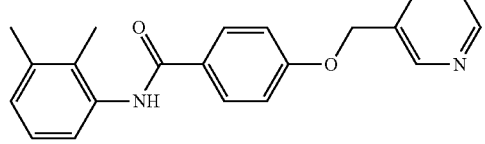 |
| Compound 62 | 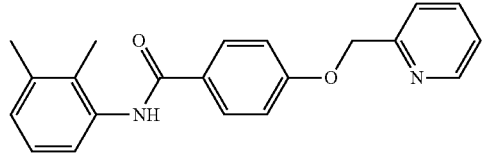 [SMILES: Cc1cccc(NC(=O)c2ccc(OCc3ccccn3)cc2)c1C] |
| Compound 63 | 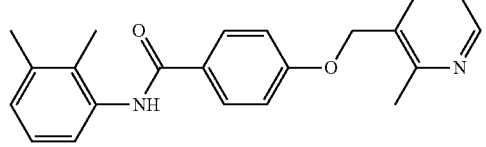 |
| Compound 64 | 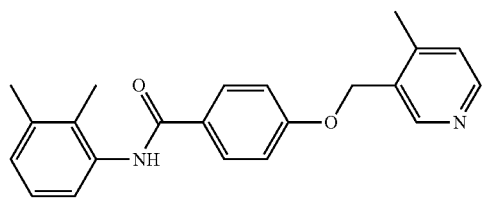 |
| Compound 65 | 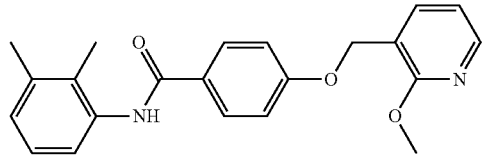 |

TABLE 2-continued
| Compound Name | Structure |
| --- | --- |
| Compound 66 | 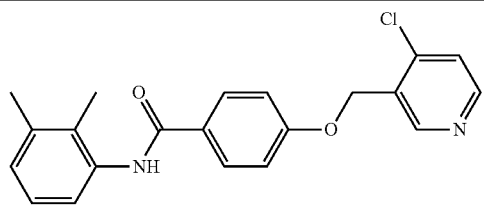 |
| Compound 67 | 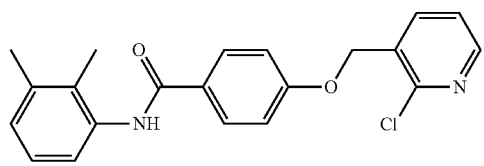 [SMILES: Cc1cccc(NC(=O)c2ccc(OCc3cccnc3C)cc2)c1C] |
| Compound 68 | 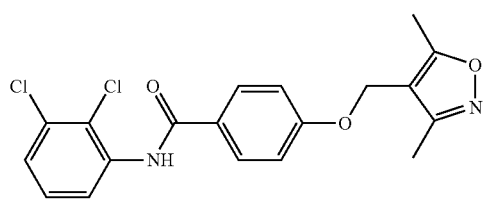 [SMILES: Cc1noc(C)c1COc1ccc(C(=O)Nc2cccc(Cl)c2Cl)cc1] |
| Compound 69 | 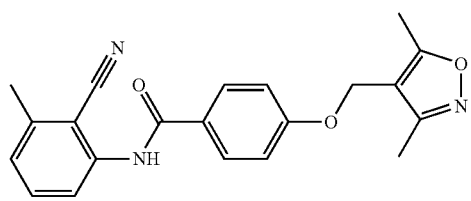 [SMILES: Cc1cccc(NC(=O)c2ccc(OCc3c(C)noc3C)cc2)c1C#N] |
| Compound 70 | 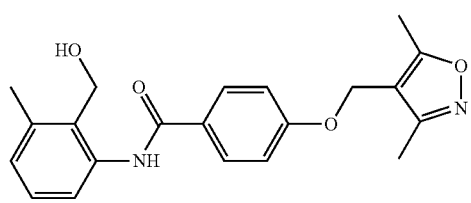 [SMILES: Cc1cccc(NC(=O)c2ccc(OCc3c(C)noc3C)cc2)c1CO] |
| Compound 71 | 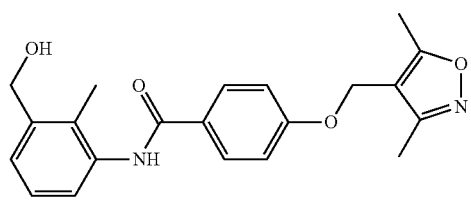 [SMILES: Cc1noc(C)c1COc1ccc(C(=O)Nc2cccc(CO)c2C)cc1] |
| Compound 72 | 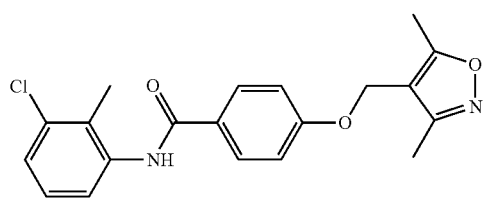 |
| Compound 73 | 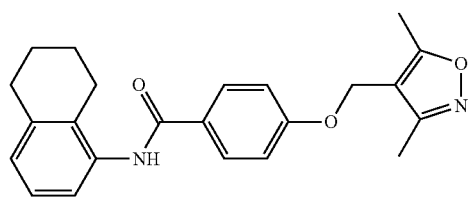 [SMILES: Cc1noc(C)c1COc1ccc(C(=O)Nc2cccc3c2CCCC3)cc1] |

TABLE 2-continued
| Compound Name | Structure |
| --- | --- |
| Compound 74 | 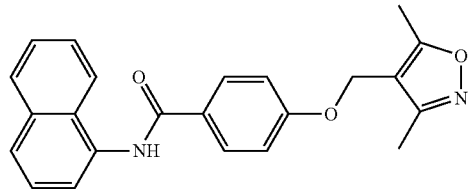 [SMILES: Cc1noc(C)c1COc1ccc(C(=O)Nc2cccc3ccccc23)cc1] |
| Compound 75 | 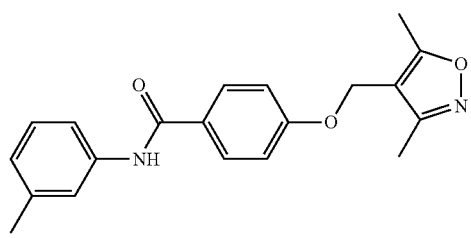 [SMILES: Cc1cccc(NC(=O)c2ccc(OCc3c(C)noc3C)cc2)c1] |
| Compound 76 | 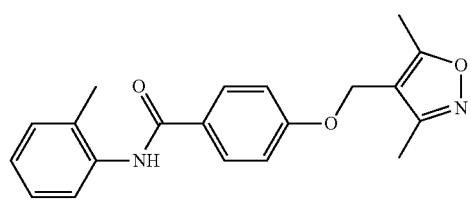 [SMILES: Cc1ccccc1NC(=O)c1ccc(OCc2c(C)noc2C)cc1] |
| Compound 77 | 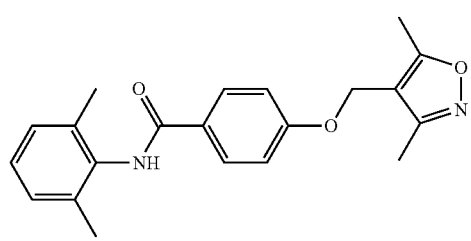 [SMILES: Cc1cccc(C)c1NC(=O)c1ccc(OCc2c(C)noc2C)cc1] |
| Compound 78 | 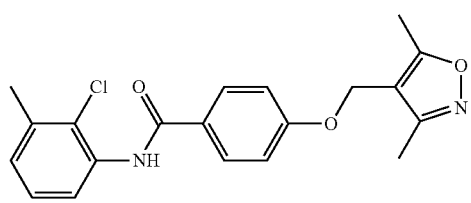 [SMILES: Cc1cccc(NC(=O)c2ccc(OCc3c(C)noc3C)cc2)c1Cl] |
| Compound 79 | 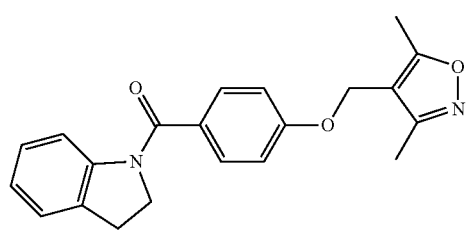 [SMILES: Cc1noc(C)c1COc1ccc(C(=O)N2CCc3ccccc32)cc1] |
| Compound 80 | 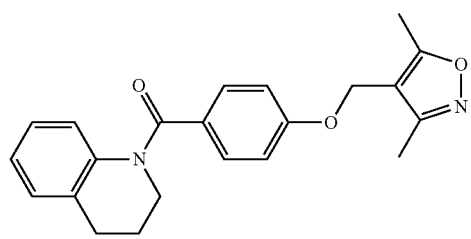 [SMILES: Cc1noc(C)c1COc1ccc(C(=O)N2CCCc3ccccc32)cc1] |

TABLE 2-continued
Compound Name  Structure
Compound 81
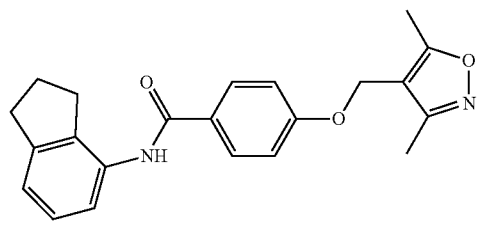 [SMILES: Cc1noc(C)c1COc1ccc(C(=O)Nc2cccc3c2CCC3)cc1]
Compound 82
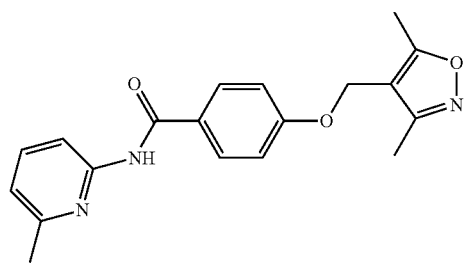 [SMILES: Cc1cccc(NC(=O)c2ccc(OCc3c(C)noc3C)cc2)n1]
Compound 83
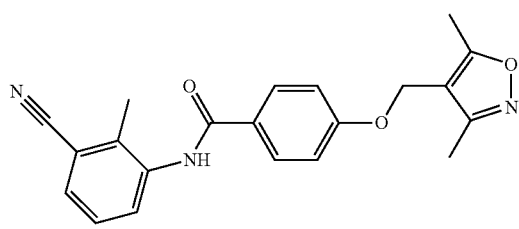 [SMILES: Cc1noc(C)c1COc1ccc(C(=O)Nc2cccc(C#N)c2C)cc1]
Compound 84
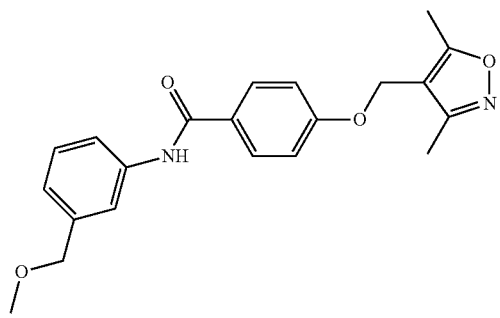 [SMILES: COCc1cccc(NC(=O)c2ccc(OCc3c(C)noc3C)cc2)c1]
Compound 85
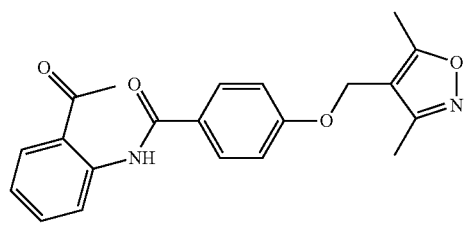 [SMILES: CC(=O)c1ccccc1NC(=O)c1ccc(OCc2c(C)noc2C)cc1]
Compound 86
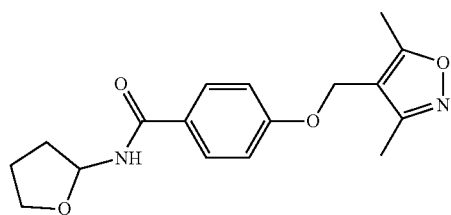 [SMILES: Cc1noc(C)c1COc1ccc(C(=O)NC2CCCO2)cc1]

TABLE 2-continued
| Compound Name | Structure |
| --- | --- |
| Compound 87 | 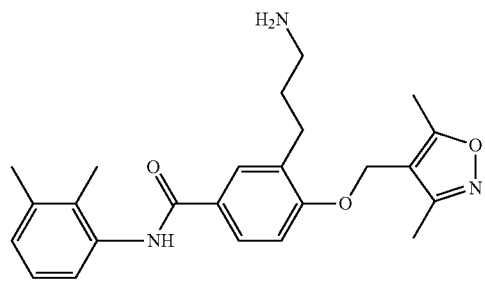 [SMILES: Cc1cccc(NC(=O)c2ccc(OCc3c(C)noc3C)c(CCCN)c2)c1C] |
| Compound 88 | 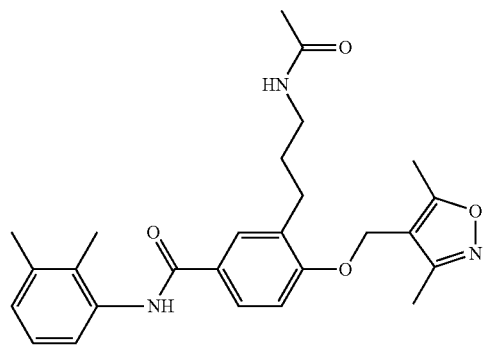 [SMILES: CC(=O)NCCCc1cc(C(=O)Nc2cccc(C)c2C)ccc1OCc1c(C)noc1C] |
| Compound 89 | 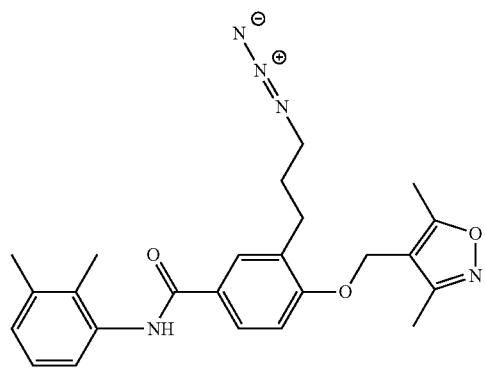 [SMILES: Cc1cccc(NC(=O)c2ccc(OCc3c(C)noc3C)c(CCCN=[NH+][NH-])c2)c1C] |
| Compound 90 | 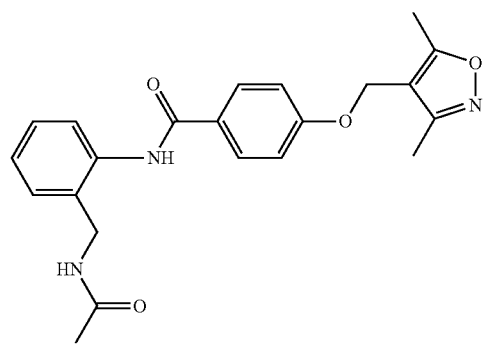 [SMILES: CC(=O)NCc1ccccc1NC(=O)c1ccc(OCc2c(C)noc2C)cc1] |

TABLE 2-continued
| Compound Name | Structure |
|---|---|
| Compound 91 | 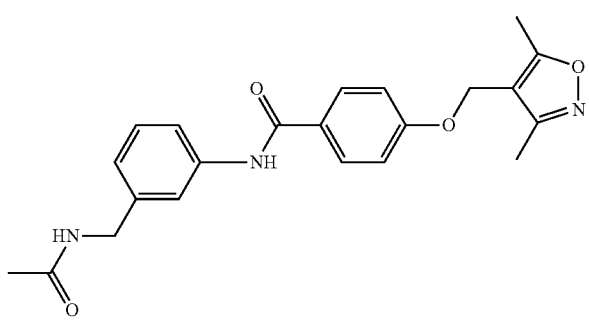 [SMILES: CC(=O)NCc1cccc(NC(=O)c2ccc(OCc3c(C)noc3C)cc2)c1] |
| Compound 92 | 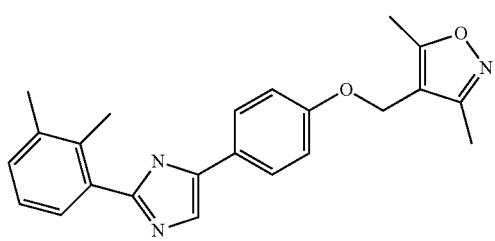 [SMILES: Cc1cccc(-c2ncc(-c3ccc(OCc4c(C)noc4C)cc3)[nH]2)c1C] |
| Compound 93 | 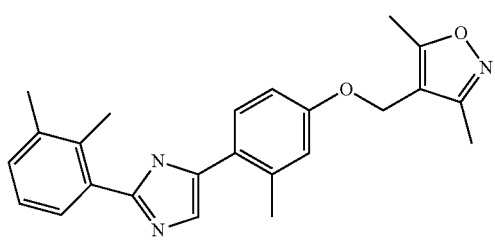 [SMILES: Cc1cc(OCc2c(C)noc2C)ccc1-c1cnc(-c2cccc(C)c2C)[nH]1] |
| Compound 94 | 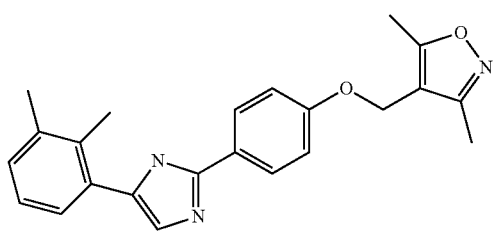 [SMILES: Cc1cccc(-c2cnc(-c3ccc(OCc4c(C)noc4C)cc3)[nH]2)c1C] |
| Compound 95 | 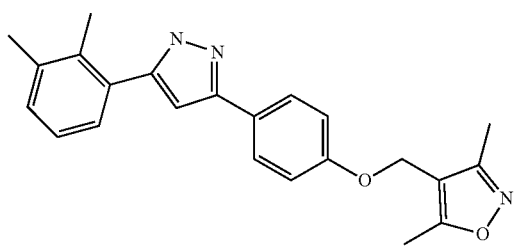 [SMILES: Cc1cccc(-c2cc(-c3ccc(OCc4c(C)noc4C)cc3)n[nH]2)c1C] |
| Compound 96 | 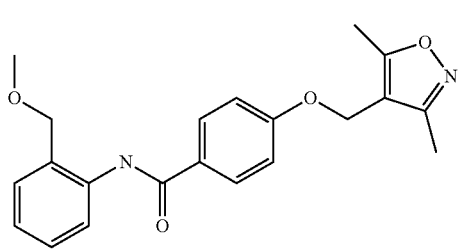 [SMILES: COCc1ccccc1NC(=O)c1ccc(OCc2c(C)noc2C)cc1] |

TABLE 2-continued

| Compound Name | Structure |
| --- | --- |
| Compound 97 | 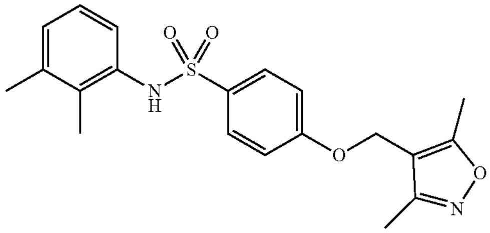 [SMILES: Cc1cccc(NS(=O)(=O)c2ccc(OCc3c(C)noc3C)cc2)c1C] |
| Compound 98 | 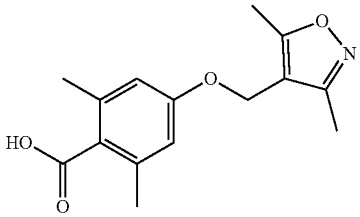 [SMILES: Cc1cc(OCc2c(C)noc2C)cc(C)c1C(=O)O] |
| Compound 99 | 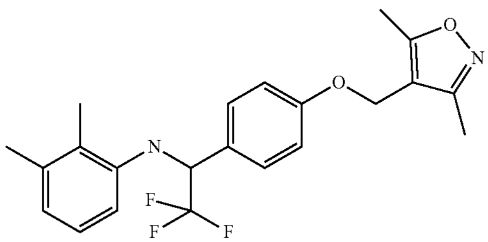 [SMILES: Cc1cccc(NC(c2ccc(OCc3c(C)noc3C)cc2)C(F)(F)F)c1C] |

The compounds can be prepared from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations*, 2d. ed., Wiley-VCH Publishers (1999); P. G. M. Wuts and T. W. Greene, *Protective Groups in Organic Synthesis*, 4th Ed., John Wiley and Sons (2007); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy (FT-IR), spectrophotometry (e.g., UV-visible), or mass spectrometry (MS), or by chromatography such as high performance liquid chromatography (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis*, 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

In some embodiments, the compound has a Z-score of greater than 3 in hyperglycemic conditions. In some embodiments, the compound has a Z-score of greater than 3 in hyperglycemic conditions and a Z score of less than 3 in normoglycemic conditions.

Pharmaceutical Compositions

In some embodiments, provided herein are pharmaceutical compositions comprising one or more compounds as disclosed herein, or a pharmaceutically acceptable form thereof (e.g., pharmaceutically acceptable salts, hydrates, solvates, isomers, prodrugs, and isotopically labeled derivatives), and one or more pharmaceutically acceptable excipients, carriers, including inert solid diluents and fillers, diluents, including sterile aqueous solution and various organic solvents, permeation enhancers, solubilizers and adjuvants. In some embodiments, a pharmaceutical composition described herein includes a second active agent such as an additional therapeutic agent, (e.g., metformin, SGLT2 inhibitor, DPP4 inhibitor, or thiazolidinedione).

As described herein, the disclosed compositions comprise a disclosed compound together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the dosage form desired. Except insofar as any conventional carrier medium is incompatible with the compounds provided herein, such as by producing any undesirable biological effect or otherwise interacting in a deleterious manner with any other component(s) of the pharmaceutical composition, the carrier is contemplated to be within the scope of this disclosure.

1. Formulations

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or another therapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

1A. Formulations for Oral Administration

In some embodiments, provided herein are pharmaceutical compositions for oral administration containing a compound as disclosed herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. In some embodiments, compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol for subsequent formulation. For example, suitable carriers include powders, capsules, and tablets, with the solid oral preparations. In some embodiments, tablets can be coated by standard aqueous or nonaqueous techniques.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

1B. Formulations for Parenteral Administration

In some embodiments, provided herein are pharmaceutical compositions for parenteral administration containing a compound as disclosed herein, and one or more pharmaceutical excipients suitable for parenteral administration. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, benzyl alcohol, and the like (and suitable mixtures thereof), cyclodextrin derivatives, sodium chloride, tragacanth gum, buffers, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

In some embodiments, the active ingredient may also be administered by injection as a composition with suitable carriers including saline, dextrose, or water, or with cyclodextrin (e.g., Captisol), cosolvent solubilization (e.g., propylene glycol) or micellar solubilization (e.g., Tween 80).

1C. Formulations for Topical Administration

In some embodiments, provided herein are pharmaceutical compositions for topical (e.g., transdermal) administration containing a compound as disclosed herein, and one or more pharmaceutical excipients suitable for topical administration. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, liniments, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area. For example, an ointment formulation can have either a paraffinic or a water-miscible base. Alternatively, the active ingredient may be formulated in a cream with an oil-in-water cream base. The aqueous phase of the cream base may include, for example at least about 30% w/w of a polyhydric alcohol such as propylene glycol, butane-1,3-diol, mannitol, sorbitol, glycerol, polyethylene glycol and mixtures thereof.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent. Patchs can be either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

1F. Formulations for Controlled Release Administration

In some embodiments, provided herein are pharmaceutical compositions for controlled release administration containing a compound as disclosed herein, and one or more pharmaceutical excipients suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

2. Dosage

A compound described herein can be delivered in the form of pharmaceutically acceptable compositions which comprise a therapeutically effective amount of one or more compounds described herein and/or one or more additional therapeutic agents, formulated together with one or more pharmaceutically acceptable excipients. In some embodiments, only a compound provided herein without an additional therapeutic agent is included in the dosage form. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the compound employed, the severity of the condition, the route of administration, the time of administration, the rate of excretion or metabolism of the compound being employed, the rate and extent of absorption, the duration of the treatment, administration of other drugs, compounds and/or materials used in combination with the compound employed, the age, sex, weight, condition, general health and prior medical history of the patient being treated, and like factors well known in the medical arts.

The dosage level can also be informed by in vitro or in vivo assays which can optionally be employed to help identify optimal dosage ranges. A rough guide to effective doses can be extrapolated from dose-response curves derived from in vitro or animal model test systems.

3. Kits

In some embodiments, provided herein are kits. The kits can include a compound or pharmaceutical composition as described herein, in suitable packaging, and written material that can include instructions for use, discussion of clinical studies, listing of side effects, and the like. Kits are well suited for the delivery of solid oral dosage forms such as tablets or capsules. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . . Second Week, Monday, Tuesday, . . . " etc. Other variations of memory aids will be readily apparent. A "daily dose" can be a single tablet or capsule or several tablets or capsules to be taken on a given day.

The kit can further contain another agent. In some embodiments, the compound as disclosed herein and the agent are provided as separate pharmaceutical compositions in separate containers within the kit. In some embodiments, the compound as disclosed herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that is to be reconstituted for parenteral administration, the kit can comprise a sealed container of a suitable vehicle in which the active agent can be dissolved to form a particulate free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

4. Methods

Provided herein are methods of treating disease and/or disorders or symptoms thereof which include administering a therapeutically effective amount of a compound, or a pharmaceutical composition comprising a compound of the formulae provided herein to a subject. In some embodiments, the subject is a mammal, such as a human. Such treatment will be suitably administered to subjects suffering from, having, susceptible to, or at risk for a disease, disorder, or symptom thereof. Identifying a subject in need of such treatment can be in the judgment of a subject or a health care professional and can be subjective (e.g. opinion) or objective (e.g. measurable by a test or diagnostic method). Determination of those subjects "at risk" can be made by any objective or subjective determination by a diagnostic test or opinion of a subject or health care provider (e.g., blood sugar, hemoglobin A1c, insulin level, genetic test, enzyme or protein marker, family history, and the like).

Diabetes mellitus type 2 is a long term metabolic disorder characterized by high blood sugar, insulin resistance and a relative lack of insulin. Long-term complications from high blood sugar include heart disease, stroke, diabetic retinopathy which can result in blindness, kidney failure, and poor blood flow in the limbs which may lead to amputations. It makes up about 90% of cases of diabetes, with the other 10% due primarily to diabetes mellitus type 1 and gestational diabetes. Type 2 diabetes is typically a chronic disease associated with a ten-year-shorter life expectancy. This is partly due to a number of complications with which it is associated, including: two to four times the risk of cardiovascular disease, including ischemic heart disease and stroke; a 20-fold increase in lower limb amputations, and increased rates of hospitalizations. Tissues and organs affected by type 2 diabetes include striated muscle, adipose tissue, liver, gastrointestinal tract, pancreas and brain (See, FIG. 1).

Type 2 diabetes is due to insufficient insulin production from beta cells in the setting of insulin resistance. Insulin resistance, which is the inability of cells to respond adequately to normal levels of insulin, occurs primarily within the muscles, liver, and fat tissue. In the liver, insulin normally suppresses glucose release. However, in the setting of insulin resistance, the liver inappropriately releases glucose into the blood. The proportion of insulin resistance versus beta-cell dysfunction differs among individuals, with some having primarily insulin resistance and only a minor defect in insulin secretion, and others with slight insulin resistance and primarily a lack of insulin secretion. Regardless of the primary etiology, progression of the disease correlates closely with decreases in glucose-stimulated insulin secretion from the pancreas.

Figure 2A:
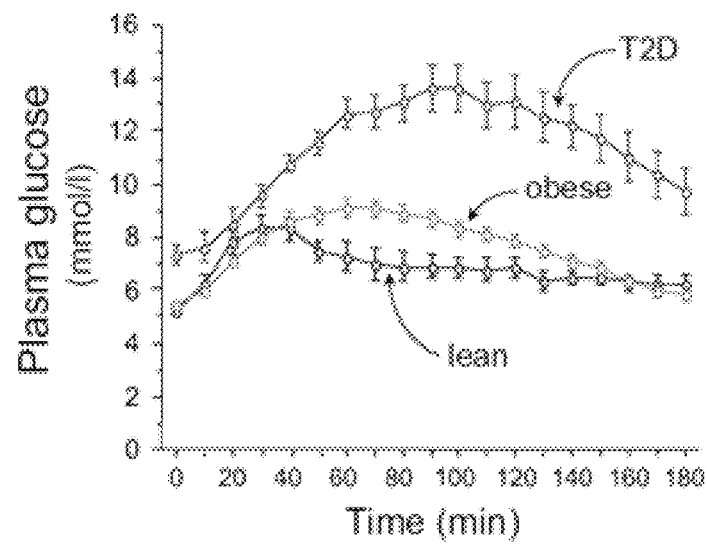
FIG. 2A is a graph showing the results of an oral glucose challenge in human subjects that were lean, obese or had type 2 diabetes (T2D).
Figure 2B:
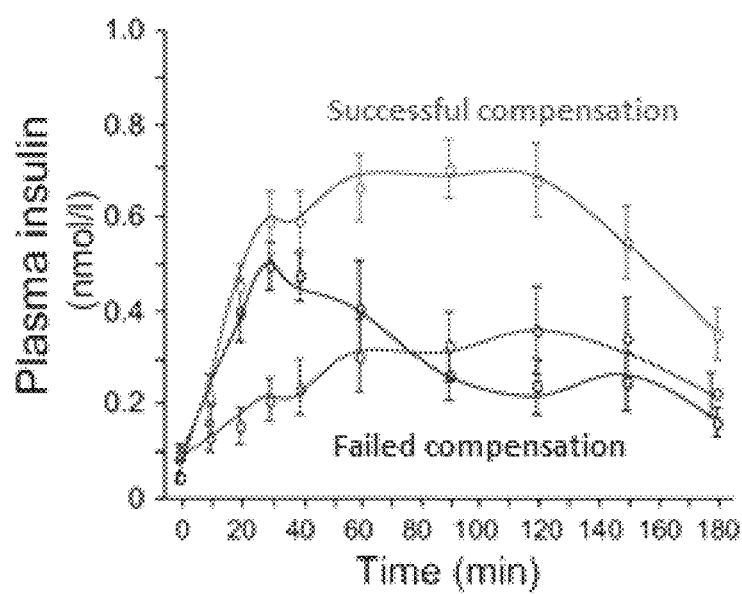
FIG. 2B depicts the results of insulin secretion in response to the glucose challenge. Successful compensation was demonstrated in a higher level of secretion than those subjects who failed to compensate by insulin secretion.

Given an oral glucose challenge, patients with type 2 diabetes have significantly higher plasma glucose levels than otherwise healthy obese and lean patients. In response, type 2 diabetes patients do not secrete sufficient insulin in the plasma and fail to compensate for the administered glucose. Obese but non-diabetic patients show the highest level of insulin secretion, suggesting compensation for insulin resistance. (see, FIGS. 2A and 2B). The relatively low insulin levels seen in type 2 diabetic patients is the primary driver of hyperglycemia, which ultimately leads to the symptoms and complications of the disease.

Other potentially important mechanisms associated with type 2 diabetes and insulin resistance include: increased breakdown of lipids within fat cells, resistance to and lack of incretin, high glucagon levels in the blood, increased retention of salt and water by the kidneys, and inappropriate regulation of metabolism by the central nervous system. However, not all people with insulin resistance develop diabetes, since an impairment of insulin secretion by pancreatic beta cells is also required. Diagnosis of type 2 diabetes is well known in the art, defined by the World Health Organization using blood glucose tests.

Currently, no cure for type 2 diabetes exists. However, the disorder can be managed using a combination of lifestyle interventions such as proper diet and exercise, lowering other cardiovascular risk factors such as hypertension and high cholesterol, and maintaining blood glucose levels in the normal range. A number of medications for treating type 2 diabetes are available, such as sulfonylureas, thiazolidinediones, dipeptidyl peptidase-4 inhibitors, SGLT2 inhibitors, and glucagon-like peptide-1 (GLP-1) analogs. Many of these drugs require injection administration. Patients may also be injected with various forms of insulin based on blood glucose levels, but hypoglycemia remains a danger. The orally available drugs that act to stimulate insulin secretion do so regardless of whether the blood glucose level is abnormally high. A patient could become hypoglycemic if their blood glucose level was reduced too far, leading to dizziness, weakness, confusion, falls, seizures or death. While GLP-1 analogues are considered to be glucose-dependent in their effects on augmenting insulin secretion, this class of medication requires painful subcutaneous injections and has limiting side effects, most notably nausea and vomiting. Other classes of drugs are administered to patients showing insulin resistance, where the pancreas produces insulin but the body does not effectively use it to capture glucose from the bloodstream, leading to high circulating glucose levels. To date, no oral treatments have been developed to safely augment insulin secretion by the pancreas in a glucose-dependent manner.

Provided herein are small molecule modulators of insulin secretion that act in a glucose-dependent manner. Desirably, compounds of the invention are small molecules amenable to oral administration, potent in lowering sugars, and cell-type selective. Most notably, they are also safely glucose-dependent in their augmentation of insulin secretion. Rather than constantly stimulating insulin secretion, independent of blood sugar levels, these compounds act on beta-cells to increase insulin secretion only when the circulating blood sugar levels are high. By avoiding chronic overstimulation of the beta-cells, these drugs are less likely to exhibit detrimental effects on long term beta-cell viability, weight gain and iatrogenic insulin resistance.

The disclosed compounds can be synthesized using techniques well-known in the art of organic synthesis. The starting materials and intermediates required for the synthesis can be obtained from commercial sources, and/or synthesized according to methods known to those skilled in the art and/or disclosed elsewhere herein.

Those skilled in the art will recognize, or be able to ascertain using no more than routine experimentation, numerous equivalents to the specific procedures, embodiments, claims, and examples described herein. Such equivalents are considered to be within the scope and covered by the claims appended hereto. For example, it should be understood that modifications in reaction conditions, including, but not limited to, reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a disclosure and description of how to make and use the assays and methods provided herein, and are not intended to limit the scope of what the inventors regard as the invention.

EXAMPLES

These Examples are provided for the purpose of illustration only, and the disclosure is not limited to these Examples, but rather encompasses all variations that are evident as a result of the teachings provided herein.

Unless noted otherwise, the starting materials for the synthesis described herein were obtained from commercial sources or known synthetic procedures and were used without further purification.

BIOLOGICAL EXAMPLES

Example 1: Identification of Insulin Secretagogues

Figure 3:
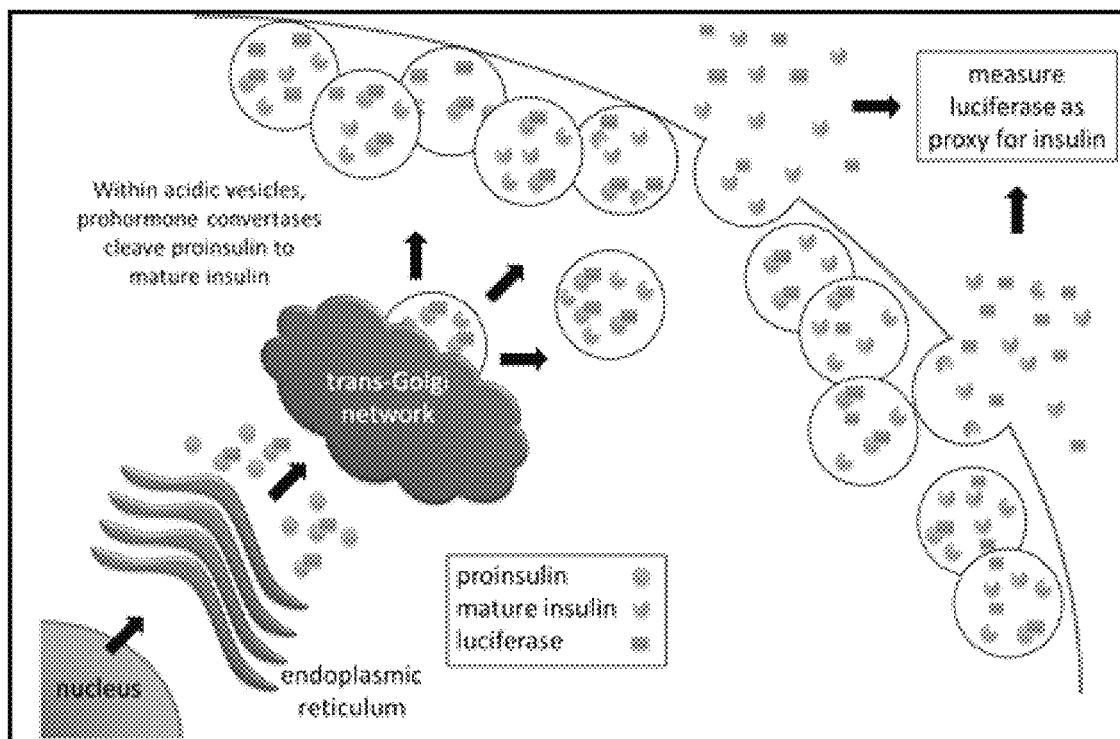
FIG. 3 depicts a diagram of the high throughput compound screening assay for insulin secretion as described in Example 1 (Luciferase Insulin Secretion Assay).

A high-throughput luminescent insulin secretion assay was developed and performed to identify compounds that amplified insulin secretion only in the presence of a permissive glucose environment (FIG. 3). The assay used in compound screening is described in International Patent Publication No. WO2013070796A3, PCT/US2012/063982, and in Burns et al., High-Throughput Luminescent Reporter of Insulin Secretion for Discovering Regulators of Pancreatic Beta-Cell Function. Cell Metab. 2015 Jan. 6; 21(1):126-37.

Figure 4:
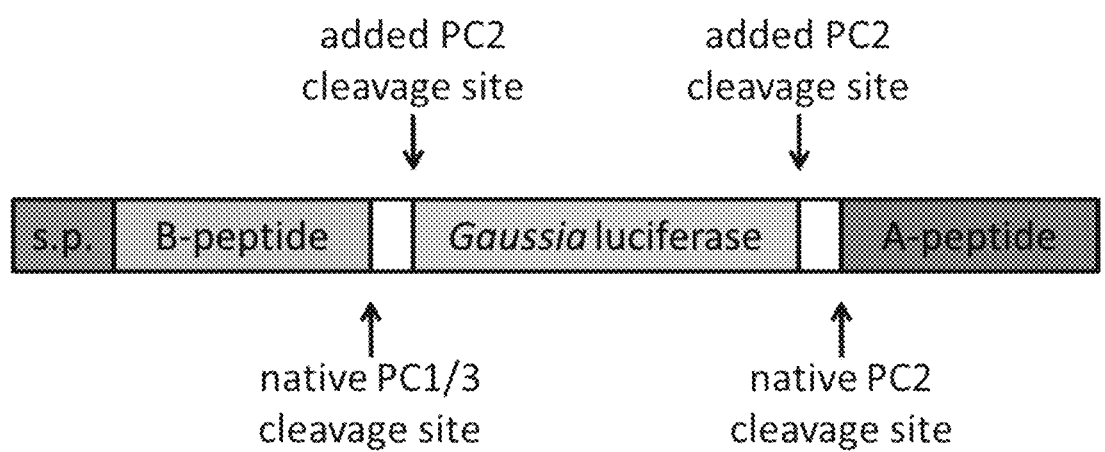
FIG. 4 depicts a diagram of a pro-insulin luciferase reporter to be used the Luciferase Insulin Secretion Assay.

The assay is a luminescent insulin secretion assay created by inserting *Gaussia* luciferase within the C-peptide portion of the insulin prohormone. *Gaussia* luciferase was chosen because of its small size and bright luciferase signal. To ensure full activity of the luciferase, a version was used that was codon-optimized for expression in mammalian cells. The enzyme was flanked with additional cleavage sites for prohormone convertase 2 (PC2), such that no extra amino acids should be present on the ends of the enzyme after processing within the vesicles (FIG. 4). Rat (INS-1E; Merglen et al., 2004) beta-cell lines stably expressing the reporter construct were generated. Assays using this cell type are referred to herein as Luciferase Insulin Secretion Assay.

Figure 5:
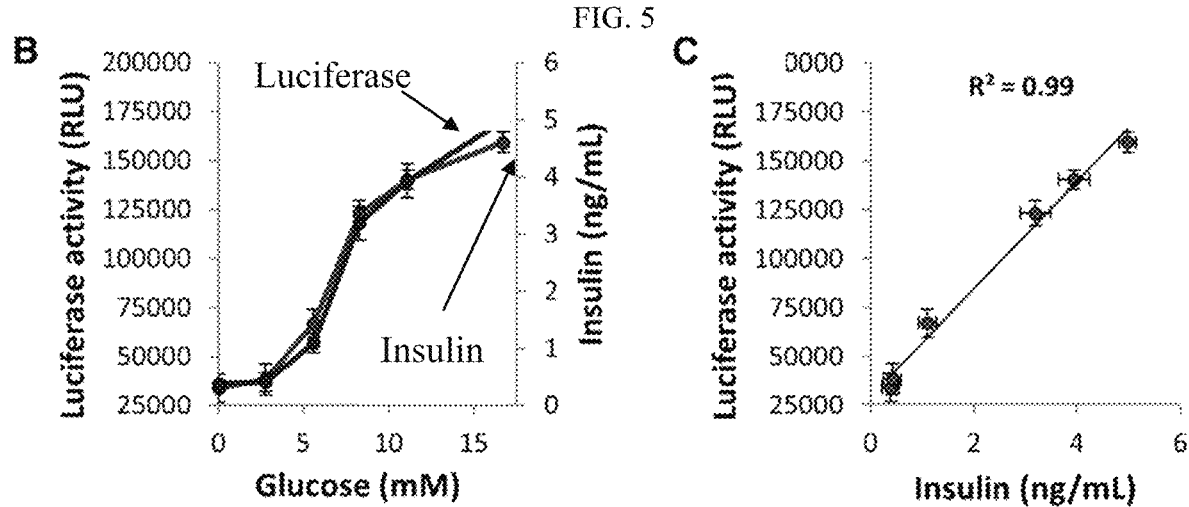
FIG. 5 depicts the strong correlation between insulin secretion (as measured by ELISA) and luciferase secretion (as measured by luminometer) from a rodent beta-cell line.

Upon stimulation with known insulin secretagogues, beta cells expressing this reporter secrete luciferase in close correlation with insulin (FIG. 5).

Figure 6:
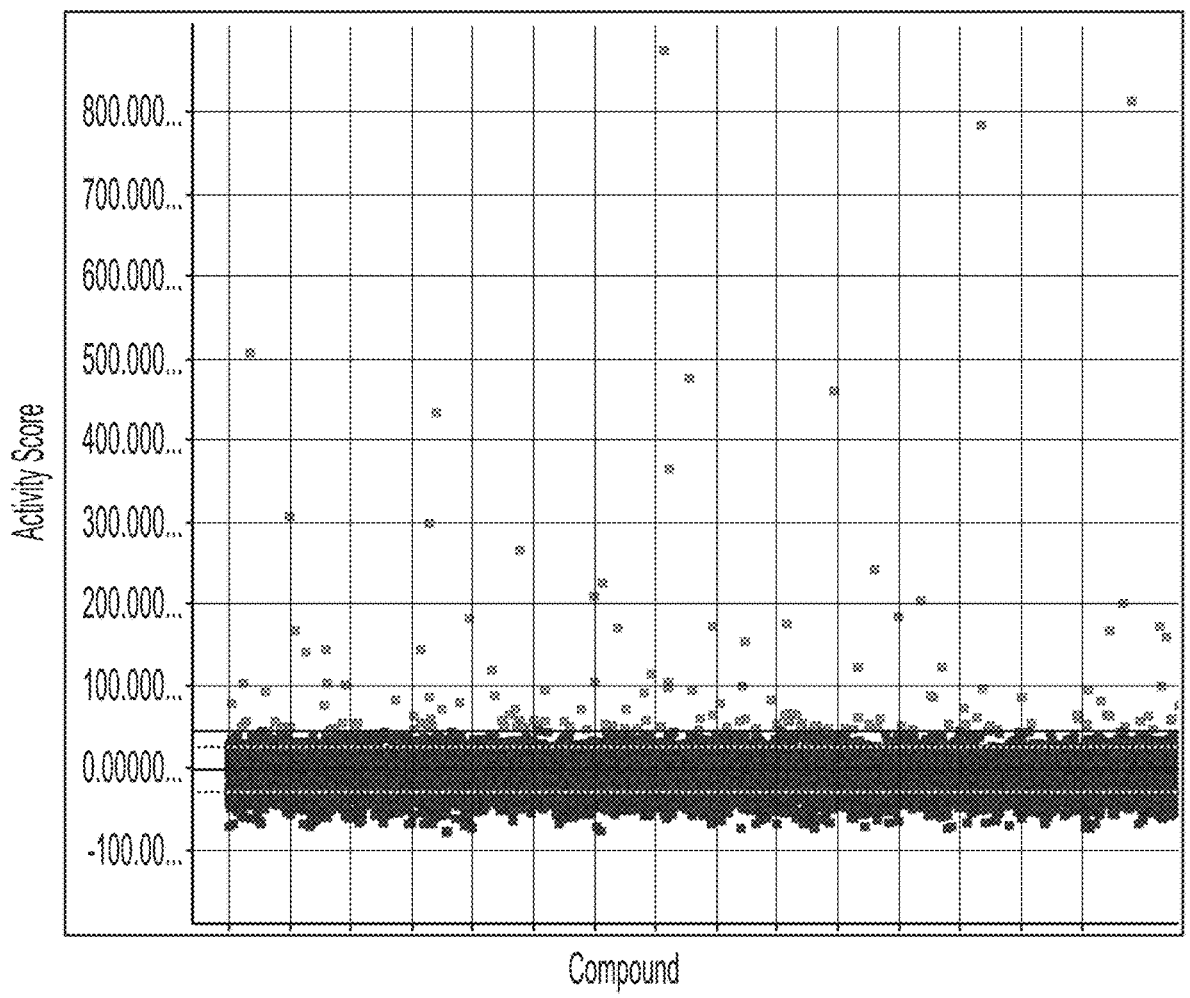
FIG. 6 depicts the Z-score results of the high throughput insulin secretion assay using test compounds. DMSO was used as a negative control.
Figure 7:
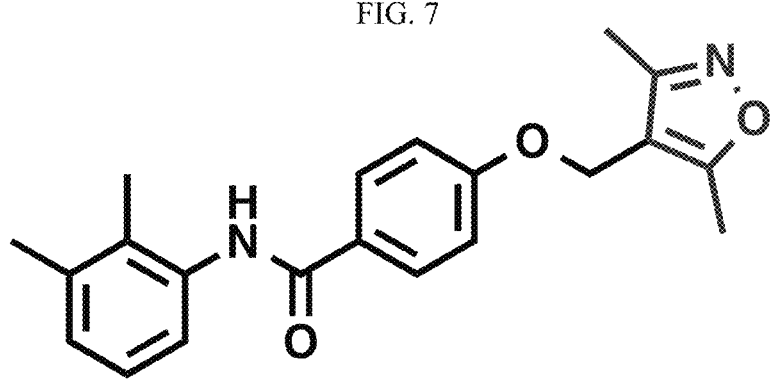
FIG. 7 depicts the structure of dimethylisoxazole-containing Compound 8, and the dose-dependent effect of Compound 8 on insulin secretion as measured in the Luciferase Insulin Secretion Assay in INS-1E cells. Forskolin is included as a positive control.
Figure 7:
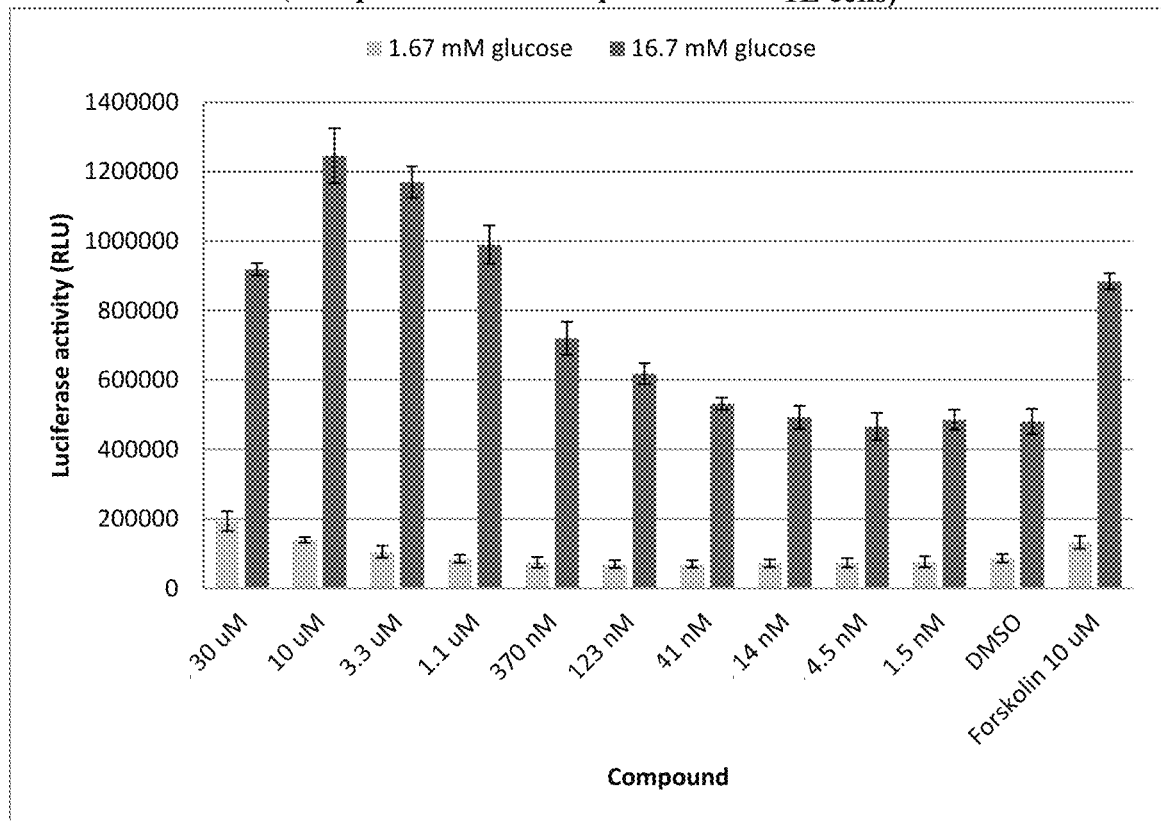
Figure 8:
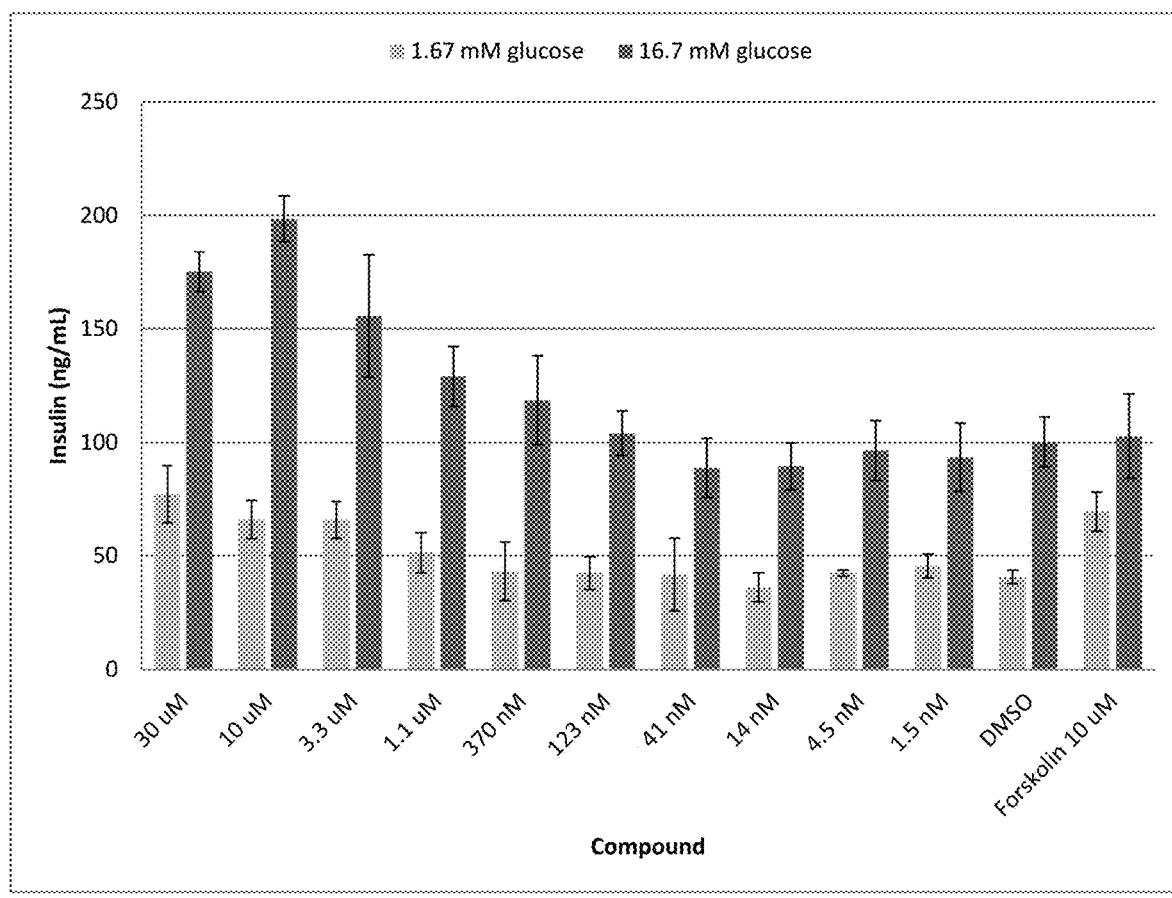
FIG. 8 depicts the dose-dependent effect of Compound 8 on insulin secretion as measured by insulin ELISA from dissociated human islets from nondiabetic donors (top). Forskolin is included as a positive control. Compound 8 similarly increases insulin secretion from human islets derived from type 2 diabetic donors (bottom).
Figure 8:
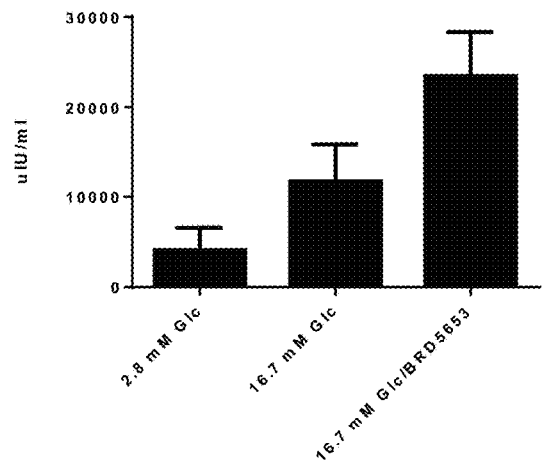

A search for glucose-dependent insulin secretagogues was conducting by screening 384,216 compounds at a single concentration (10 µM) in duplicate using the Luciferase Insulin Secretion Assay, to identify those that increase insulin secretion only in the presence of high glucose (11.1 mM) (FIG. 6). These assays were performed in 1536 well format. A Z' factor of 0.35 was obtained with respect the positive control (300 µM IBMX). The cutoff value selected was 45% activation, which was 3-4 standard deviations above background (solid uppermost line; FIG. 6). Exemplary results of the dose-dependent effects of one of these compounds (Compound 8) are shown at FIG. 7. Interestingly, Compound 8 is able to induce significant increase in glucose-dependent insulin secretion in INS-1E cells (FIG. 7) and both normal and type 2 diabetes human islets (FIG. 8).

Further investigation into Compound 8 included measuring levels of the secondary messengers cAMP (FIG. 9) and IP-1 (not shown) in treated cells, as compounds that increase these secondary messengers are known to augment insulin secretion, though often in ways that are not beta-cell specific. Compound 8 did not increase levels of either of these secondary messengers.

Figure 10:
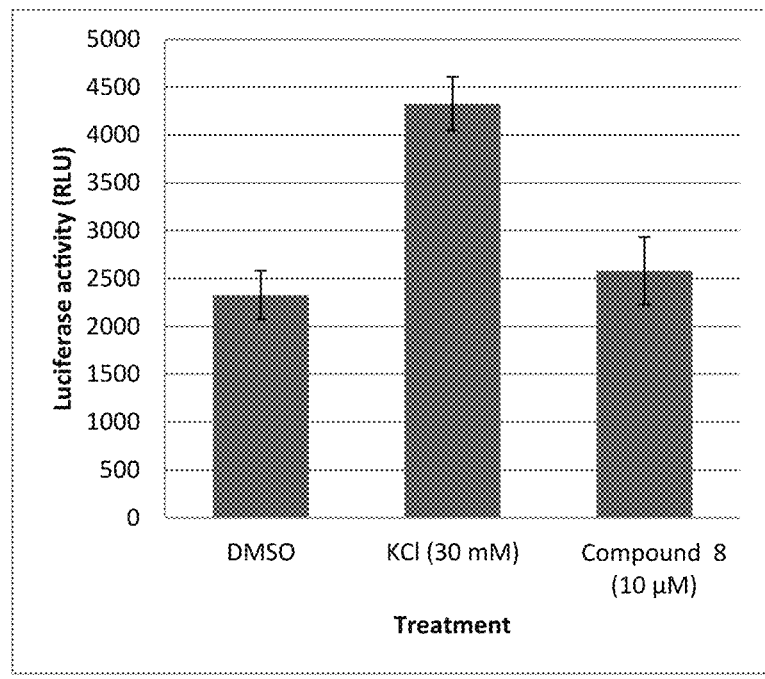
FIG. 10 depicts the quantification of α-cell secretory activity in cells treated with DMSO, KCl, or Compound 8, using a luminescent assay for glucagon secretion. While potassium chloride (KCl) causes secretion, Compound 8 does not (insignificant change from DMSO negative control).

To investigate the cell-type specificity of the compound, and to exclude the possibility that Compound 8 acts as a generic secretagogue, the compound was tested on secretion from a rodent alpha-cell line, "alpha-TC-1-6," using a luciferase reporter for glucagon secretion that mirrors the insulin secretion assay (FIG. 10). Compound 8 was shown not to augment luciferase secretion in this setting.

Figure 11:
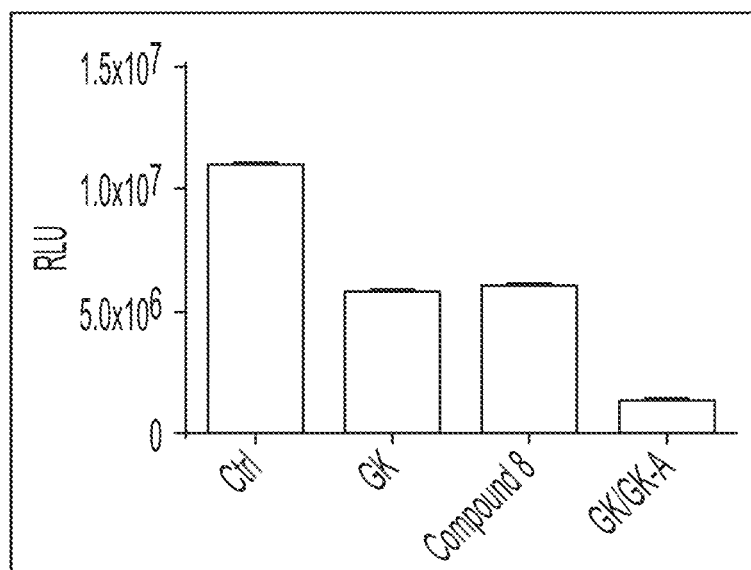
FIG. 11 depicts the lack of effect of Compound 8 on glucokinase activity in cells treated with the indicated compounds. The assay is based on the measurement of ATP level. In presence of GK we observe a reduction of level of ATP with respect to the negative control (DMSO). In contrast to the positive control, labelled GK-A, no change in assay signal is observed for Compound 8, indicating that it does not activate glucokinase.

To rule out the possibility of Compound 8 acting as a glucokinase agonist, another well-established mechanism of augmenting insulin secretion, the compound was subjected to a glucokinase activation assay (FIG. 11). Interestingly Compound 8 did not show any significant activation effect on pancreatic glucokinase.

Figure 9:
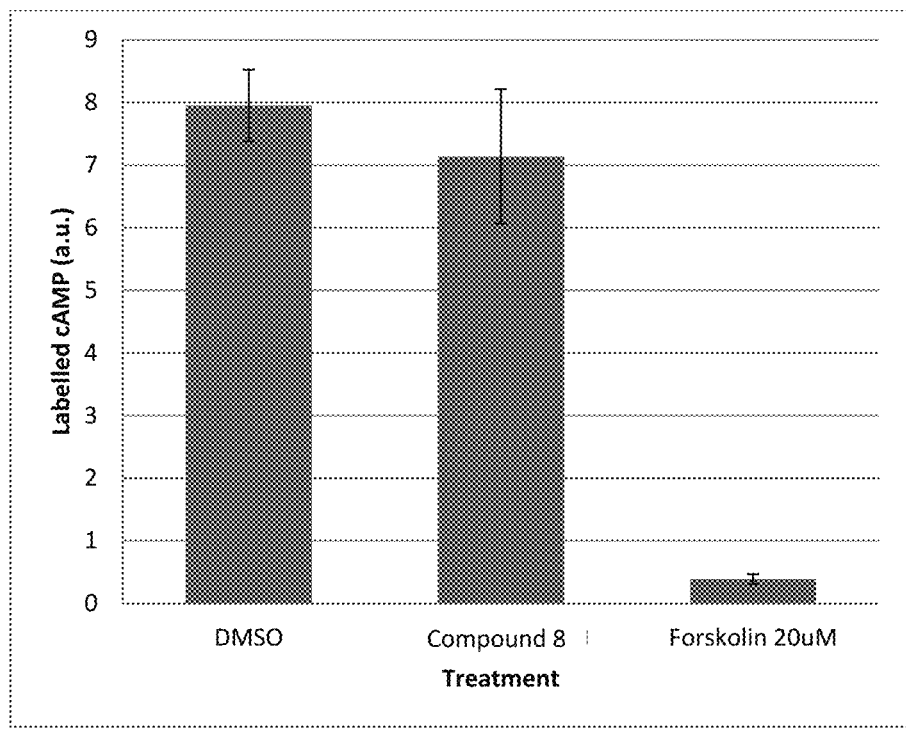
FIG. 9 depicts the quantification of cAMP activity in cells treated with the indicated compound in a HTRF assay from Cisbio. In this competition assay, an increase in cAMP is seen as a decrease in assay signal, as shown by the positive control, forskolin.
Figure 12:
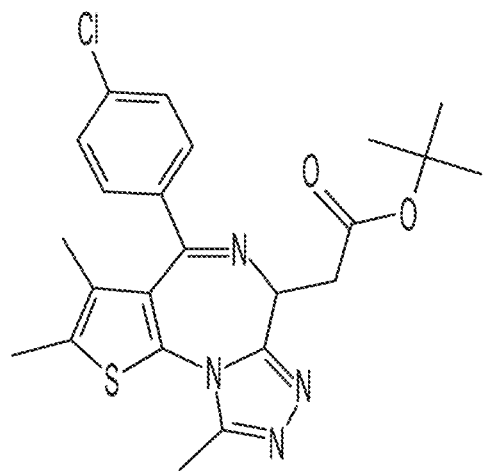
FIG. 12 depicts the effect of various concentrations of compound JQ1, a known bromodomain inhibitor, on glucose-stimulated insulin secretion from INS-1E cells, as measured in the Luciferase Insulin Secretion Assay. No increase in secretion is observed at lower concentration, whereas at higher concentrations tested, a decrease in glucose-stimulated secretion is observed. In the bar graph, the 2.8 mM glucose is shown on the left for each compound concentration, and the 16.7 mM glucose sample is shown on the right.
Figure 12:
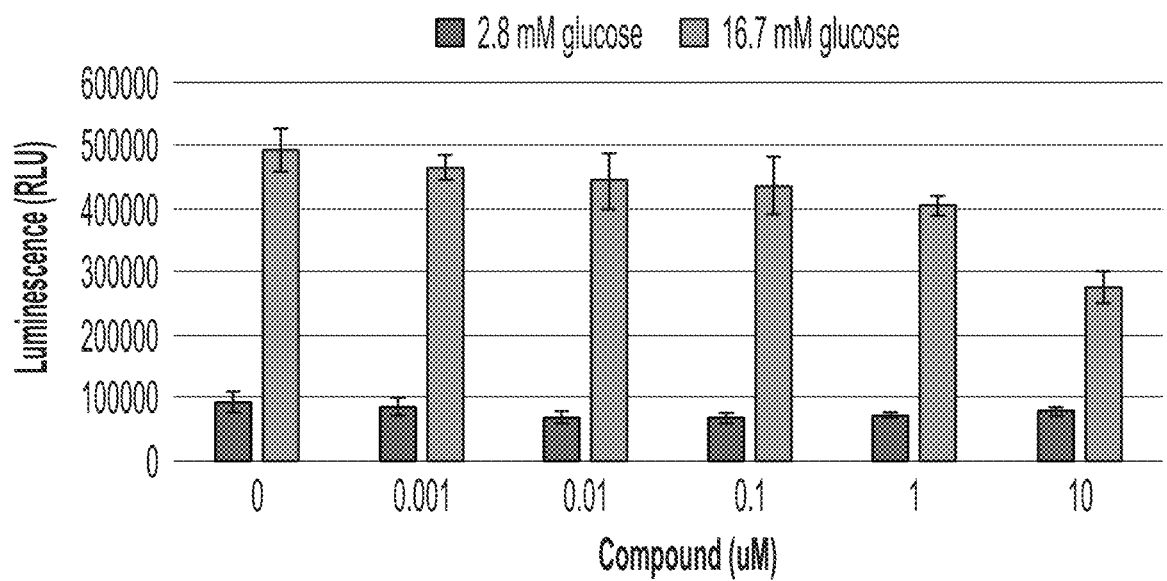
Figure 13B:
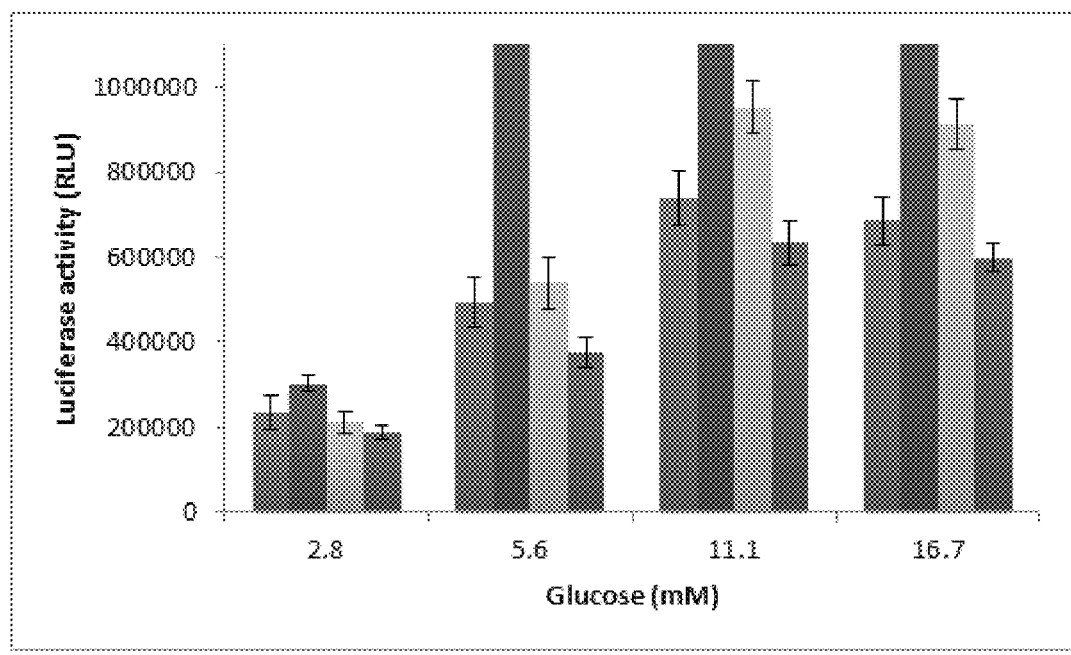

Upon structural analysis, Compound 8 was found to share some structural characteristics with known BET bromodomain inhibitors. To investigate the possibility that glucose-dependent insulin secretion induced by Compound 8 related to BET bromodomain inhibition, well known and potent BET bromodomain inhibitors (e.g., JQ1, PF-1 and SGC-CBP30) were tested in the Lucifersase Insulin Secretion assay. None of the compounds assayed increased glucose-dependent insulin secretion at any of the concentration used, and showed inhibitory effects when used at high concentrations (FIGS. 12, 13A, and 13B). Accordingly, disclosed herein are compounds that may also be PDE inhibitors. Other embodiments disclosed herein are compounds that do not affect PDE activity or cAMP levels (FIG. 9). In addition, some compounds do not exhibit glucokinase activation (FIG. 10) activity or alpha-cell secretion. (FIG. 11). Known bromodomain inhibitors did not induce insulin secretion at any concentration in a Luciferase Insulin Secretion Assay. See, FIGS. 12 and 13.

Figure 14A:
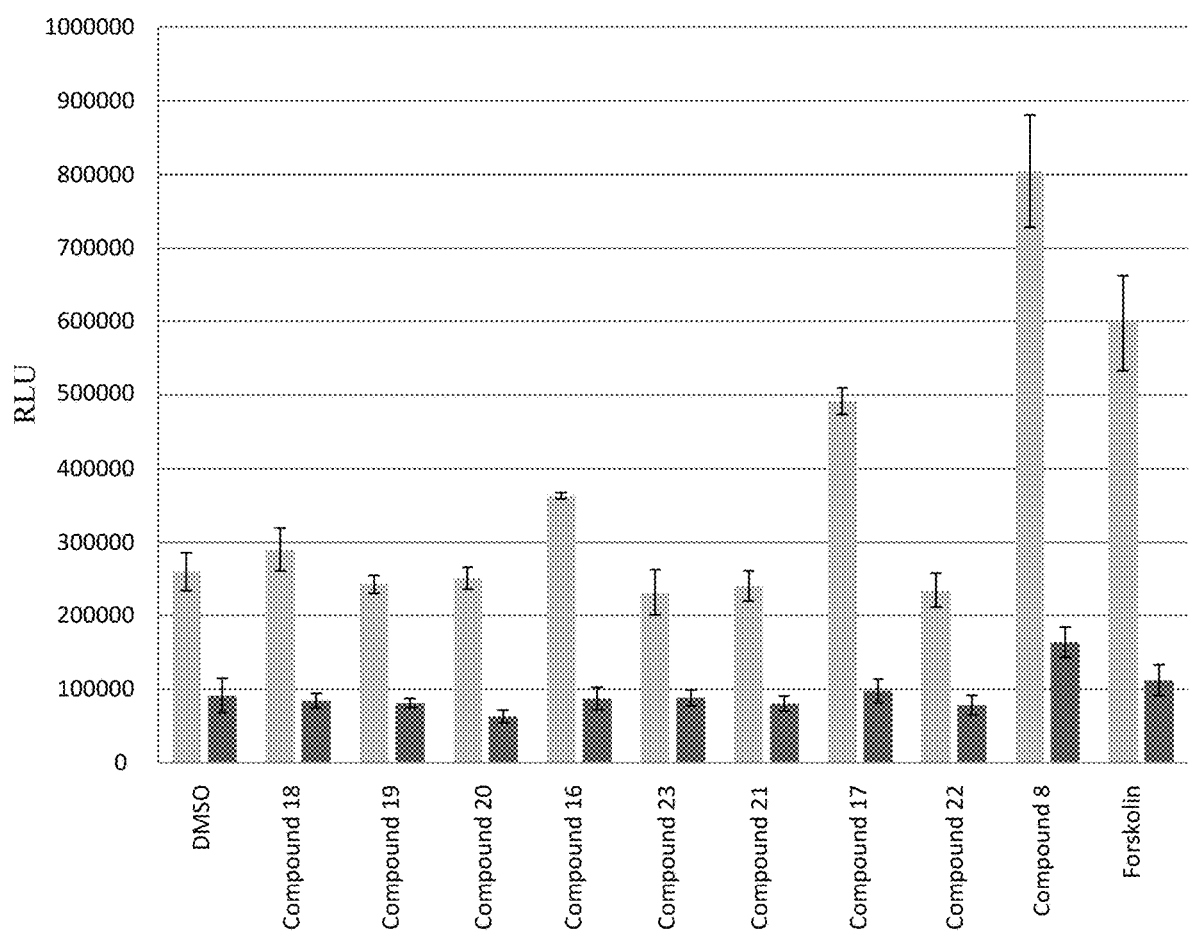
FIG. 14A details the effect of Compound 8 and related analogues on secretion from the INS-1E beta-cell line (using the luciferase reporter), performed to explore the structure-activity relationship (SAR) of the compound. In the bar graph, the 2.8 mM glucose is shown on the left, and the 16.7 mM glucose sample is shown on the right. Though a couple of analogues (e.g., Compound 16, Compound 17) appear to have some positive effect on secretion, none are as effective as Compound 8 at increasing glucose-stimulated secretion, which appears to be more effective than even the positive control, forskolin.
Figure 14B:
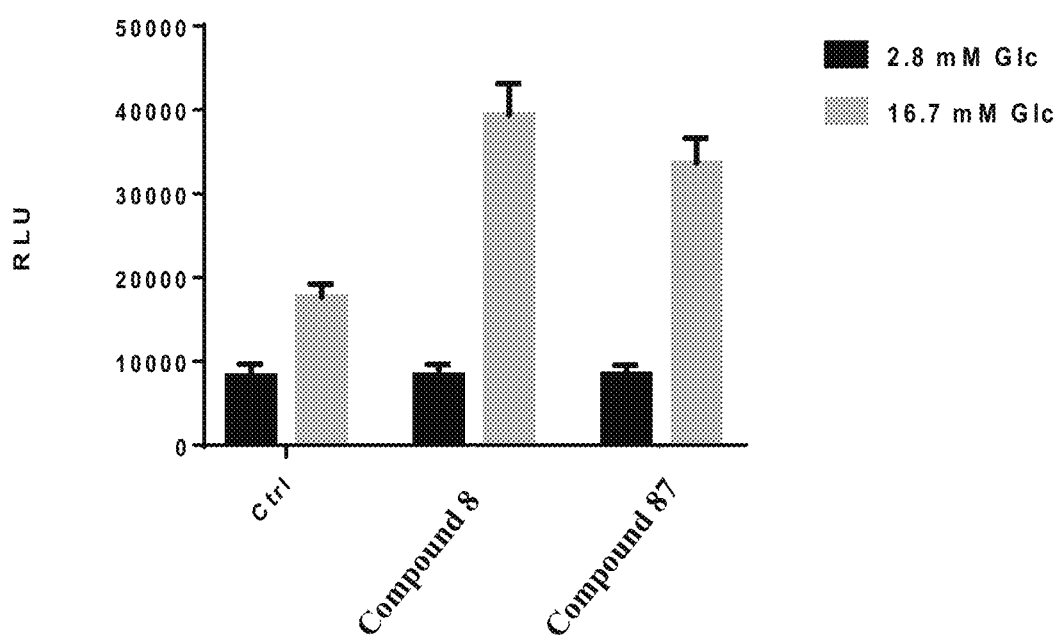
FIG. 14B compares the effect of Compound 8 to Compound 87 (which comprises a free amine for conjugation to a solid support).
Figure 15B:
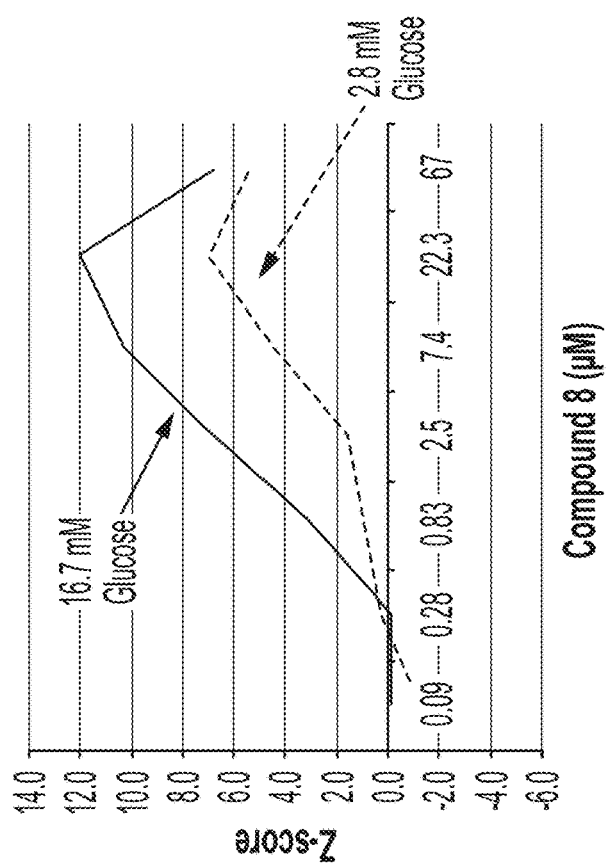
FIGS. 15A-E illustrate the effect of additional analogues of Compound 8 on secretion from the INS-1E beta-cell line using the luciferase reporter.
Figure 15A:
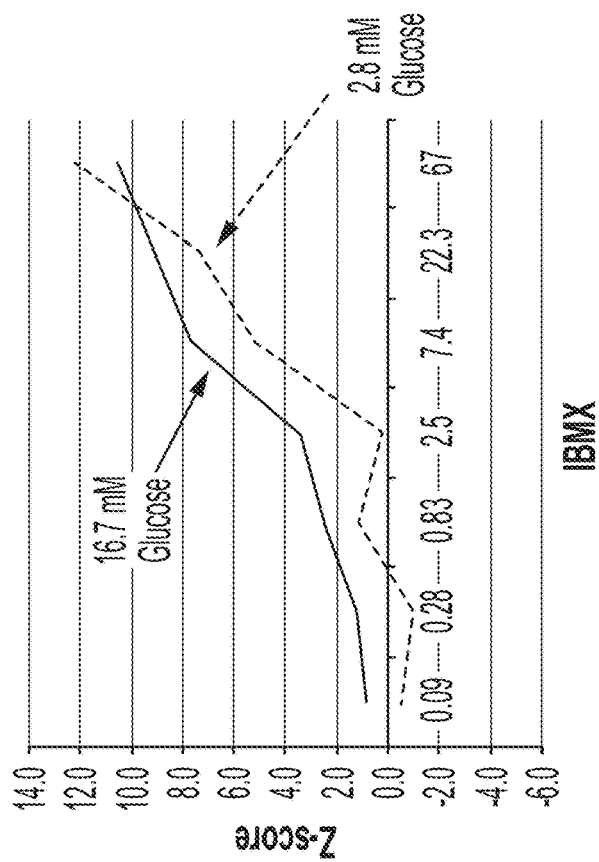
Figure 15D:
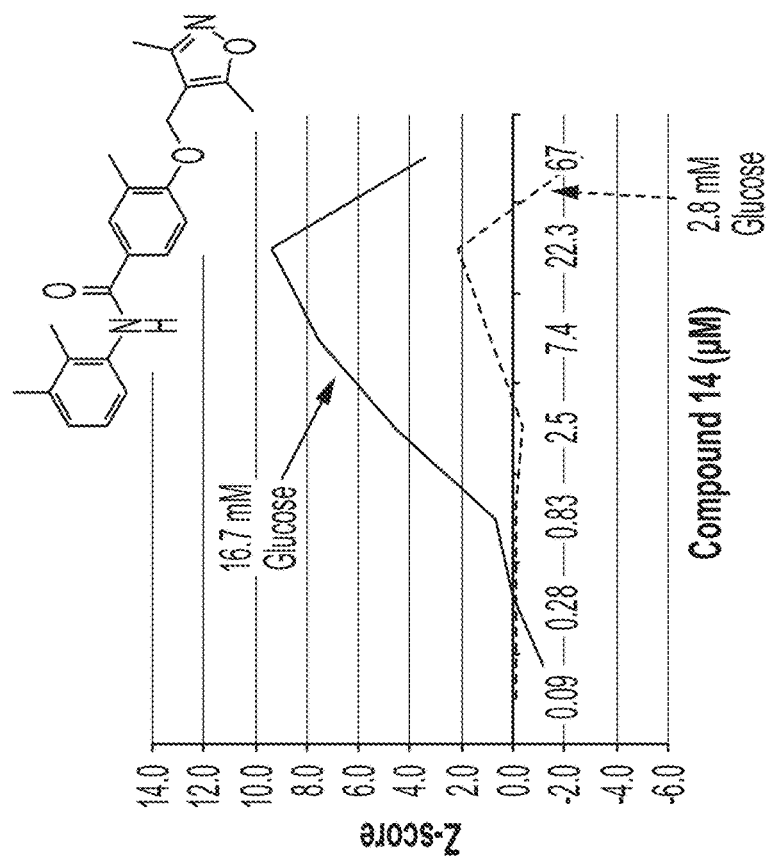
Figure 15C:
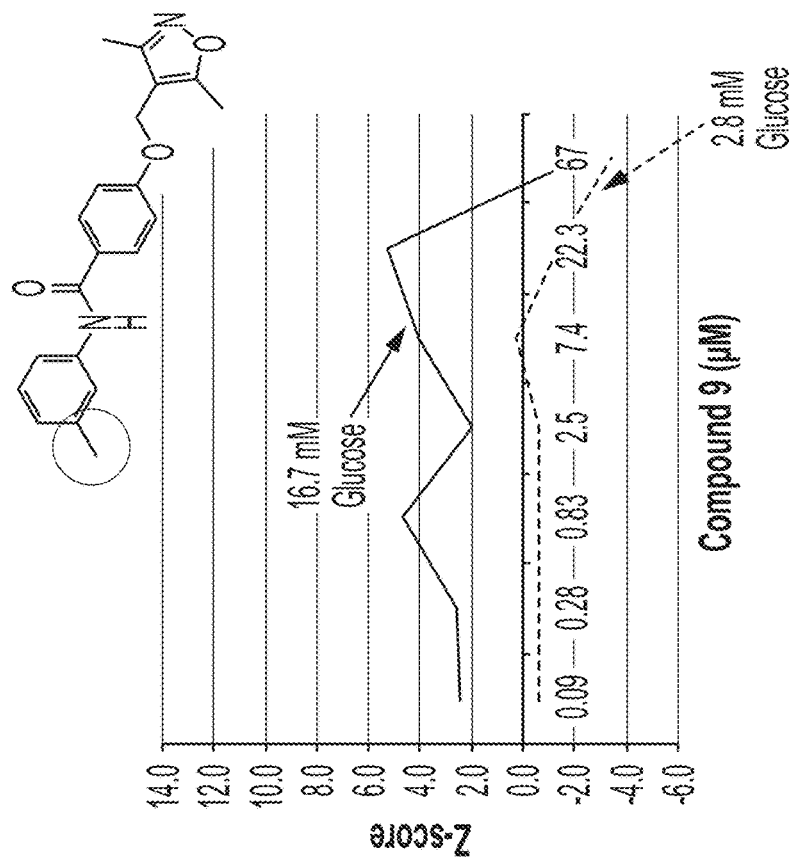
Figure 15E:
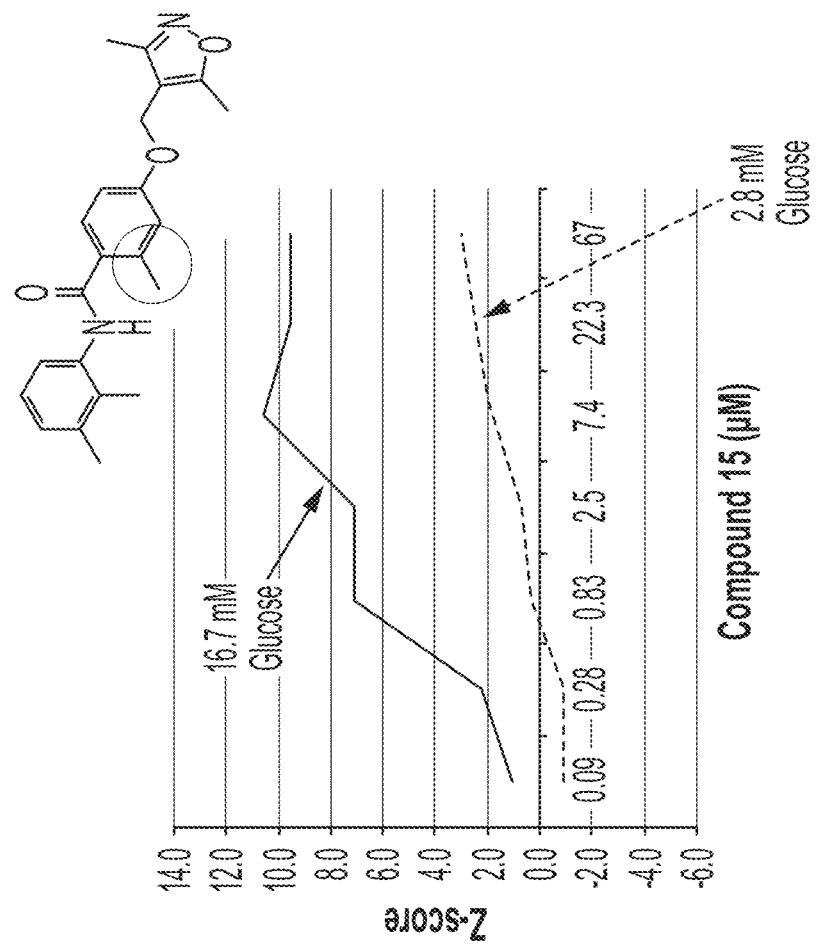
Figure 16:
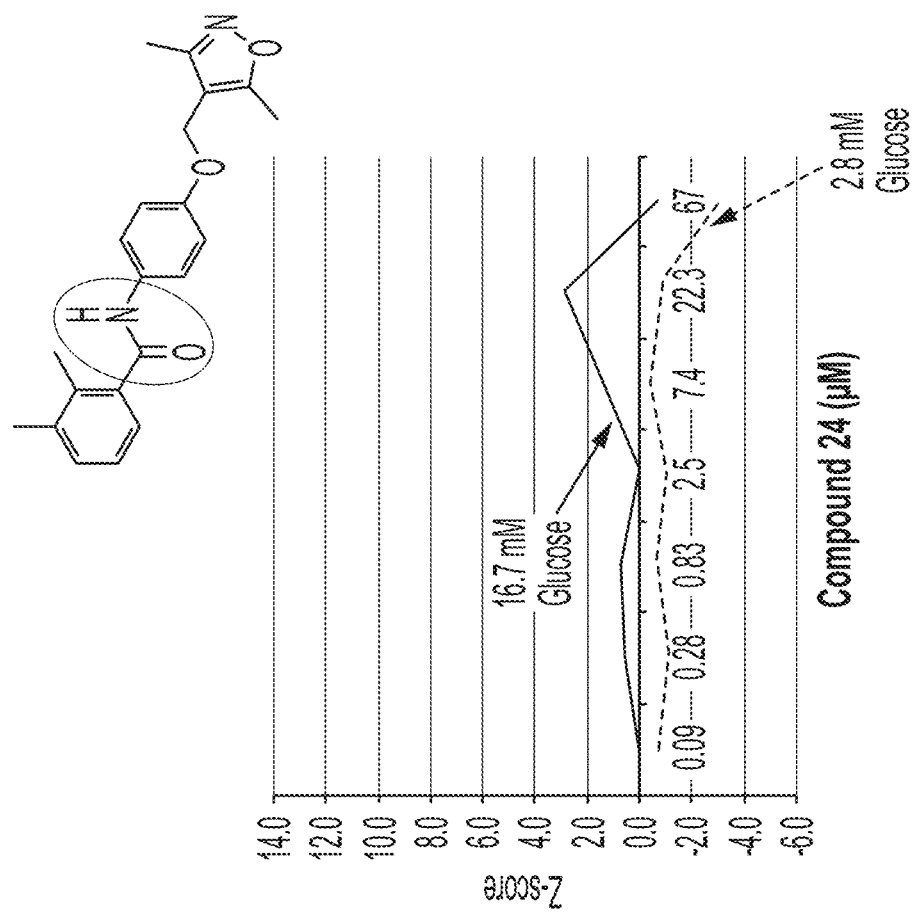
FIG. 16 illustrates the effect of Compound 24 on secretion from the INS-1E beta-cell line using the luciferase reporter.
Figure 17B:
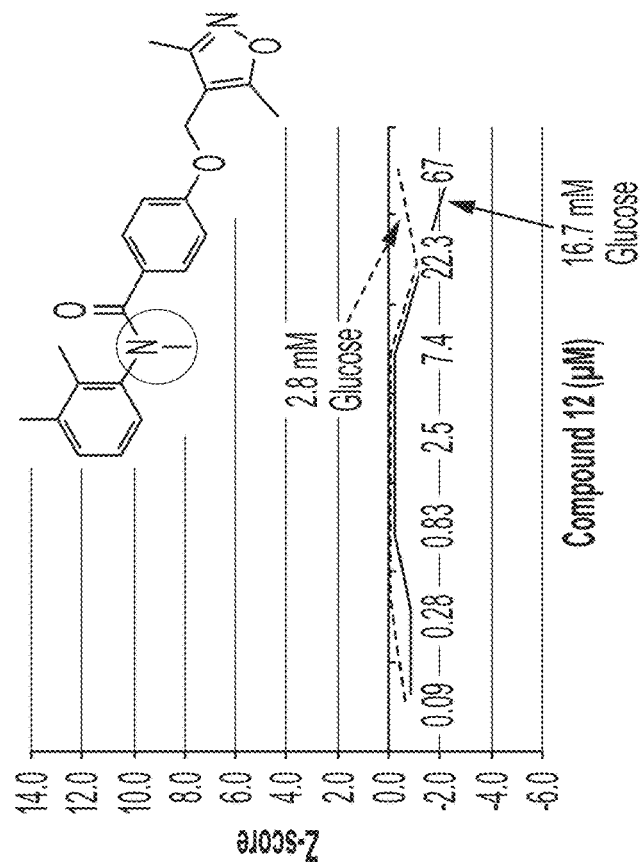
FIGS. 17A-17L illustrate the effect of additional analogues of various compounds on secretion from the INS-1E beta-cell line using the luciferase reporter.
Figure 17A:
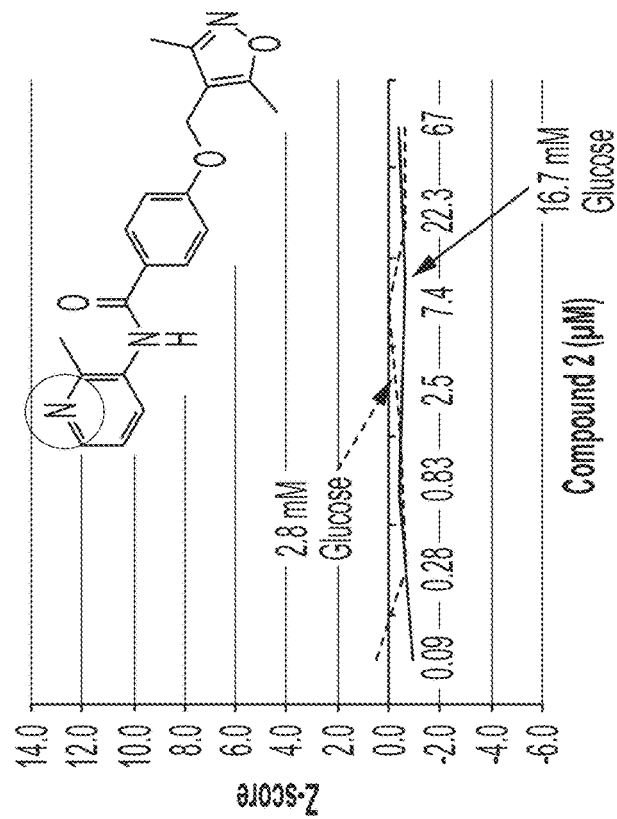
Figure 17D:
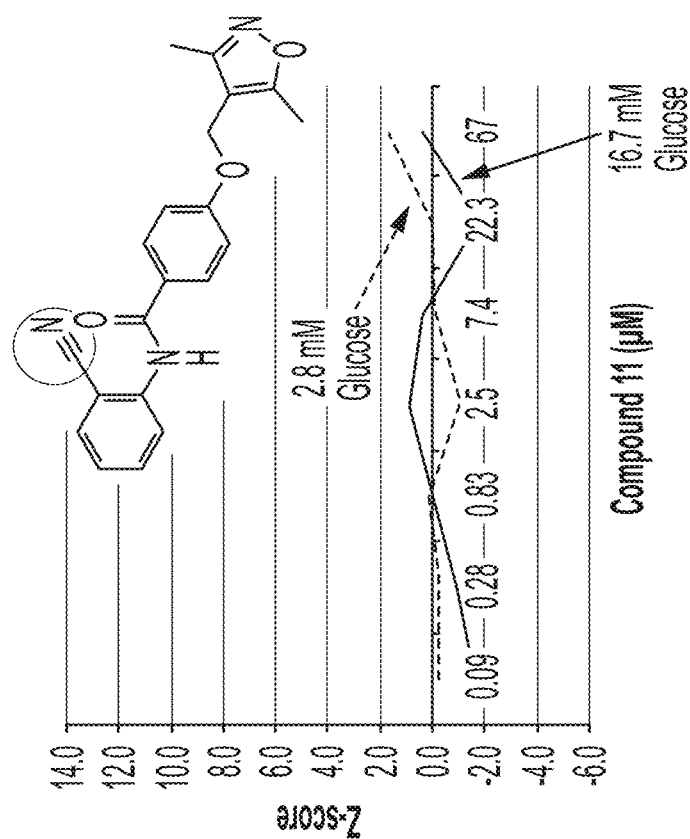
Figure 17C:
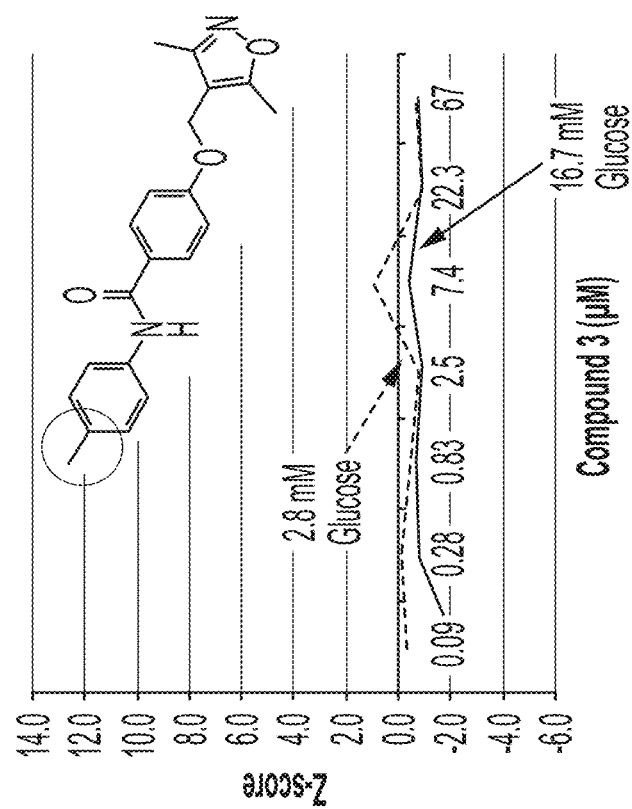
Figure 17F:
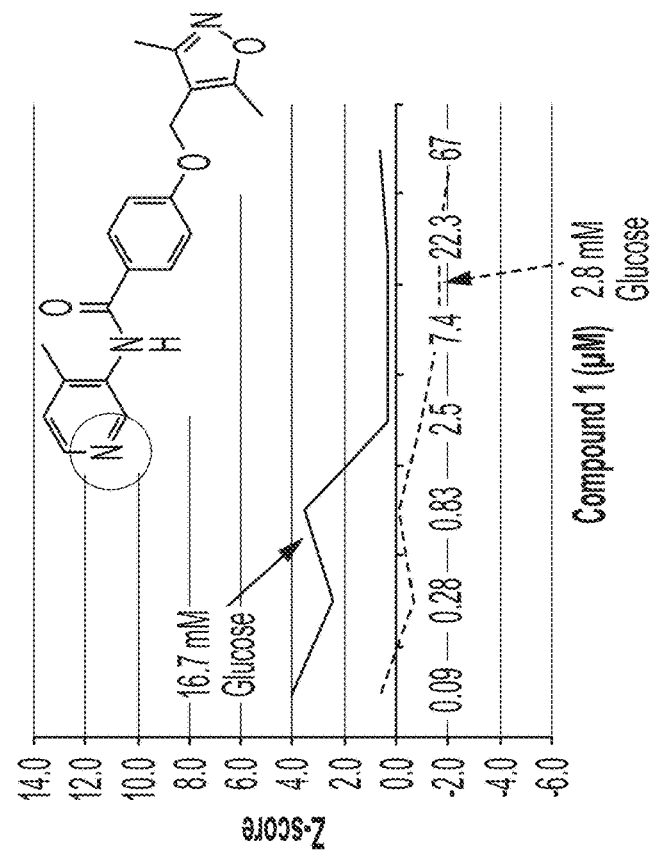
Figure 17E:
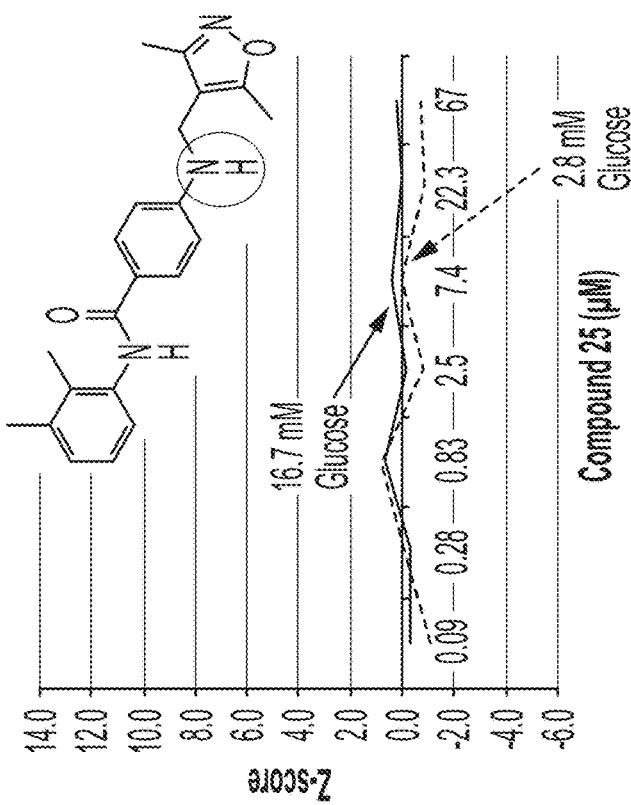
Figure 17H:
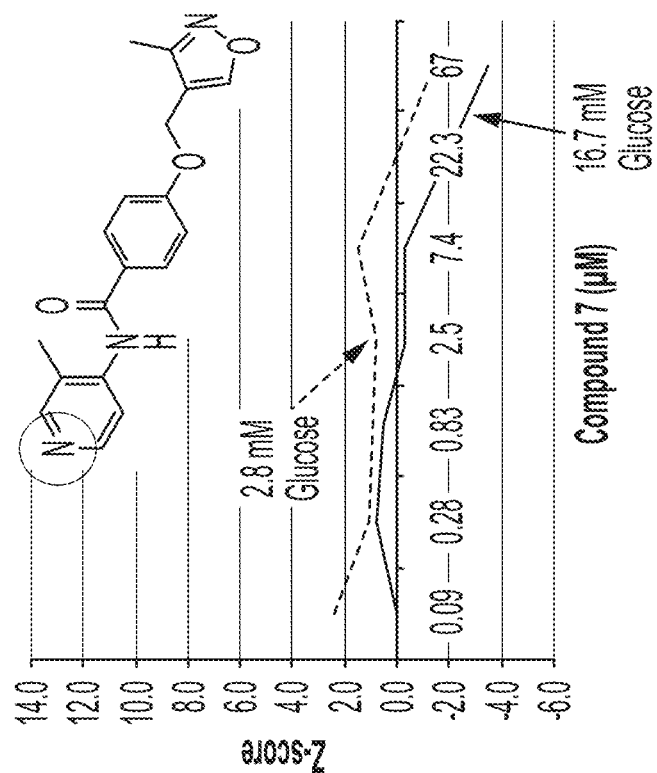
Figure 17G:
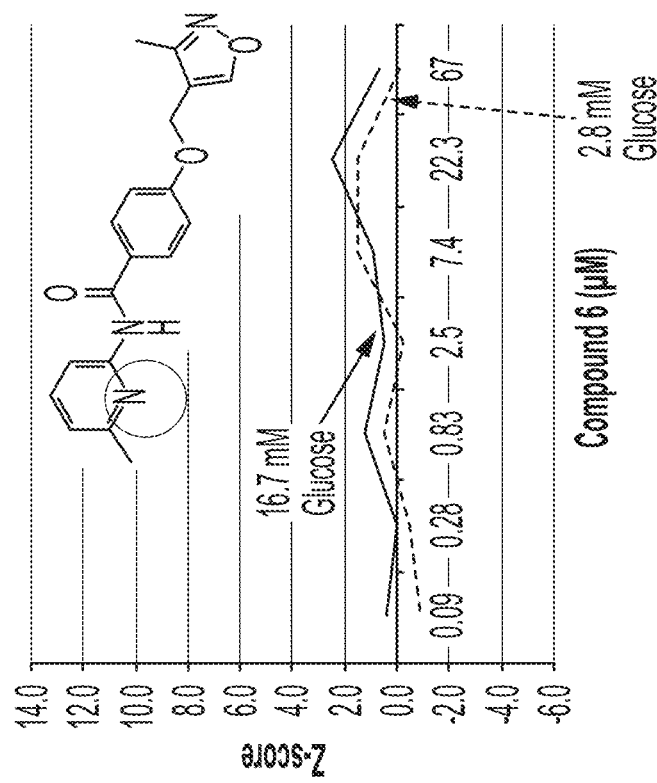
Figure 17I:
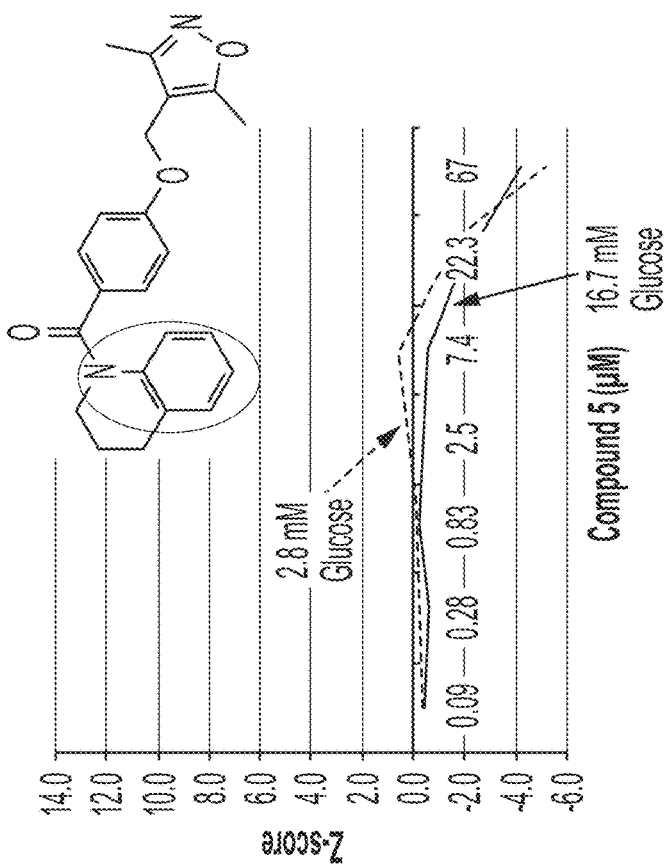
Figure 17J:
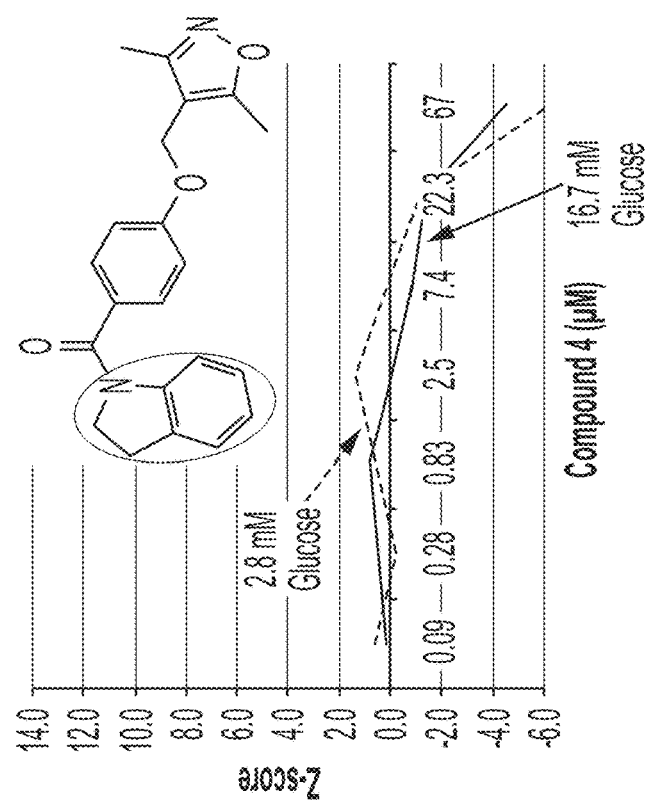
Figure 17L:
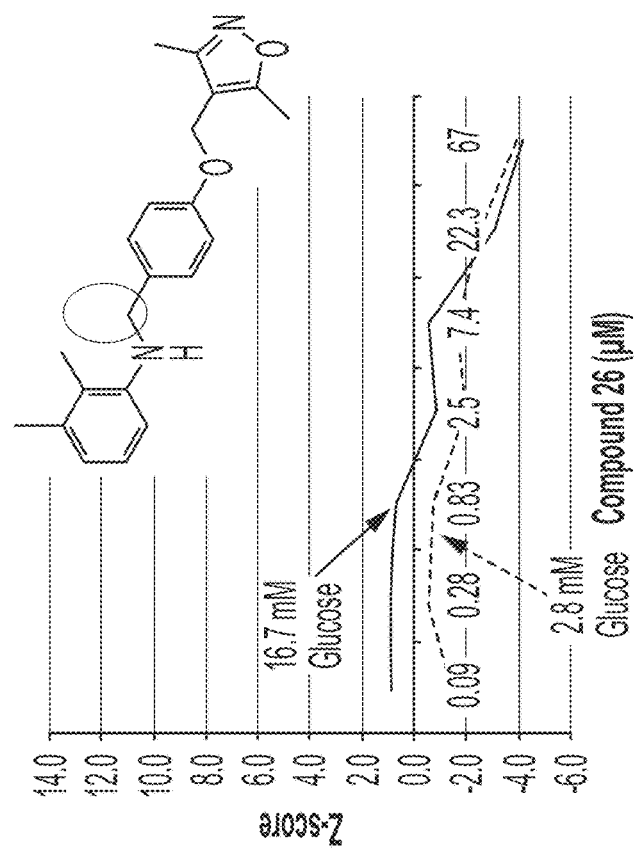
Figure 17K:
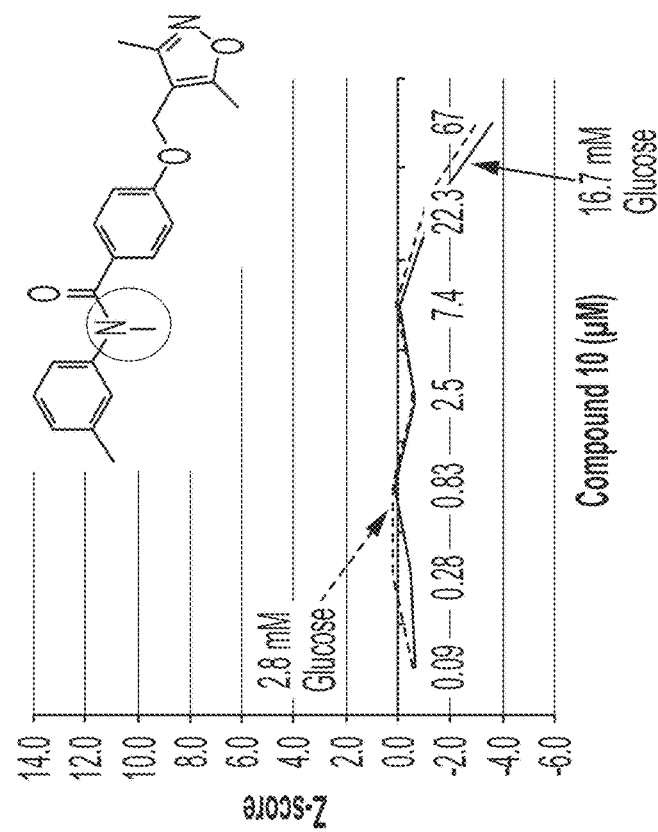

Measurements were performed on a variety of other compounds assayed in the Luciferase Insulin Secretion Assay (FIGS. 14A and 14B). FIG. 14B compares Compound 8 to compound 87 which comprise an amine functional group capable of conjugation to solid support (e.g., affi-gel). As can be seen, compound 87 has similar activity to Compound 8. The insulin secretion activity of several compounds can be seen in FIGS. 15A-E, 16 and 17A-L. In all graphs in FIGS. 16A-E, 16 and 17A-L, the x-axis represents the concentration of compound (µM), and the y-axis represents the Z-score of the compound in the assay. In some embodiments, the compounds disclosed herein increase activity in a Luciferase Insulin Secretion Assay in a glucose-dependent manner without notable toxicity. Thus, the disclosed compounds are quite specific in their action as glucose-dependent insulin secretagogues without significant off-target activity.

Measurements on the glucose dependence of several compounds are summarized in Table 3. In Table 3, a compound is identified as active if the compound has a Z-score greater than 3 in the presence of 16.7 mM glucose. Partial activity indicates that the compound does promote insulin secretion (at lower Z-scores). In some cases, insulin secretion was promoted at both measured insulin concentrations.

TABLE 3

| Compound Name | Structure | Activity |
|---|---|---|
| Compound 27 | 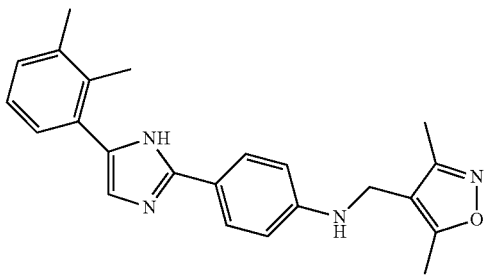 [SMILES: Cc1cccc(-c2cnc(-c3ccc(NCc4c(C)noc4C)cc3)[nH]2)c1C] | Inactive |
| Compound 28 | 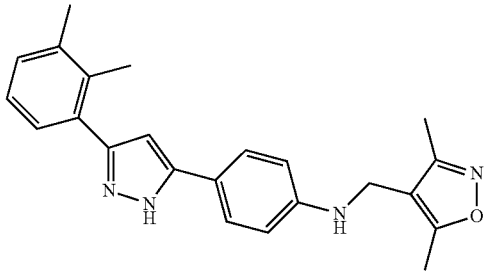 [SMILES: Cc1cccc(-c2cc(-c3ccc(NCc4c(C)noc4C)cc3)[nH]n2)c1C] | Inactive |

TABLE 3-continued

| Compound Name | Structure | Activity |
|---|---|---|
| Compound 29 | 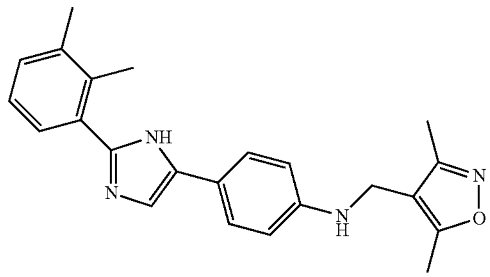 [SMILES: Cc1cccc(-c2ncc(-c3ccc(NCc4c(C)noc4C)cc3)[nH]2)c1C] | Inactive |
| Compound 30 | 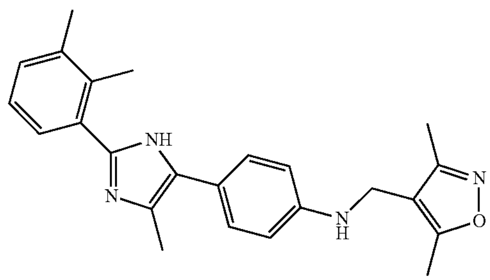 [SMILES: Cc1cccc(-c2nc(C)c(-c3ccc(NCc4c(C)noc4C)cc3)[nH]2)c1C] | Inactive |
| Compound 31 | 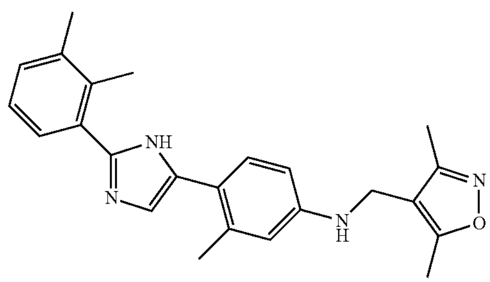 [SMILES: Cc1cc(NCc2c(C)noc2C)ccc1-c1cnc(-c2cccc(C)c2C)[nH]1] | Inactive |
| Compound 32 | 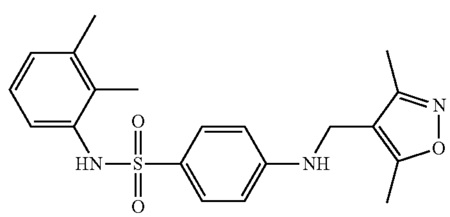 [SMILES: Cc1cccc(NS(=O)(=O)c2ccc(NCc3c(C)noc3C)cc2)c1C] | Inactive |
| Compound 33 | 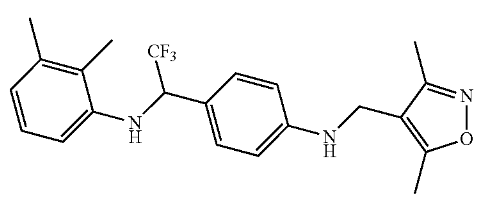 [SMILES: Cc1cccc(NC(c2ccc(NCc3c(C)noc3C)cc2)C(F)(F)F)c1C] | Inactive |
| Compound 34 | 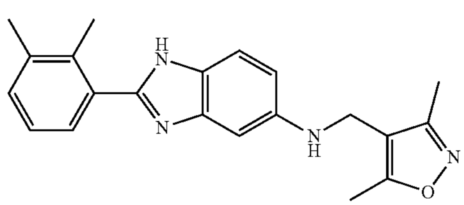 [SMILES: Cc1cccc(-c2nc3cc(NCc4c(C)noc4C)ccc3[nH]2)c1C] | Inactive |

TABLE 3-continued

| Compound Name | Structure | Activity |
|---|---|---|
| Compound 35 | 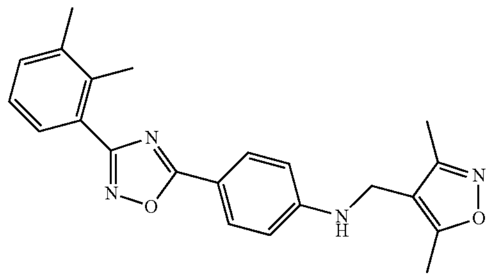 [SMILES: Cc1cccc(-c2noc(-c3ccc(NCc4c(C)noc4C)cc3)n2)c1C] | Inactive |
| Compound 36 | 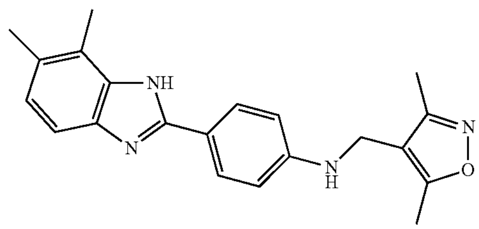 [SMILES: Cc1ccc2nc(-c3ccc(NCc4c(C)noc4C)cc3)[nH]c2c1C] | Inactive |
| Compound 13 | 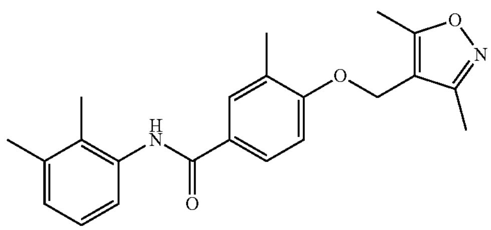 [SMILES: Cc1cc(C(=O)Nc2cccc(C)c2C)ccc1OCc1c(C)noc1C] | Active |
| Compound 14 | 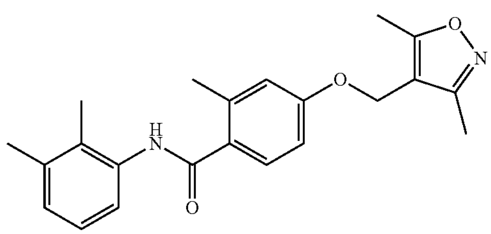 [SMILES: Cc1cc(OCc2c(C)noc2C)ccc1C(=O)Nc1cccc(C)c1C] | Active |
| Compound 39 | 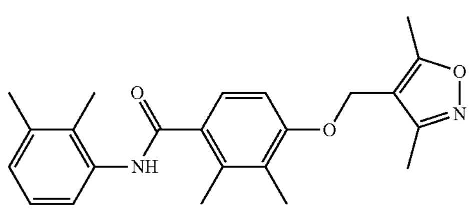 [SMILES: Cc1cccc(NC(=O)c2ccc(OCc3c(C)noc3C)c(C)c2C)c1C] | Active |
| Compound 40 | 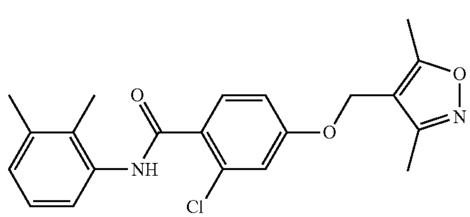 [SMILES: Cc1cccc(NC(=O)c2ccc(OCc3c(C)noc3C)cc2Cl)c1C] | Active |

TABLE 3-continued
| Compound Name | Structure | Activity |
|---|---|---|
| Compound 41 | 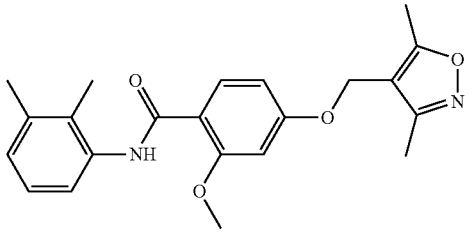 [SMILES: COc1cc(OCc2c(C)noc2C)ccc1C(=O)Nc1cccc(C)c1C] | Active |
| Compound 42 | 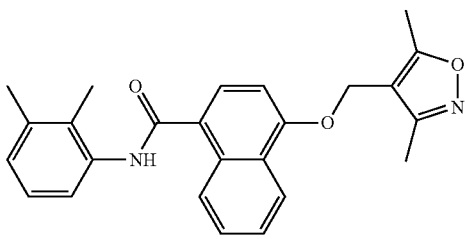 [SMILES: Cc1cccc(NC(=O)c2ccc(OCc3c(C)noc3C)c3ccccc23)c1C] | Inactive |
| Compound 43 | 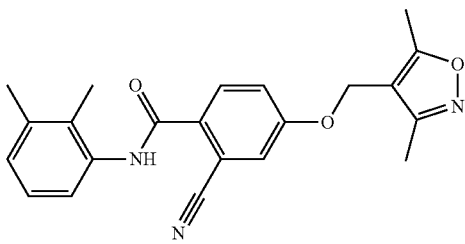 [SMILES: Cc1cccc(NC(=O)c2ccc(OCc3c(C)noc3C)cc2C#N)c1C] | Inactive |
| Compound 44 | 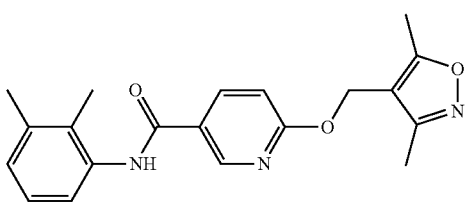 [SMILES: Cc1cccc(NC(=O)c2ccc(OCc3c(C)noc3C)nc2)c1C] | Inactive |
| Compound 45 | 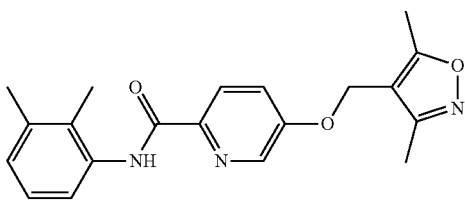 [SMILES: Cc1cccc(NC(=O)c2ccc(OCc3c(C)noc3C)cn2)c1C] | Inactive |
| Compound 46 | 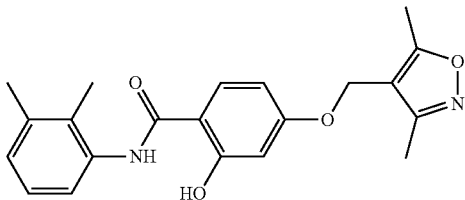 | Inactive |
| Compound 47 | 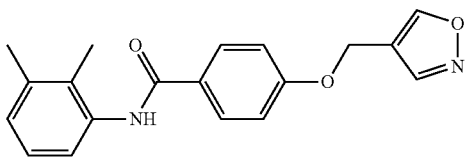 [SMILES: Cc1cccc(NC(=O)c2ccc(OCc3cnoc3)cc2)c1C] | Inactive |

TABLE 3-continued

| Compound Name | Structure | Activity |
| --- | --- | --- |
| Compound 48 | 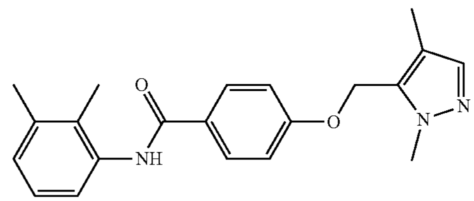 [SMILES: Cc1cccc(NC(=O)c2ccc(OCc3c(C)cnn3C)cc2)c1C] | Inactive |
| Compound 49 | 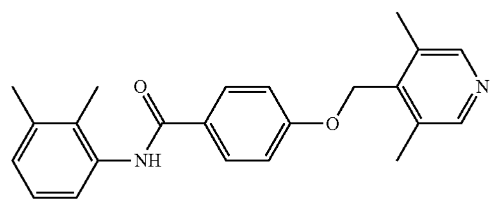 [SMILES: Cc1cccc(NC(=O)c2ccc(OCc3c(C)cncc3C)cc2)c1C] | Inactive |
| Compound 50 | 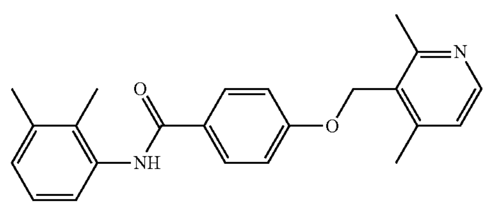 [SMILES: Cc1cccc(NC(=O)c2ccc(OCc3c(C)ccnc3C)cc2)c1C] | Inactive |
| Compound 51 | 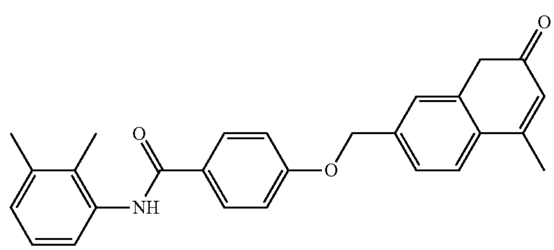 [SMILES: CC1=CC(=O)Cc2cc(COc3ccc(C(=O)Nc4cccc(C)c4C)cc3)ccc21] | Partial activity, Lost Glucose Dependence |
| Compound 52 | 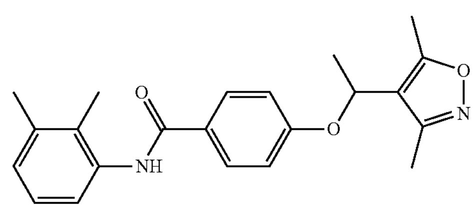 [SMILES: Cc1cccc(NC(=O)c2ccc(OC(C)c3c(C)noc3C)cc2)c1C] | Inactive |
| Compound 53 | 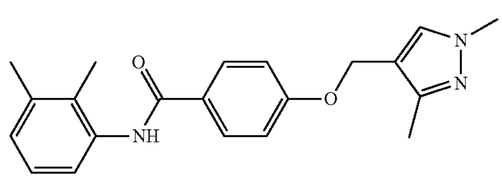 [SMILES: Cc1cccc(NC(=O)c2ccc(OCc3cn(C)nc3C)cc2)c1C] | Inactive |
| Compound 54 | 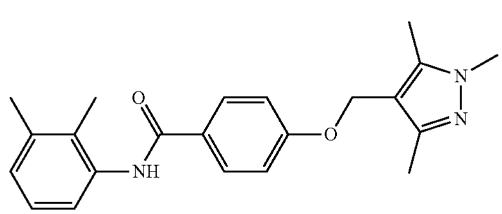 [SMILES: Cc1cccc(NC(=O)c2ccc(OCc3c(C)nn(C)c3C)cc2)c1C] | Inactive |

TABLE 3-continued

| Compound Name | Structure | Activity |
| --- | --- | --- |
| Compound 55 | 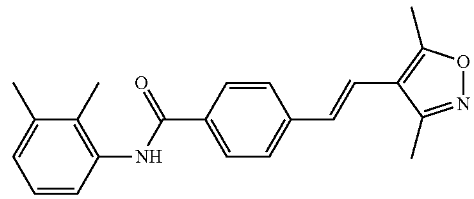 [SMILES: Cc1cccc(NC(=O)c2ccc(/C=C/c3c(C)noc3C)cc2)c1C] | Partial activity, Lost Glucose Dependence |
| Compound 56 | 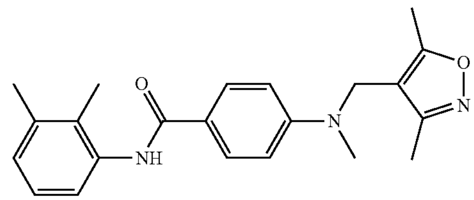 [SMILES: Cc1cccc(NC(=O)c2ccc(N(C)Cc3c(C)noc3C)cc2)c1C] | Inactive |
| Compound 57 | 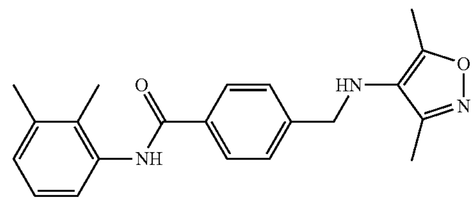 [SMILES: Cc1cccc(NC(=O)c2ccc(CNc3c(C)noc3C)cc2)c1C] | Inactive |
| Compound 58 | 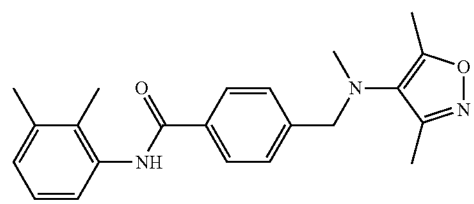 [SMILES: Cc1cccc(NC(=O)c2ccc(CN(C)c3c(C)noc3C)cc2)c1C] | Inactive |
| Compound 59 | 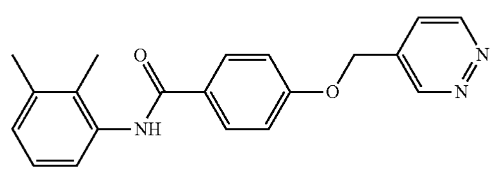 [SMILES: Cc1cccc(NC(=O)c2ccc(OCc3ccnnc3)cc2)c1C] | Inactive |
| Compound 60 | 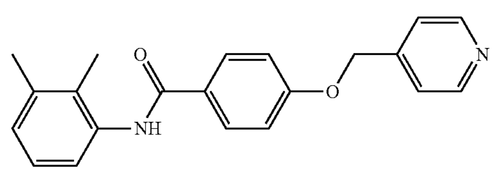 | Inactive |
| Compound 61 | 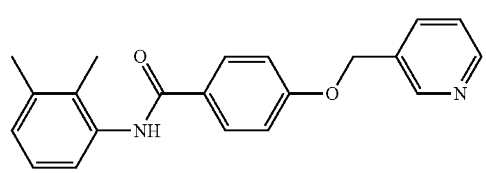 [SMILES: Cc1cccc(NC(=O)c2ccc(OCc3cccnc3)cc2)c1C] | Inactive |
| Compound 62 | 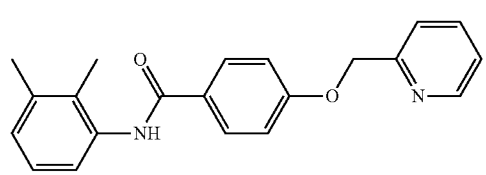 [SMILES: Cc1cccc(NC(=O)c2ccc(OCc3ccccn3)cc2)c1C] | Inactive |

TABLE 3-continued

| Compound Name | Structure | Activity |
|---|---|---|
| Compound 63 | 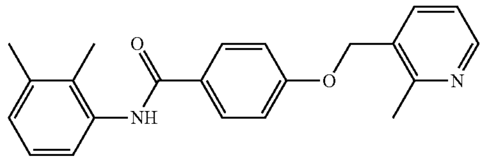 [SMILES: Cc1cccc(NC(=O)c2ccc(OCc3cccnc3C)cc2)c1C] | Inactive |
| Compound 64 | 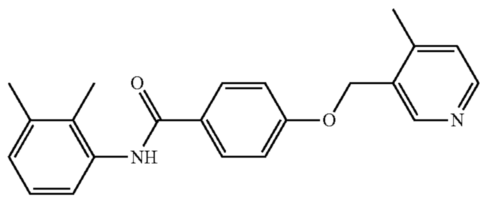 [SMILES: Cc1ccncc1COc1ccc(C(=O)Nc2cccc(C)c2C)cc1] | Inactive |
| Compound 65 | 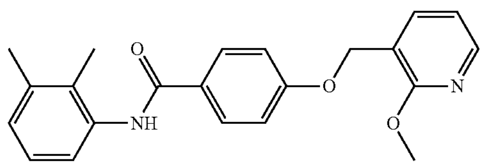 [SMILES: COc1ncccc1COc1ccc(C(=O)Nc2cccc(C)c2C)cc1] | Inactive |
| Compound 66 | 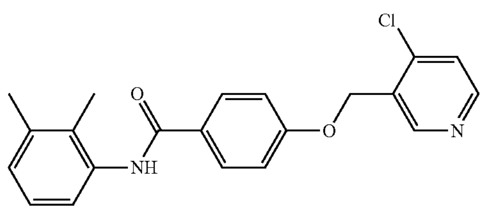 [SMILES: Cc1cccc(NC(=O)c2ccc(OCc3cnccc3Cl)cc2)c1C] | Inactive |
| Compound 67 | 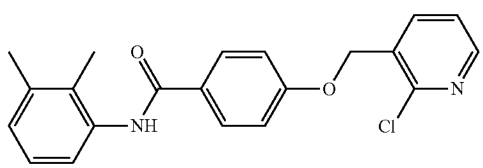 | Inactive |
| Compound 68 | 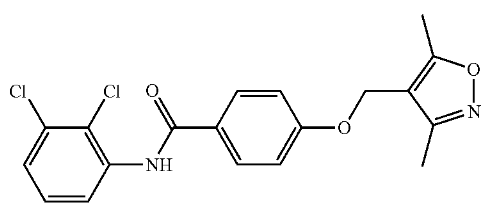 [SMILES: Cc1noc(C)c1COc1ccc(C(=O)Nc2cccc(Cl)c2Cl)cc1] | Active |
| Compound 69 | 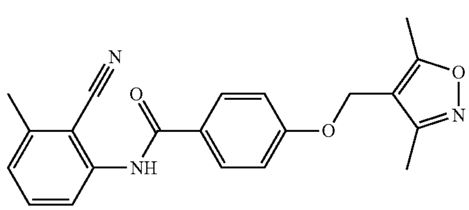 [SMILES: Cc1cccc(NC(=O)c2ccc(OCc3c(C)noc3C)cc2)c1C#N] | Active |
| Compound 70 | 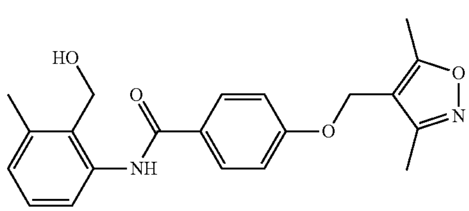 [SMILES: Cc1cccc(NC(=O)c2ccc(OCc3c(C)noc3C)cc2)c1CO] | Active |

TABLE 3-continued

| Compound Name | Structure | Activity |
| --- | --- | --- |
| Compound 71 | 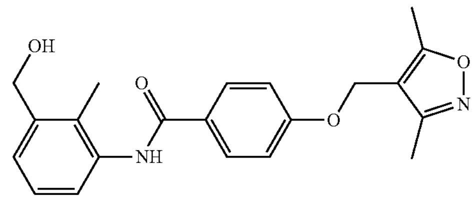 [SMILES: Cc1noc(C)c1COc1ccc(C(=O)Nc2cccc(CO)c2C)cc1] | Active |
| Compound 72 | 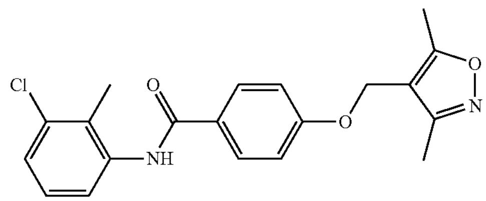 [SMILES: Cc1noc(C)c1COc1ccc(C(=O)Nc2cccc(Cl)c2C)cc1] | Active |
| Compound 73 | 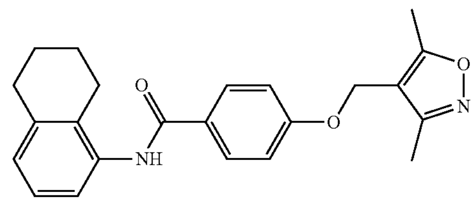 [SMILES: Cc1noc(C)c1COc1ccc(C(=O)Nc2cccc3c2CCCC3)cc1] | Inactive |
| Compound 74 | 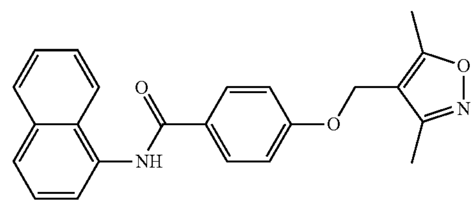 [SMILES: Cc1noc(C)c1COc1ccc(C(=O)Nc2cccc3ccccc23)cc1] | Inactive |
| Compound 75 | 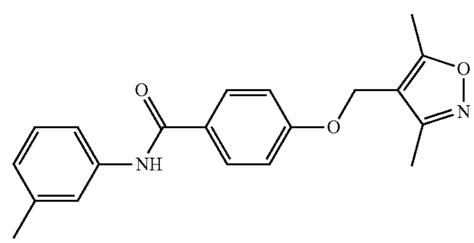 [SMILES: Cc1cccc(NC(=O)c2ccc(OCc3c(C)noc3C)cc2)c1] | Inactive |
| Compound 76 | 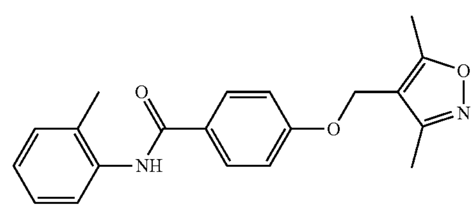 [SMILES: Cc1ccccc1NC(=O)c1ccc(OCc2c(C)noc2C)cc1] | Inactive |
| Compound 77 | 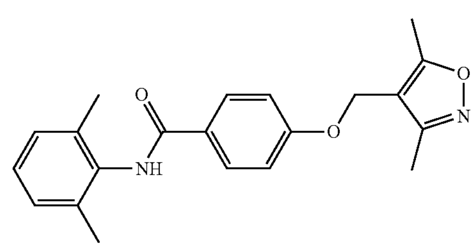 [SMILES: Cc1cccc(C)c1NC(=O)c1ccc(OCc2c(C)noc2C)cc1] | Inactive |

TABLE 3-continued

| Compound Name | Structure | Activity |
| --- | --- | --- |
| Compound 78 | 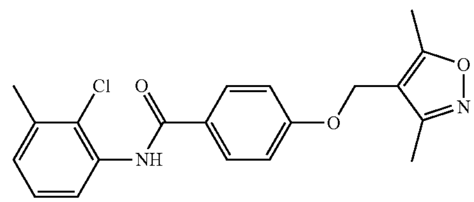 [SMILES: Cc1cccc(NC(=O)c2ccc(OCc3c(C)noc3C)cc2)c1Cl] | Inactive |
| Compound 79 | 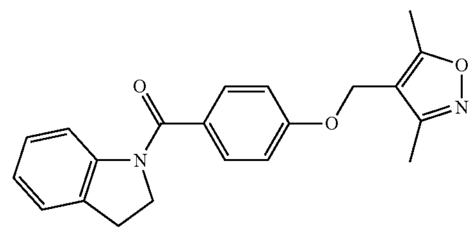 [SMILES: Cc1noc(C)c1COc1ccc(C(=O)N2CCc3ccccc32)cc1] | Inactive |
| Compound 80 | 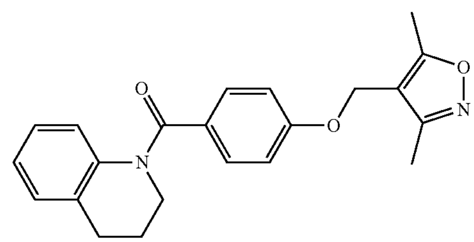 [SMILES: Cc1noc(C)c1COc1ccc(C(=O)N2CCCc3ccccc32)cc1] | Inactive |
| Compound 81 | 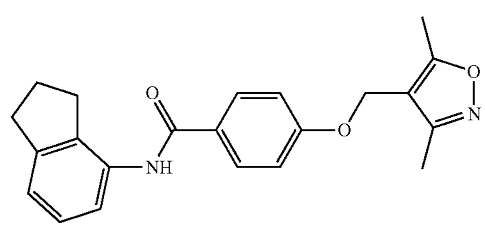 [SMILES: Cc1noc(C)c1COc1ccc(C(=O)Nc2cccc3c2CCC3)cc1] | Inactive |
| Compound 82 | 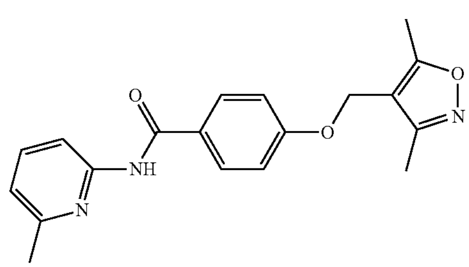 [SMILES: Cc1cccc(NC(=O)c2ccc(OCc3c(C)noc3C)cc2)n1] | Inactive |
| Compound 83 | 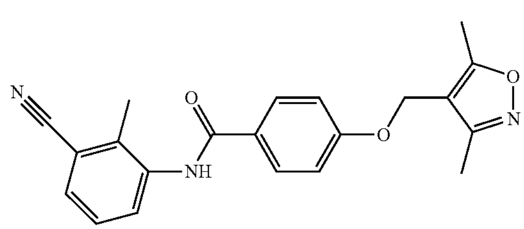 [SMILES: Cc1noc(C)c1COc1ccc(C(=O)Nc2cccc(C#N)c2C)cc1] | Inactive |

TABLE 3-continued

| Compound Name | Structure | Activity |
|---|---|---|
| Compound 84 | 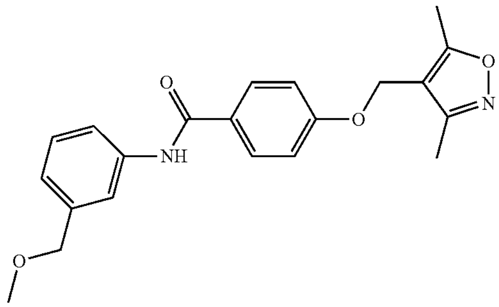 [SMILES: COCc1cccc(NC(=O)c2ccc(OCc3c(C)noc3C)cc2)c1] | Inactive |
| Compound 85 | 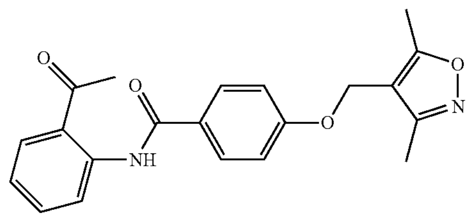 [SMILES: CC(=O)c1ccccc1NC(=O)c1ccc(OCc2c(C)noc2C)cc1] | Inactive |
| Compound 86 | 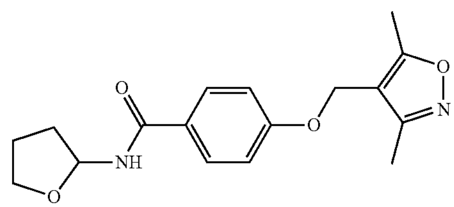 [SMILES: Cc1noc(C)c1COc1ccc(C(=O)NC2CCCO2)cc1] | Inactive |
| Compound 87 | 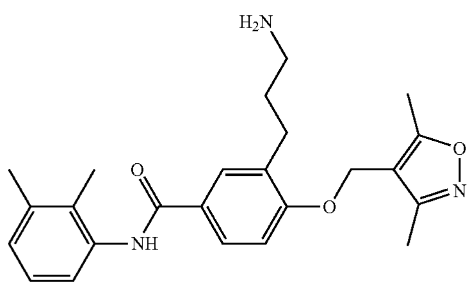 [SMILES: Cc1cccc(NC(=O)c2ccc(OCc3c(C)noc3C)c(CCCN)c2)c1C] | Active |
| Compound 88 | 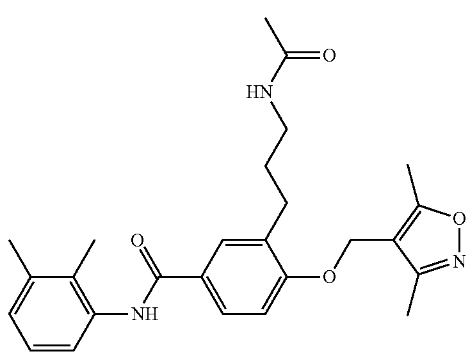 [SMILES: CC(=O)NCCCc1cc(C(=O)Nc2cccc(C)c2C)ccc1OCc1c(C)noc1C] | Active |

TABLE 3-continued

| Compound Name | Structure | Activity |
| --- | --- | --- |
| Compound 89 | 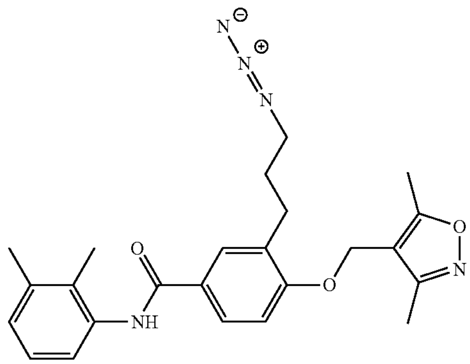 [SMILES: Cc1cccc(NC(=O)c2ccc(OCc3c(C)noc3C)c(CCCN=[NH+][NH-])c2)c1C] | Inactive |
| Compound 90 | 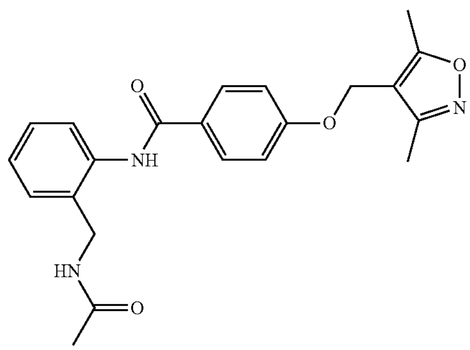 [SMILES: CC(=O)NCc1ccccc1NC(=O)c1ccc(OCc2c(C)noc2C)cc1] | Inactive |
| Compound 91 | 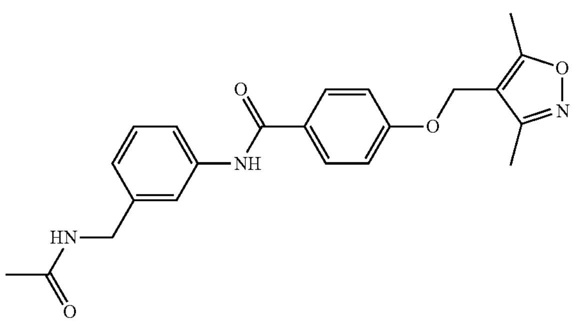 [SMILES: CC(=O)NCc1cccc(NC(=O)c2ccc(OCc3c(C)noc3C)cc2)c1] | Inactive |
| Compound 92 | 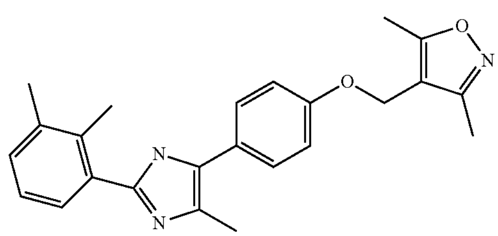 [SMILES: Cc1cccc(-c2nc(C)c(-c3ccc(OCc4c(C)noc4C)cc3)[nH]2)c1C] | Inactive |
| Compound 93 | 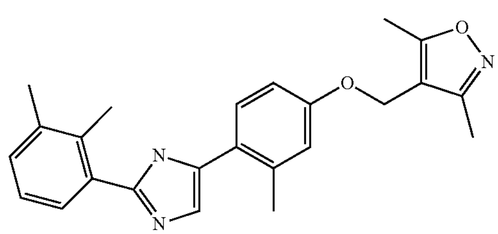 [SMILES: Cc1cc(OCc2c(C)noc2C)ccc1-c1cnc(-c2cccc(C)c2C)[nH]1] | Inactive |

TABLE 3-continued

| Compound Name | Structure | Activity |
|---|---|---|
| Compound 94 | 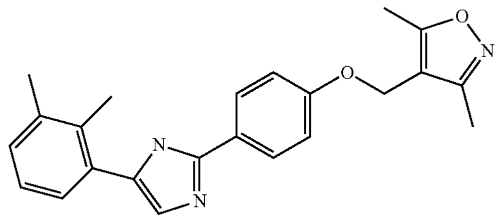 [SMILES: Cc1cccc(-c2cnc(-c3ccc(OCc4c(C)noc4C)cc3)[nH]2)c1C] | Inactive |
| Compound 95 | 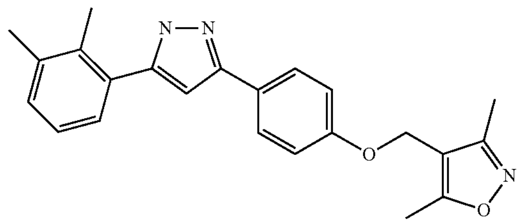 [SMILES: Cc1cccc(-c2cc(-c3ccc(OCc4c(C)noc4C)cc3)n[nH]2)c1C] | Inactive |
| Compound 96 | 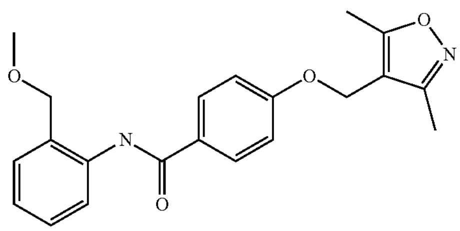 [SMILES: COCc1ccccc1NC(=O)c1ccc(OCc2c(C)noc2C)cc1] | Inactive |
| Compound 97 | 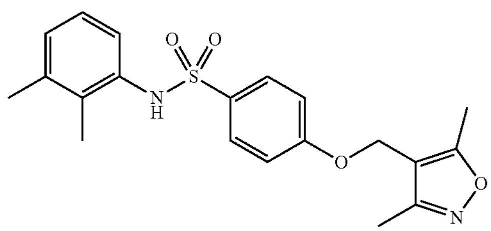 [SMILES: Cc1cccc(NS(=O)(=O)c2ccc(OCc3c(C)noc3C)cc2)c1C] | Inactive |
| Compound 55 (cis) | 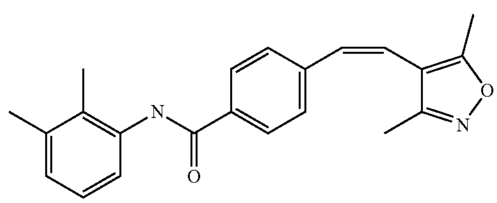 [SMILES: Cc1cccc(NC(=O)c2ccc(/C=C\c3c(C)noc3C)cc2)c1C] | Inactive |

As can be seen, compound activity is maintained through modification of several moieties of Compound 8 representing the genus defined by Formula I.

Example 2: Pharmacokinetic Assay

The pharmacokinetic activity profile of Compound 8 was assessed by various standard in vitro measurements. Measurements were performed on human, mouse (CD-1) and rat (SD) microsomes to determine the $t_{1/2}$, the plasma protein binding ("PPB") and the plasma stability ("PS"). Results of the PK measurements are shown below in Table 4. $t_{1/2}$ measurements were performed with imipramine and propranolol, cerapamil, or terfeadine as controls for high stability, medium stability and low stability, respectively. Plasma measurements were performed on Compound 8 and known compound verapamil, lidocaine, and eucatropine for comparison.

TABLE 4

| | Compound | Human | Mouse | Rat |
|---|---|---|---|---|
| $t_{1/2}$ (min) | Compound 8 | 1158 | 276 | 217 |
| PPB (% remaining) | Compound 8 | 96.9 | 94.0 | 97.1 |
| PPB (% remaining) | verapamil | 96.5 | 94.6 | 98.8 |
| PPB (% remaining) | lidocaine | 68.8 | 52.8 | 57.8 |
| PS (% remaining) | Compound 8 | 106.2 | 96.0 | 97.5 |
| PS (% remaining) | verapamil | 104.8 | 97.6 | 105.1 |
| PS (% remaining) | eucatropine | 1.1 | 24.6 | 32.4 |

Example 3: In Vivo Pharmacokinetic Measurements

A group of 36 male mice were divided into four groups of nine mice each and administered a compound solution via varying administration routes. Compound in 7.5% NMP, 7.5% Solutol HS-15, 85% normal saline as administered through intravenous ("i.v.," 2 mg/kg), subcutaneous ("s.c.," 10 mg/kg), intraperitoneal ("i.p.," 10 mg/kg), or oral ("p.o.," 10 mg/kg) dose administration. Blood samples (approximately 100 µL) were collected from each group under light isoflurane anesthesia from the retro-orbital plexus of mice at 0.083, 0.25, 0.5, 1, 2, 4, 8, 12 and 24 hr following administration for i.v., s.c., and i.p. groups and 0.25, 0.5, 1, 2, 4, 6, 8, 12 and 24 hr following administration for the p.o. group. Plasma samples were separated by centrifugation of whole blood and stored below −70° C. until bioanalysis. All samples were processed for analysis by protein precipitation using acetonitrile and analyzed with fit-for-purpose LC/MS/MS method (LLOQ—2.44 ng/mL). Pharmacokinetic parameters were calculated using the non-compartmental analysis tool of Phoenix WinNonlin (Version 6.3).

Figure 18:
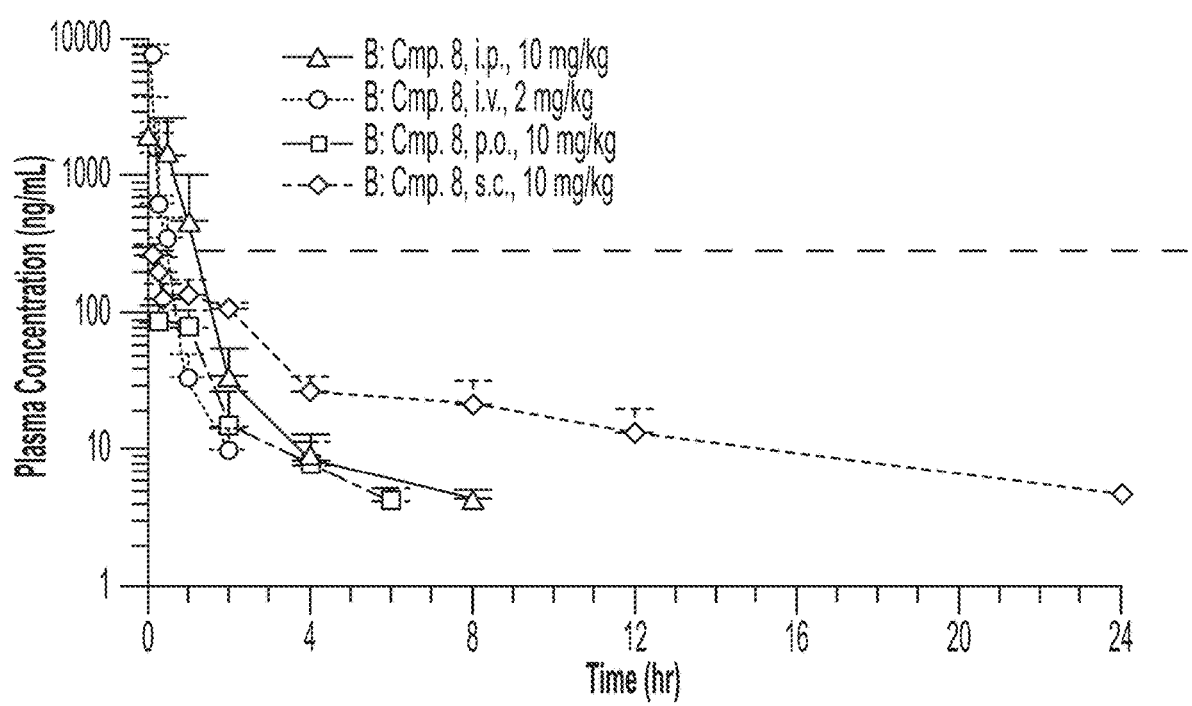
FIG. 18 shows the concentration of Compound 8 ("Cmp. 8") in mice at time points following intraperitoneal ("i.p."), intraveneous ("i.v."), subcutaneous ("s.c."), or oral ("p.o.") administration.

FIG. 18 illustrates the results of the pharmacokinietic measurements with Compound 8. The plasma concentration of Compound 8 at the measured time points for each administration route can be seen. The dotted line in FIG. 18 is indicative of a 10 µM concentration of Compound 8. Additionally, medicinal chemistry measurements on Compound 49 showed that Compound 49 may have greater potency for insulin secretion ($EC_{50}$~82 nM measured at a glucose concentration of 16.7 mM). However, Compound 49 has lower solubility than Compound 8.

Example 4: In Vivo Efficacy

Animals

Three-month-old male C57B6/J mice of body weight ranging from 20 to 25 g were housed in plastic polycarbonate cages. The animals were maintained at 25° C. with a 12-hour dark, 12-hour light schedule with food and water available ad libitum.

Experimental Protocol

Figure 19A:
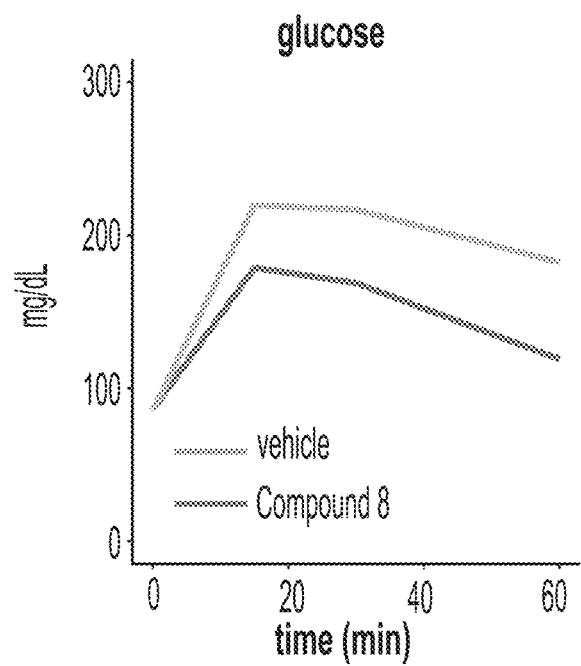
FIGS. 19A-19D shows the results of the in vivo efficacy measurements of Compound 8 on mice measuring glucose and insulin levels following administration.
Figure 19B:
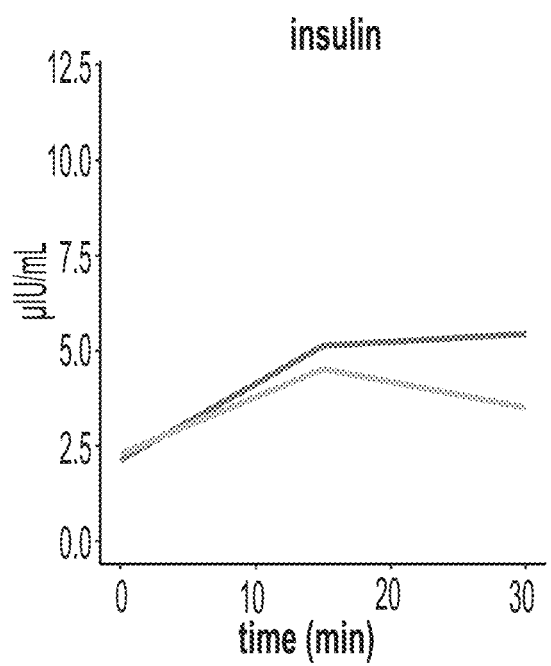
Figure 19C:
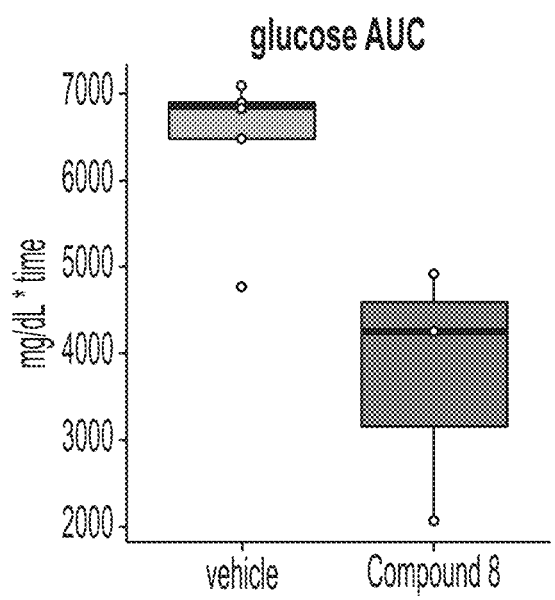
Figure 19D:
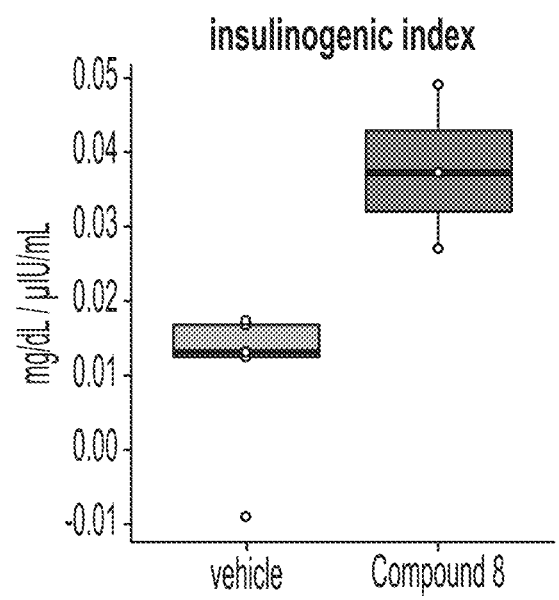

After two weeks of adaptation, the animals were randomly divided into two treatment groups (vehicle and Compound 8 in vehicle) with 5 mice per group. Mice were fasted for 16 hours (overnight) and basal blood glucose level was measured by tail vein nick using the AlphaTRAK 2 glucometer. Animals were given Compound 8 (2 mg/kg body weight) in vehicle or vehicle alone (7.5% NMP, 7.5% Solutol HS-15, 85% normal saline) by tail vein injection. Glucose tolerance tests (GTT) were performed 10 minutes after injection. Animals were given glucose at a dose of 1 g/kg body weight by intraperitoneal injection. Blood glucose was measured using the glucometer immediately before glucose injection, and at 15, 30, 60, and 120 minutes after injection (FIGS. 19A and 19C). At the 0, 15, and 30 minute time points, blood samples for insulin measurements were collected into EDTA-coated tubes and centrifuged at 9000 rpm to separate plasma, which was then stored at −80° C. until analysis. Insulin levels in plasma were analyzed using the ultra-sensitive mouse insulin ELISA kit (Crystal Chem) (FIGS. 19B and 19D). The animals were sacrificed at the end of the glucose tolerance test. Liver and pancreas of the mice were frozen immediately in liquid nitrogen and stored at −80° C. for future analyses. A part of the liver tissue was fixed in 4% PFA for histopathological analysis. As can be seen in FIGS. 19A-19D, the glucose concentration area under the curve (AUC) is decreased when Compound 8 is administered as compared to control, while also showing an increase in the insulinogenic index as compared to control.

Example 5: Calcium Influx Assay

Figure 20:
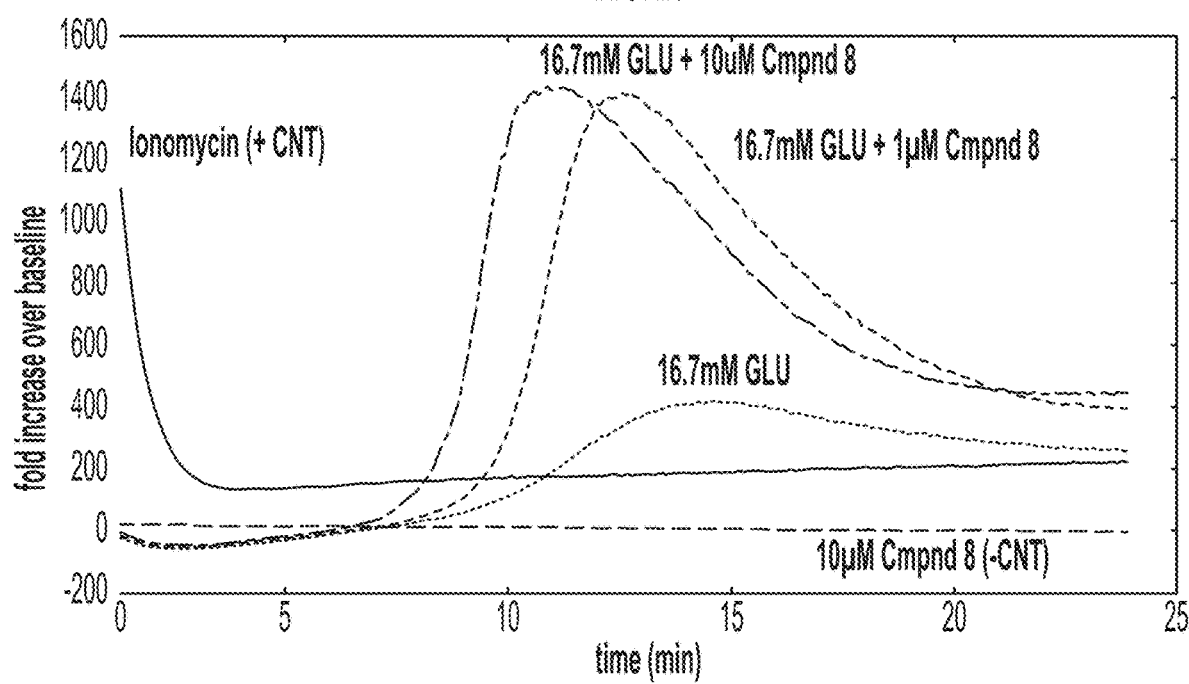
FIG. 20 shows the results of a calcium influx assay of beta cells in glucose stimulating conditions (16.7 mM glucose) without an insulin secretagogue, at a concentration of 1 μM, 10 μM of an insulin secretagogoue (Compound 8), and in the presence of ionomycin, an ionophore which raises the intracellular level of $Ca^{2+}$.

Mouse MING insulinoma cells were cultured in DMEM medium supplemented with 10% FBS, 100 U/mL penicillin, 100 µg/mL streptomycin, and 55 µM β-mercaptoethanol. Two days prior to the experiment, cells were seeded in 384-well clear-bottom microplates at 17,500 cells/well. For calcium imaging, microplates were washed three times with Hanks' Balanced Salt Solution (HBSS, containing $Ca^{2+}$/$Mg^{2+}$) using the CyBio Well vario plate washer. Cells were loaded with 2 µM of the calcium indicator Fluo-4 for 1 hour at 37° C. in Krebs-Ringer buffer (KRB) with 3 g/L glucose. After dye loading, the cells were washed again with HBSS and incubated in KRB with 0.5 g/L glucose for 30 minutes at 37° C. (glucose starvation conditions). After glucose starvation, microplates were transferred to FLIPR Tetra, where an automated 384-well dispensing unit added glucose (glucose stimulation conditions) together with Compound 8. Positive control measurements ("+CNT") were performed in wells with ionomycin to prompt calcium influx without the presence of glucose. Negative control measurements ("−CNT") were also performed in wells with Compound 8 present in and without glucose. All wells were read simultaneously at 1 Hz intervals. FIG. 20 illustrates the fold increase of measured calcium over baseline measurements performed in the absence of glucose. As can be seen, glucose invoked calcium influx in β-cells, but Compound 8 does not invoke a calcium influx in β-cells in the absence of glucose. However, Compound 8 does promote calcium influx in β-cells in the presence of glucose. Moreover, Compound 8 has a dose dependent response to increasing calcium influx in beta cells, but only in the presence of glucose. Without wishing to be bound by theory, it is believed that insulin secretagogues acts between KATP channels stimulated by glucose, and the calcium channels that induce insulin secretion.

Example 6: Proteomics Analysis for Target Identification

On-Bead Digest:

Compound 87 (which displays similar secretagogue activity to Compound 8) was immobilized on solid support (beads) and incubated with cell lysate from INS-1E rat insulinoma cells. Incubation occurred in either the absence or presence of 10× soluble competitor (sol comp). Beads with Compound 8 immobilized thereon were washed once with IP lysis buffer, then three times with PBS. Four duplicate lysates prepared in the presence of sol comp and another four duplicate lysate prepared in the absence of sol comp were resuspended in 90 µL digestion buffer (2 M Urea, 50 mM Tris-HCl), reduced (2 µL of 500 mM DTT, 30 minutes, room temperature), and alkylated (4 µL of 500 mM IAA, 45 minutes, dark). 2 µg of sequencing-grade trypsin were added to each lysate, followed by overnight shaking at 700 rpm. The samples were then quenched with 20 µL of 10% formic acid and desalted on 10 mg Oasis cartridges to form desalted peptides.

iTRAQ Labeling of Peptides and Basic Reversed Phase (Brp) Fractionation

Desalted peptides were labeled with isbaric tage for relative and absolute concentration ("iTRAQ") reagents according to the manufacturer's instructions (AB Sciex, Foster City, Calif.). Peptides were dissolved in 30 µL of 0.5 M TEAB solution (pH 8.5) and labeling reagent was added in 70 µL of ethanol. After 1-hour incubation, the reaction was stopped with 50 mM Tris-HCl pH 7.5. Differentially labeled peptides were mixed and subsequently desalted on 10 mg Oasis cartridges for pull-down measurements for replicate groups 1 and 2. Table 5 illustrates the iTRAQ label and each sample measured.

TABLE 5

| iTRAQ label | Sample |
|---|---|
| 114 | no Sol Comp Rep1 |
| 115 | 10X Sol Comp Rep1 |
| 116 | no Sol Comp Rep2 |
| 117 | 10X Sol Comp Rep2 |

Differentially labeled and combined peptides were basic reverse-phase-fractionated as described in Rappsilber et al. Nat Protoc 2(8):1896-906 (2012), with six steps of % acetonitrile (ACN) (10;15;20;35;50;80%). Peptides were dried down and re-constituted in 9 μL of 3% ACN and 0.1% formic acid.

MS Analysis

Reconstituted peptides were separated on an online nano-flow EASY-nLC 1000 UHPLC system and analyzed on a benchtop Orbitrap Q Exactive mass spectrometer (the "Q Exactive instrument"). The peptide samples were injected onto a capillary column (Picofrit with 10 m tip opening/75 μm diameter, New Objective) packed in-house with 20 cm C18 silica material (1.9 μm ReproSil-Pur C18-AQ medium). The UHPLC setup was connected with a custom-fit micro-adapting tee (360 IDEX Health & Science, UH-753), and capillary columns were heated to 50° C. in column heater sleeves to reduce backpressure during UHPLC separation. Injected peptides were separated at a flow rate of 200 nL/min with a linear 80-minute gradient from 100% solvent A (3% acetonitrile, 0.1% formic acid) to 30% solvent B (90% acetonitrile, 0.1% formic acid), followed by a linear 6-minute gradient from 30% solvent B to 90% solvent B. Each sample was run for 120 minutes, including sample loading and column equilibration times. The Q Exactive instrument was operated in data-dependent mode, acquiring HCD MS/MS scans (R=17,500) after each MS1 scan (R=70,000) on the twelve most abundant ions in each sample using an MS1 ion target of $3\times10^6$ ions, an MS2 target of $5\times10^4$ ions, and an isolation window of 1.6 m/z. The maximum ion time utilized for the MS/MS scans was 120 msec; the HCD-normalized collision energy was set to 27; the dynamic exclusion time was set to 20 sec, and the peptide match and isotope exclusion functions were enabled.

Quantification and Identification of Peptides and Proteins

All mass spectra were processed using the Spectrum Mill software package v6.0 pre-release, with additional modules for iTRAQ-based quantification. Precursor ion quantification was done using extracted ion chromatograms (XIC's) for each precursor ion. The peak area for the XIC of each precursor ion subjected to MS/MS was calculated automatically by the Spectrum Mill software in the intervening high-resolution MS1 scans of the LC-MS/MS runs using narrow windows around each individual member of the isotope cluster. Peak widths in both the time and m/z domains were dynamically determined based on MS scan resolution, precursor charge and m/z, subject to quality metrics on the relative distribution of the peaks in the isotope cluster vs a theoretical calculation of peak parameters. Similar MS/MS spectra acquired on the same precursor m/z in the same dissociation mode within +/−60 sec were merged. MS/MS spectra with precursor charge >7 and poor quality MS/MS spectra, which failed the quality filter by not having a sequence tag length >1 (i.e., minimum of 3 masses separated by the in-chain mass of an amino acid) were excluded from searching.

For peptide identification, these MS/MS spectra were searched against a rat Uniprot database to which a set of common laboratory contaminant proteins was appended. Search parameters included: ESI-QEXACTIVE-HCD scoring parameters, trypsin enzyme specificity with a maximum of two missed cleavages, 40% minimum matched peak intensity, +/−20 ppm precursor mass tolerance, +/−20 ppm product mass tolerance, and carbamidomethylation of cysteines and iTRAQ labeling of lysines and peptide n-termini as fixed modifications. Allowed variable modifications were oxidation of methionine, N-terminal acetylation, pyroglutamic acid (N-termQ), deamidated (N), pyrocarbamidomethyl Cys (N-termC), with a precursor MH+ shift range of −18 to 64 Da. Protein identities interpreted for individual spectra were automatically designated as valid by optimizing score and delta rank1-rank2 score thresholds separately for each precursor charge state in each LC-MS/MS while allowing a maximum target-decoy-based false-discovery rate (FDR) of 1.0% at the spectrum level.

Figure 21:
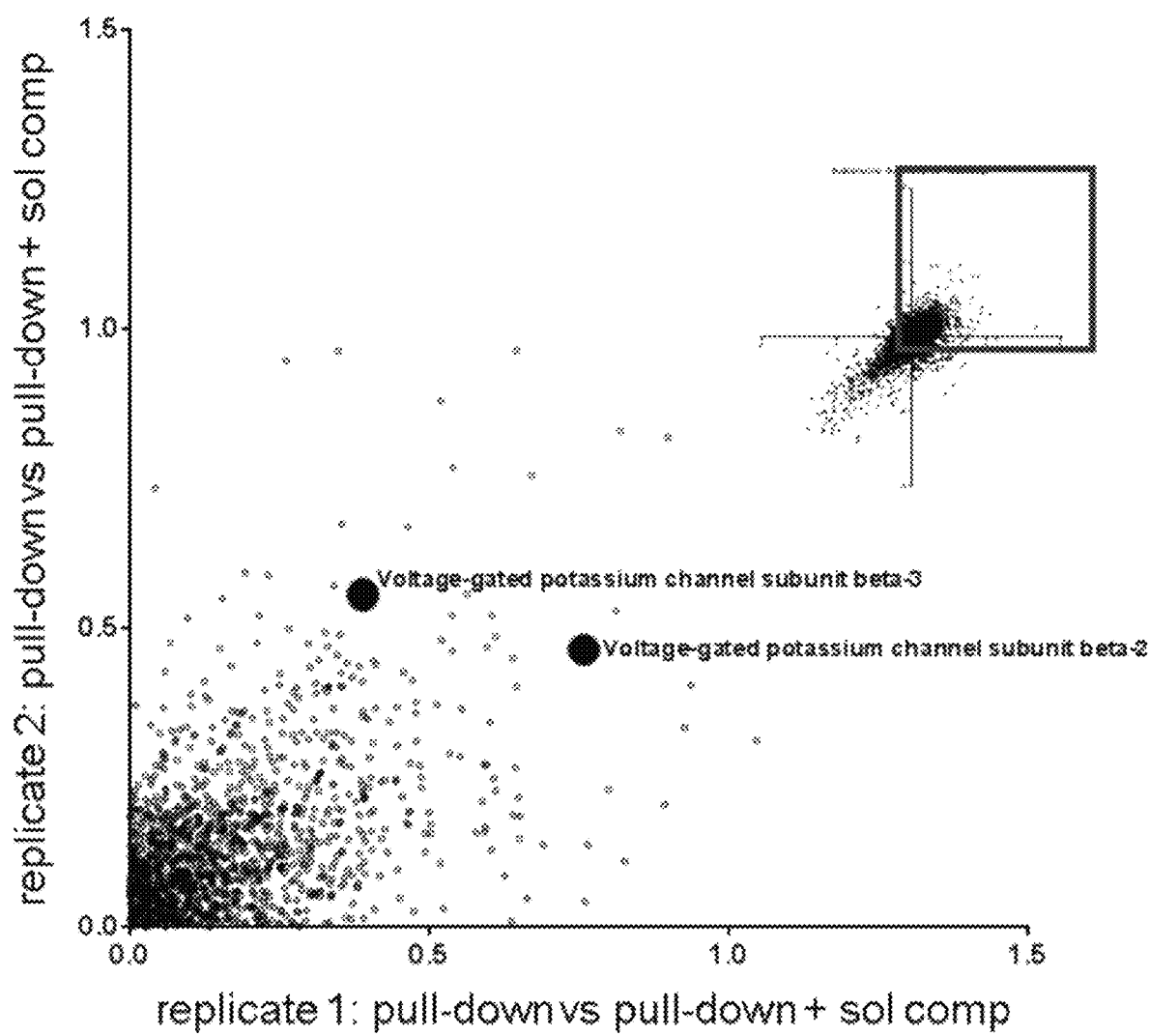
FIG. 21 shows a comparison of the iTRAQ ratios of two replicate groups to identify those proteins which interact with Compound 87 conjugated to a solid support. This identification was performed using proteomics analysis.

In calculating scores at the protein level and reporting the identified proteins, redundancy is addressed in the following manner: the protein score is the sum of the scores of distinct peptides. A distinct peptide is the single highest scoring instance of a peptide detected through an MS/MS spectrum. MS/MS spectra for a particular peptide may have been recorded multiple times (i.e., as different precursor charge states, isolated from adjacent SCX fractions, modified by oxidation of Met) but are still counted as a single distinct peptide. When a peptide sequence >8 residues long is contained in multiple protein entries in the sequence database, the proteins are grouped together and the highest scoring one and its accession number are reported. In some cases, when the protein sequences are grouped in this manner, there are distinct peptides which uniquely represent a lower scoring member of the group (isoforms or family members). Each of these instances of grouped proteins spawns a subgroup. Multiple subgroups are reported and counted towards the total number of proteins. iTRAQ ratios were obtained from the protein-comparisons export table in Spectrum Mill. FIG. 21 illustrates a comparison of the iTRAQ ratios for each identified protein in the replicate groups. Two strongly enriched hits identified were the voltage-gated potassium channel subunit β-3 (Kvβ3) and voltage-gated potassium channel subunit β-2 (Kvβ2) which are encoded by the genes Kcnab3 and Kcnab2, respectively. To obtain iTRAQ protein ratios the median was calculated over all distinct peptides assigned to a protein subgroup in each replicate. Interacting proteins were assigned using the Limma package in the R environment to calculate moderated t-test p, as described in Udeshi N D et al. Mol. Cell Proteomics 11:148-159 (2012).

Example 7: Genetic Knock-Downs

Figure 22:
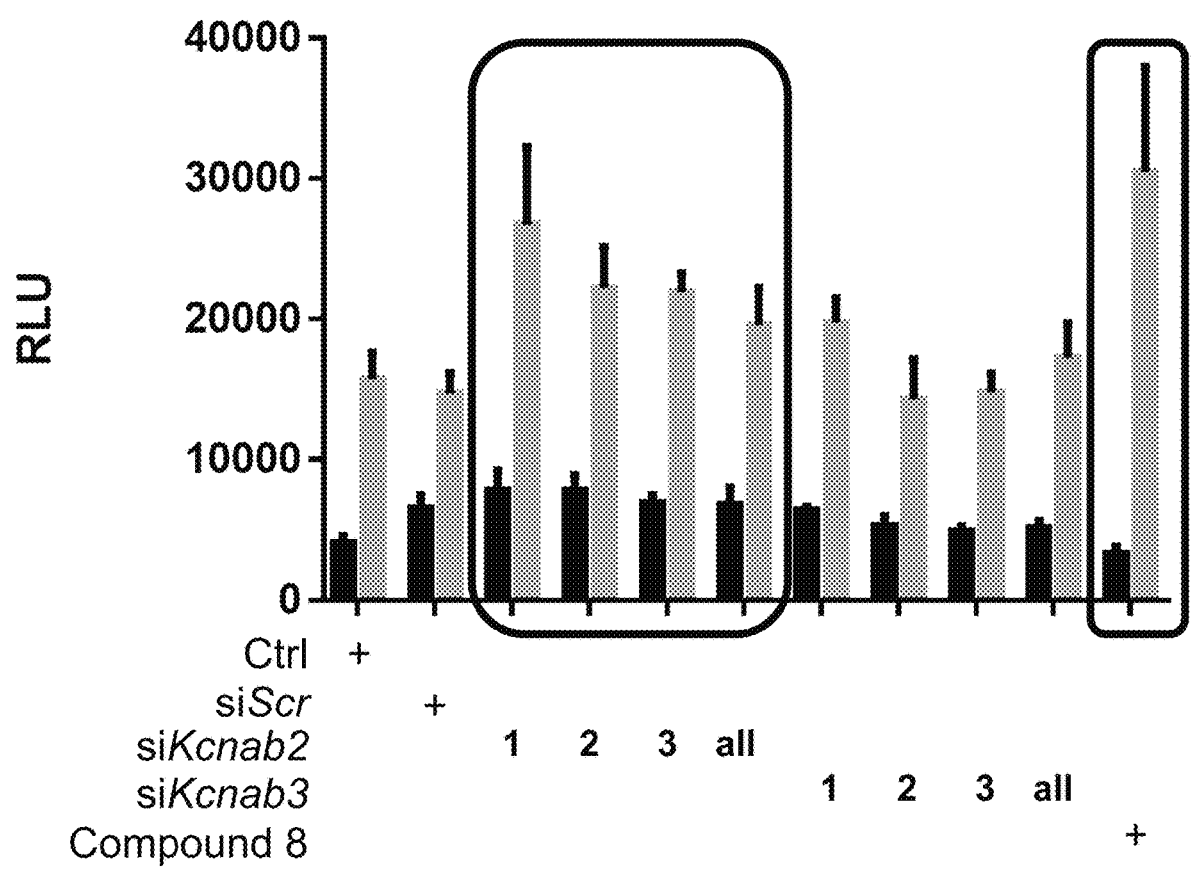
FIG. 22 illustrates the results genetic knockdown experiments measuring the luminescence of luciferase in cells with portions of Kncab2 or Kncab3 targeted. Results from measurements performed at the 2.8 mM glucose concentration are shown on the left in black, and measurements performed at the 16.7 mM glucose concentration is shown on the right in grey. For comparison, the luminescence of cells in contact with Compound 8 is also provided.

Rat INS-1E insulinoma cells stably expressing Gaussia luciferase inserted into the C-peptide portion of proinsulin (INS1E-PIG) were obtained as described previously (Burns et al. Cell Met. 2015). INS1E-PIG cells were seeded at 10,000 cells/well in 96-well plates. 30 nM of scrambled siRNA ("siSCR") or siRNAs targeting portions of rat Kcnab2 and Kcnab3 ("1," "2," and "3" refer to different portions of the specified gene, and "all" refers to a pool for siRNA targeting portions 1, 2, and 3) were transfected using Lipofectamine2000 reagent. Transfected cells were cultured for 72 hours, and subjected to glucose-stimulated luciferase secretion (GSLS). The 96-well plates were treated for 1 hour with 100 μL of KRBH buffer (135 mM NaCl, 3.6 mM KCl, 5 mM $NaHCO_3$, 0.5 mM $NaH_2PO_4$, 0.5 mM $MgCl_2$, 1.5 mM $CaCl_2$, 10 mM HEPES, pH 7.4, 0.1% BSA) containing 2.8 mM glucose. Cells were subsequently incubated with KRBH buffer containing 16.7 mM glucose for 2 hours. The supernatants (50 mL) were collected for measurement of secreted luciferase and transferred to a new plate containing 50 μL of 40 μM (2×) Coelenterazine in PBS. The resulting luminescence was measured using a Synergy microplate reader and shown in FIG. 22. Black bars on the left at each measurement type represent measurements taken in 2.8 mM glucose and grey bars on the right represent measurements in 16.7 mM glucose. For comparison, the luciferase measurements performed on Compound 8 are shown as well (see, FIGS. 14A and 14B). As can be seen, genetic knockdown of Kcnab2 by siRNA phenocopies the effect of Compound 8.

Example 8: Immunoprecipitation and Western Blotting

Figure 23:
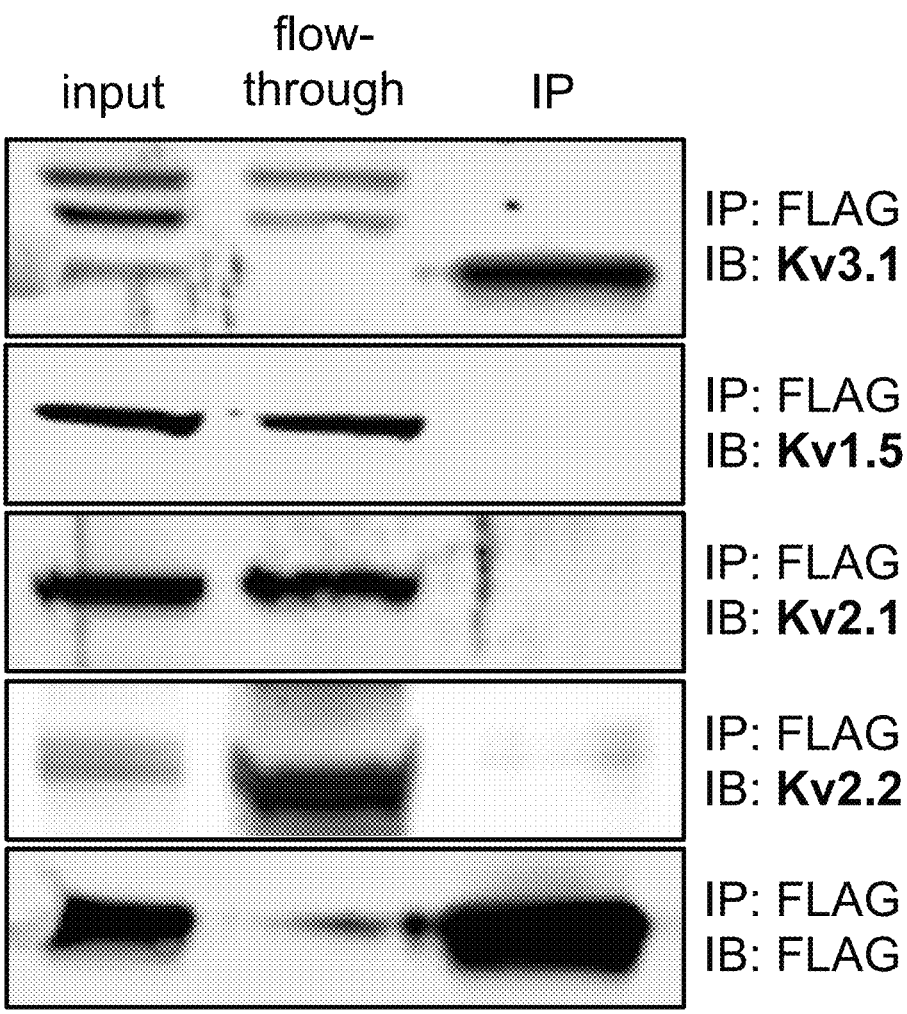
FIG. 23 shows images from immunoprecipitation and western blotting experiments on FLAG-tagged Kcnab2 cells with various antibody probes.
Figure 24:
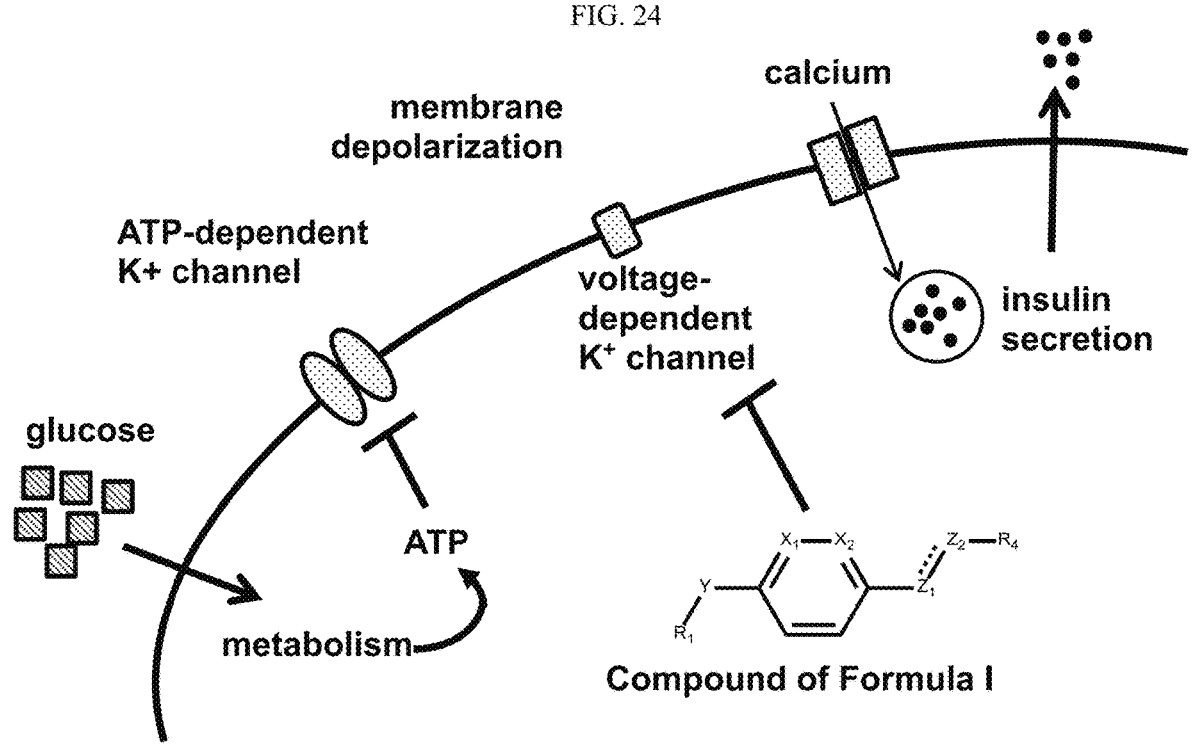
FIG. 24 is a schematic of the mechanism by which insulin secretagogues (in this case compounds of Formula I) may be able to promote secretion in a glucose dependent manner.

To determine which potassium channel member may be associating with Kvβ2, immunoprecipitation on overexpressed FLAG-tagged Kcnab2 was performed. K Rat INS1E insulinoma cells stably expressing rat Kvβ2-FLAG were seeded in 150-mm culture dishes until confluent. Cells were then washed twice with cold PBS and lysed with 10 mL of IP/Lysis Buffer (Thermo Fisher) containing protease inhibitor cocktail. After centrifugation for 30 min at 20,000×g, the supernatants were recovered and protein concentration was measured using BCA Protein Assay kit. 50 μl of resuspended anti-FLAG M2 magnetic beads were equilibrated with 5 packed gel volumes of TBS (50 mM Tris-HCl, 150 mM NaCl, pH 7.4). Beads were collected by placing the tube in the appropriate magnetic separator and washed twice with TB S. 1 mg of protein extract in 1 mL of IP/Lysis buffer was added to the beads and incubated overnight at 4° C. under rotation. Beads were collected by placing the tube in the appropriate magnetic separator and the supernatants transferred to fresh tubes (flow-through). Beads were washed with 20 gel volumes of TBS and proteins were eluted using 5 packed volumes of 150 ng/mL of 3×FLAG peptide in TBS. Samples were incubated overnight at 4° C. under rotation. Beads were collected by placing the tube in the appropriate magnetic separator and supernatants transferred to fresh tubes (IPs). 50 μl of each protein extracts (input), flow-through and IP were separated by 4-12% SDS-PAGE and transferred to a PVDF membrane and probed with the appropriate primary antibody (1:1000 each of either rabbit anti-Kv3.1, rabbit anti-Kv3.2, rabbit anti-Kv2.1, rabbit anti-Kv2.2, rabbit anti-Kv1.5, or mouse anti-FLAG). Blots were probed with 1:5000 goat anti-rabbit IRDye800CW, and donkey anti-mouse IRDye680CD. Images captured using the Odyssey CLx (LI-COR). FIG. 23 shows the images captured in the experiments and illustrates that Kv3.1 is enriched in the pull-down and thus may be the potassium channel responsible for compound effects. Without wishing to be bound by theory, insulin secretagogues target voltage-gated potassium channels to prevent or slow membrane repolarization. Normally, this repolarization is necessary to have a beta cell secrete the appropriate amount of insulin. By inhibiting repolarization, the compounds of the invention provide increased insulin secretion, but in a glucose dependent manner. Such a mechanism is illustrated in FIG. 24.

CHEMISTRY EXAMPLES

The following Examples illustrate the synthesis of a representative number of compounds which may be insulin secretagogues. Accordingly, the Examples are intended to illustrate but not to limit the disclosure. Additional compounds not specifically exemplified may be synthesized using conventional methods in combination with the methods described herein.

Example 1

Shown below are non-limiting synthetic schemes which may be used to prepare selected, non-limiting examples of compounds of the invention from commercially available starting materials.

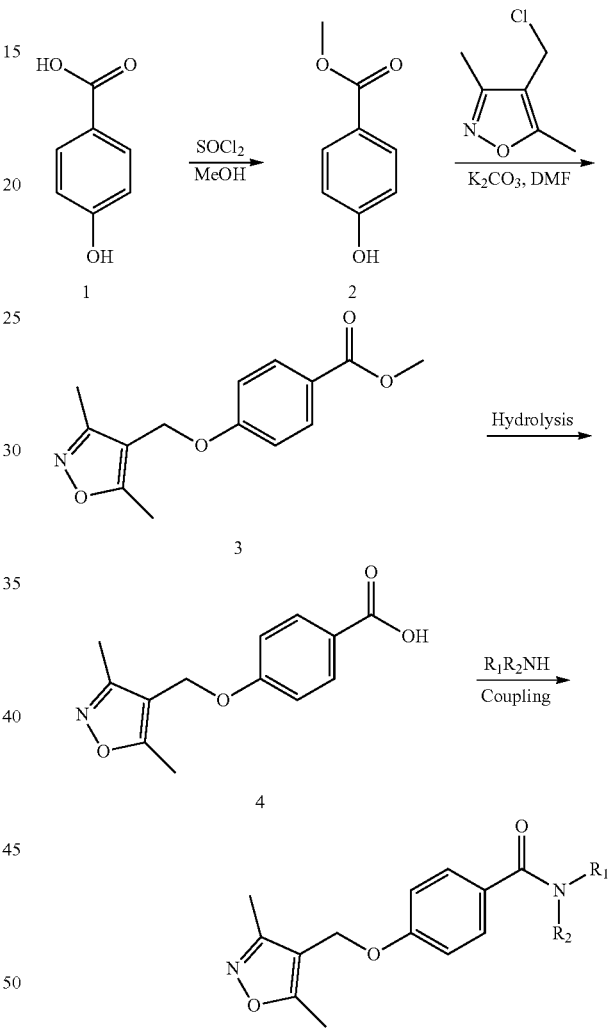

Preparation of Methyl 4-hydroxybenzoate (Intermediate 2)

To a solution of 4-hydroxybenzoic acid (10.0 g, 72.4 mmol, 1.0 eq) in MeOH (200 mL) was added thionyl chloride (43.07 g, 362.0 mmol, 5.0 eq) dropwise at 0° C., and the reaction was heated to reflux overnight. Solvent was removed under reduced pressure after the starting material was consumed completely by TLC monitoring. The semi-solid residue was added sat. NaHCO₃ solution to adjust pH 9-10 to precipitate the target product. The obtained solid product (6.0 g, 54.5%) was collected and dried under vacuum, which was pure enough for the next step reaction.

Preparation of Methyl 4-((3,5-dimethylisoxazol-4-yl)methoxy)benzoate (Intermediate 3)

To a solution of methyl 4-hydroxybenzoate (0.5 g, 3.29 mmol, 1.0 eq) in DMF (10 mL) was added K$_2$CO$_3$ (0.683 g, 4.94 mmol, 1.50 eq). The reaction was stirred at rt for 30 min. 4-(Chloromethyl)-3,5-dimethylisoxazole (0.575 g, 3.95 mmol, 1.20 eq) was added, and the resulting solution was stirred at 80° C. for 6 hrs. After being cooled to rt, the reaction was diluted with ethyl acetate, washed with brine for 5 times. The organic layer was dried and concentrated to afford the crude product, which was triturated with PE/EA (50:1) for 3 times. The suspension was filtered and the solid was collected and dried to give the title compound (1.0 g, 99%).

Preparation of 4-((3,5-dimethylisoxazol-4-yl)methoxy)benzoic acid (Intermediate 4)

To a solution of methyl 4-((3,5-dimethylisoxazol-4-yl)methoxy)benzoate (12.0 g, 46.0 mmol, 1.0 eq) in THF/MeOH (240 ml, v:v=1:1) was added 10% NaOH aq. solution (9.0 g, 92 mL, 229.0 mmol, 5.0 eq) at rt. The reaction was stirred for 3 hrs. Solvent was removed under reduced pressure after the starting material was consumed completely by TLC monitoring. The semi-solid residue was added diluted HCl solution (1 M) to adjust pH 5-6 to precipitate the target product. The solid product was collected and dried under vacuum oil pump to give the title compound (9.9 g, 87%).

Preparation of 4-((3,5-dimethylisoxazol-4-yl)methoxy)-N-(6-methylpyridin-2-yl)benzamide (Compound 1)

To a solution of 4-((3,5-dimethylisoxazol-4-yl)methoxy)benzoic acid (100 mg, 0.4 mmol, 1.0 eq) in DCM (10 mL) was added oxalyl chloride (0.5 mL, 5.0 eq) at rt, and the reaction was stirred for 30 min. The solvent was removed under reduced pressure. To a solution of 6-methylpyridin-2-amine (43.7 mg, 0.4 mmol, 1.0 eq) and TEA (150 mg, 1.5 mg, 3.5 eq) in DCM (2 mL) was added dropwise the obtained acyl chloride in DCM (10 mL), and the reaction mixture was stirred for 2 hrs, and washed with water, brine, and dried to give a residue, which was purified by pre-TLC to give the title compound (24.7 mg, 18%).

Alternate Synthesis of Intermediate 4

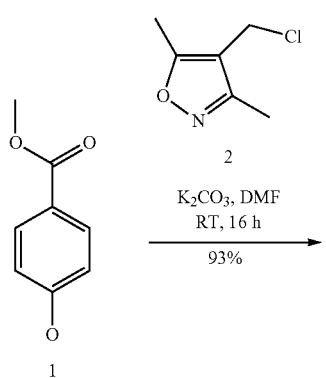

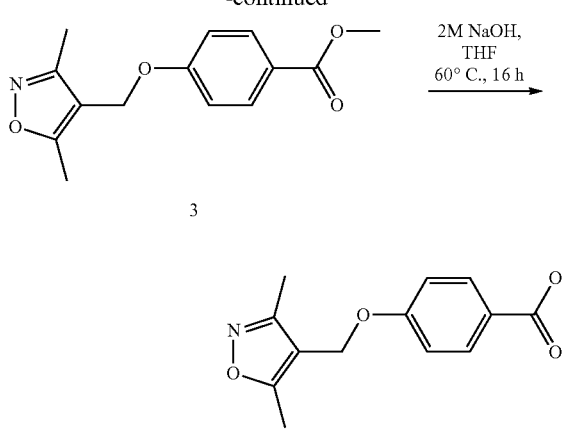

To a stirred solution of 4-Hydroxy-benzoic acid methyl ester (1) (3 g, 19.724 mmol) in DMF (30 mL), K$_2$CO$_3$ (3 g, 39.448 mmol) and 4-Chloromethyl-3,5-dimethyl-isoxazole (2) (2.74 mL, 21.696 mmol) were added and the reaction mixture was stirred at RT for 16 hours. The reaction mixture was diluted with ethyl acetate, washed with water, brine, dried over sodium sulfate and concentrated. The crude was triturated with hexane to afford Intermediate 3 (4-(3,5-Dimethyl-isoxazol-4-ylmethoxy)-benzoic acid methyl ester, 4.8 g, 93%) as white solid.

To a stirred solution of 4-(3,5-Dimethyl-isoxazol-4-ylmethoxy)-benzoic acid methyl ester (3) (2.5 g, 10.331 mmol) in THF (20 mL) was added an aqueous solution (5 mL) of NaOH (0.826 g, 20.662 mmol) and the reaction mixture was heated at 60° C. for 16 hours. It was then brought to room temperature and evaporated to dryness under reduced pressure. Residue was taken in water and acidified with 2N HCl solution. The white precipitate that formed was collected by filtration and dried well under vacuum to afford Intermediate 4 (1.8 g, 70%) as white solid.

Synthesis of Compound 81 (4-(3,5-Dimethyl-isoxazol-4-ylmethoxy)-N-indan-4-yl-benzamide)

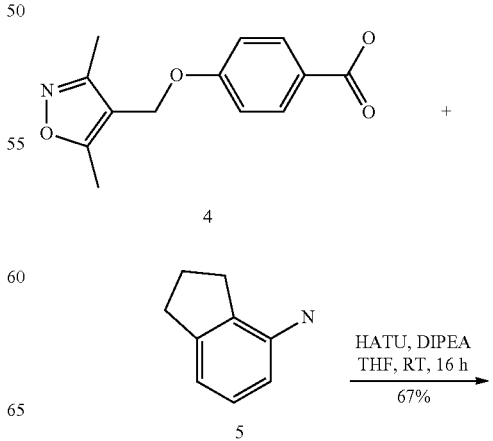

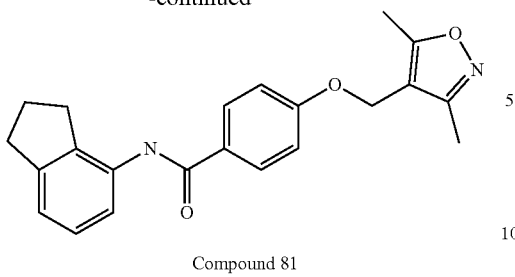

Compound 81

To a stirred solution of 4-(3,5-Dimethyl-isoxazol-4-yl-methoxy)-benzoic acid (4) (150 mg, 0.658 mmol) and Indan-4-ylamine (5) (0.119 mL, 0.658 mmol) in THF (5 mL) were added HATU (375 mg, 0.987 mmol) and DIPEA (0.455 mL, 2.632 mmol) and the resulting mixture was stirred at ambient temperature for 16 hours. The reaction mixture was diluted with EtOAc, washed with saturated NaHCO$_3$ solution, water, dried over sodium sulfate and concentrated. Crude thus obtained was purified by CombiFlash ISCO column (gradient: 30% EtOAc in Hexane) to afford the desired Compound 81 (160 mg, 67%) as off white solid.

Synthesis of Compound 73 (4-(3,5-Dimethyl-isoxazol-4-ylmethoxy)-N-(5,6,7,8-tetrahydro-naphthalen-1-yl)benzamide)

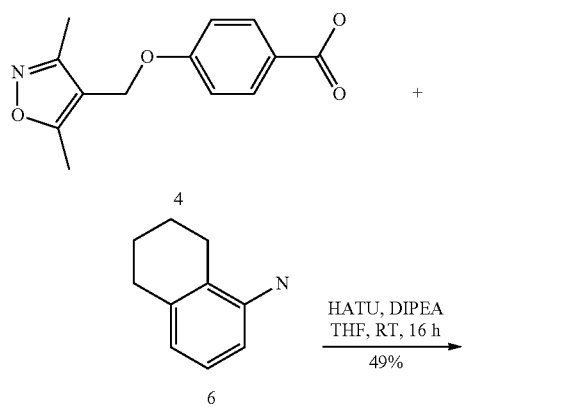

Compound 73

To a stirred solution of 4-(3,5-Dimethyl-isoxazol-4-yl-methoxy)-benzoic acid (4) (150 mg, 0.658 mmol) and 5,6,7,8-Tetrahydro-naphthalen-1-ylamine (6) (0.091 mL, 0.658 mmol) in THF (5 mL) were added HATU (375 mg, 0.987 mmol) and DIPEA (0.455 mL, 2.632 mmol) and the resulting mixture was stirred at ambient temperature for 16 hours. The reaction mixture was diluted with EtOAc, washed with saturated NaHCO$_3$ solution, water, dried over sodium sulfate and concentrated. Crude thus obtained was purified by CombiFlash ISCO column (gradient: 30% EtOAc in Hexane) to afford the desired Compound 73 (110 mg, 49%) as off white solid.

Synthesis of Compound 74 (4-(3,5-Dimethyl-isoxazol-4-ylmethoxy)-N-naphthalen-1-yl-benzamide)

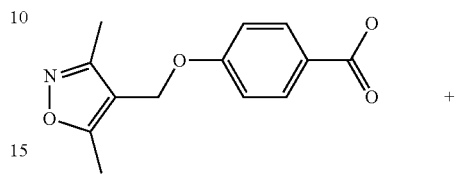

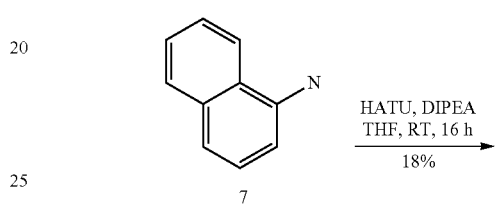

Compound 74

To a stirred solution of 4-(3,5-Dimethyl-isoxazol-4-yl-methoxy)-benzoic acid (4) (150 mg, 0.658 mmol) and Naphthalen-1-ylamine (7) (0.094 mL, 0.658 mmol) in THF (5 mL) were added HATU (375 mg, 0.987 mmol) and DIPEA (0.455 mL, 2.632 mmol) and the resulting mixture was stirred at ambient temperature for 16 hours. The reaction mixture was diluted with EtOAc, washed with saturated NaHCO$_3$ solution, water, dried over sodium sulfate and concentrated. Crude thus obtained was purified by CombiFlash ISCO column (gradient: 30% EtOAc in Hexane) to afford the desired Compound 74 (44 mg, 18%) as off white solid.

Synthesis of Compound 78 (N-(2-Chloro-3-methyl-phenyl)-4-(3,5-dimethyl-isoxazol-4-ylmethoxy)-benzamide)

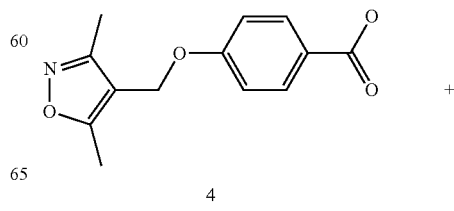

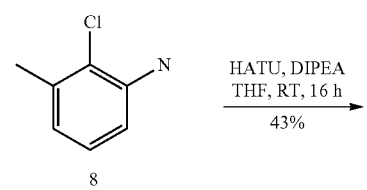

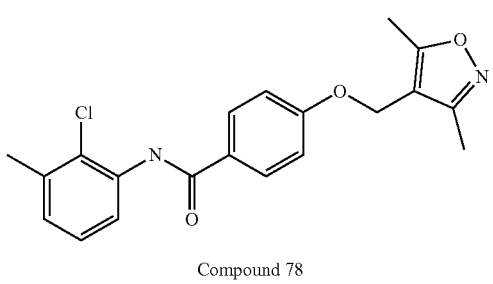

Compound 78

To a stirred suspension of 4-(3,5-Dimethyl-isoxazol-4-ylmethoxy)-benzoic acid (4) (150 mg, 0.658 mmol) in DCM (3 mL) was added Oxalyl chloride (0.085 mL, 0.987 mmol) at 0° C. followed by the addition of catalytic amount of DMF. The reaction mixture was slowly warmed to room temperature and stirred for 3 hours. It was then evaporated under inert atmosphere. The residue was again dissolved in DCM (3 mL) and was added to a solution of 2-Chloro-3-methyl-phenylamine (8) (93 mg, 0.658 mmol) and Et$_3$N (0.455 mL, 2.632 mmol) in DCM (3 mL) at 0° C. The resultant solution was further stirred at room temperature for 16 hours. It was then diluted with EtOAc, washed with saturated NaHCO$_3$ solution, water, dried over sodium sulfate and concentrated. Crude thus obtained was purified by CombiFlash ISCO column (gradient: 30-40% EtOAc in Hexane) to afford the desired Compound 78 (105 mg, 43%) as white solid.

Synthesis of Compound 69 (N-(2-Cyano-3-methyl-phenyl)-4-(3,5-dimethyl-isoxazol-4-ylmethoxy)-benzamide)

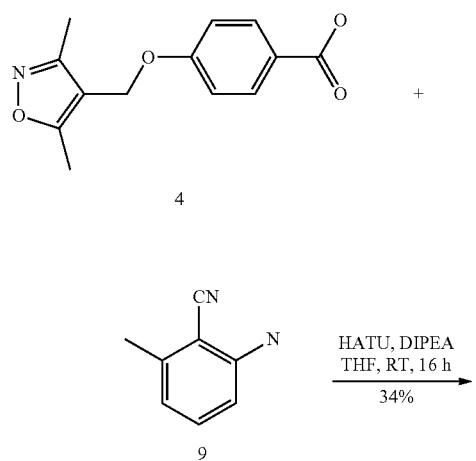

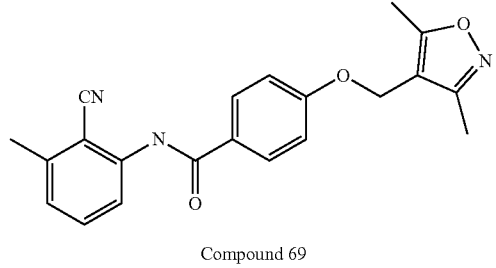

Compound 69

To a stirred suspension of 4-(3,5-Dimethyl-isoxazol-4-ylmethoxy)-benzoic acid (4) (150 mg, 0.658 mmol) in DCM (3 mL) was added Oxalyl chloride (0.085 mL, 0.987 mmol) at 0° C. followed by the addition of catalytic amount of DMF. The reaction mixture was slowly warmed to room temperature and stirred for 3 hours. It was then evaporated under inert atmosphere. The residue was again dissolved in DCM (3 mL) and was added to a solution of 2-Amino-6-methyl-benzonitrile (9) (86 mg, 0.658 mmol) and Et$_3$N (0.455 mL, 2.632 mmol) in DCM (3 mL) at 0° C. The resultant solution was further stirred at room temperature for 16 hours. It was then diluted with EtOAc, washed with saturated NaHCO$_3$ solution, water, dried over sodium sulfate and concentrated. Crude thus obtained was purified by CombiFlash ISCO column (gradient: 30-40% EtOAc in Hexane) to afford the desired Compound 69 (80 mg, 34%) as white solid.

Synthesis of Compound 83 (N-(3-Cyano-2-methyl-phenyl)-4-(3,5-dimethyl-isoxazol-4-ylmethoxy)-benzamide)

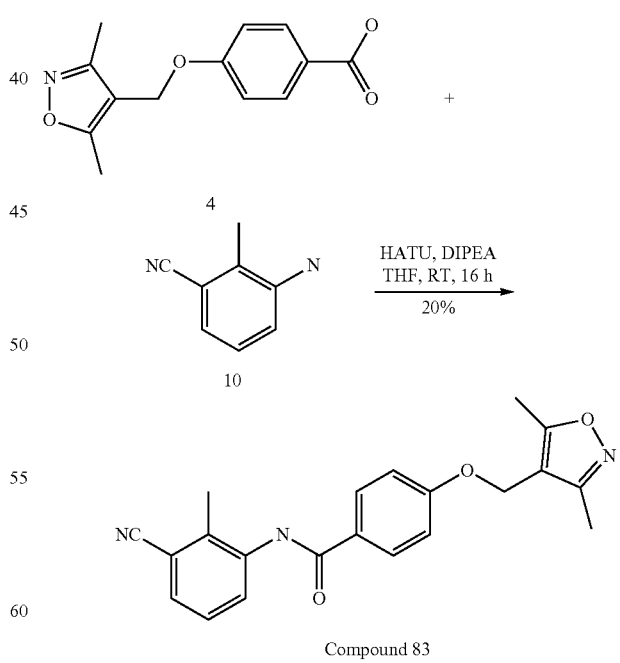

Compound 83

To a stirred suspension of 4-(3,5-Dimethyl-isoxazol-4-ylmethoxy)-benzoic acid (4) (150 mg, 0.658 mmol) in DCM (3 mL) was added Oxalyl chloride (0.085 mL, 0.987 mmol) at 0° C. followed by the addition of catalytic amount of DMF. The reaction mixture was slowly warmed to room temperature and stirred for 3 hours. It was then evaporated under inert atmosphere. The residue was again dissolved in DCM (3 mL) and was added to a solution of 3-Amino-2-methyl-benzonitrile (10) (86 mg, 0.658 mmol) and Et$_3$N (0.455 mL, 2.632 mmol) in DCM (3 mL) at 0° C. The resultant solution was further stirred at room temperature for 16 hours. It was then diluted with EtOAc, washed with saturated NaHCO$_3$ solution, water, dried over sodium sulfate and concentrated. Crude thus obtained was purified by CombiFlash ISCO column (gradient: 30-40% EtOAc in Hexane) to afford the desired Compound 83 (48 mg, 20%) as white solid.

Synthesis of Compound 68 (N-(2,3-Dichloro-phenyl)-4-(3,5-dimethyl-isoxazol-4-ylmethoxy)-benzamide)

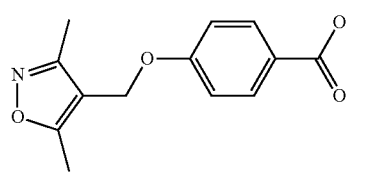

4

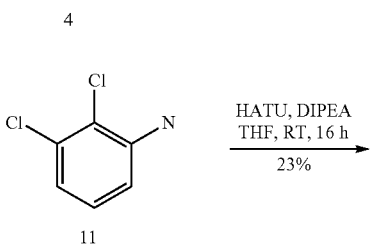

11

HATU, DIPEA
THF, RT, 16 h
23%

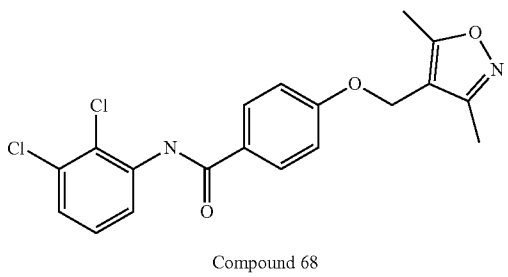

Compound 68

To a stirred suspension of 4-(3,5-Dimethyl-isoxazol-4-ylmethoxy)-benzoic acid (4) (150 mg, 0.658 mmol) in DCM (3 mL) was added Oxalyl chloride (0.085 mL, 0.987 mmol) at 0° C. followed by the addition of catalytic amount of DMF. The reaction mixture was slowly warmed to room temperature and stirred for 3 hours. It was then evaporated under inert atmosphere. The residue was again dissolved in DCM (3 mL) and was added to a solution of 2,3-Dichloroaniline (11) (106 mg, 0.658 mmol) and Et$_3$N (0.455 mL, 2.632 mmol) in DCM (3 mL) at 0° C. The resultant solution was further stirred at room temperature for 16 hours. It was then diluted with EtOAc, washed with saturated NaHCO$_3$ solution, water, dried over sodium sulfate and concentrated. Crude thus obtained was purified by CombiFlash ISCO column (gradient: 30-40% EtOAc in Hexane) to afford the desired Compound 68 (60 mg, 23%) as white solid.

Synthesis of Compound 72 (N-(3-Chloro-2-methylphenyl)-4-(3,5-dimethyl-isoxazol-4-ylmethoxy)-benzamide)

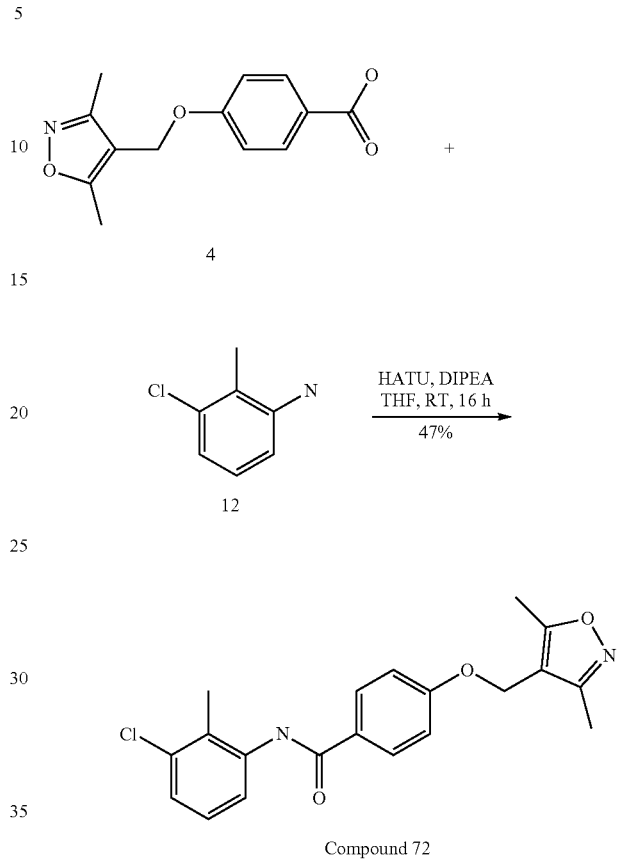

Compound 72

To a stirred solution of 4-(3,5-Dimethyl-isoxazol-4-ylmethoxy)-benzoic acid (4) (150 mg, 0.658 mmol) and 3-Chloro-2-methyl-phenylamine (12) (92 mg, 0.658 mmol) in THF (5 mL) were added HATU (375 mg, 0.987 mmol) and DIPEA (0.455 mL, 2.632 mmol) and the resulting mixture was stirred at ambient temperature for 16 hours. The reaction mixture was diluted with EtOAc, washed with saturated NaHCO$_3$ solution, water, dried over sodium sulfate and concentrated. Crude thus obtained was purified by CombiFlash ISCO column (gradient: 30% EtOAc in Hexane) to afford the desired Compound 72 (115 mg, 47%) as white solid.

Synthesis of Compound 71 (4-((3,5-dimethylisoxazol-4-yl)methoxy)-N-(3-(hydroxymethyl)-2-methylphenyl)benzamide)

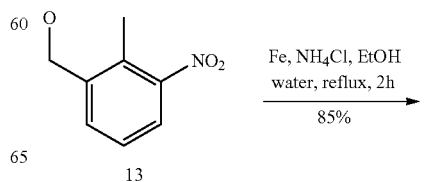

13

Fe, NH$_4$Cl, EtOH
water, reflux, 2h
85%

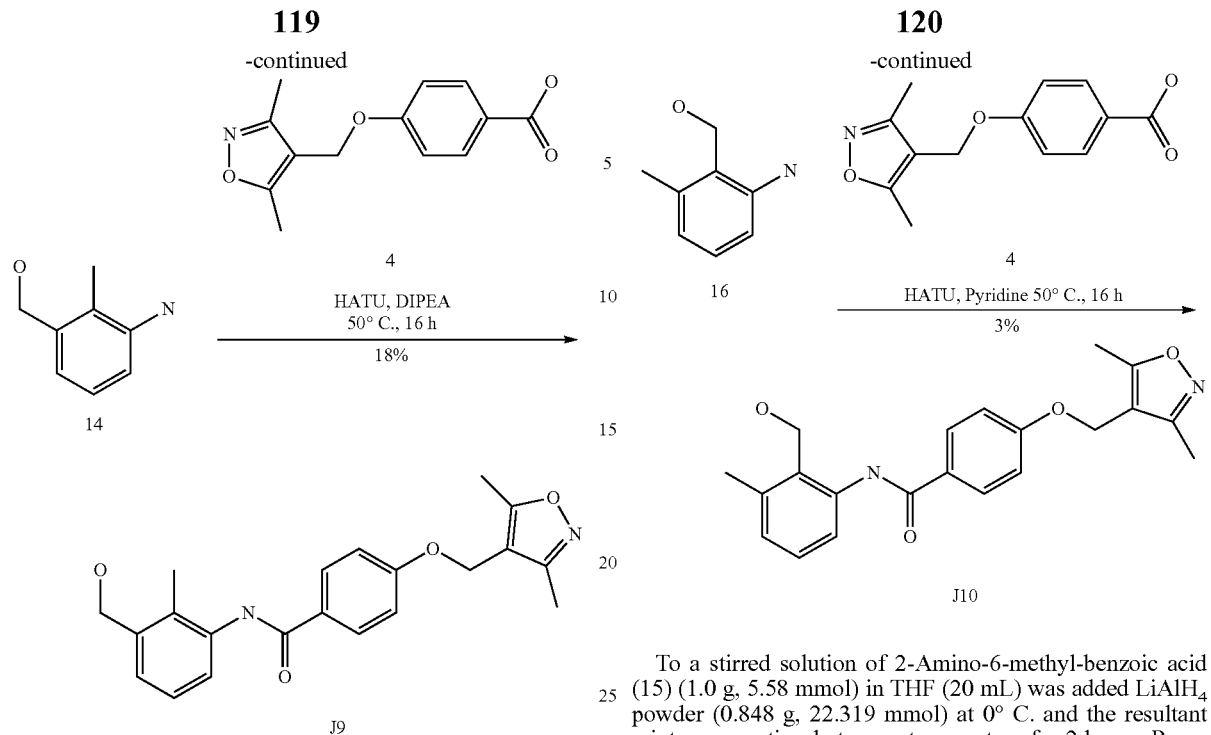

To a stirred solution of (2-Methyl-3-nitro-phenyl)-methanol (13) (100 mg, 0.598 mmol) in EtOH (5 mL) and water (1 mL) were added iron powder (183 mg, 3.29 mmol) and ammonium chloride (22 mg, 0.419 mmol) and the resultant mixture was refluxed for 2 hours. Reaction mixture was then brought to room temperature and filtered through a bed of celite. Filtrate was diluted with EtOAc, washed with water, dried over sodium sulfate and concentrated under reduced pressure to afford Intermediate 14 (70 mg, 85%) as yellow gum.

To a stirred solution of 4-(3,5-Dimethyl-isoxazol-4-yl-methoxy)-benzoic acid (4) (125 mg, 0.51 mmol) and (3-Amino-2-methyl-phenyl)-methanol (14) (70 mg, 0.51 mmol) in Pyridine (1 mL) was added HATU (290 mg, 0.765 mmol) and the reaction mixture was stirred at 50° C. for 16 hours. It was then diluted with EtOAc, washed with 2N HCl, saturated NaHCO$_3$ solution, water, dried over sodium sulfate and concentrated under reduced pressure. Crude thus obtained was purified by column chromatography (silica, gradient: 25-30% EtOAc in Hexane) to afford desired Compound 71 (35 mg, 18%) as off white solid.

Synthesis of Compound 71 (4-((3,5-dimethylisoxazol-4-yl)methoxy)-N-(2-(hydroxymethyl)-3-methylphenyl)benzamide)

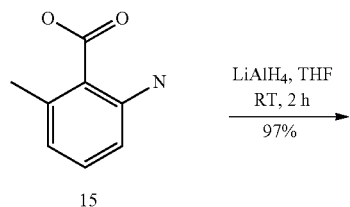

To a stirred solution of 2-Amino-6-methyl-benzoic acid (15) (1.0 g, 5.58 mmol) in THF (20 mL) was added LiAlH$_4$ powder (0.848 g, 22.319 mmol) at 0° C. and the resultant mixture was stirred at room temperature for 2 hours. Reaction mixture was then quenched with water, stirred for 30 minutes and filtered. Filtrate was diluted with EtAOc, washed with water, brine, dried over sodium sulfate and concentrated under reduced pressure to afford desired intermediate 16 (750 mg, 97%) as yellow gum.

To a stirred solution of 4-(3,5-Dimethyl-isoxazol-4-yl-methoxy)-benzoic acid (4) (360 mg, 1.458 mmol) and (2-Amino-6-methyl-phenyl)-methanol (16) (200 mg, 1.458 mmol) in Pyridine (2 mL) was added HATU (831 mg, 2.187 mmol) and the reaction mixture was stirred at 50° C. for 16 hours. It was then diluted with EtOAc, washed with 2N HCl, saturated NaHCO$_3$ solution, water, dried over sodium sulfate and concentrated under reduced pressure. Crude thus obtained was purified by column chromatography (silica, gradient: 25-30% EtOAc in Hexane) to afford desired Compound 71 (15 mg, 3%) as off white solid.

Synthesis of Compound 84 (4-(3,5-Dimethyl-isoxazol-4-ylmethoxy)-N-(3-methoxymethyl-phenyl)-benzamide)

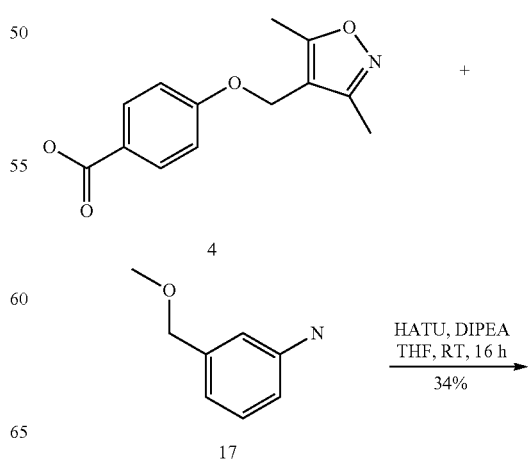

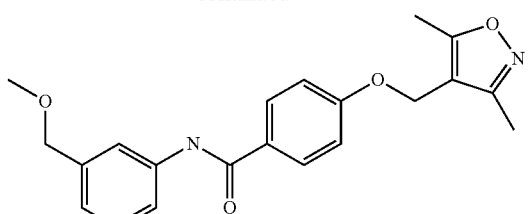

Compound 84

To a stirred solution of 4-(3,5-Dimethyl-isoxazol-4-yl-methoxy)-benzoic acid (4) (100 mg, 0.404 mmol) and 3-Methoxymethyl-phenylamine (17) (55 mg, 0.404 mmol) in THF (3 mL) were added HATU (230 mg, 0.607 mmol) and DIPEA (0.209 mL, 1.213 mmol) and the resulting mixture was stirred at ambient temperature for 16 hours. The reaction mixture was diluted with EtOAc, washed with saturated NaHCO₃ solution, water, dried over sodium sulfate and concentrated. Crude compound was purified by reverse phase Prep HPLC to afford desired compound J17 (50 mg, 34%) as pinkish solid.

Prep HPLC was carried out on Waters auto purification instrument. Column name: YMC Prep C18 (250×20 mm, 5µ) operated at ambient temperature with a flow rate of 14.0 mL/min. A=10 mM NH₄OAc in H₂O, B=Acetonitrile. Mobile phase initial from 90% of 10 mM NH₄OAc in H₂O and 10% acetonitrile composition then 55% 10 mM NH₄OAc in H₂O and 45% acetonitrile in 3.00 min, then 50% of 10 mM NH₄OAc in H₂O and 50% acetonitrile in 10.00 min, then 40% of 10 mM NH₄OAc in H₂O and 60% acetonitrile in 30.00 min to 5% of 10 mM NH₄OAc in H₂O and 95% acetonitrile in 32.0 min, held in this composition up to 35.0 min, then returned to initial composition in 36.0 min.

Synthesis of Compound 96 (4-(3,5-Dimethyl-isoxazol-4-ylmethoxy)-N-(2-methoxymethyl-phenyl)-benzamide)

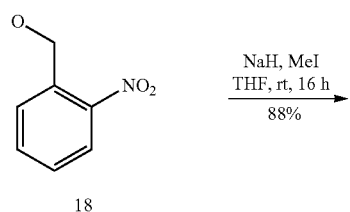

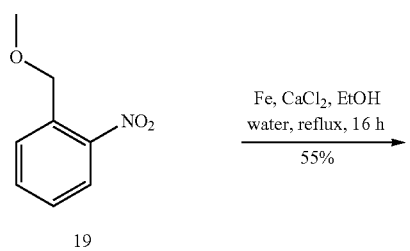

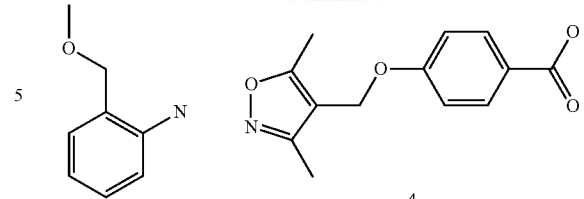

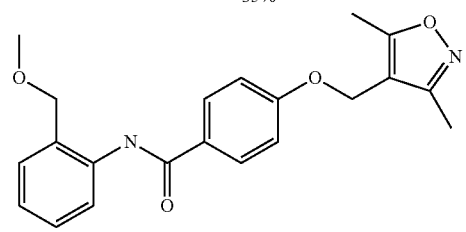

J18

To a stirred solution of (2-Nitro-phenyl)-methanol (18) (500 mg, 3.268 mmol) in THF (10 mL) was added NaH (117 mg, 4.902 mmol) at room temperature and the resultant mixture was stirred for 30 min. Methyl iodide (0.607 mL, 9.804 mmol) was then added to it and the reaction mixture was stirred at ambient temperature for 16 hours. It was then quenched with water, diluted with ethyl acetate, washed with water, dried over sodium sulfate and concentrated under reduced pressure. Crude thus obtained was purified by column chromatography (silica, gradient: 20-30% EtOAc in Hexane) to afford intermediate 19 (470 mg, 86%) as yellow gum.

To a stirred solution of 2-Methoxymethyl-nitrobenzene (19) (250 mg, 1.632 mmol) in EtOH (4 mL) and water (1 mL) were added iron powder (455 mg, 8.162 mmol) and Calcium chloride (217 mg, 1.959 mmol) and the resulting mixture was refluxed for 16 hours. Reaction mixture was then brought to room temperature and filtered through a short bed of celite. The filtrate was diluted with excess EtOAc, washed with water, dried over sodium sulfate and concentrated under reduced pressure. Crude thus obtained was purified by column chromatography (silica, gradient: 30-40% EtOAc in Hexane) to afforded intermediate 20 (124 mg, 55%) as yellow gum.

To a stirred solution of 4-(3,5-Dimethyl-isoxazol-4-yl-methoxy)-benzoic acid (4) (100 mg, 0.404 mmol) and 2-Methoxymethyl-phenylamine (20) (55 mg, 0.404 mmol) in THF (3 mL) were added HATU (230 mg, 0.607 mmol) and DIPEA (0.209 mL, 1.213 mmol) and the resulting mixture was stirred at ambient temperature for 16 hours. The reaction mixture was diluted with EtOAc, washed with saturated NaHCO₃ solution, water, dried over sodium sulfate and concentrated. Crude compound was purified by reverse phase Prep HPLC to afford desired compound J18 (35 mg, 35%) as white solid. Prep HPLC was carried out on Waters auto purification instrument. Column name: YMC Prep C18 (100×30 mm, 5µ) is operating at ambient temperature and flow rate of 30.0 mL/min. A=10 mM NH₄OAc in H₂O, B=Acetonitrile. Mobile phase initial from 90% of 10 mM NH₄OAc in H₂O and 10% acetonitrile composition then 55% 10 mM NH4OAc in H2O and 45% acetonitrile in 1.00 min, then 25% of 10 mM NH₄OAc in H₂O and 75% acetonitrile in 15.00 min to 5% of 10 mM NH₄OAc in H₂O

Synthesis of Compound 91 (N-[3-(Acetylamino-methyl)-phenyl]-4-(3,5-dimethyl-isoxazol-4-yl-methoxy)-benzamide)

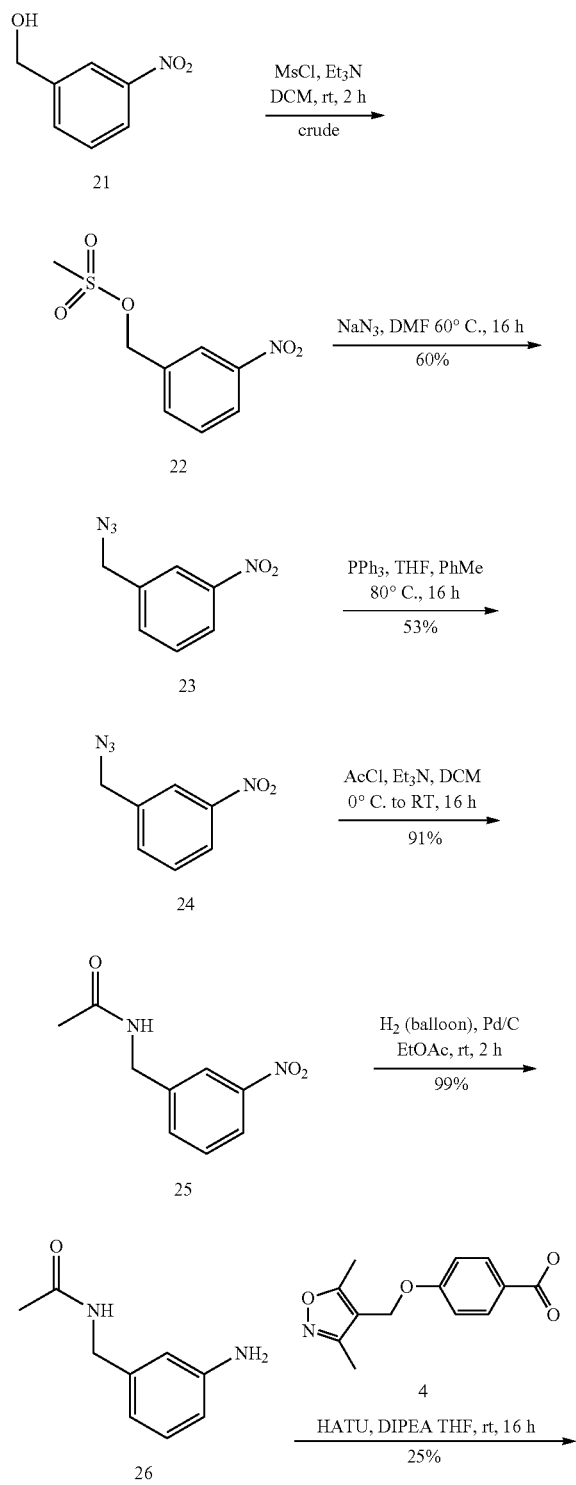

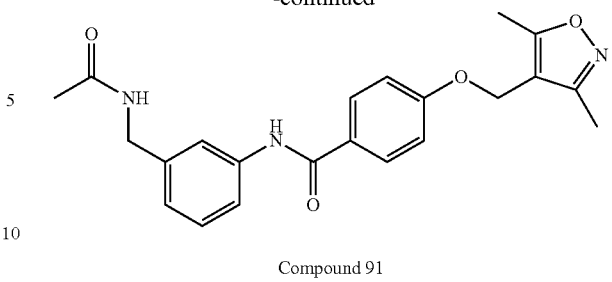

Compound 91

To a stirred solution of (3-Nitro-phenyl)-methanol (21) (1.0 g, 6.53 mmol) in DCM (10 mL) was added $Et_3N$ (1.81 mL, 13.06 mmol) at 0° C. followed by the addition of Methanesulfonyl chloride (0.607 mL, 7.836 mmol). The resultant mixture was then slowly warmed to room temperature and stirred for 2 hours. Reaction mass was then diluted with DCM, washed with saturated $NaHCO_3$ solution, water, dried over sodium sulfate and concentrated under reduced pressure to afford intermediate 22 (1.5 g, crude) as yellow gum.

To a stirred solution of Methanesulfonic acid 3-nitro-benzylester (22) (1.5 g, 6.49 mmol) in DMF (10 mL) was added sodium azide (0.844 g, 12.98 mmol) and the reaction mixture was stirred at 60° C. for 16 hours. It was then brought to room temperature, diluted with EtOAc, washed with water, dried over sodium sulfate and concentrated under reduced pressure. The crude was purified by column chromatography (silica, gradient: 40-50% EtOAc in Hexane) to afford intermediate 23 (700 mg; 60%) as colorless oil.

To a stirred solution of 1-Azidomethyl-3-nitro-benzene (23) (700 mg, 3.929 mmol) in THF:Toluene (1:1; 10 mL) were added Triphenyphosphine (3.08 g, 11.788 mmol) and one drop of water and the resultant reaction mixture was stirred at 80° C. for 16 hours. It was then brought to room temperature, acidified with 2N HCl and washed with DCM. The aqueous layer was then basified with solid sodium bicarbonate and extracted with ethyl acetate. The EtOAc layer was dried over sodium sulfate and concentrated under reduced pressure to afford desired intermediate 24 (320 mg, 53%) as wine red oil.

To a stirred solution of 3-Nitro-benzylamine (24) (320 mg, 1.697 mmol) in DCM (5 mL) was added Triethylamine (0.707 mL, 5.09 mmol) and acetyl chloride (199 mg, 2.545 mmol) sequentially at 0° C. The resulting mixture was warmed to room temperature and 16 hours. It was then diluted with DCM, washed with saturated $NaHCO_3$ solution, dried over sodium sulfate and concentrated under reduced pressure to afford the desired intermediate 25 (300 mg, 91%) as off white solid.

A stirred solution of N-(3-Nitro-benzyl)-acetamide (25) (250 mg, 1.289 mmol) in EtOAc (7 mL) was degassed with argon for about for 10 minutes followed by the addition of 10% Pd—C (50 mg). The resulting mixture was stirred at room temperature under hydrogen atmosphere (balloon) for 2 hours. It was then filtered through a short pad of celite and the filtrate was concentrated under reduced pressure to afford desired intermediate 26 (210 mg, 99%) as off white solid.

To a stirred solution of 4-(3,5-Dimethyl-isoxazol-4-yl-methoxy)-benzoic acid (4) (100 mg, 0.404 mmol) and N-(3-Amino-benzyl)-acetamide (26) (55 mg, 0.404 mmol) in THF (3 mL) were added HATU (230 mg, 0.607 mmol) and DIPEA (0.209 mL, 1.213 mmol) and the resulting mixture was stirred at ambient temperature for 16 hours. The reaction mixture was diluted with EtOAc, washed with saturated NaHCO$_3$ solution, water, dried over sodium sulfate and concentrated. Crude compound was purified by reverse phase Prep HPLC to afford desired Compound 91 (40 mg, 25%) as white solid.

Prep HPLC was carried out on Waters auto purification instrument. Column name: YMC Prep C18 (100×30 mm, 5μ) is operating at ambient temperature and flow rate of 30.0 mL/min. A=10 mM NH$_4$OAc in H$_2$O, B=Acetonitrile. Mobile phase initial from 90% of 10 mM NH4OAc in H$_2$O and 10% acetonitrile composition then 55% 10 mM NH$_4$OAc in H$_2$O and 45% acetonitrile in 1.00 min, then 25% of 10 mM NH$_4$OAc in H$_2$O and 75% acetonitrile in 15.00 min to 5% of 10 mM NH$_4$OAc in H$_2$O and 95% acetonitrile in 16.0 min, held in this composition up to 17.0 min, then returned to initial composition in 18.0 min.

Synthesis of Compound 90 (N-[2-(Acetylamino-methyl)-phenyl]-4-(3,5-dimethyl-isoxazol-4-yl-methoxy)-benzamide)

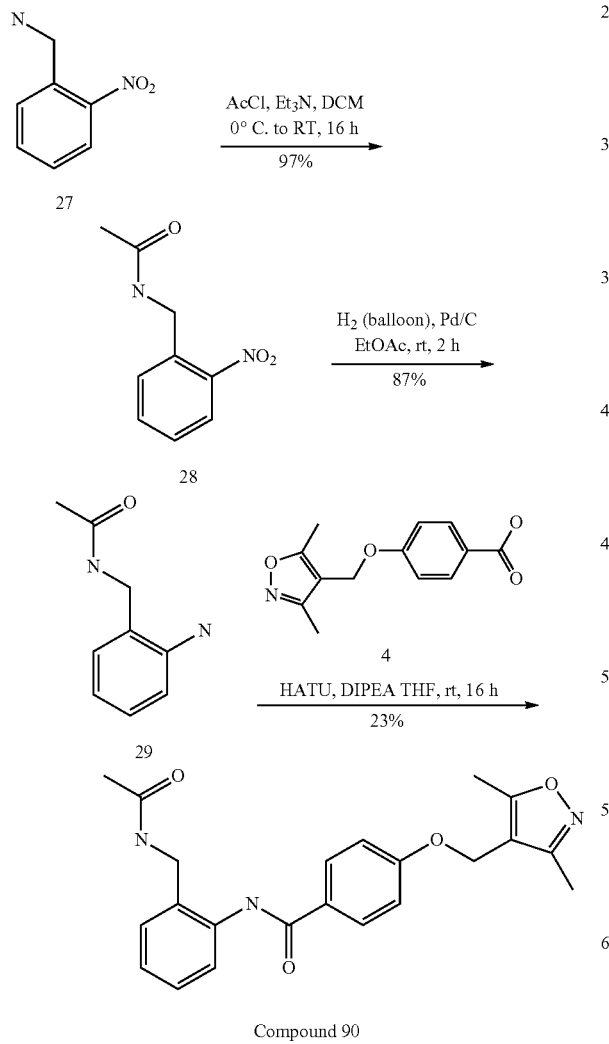

Compound 90

To a stirred solution of 2-Nitro-benzylamine (27) (500 mg, 2.651 mmol) in DCM (5 mL) was added Triethylamine (1.10 mL, 7.952 mmol) and acetyl chloride (0.283 mL, 3.976 mmol) sequentially at 0° C. The resulting mixture was warmed to room temperature and 16 hours. It was then diluted with DCM, washed with saturated NaHCO$_3$ solution, dried over sodium sulfate and concentrated under reduced pressure to afford the desired Intermediate 28 (500 mg, 97%) as off white solid.

A stirred solution of N-(2-Nitro-benzyl)-acetamide (28) (250 mg, 1.289 mmol) in EtOAc (7 mL) was degassed with argon for about for 10 minutes followed by the addition of 10% Pd—C (50 mg). The resulting mixture was stirred at room temperature under hydrogen atmosphere (balloon) for 2 hours. It was then filtered through a short pad of celite and the filtrate was concentrated under reduced pressure to afford desired Intermediate 29 (185 mg, 87%) as off white solid.

To a stirred solution of 4-(3,5-Dimethyl-isoxazol-4-yl-methoxy)-benzoic acid (4) (120 mg, 0.485 mmol) and N-(2-Amino-benzyl)-acetamide (29) (79 mg, 0.485 mmol) in THF (3 mL) were added HATU (276 mg, 0.728 mmol) and DIPEA (0.252 mL, 1.456 mmol) and the resulting mixture was stirred at ambient temperature for 16 hours. The reaction mixture was diluted with EtOAc, washed with saturated NaHCO$_3$ solution, water, dried over sodium sulfate and concentrated. Crude compound was purified by reverse phase Prep HPLC to afford desired Compound 90 (45 mg, 23%) as white solid. Prep HPLC was carried out on Waters auto purification instrument. Column name: YMC Prep C18 (100×30 mm, 5μ) is operating at ambient temperature and flow rate of 30.0 mL/min. A=20 mM NH$_4$HCO$_3$ in H$_2$O, B=Acetonitrile. Mobile phase initial from 90% of 20 mM NH$_4$HCO$_3$ in H$_2$O and 10% acetonitrile composition then 60% 20 mM NH$_4$HCO$_3$ in H$_2$O and 40% acetonitrile in 1.00 min, then 30% of 20 mM NH$_4$HCO$_3$ in H$_2$O and 70% acetonitrile in 15.00 min to 5% of 20 mM NH$_4$HCO$_3$ in H$_2$O and 95% acetonitrile in 16.0 min, held in this composition up to 17.0 min, then returned to initial composition in 18.0 min.

Synthesis of Compound 97 (4-(3,5-Dimethyl-isoxazol-4-ylmethoxy)-N-(2,3-dimethyl-phenyl)-benzenesulfonamide)

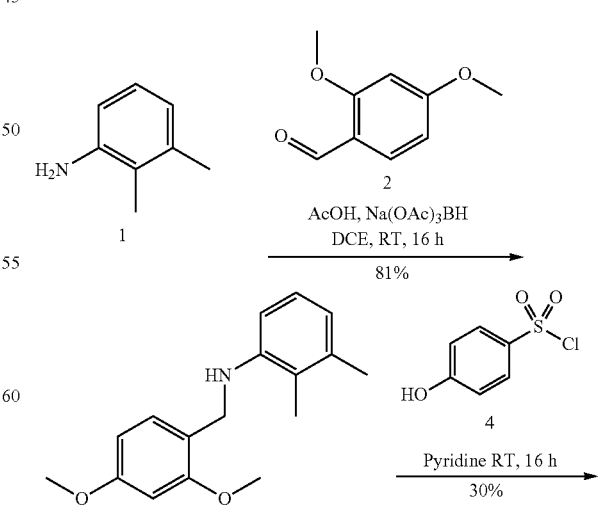

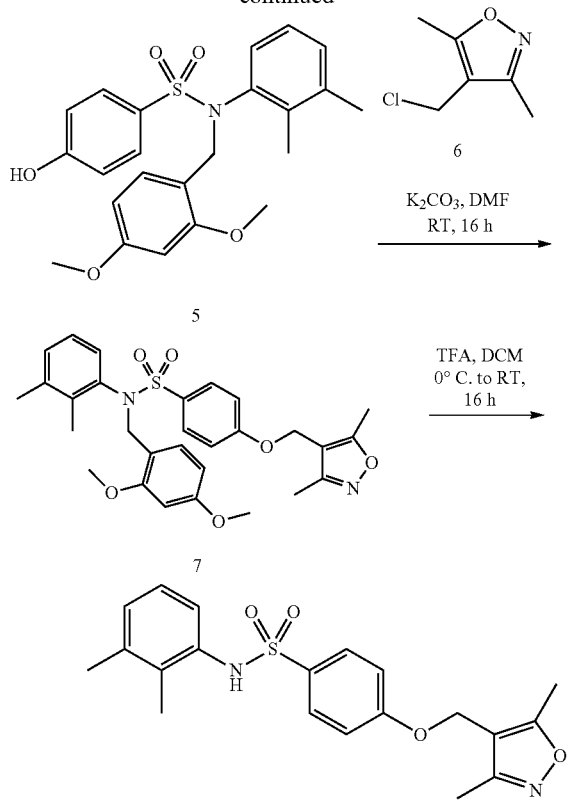

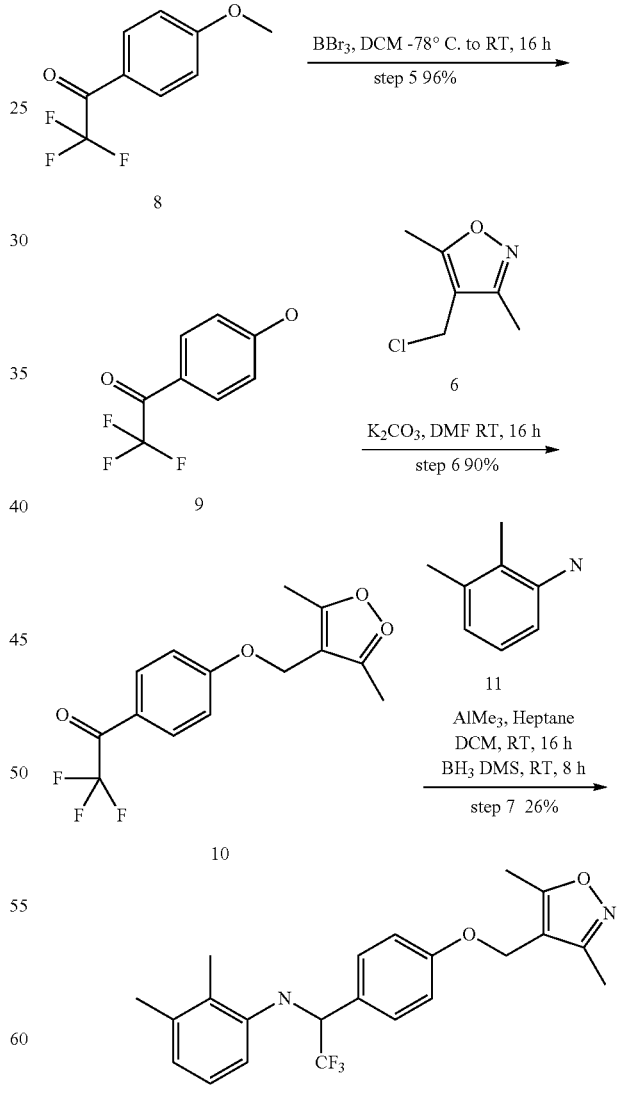

matography (silica, gradient: 20-30% EtOAc in Hexane) to afford the Intermediate 7 (25 mg, 19%) as yellow gum.

To a stirred solution of N-(2,4-Dimethoxy-benzyl)-4-(3,5-dimethyl-isoxazol-4-ylmethoxy)-N-(2,3-dimethyl-phenyl) benzenesulfonamide (7) (25 mg, 0.047 mmol) in DCM (1 mL) was added TFA (0.036 mL, 0.466 mmol) at 0° C. and the resulting solution was slowly warmed to room temperature and stirred for 16 hours. All the volatiles were evaporated under reduced pressure and the residue was taken in Ethyl acetate, washed with aqueous saturated $NaHCO_3$ solution, dried over $Na_2SO_4$ and concentrated. Crude thus obtained was purified over preparative TLC plate eluting with 5% MeOH in DCM to afford Compound 97 (14 mg, 77%) as yellow solid.

Synthesis of Compound 99 ({1-[4-(3,5-Dimethyl-isoxazol-4-ylmethoxy)-phenyl]-2,2,2-trifluoro-ethyl}-(2,3-dimethylphenyl)amine)

To stirred solution of 2,3-Dimethyl-phenylamine (1) (300 mg, 1.806 mmol) in DCE (5 mL) were added 2,4-Dimethoxy-benzaldehyde (2) (218 mg, 1.806 mmol) and Acetic acid (0.103 mL, 1.806 mmol) and it was stirred for 15 minutes. To it was then added Sodium triacetoxyborohydride (765 mg, 3.612 mmol) and the reaction mixture was stirred at ambient temperature for 16 hours. It was then diluted with DCM, washed with saturated aqueous $NaHCO_3$ solution, water, dried over $Na_2SO_4$ and concentrated under reduced pressure. Crude thus obtained was purified by column chromatography (silica, gradient: 20-25% EtOAc in Hexane) to afford the Intermediate 3 (400 mg, 81%) as yellow gum.

To a stirred solution of (2,4-Dimethoxy-benzyl)-(2,3-dimethyl-phenyl)-amine (3) (300 mg, 1.806 mmol) in Pyridine (5 mL) was added 4-Hydroxy-benzenesulfonyl chloride (4) (150 mg, 0.779 mmol) and the resulting solution was stirred at ambient temperature for 16 hours. The reaction mixture was then diluted with EtOAc, washed with 2N HCl, water, dried over $Na_2SO_4$ and concentrated under reduced pressure. Crude thus obtained was purified by column chromatography (silica, gradient: 20-25% EtOAc in Hexane) to afford the Intermediate 5 (100 mg, 30%) as yellow gum.

To a stirred solution of N-(2,4-Dimethoxy-benzyl)-N-(2,3-dimethyl-phenyl)-4-hydroxy-benzenesulfonamide (5) (100 mg, 0.253 mmol) in DMF (2 mL) were added $K_2CO_3$ (69 mg, 0.506 mmol) and 4-Chloromethyl-3,5-dimethyl-isoxazole (6) (0.032 mL, 0.253 mmol) and the reaction mixture was stirred at ambient temperature for 16 hours. It was then diluted with Ethyl acetate, washed with water and brine, dried over $Na_2SO_4$ and concentrated under reduced pressure. Crude thus obtained was purified by column chro- To a stirred solution of 2,2,2-Trifluoro-1-(4-methoxyphenyl)-ethanone (8) (500 mg, 2.45 mmol) in DCM (5 mL)

was added BBr₃ (1M in DCM, 24.4 mL, 24.4 mmol) drop wise at −78° C. and the reaction mixture was slowly warmed to room temperature and stirred for 16 hours. It was then quenched with aqueous NaHCO₃ solution and partitioned between Ethyl acetate and water. The organic layer was separated, water, dried over Na₂SO₄ and concentrated under reduced pressure to afford Intermediate 9 (450 mg, 96%) as yellow gum.

To a stirred solution of,2,2-Trifluoro-1-(4-hydroxy-phenyl)-ethanone (9) (450 mg, 2.394 mmol) in DMF (5 mL) were added K₂CO₃ (661 mg, 4.787 mmol) and 4-Chloromethyl-3,5-dimethyl-isoxazole (6) (0.333 mL, 2.633 mmol) and the reaction mixture was stirred at ambient temperature for 16 hours. It was then diluted with Ethyl acetate, washed with water and brine, dried over Na₂SO₄ and concentrated under reduced pressure. Residue was triturated with hexane, decanted and dried well to afford Intermediate 10 (650 mg, 90%) as yellow solid.

To a stirred solution of 1-[4-(3,5-Dimethyl-isoxazol-4-ylmethoxy)-phenyl]-2,2,2-trifluoro-ethanone (10) (200 mg, 0.669 mmol) and 2,3-Dimethyl-phenylamine (11) (0.083 mL, 0.669 mmol) in DCM (3 mL) was added Trimethylaluminium (2M in Heptane, 0.501 mL, 1.003 mmol) at 0° C. and the resulting mixture was slowly warmed to room temperature and stirred for 16 hours. Borane-DMS (0.167 mL, 3.34 mmol) was then added to the reaction mixture and it was allowed to stir at room temperature for another 8 hours. The reaction mass was quenched with 2N NaOH and extracted with Ethyl acetate. The combined Ethyl acetate layer was then washed with water, brine, dried over Na₂SO₄ and concentrated under reduced pressure. Crude thus obtained was purified over preparative TLC plate eluting with 60% DCM in Hexane to afford the Compound 99 (70 mg, 26%) as yellow gum.

Synthesis of Compound 57 (4-[(3,5-Dimethyl-isoxazol-4-ylamino)-methyl]-N-(2,3-dimethyl-phenyl)-benzamide)

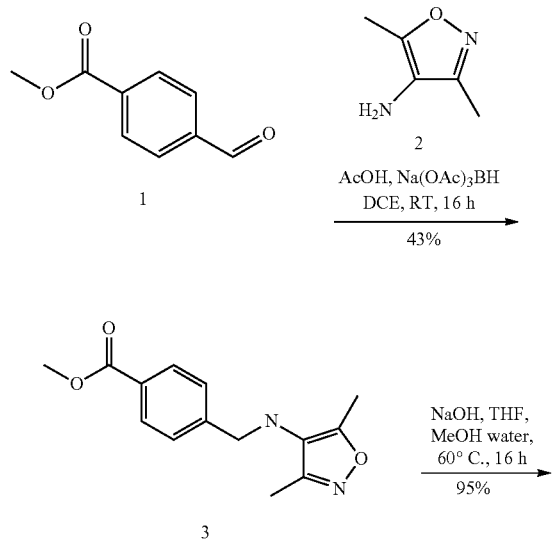

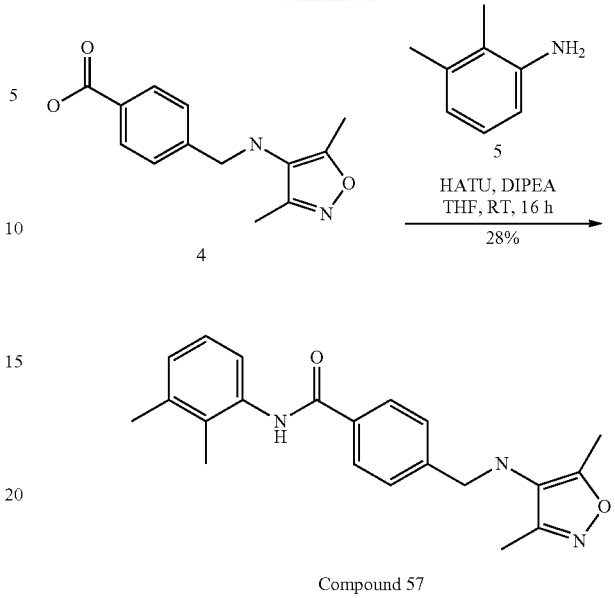

Compound 57

To stirred solution of 4-Formyl-benzoic acid methyl ester (1) (500 mg, 4.452 mmol) in DCE (10 mL) were added 3,5-Dimethyl-isoxazol-4-ylamine (2) (543 mg, 4.452 mmol) and AcOH (0.252 mL, 4.452 mmol) and the resulting mixture was stirred for 15 minutes. To it was then added Sodium triacetoxyborohydride (1.41 g, 6.679 mmol) and the reaction mixture was stirred at room temperature for 16 hours. It was then diluted with DCM, washed with aqueous saturated NaHCO₃ solution, water, dried over Na₂SO₄ and concentrated under reduced pressure. Crude thus obtained was purified by column chromatography (silica, gradient: 30-40% EtOAc in Hexane) to afford the Intermediate 3 (500 mg, 43%) as yellow oil.

To a stirred solution of 4-[(3,5-Dimethyl-isoxazol-4-ylamino)-methyl]-benzoic acid methyl ester (3) (200 mg, 0.769 mmol) in THF (4 mL) and MeOH (2 mL) was added 1.5M NaOH (1 mL) and the resulting mixture was heated at 60° C. for 16 hours. It was then brought to room temperature and concentrated under reduced pressure. Residue was taken into water and acidified with 2N HCl to attain pH~5 and extracted with Ethyl acetate. The combined Ethyl acetate extract was dried over Na₂SO₄ and concentrated to afford Intermediate 4 (180 mg, 95%) as yellow gum.

To a stirred solution of 4-[(3,5-Dimethyl-isoxazol-4-ylamino)-methyl]-benzoic acid (4) (150 mg, 0.61 mmol) and 2,3-Dimethyl-phenylamine (5) (0.11 mL, 0.61 mmol) in THF (5 mL) were added HATU (347 mg, 0.915 mmol) and DIPEA (0.422 mL, 2.439 mmol) and the reaction mixture was stirred at ambient temperature for 16 hours. It was then diluted with EtOAc, washed with aqueous saturated NaHCO₃ solution, water and brine. The organic layer was dried over Na₂SO₄ and concentrated. Crude thus obtained was purified by CombiFlash ISCO column (gradient: 30% EtOAc in Hexane) to afford the Compound 57 (60 mg, 28%) as sticky solid.

Synthesis of Compound 58 (4-{[(3,5-Dimethyl-isoxazol-4-yl)-methyl-amino]-methyl}-N-(2,3-dimethyl-phenyl)-benzamide)

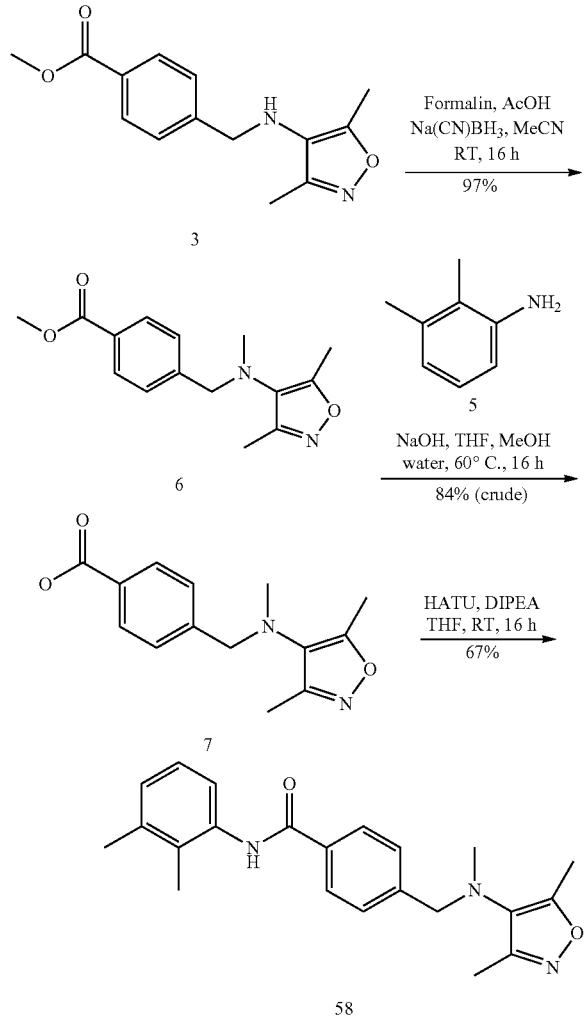

To a stirred solution of 4-[(3,5-Dimethyl-isoxazol-4-ylamino)-methyl]-benzoic acid methyl ester (3) (100 mg, 0.385 mmol) in MeCN (3 mL) were added Formalin (37% aqs solution; 0.107 mL) and AcOH (0.305 mL, 5.385 mmol) and the resulting mixture was stirred at room temperature for 30 minutes. To it was then added Sodium cyanoborohydride (33 mg, 0.538 mmol) and the reaction mixture was stirred at room temperature for 16 hours. It was then diluted with EtOAc, washed with aqueous saturated NaHCO₃ solution, water and brine. The organic layer was dried over Na₂SO₄ and concentrated to afford the Intermediate 6 (100 mg, 97%) as colorless oil.

To a stirred solution of 4-{[(3,5-Dimethyl-isoxazol-4-yl)-methyl-amino]-methyl}-benzoic acid methyl ester (6) (100 mg, 0.365 mmol) in THF (4 mL) and MeOH (2 mL) was added 1M NaOH (1 mL) and the resulting mixture was heated at 60° C. for 16 hours. It was then brought to room temperature and concentrated under reduced pressure. Residue was taken into water, acidified with 2N HCl to attain pH~5 and extracted with Ethyl acetate. The combined Ethyl acetate extract was dried over Na₂SO₄ and concentrated to afford Intermediate 7 (80 mg, 84%) as yellow gum.

To a stirred solution of 4-{[(3,5-Dimethyl-isoxazol-4-yl)-methyl-amino]-methyl}-benzoic acid (7) (80 mg, 0.308 mmol) and 2,3-Dimethyl-phenylamine (5) (0.056 mL, 0.308 mmol) in THF (3 mL) were added HATU (175 mg, 0.462 mmol) and DIPEA (0.213 mL, 1.231 mmol) and the reaction mixture was stirred at ambient temperature for 16 hours. It was then diluted with EtOAc, washed with aqueous saturated NaHCO₃ solution, water and brine. The organic layer was dried over Na₂SO₄ and concentrated. Crude thus obtained was purified by CombiFlash ISCO column (gradient: 30% EtOAc in Hexane) to afford the Compound 58 (75 mg, 67%) as sticky solid.

Synthesis of Compound 55 ((Z)-4-{[(3,5-Dimethyl-isoxazol-4-yl)-methyl-amino]-methyl}-N-(2,3-dimethyl-phenyl)-benzamide) and Compound 55(cis) ((E)-4-{[(3,5-Dimethyl-isoxazol-4-yl)-methyl-amino]-methyl}-N-(2,3-dimethyl-phenyl)-benzamide)

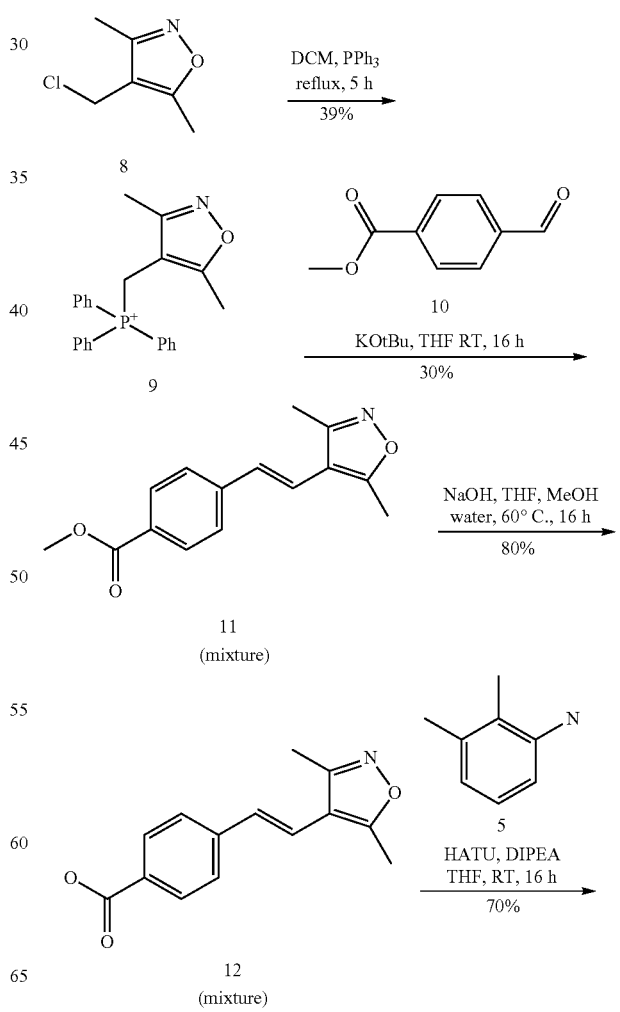

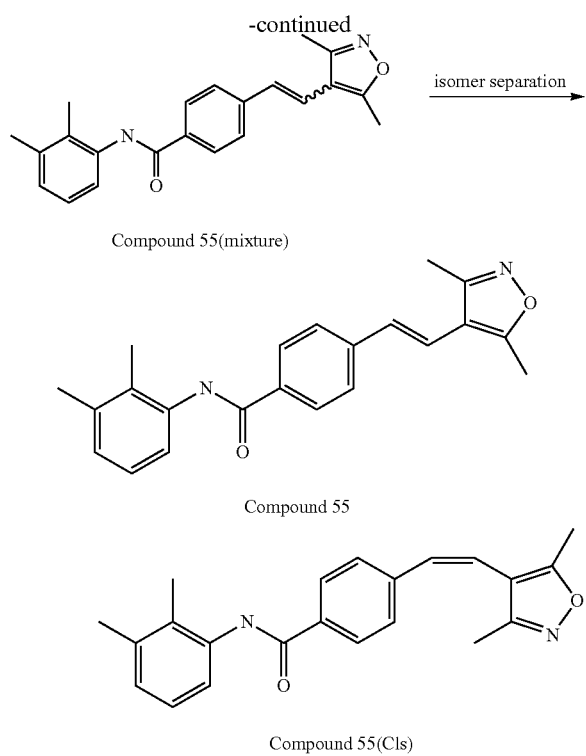

Compound 55(mixture)

Compound 55

Compound 55(Cis)

To a stirred solution of 4-Chloromethyl-3,5-dimethyl-isoxazole (8) (2 g, 13.737 mmol) in DCM (20 mL) was added Triphenylphosphine (3.60 g, 13.737 mmol) and the reaction mixture was refluxed for 5 hours. It was then cooled on an ice bath and solid formed was filtered and washed with Hexane. The solid was further dried in vacuo to afford compound 9 (2 g, 39%) as white solid.

To a stirred solution (3,5-Dimethyl-isoxazol-4-ylmethyl)-triphenyl-phosphonium (9) (1.5 g, 4.039 mmol) of in THF (15 mL) were added 4-Formyl-benzoic acid methyl ester (10) (663 mg, 4.039 mmol) and Potassium tert-butoxide (453 mg, 4.039 mmol) and the resulting mixture was stirred at ambient temperature for 16 hours. The reaction mixture was then quenched with ice-water and partitioned between DCM and water. The organic layer was separated, washed with water, brined, dried over Na$_2$SO$_4$ and concentrated. Crude thus obtained was purified by column chromatography (silica, gradient: 15-20% EtOAc in Hexane) to afford compound 11 (310 mg, 30%) (as a mixture of cis- and trans-isomers) as white solid.

To a stirred solution of 4-[(E)-2-(3,5-Dimethyl-isoxazol-4-yl)-vinyl]-benzoic acid methyl ester (11) (300 mg, 1.183 mmol) in THF (4 mL) and MeOH (2 mL) was added 2M NaOH (1 mL) and the resulting mixture was heated at 60° C. for 16 hours. It was then brought to room temperature and concentrated under reduced pressure. Residue was taken into water, acidified with 2N HCl to attain pH~5 and extracted with Ethyl acetate. The combined Ethyl acetate extract was dried over Na$_2$SO$_4$ and concentrated to afford Intermediate 12 (230 mg, 80%) (as a mixture of cis- and trans-isomers) as white solid.

To a stirred solution of 4-[(E)-2-(3,5-Dimethyl-isoxazol-4-yl)-vinyl]-benzoic acid (12) (230 mg, 0.697 mmol) and 2,3-Dimethyl-phenylamine (5) (0.085 mL, 0.697 mmol) in THF (3 mL) were added HATU (397 mg, 1.045 mmol) and DIPEA (0.482 mL, 2.788 mmol) and the reaction mixture was stirred at ambient temperature for 16 hours. It was then diluted with EtOAc, washed with aqueous saturated NaHCO$_3$ solution, water and brine. The organic layer was dried over Na$_2$SO$_4$ and concentrated. Crude thus obtained was purified by CombiFlash ISCO column (gradient: 30% EtOAc in Hexane) to afford the compound M3 (230 mg, 70%) (as a mixture of cis- and trans-isomers; 50 mg of this was shipped) as white solid. Isomeric mixture of Compound 55(mixture) (180 mg, 0.520 mmol) was subjected to chiral HPLC using Chiralpak IA (250×4.6 mm)5µ column and mobile phase: Hexane/EtOH/DEA: 80/20/0.5 with a flow rate of 20.0 mL/min. This afforded cis-isomer, eluted as first fraction, Compound 55(cis) (70 mg, 38%) and the trans-isomer, eluted as second fraction, Compound 55 (trans isomer, 30 mg, 17%) as white solids.

Synthesis of Compound 38 (2-Chloro-4-(3,5-dimethyl-isoxazol-4-ylmethoxy)-N-(2,3-dimethyl-phenyl)-benzamide)

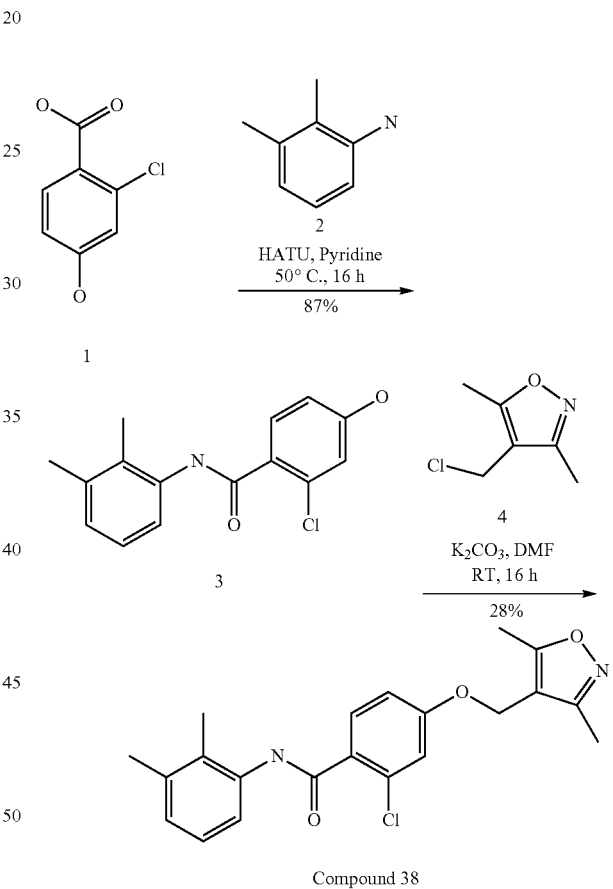

Compound 38

To a stirred solution of 2-Chloro-4-hydroxy-benzoic acid (1) (200 mg, 1.038 mmol) and 2,3-Dimethyl-phenylamine (2) (0.128 mL, 1.038 mmol) in Pyridine (3 mL), HATU (591 mg, 1.558 mmol) was added and the reaction was stirred at 50° C. for 16 hours. The reaction mixture was diluted with EtOAc and washed with 2N HCl, saturated sodium bicarbonate, water and brine, dried over sodium sulfate and concentrated. The crude LCMS showed mass peak of desired product along with the ester. The crude was then dissolved in THF:MeOH:Water (4:2:1; 10 mL) and treated with 2N NaOH (3 mL) at 60° C. for 4 hours (monitored by LCMS). The reaction mixture was again evaporated to dryness, the residue was taken in 2N HCl, extracted with ethyl acetate and evaporated to afford the Intermediate 3 (250 mg, 87%) as yellow gum.

To a stirred solution of 2-Chloro-N-(2,3-dimethyl-phenyl)-4-hydroxy-benzamide (5) (200 mg, 0.727 mmol) in DMF (2 mL), K2CO3 (200 mg, 1.455 mmol) and 4-Chloromethyl-3,5-dimethyl-isoxazole (4) (0.101 mL, 0.800 mmol) were added and the reaction was stirred at RT for 16 hours. The reaction mixture was diluted with ethyl acetate and washed with water and brine, dried over sodium sulfate and concentrated. The crude was purified by column chromatography (silica, gradient: 20-30% EtOAc in Hexane) to afford the Compound 38 (80 mg, 28%) as yellow solid.

Synthesis of Compound 41 (2-Cyano-4-(3,5-dimethyl-isoxazol-4-ylmethoxy)-N-(2,3-dimethyl-phenyl)-benzamide)

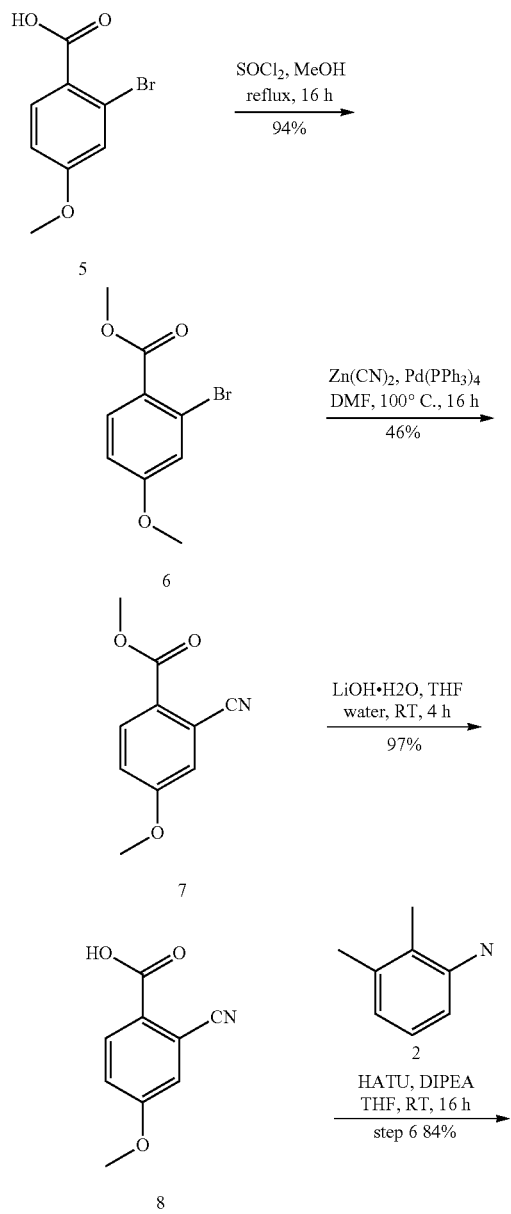

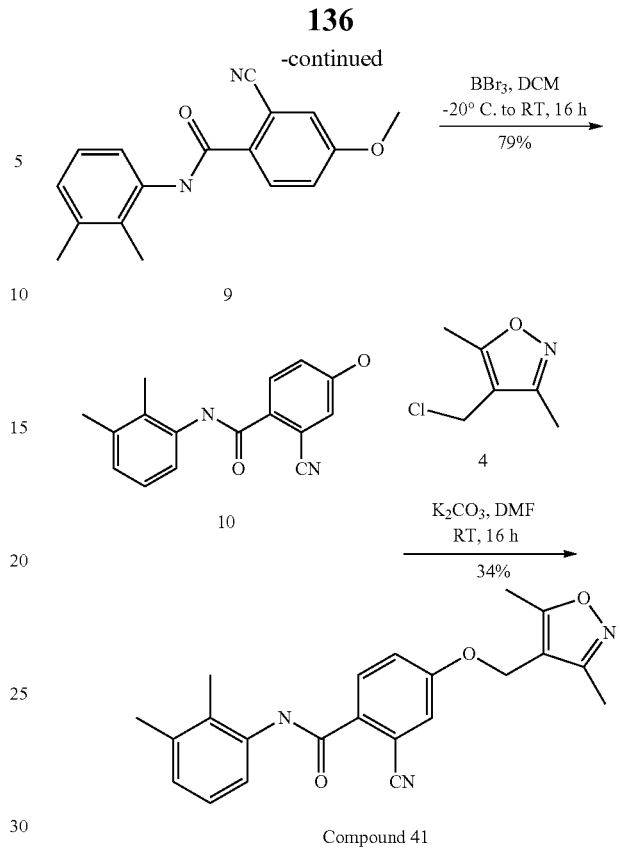

Compound 41

A stirred solution of 2-Bromo-4-methoxy-benzoic acid (5) (1.0 g, 4.329 mmol) in MeOH (15 mL) was cooled to 0° C. and to it Thionyl chloride (3.14 mL, 43.29 mmol) was added drop wise. The reaction mixture was then refluxed for 16 hours. It was then evaporated to dryness and the residue was dissolved in EtOAc, washed with saturated sodium bicarbonate solution and brine. The organic layer was dried over sodium sulfate and concentrated to afford Intermediate 6 (1.0 g; 94%) as colorless liquid.

A stirred solution of 2-Bromo-4-methoxy-benzoic acid methyl ester (6) (2.5 g, 10.201 mmol) in DMF (15 mL) was degassed for 15 minutes with argon followed by the addition of Zn(CN)$_2$ (2.39 g, 20.402 mmol) and Pd(PPh$_3$)$_4$ (1.17 g, 1.02 mmol) and the reaction mixture was stirred at 100° C. for 16 hours. The reaction mixture was diluted with Ethyl acetate, washed with water and brine, dried over sodium sulfate and concentrated. The crude was purified by column chromatography (silica, gradient: 20-30% EtOAc in Hexane) to afford the Intermediate 7 (900 mg, 46%) as white solid.

To a stirred solution of 2-Cyano-4-methoxy-benzoic acid methyl ester (7) (100 mg, 0.524 mmol) in THF (4 mL), LiOH (43 mg, 1.047 mmol) dissolved in water (1 mL) was added and the reaction was heated at RT for 4 hours. The reaction mixture was then evaporated to dryness and acidified with 2N HCl solution. The white precipitate that formed was collected by filtration, dried properly under vacuum to afford Intermediate 8 (90 mg, 97%) as white solid. The compound was taken forward to the next step on basis of TLC only, no analytical data was recorded.

To a stirred solution of 2-Cyano-4-methoxy-benzoic acid (8) (90 mg, 0.508 mmol) and 2,3-Dimethyl-phenylamine (2) (0.062 mL, 0.508 mmol) in THF (3 mL), HATU (289 mg, 0.763 mmol) and DIPEA (0.352 mL, 2.034 mmol) were added and the reaction was stirred at RT for 16 hours. The reaction mixture was diluted with EtOAc, washed with saturated sodium bicarbonate, water and brine, dried over sodium sulfate and concentrated. The crude was purified by CombiFlash ISCO column (gradient: 30% EtOAc in Hexane) to afford the Intermediate 9 (120 mg, 84%) as yellow solid.

To a stirred solution of 2-Cyano-N-(2,3-dimethyl-phenyl)-4-methoxy-benzamide (9) (120 mg, 0.429 mmol) in DCM (5 mL), BBr3 (1M in DCM, 2.1 mL, 2.1 mmol) was added drop wise at −20° C. and the reaction was slowly warmed to RT and stirred for 16 hours. After completion of the reaction (monitored by TLC/LC MS) the reaction mass was quenched with water and extracted with EtOAc. The EtOAc extract was washed with water and brine, dried over sodium sulfate and concentrated to afford the Intermediate 10 (90 mg, 79%) as yellow gum.

To a stirred solution of 2-Cyano-N-(2,3-dimethyl-phenyl)-4-hydroxy-benzamide (10) (90 mg, 0.508 mmol) in DMF (2 mL), K2CO3 (140 mg, 1.017 mmol) and 4-Chloromethyl-3,5-dimethyl-isoxazole (4) (0.064 mL, 0.508 mmol) were added and the reaction mass was stirred at RT for 16 hours. The reaction mixture was diluted with ethyl acetate, washed with water and brine, dried over sodium sulfate and concentrated. The crude was purified by column chromatography (silica, gradient: 20-30% EtOAc in Hexane) to afford the Compound N2 (50 mg, 34%) as off white solid.

Synthesis of Compound 98 (4-(3,5-Dimethyl-isoxazol-4-ylmethoxy)-2,6-dimethyl-benzoic acid)

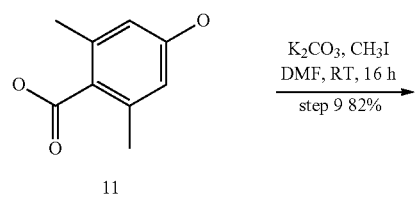

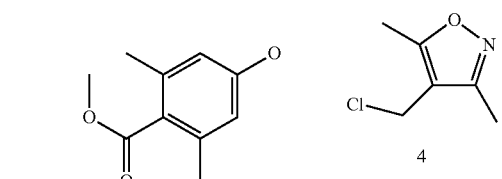

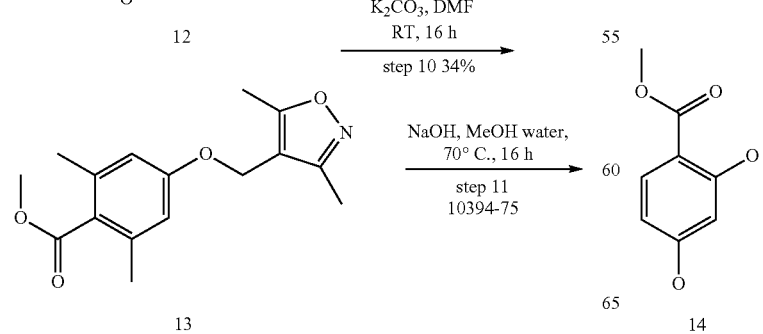

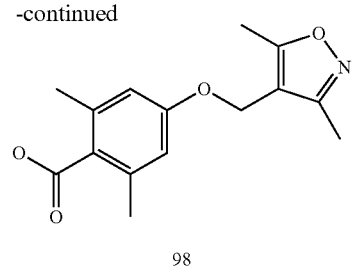

98

To a stirred solution of 4-Hydroxy-2,6-dimethyl-benzoic acid (11) (100 mg, 0.602 mmol) in DMF (2 mL), K2CO3 (249 mg, 1.806 mmol) and Methyl iodide (0.186 mL, 3.01 mmol) were added and the reaction was stirred at RT for 16 hours. The reaction mixture was diluted with ethyl acetate, washed with water and brine, dried over sodium sulfate and concentrated. The crude was purified by column chromatography (silica, gradient: 20-30% EtOAc in Hexane to) afford the Intermediate 12 (90 mg, 82%) as white solid.

To a stirred solution of 4-Hydroxy-2,6-dimethyl-benzoic acid methyl ester (12) (100 mg, 0.556 mmol) in DMF (2 mL), K2CO3 (153 mg, 1.111 mmol) and 4-Chloromethyl-3,5-dimethyl-isoxazole (4) (0.07 mL, 0.556 mmol) were added and the reaction was stirred at RT for 16 hours. The reaction mixture was diluted with ethyl acetate, washed with water and brine, dried over sodium sulfate and concentrated. The crude was purified by column chromatography (silica, gradient: 20-30% EtOAc in Hexane) to afford the Intermediate 13 (130 mg, 80%) as off white solid.

To a stirred solution of 4-(3,5-Dimethyl-isoxazol-4-ylmethoxy)-2,6-dimethyl-benzoic acid methyl ester (13) (120 mg, 0.415 mmol) in MeOH (2.5 mL), NaOH (82 mg, 2.074 mmol) dissolved in water (2.5 mL) was added and the reaction was heated at 70° C. for 16 hours. The reaction mixture was then evaporated to dryness and acidified with 2N HCl solution. The white precipitate that formed was collected by filtration, dried properly under vacuum to afford compound 98 (105 mg, 91%) as white solid.

Synthesis of Compound 39 (4-(3,5-Dimethyl-isoxazol-4-ylmethoxy)-N-(2,3-dimethyl-phenyl)-2-methoxy-benzamide) and 44 (4-(3,5-Dimethyl-isoxazol-4-ylmethoxy)-N-(2,3-dimethyl-phenyl)-2-hydroxy-benzamide)

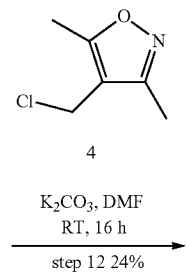

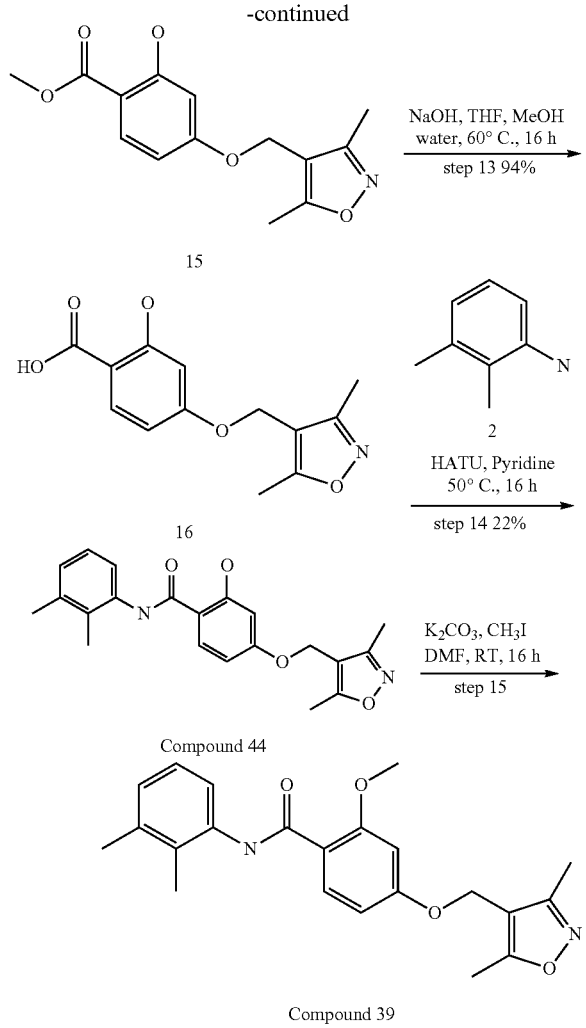

Compound 44

Compound 39

To a stirred solution of 2,4-Dihydroxy-benzoic acid methyl ester (14) (1 g, 5.949 mmol) in DMF (2 mL), K₂CO₃ (1.64 g, 11.898 mmol) and 4-Chloromethyl-3,5-dimethyl-isoxazole (4) (0.75 mL, 5.949 mmol) were added and the reaction was stirred at RT for 16 hours. The reaction mixture was diluted with ethyl acetate, washed with water and brine, dried over sodium sulfate and concentrated. The crude was purified by column chromatography (silica, gradient: 20-30% EtOAc in Hexane) to afford the Intermediate 15 (400 mg, 24%) as white solid.

To a stirred solution of 4-(3,5-Dimethyl-isoxazol-4-yl-methoxy)-2-hydroxy-benzoic acid methyl ester (15) (200 mg, 0.722 mmol) in THF (4 mL) and MeOH (2 mL), NaOH (57 mg, 1.444 mmol) dissolved in water (1 mL) was added and the reaction mass was heated at 60° C. for 16 hours. The reaction mixture was then concentrated and the residue was acidified with 2N HCl solution and extracted with EtOAc. Combined EtOAc extract was dried over sodium sulfate and concentrated under reduced pressure to afford Intermediate 16 (180 mg, 94%) as off white solid.

To a stirred solution of 4-(3,5-Dimethyl-isoxazol-4-yl-methoxy)-2-hydroxy-benzoic acid (16) (130 mg, 0.675 mmol) and 2,3-Dimethyl-phenylamine (2) (0.083 mL, 0.675 mmol) in Pyridine (3 mL), HATU (384 mg, 1.012 mmol) was added and the reaction was stirred at 50° C. for 16 hours. The reaction mixture was diluted with EtOAc, washed with 2N HCl, saturated sodium bicarbonate, water and brine, dried over sodium sulfate and concentrated. The crude was purified by column chromatography (silica, gradient: 25-30% EtOAc in Hexane) to afford the Compound 44 (55 mg, 22%) as off white solid.

To a stirred solution of 4-(3,5-Dimethyl-isoxazol-4-yl-methoxy)-N-(2,3-dimethyl-phenyl)-2-hydroxy-benzamide (44) (75 mg, 0.271 mmol) in DMF (1 mL), K₂CO₃ (74 mg, 0.542 mmol) and Methyl iodide (0.084 mL, 1.354 mmol) were added and the reaction was stirred in a sealed tube at RT for 16 hours. The reaction mixture was diluted with ethyl acetate, washed with water and brine, dried over sodium sulfate and concentrated. The crude was purified over preparative TLC plate in 50% EtOAc in Hexane to afford the Compound N4 as light yellow solid (26 mg, 25%).

Synthesis of Compound 37 (4-(3,5-Dimethyl-isoxazol-4-ylmethoxy)-naphthalene-1-carboxylic acid (2,3-dimethyl-phenyl)-amide)

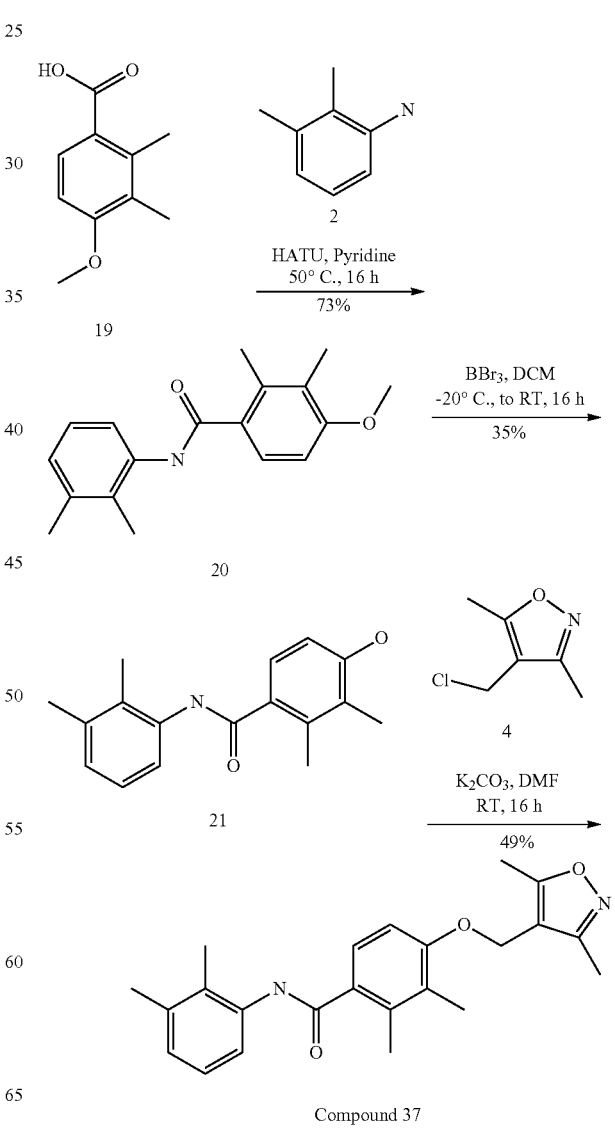

Compound 37

To a stirred solution of 4-Methoxy-2,3-dimethyl-benzoic acid (19) (200 mg, 0.769 mmol) and 2,3-Dimethyl-phenylamine (2) (0.094 mL, 0.769 mmol) in Pyridine (5 mL), HATU (438 mg, 1.153 mmol) was added and the reaction was stirred at 50° C. for 16 hours. The reaction mixture was diluted with EtOAc and washed with 2N HCl, saturated sodium bicarbonate, water and brine, dried over sodium sulfate and concentrated. The crude was purified by column chromatography (silica, gradient: 20-30% EtOAc in Hexane) to afford the Intermediate 20 (160 mg, 73%) as off white solid.

To a stirred solution of N-(2,3-Dimethyl-phenyl)-4-methoxy-2,3-dimethyl-benzamide (20) (150 mg, 0.529 mmol) in DCM (3 mL) in DCM, BBr$_3$ (1M in DCM, 2.6 mL, 2.6 mmol) was added drop wise at −20° C., and the reaction was slowly warmed to RT and stirred for 16 hours. After completion of the reaction (monitored by TLC/LC MS) the reaction mass was quenched with water and extracted with EtOAc. The combined organic extract was washed with water and brine, dried over sodium sulfate and concentrated. The crude was purified by column chromatography (silica, gradient: 20-30% EtOAc in Hexane) to afford the Intermediate 21 (50 mg, 35%) as off white solid.

To a stirred solution of compound 21 (50 mg, 0.186 mmol) in DMF (2 mL), K$_2$CO$_3$ (51 mg, 0.371 mmol) and 4-Chloromethyl-3,5-dimethyl-isoxazole (4) (0.023 mL, 0.186 mmol) were added and the reaction was stirred at RT for 16 hours. The reaction mixture was diluted with ethyl acetate, washed with water and brine, dried over sodium sulfate and concentrated. The crude was purified over preparative TLC plate eluting with 40% EtOAc in hexane to afford the Compound 37 as white solid (35 mg, 49%).

Synthesis of Compound 40 (4-(3,5-Dimethyl-isoxazol-4-ylmethoxy)-naphthalene-1-carboxylic acid (2,3-dimethyl-phenyl)-amide)

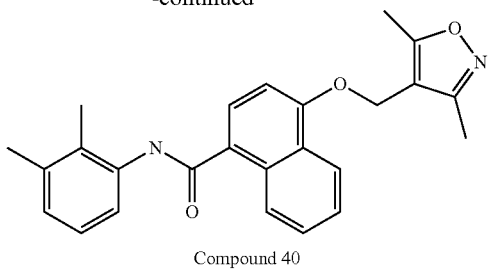

Compound 40

To a stirred solution of 4-Hydroxy-naphthalene-1-carboxylic acid (17) (125 mg, 0.649 mmol) and 2,3-Dimethyl-phenylamine (2) (0.08 mL, 0.649 mmol) in Pyridine (2 mL), HATU (369 mg, 0.974 mmol) was added and the reaction was stirred at 50° C. for 16 hours. The reaction mixture was diluted with EtOAc, washed with 2N HCl, saturated sodium bicarbonate, water and brine, dried over sodium sulfate and concentrated. The crude LCMS showed mass peak of desired product along with the ester. The crude was then dissolved in THF:MeOH:Water (4:2:1; 10 mL) and treated with 2N NaOH (3 mL) at 60° C. for 4 hours (monitored by LCMS). The reaction mixture was again evaporated to dryness, the residue was taken in 2N HCl, extracted with ethyl acetate and evaporated to afford the Intermediate 18 (170 mg, 89%) as yellow solid.

To a stirred solution of 4-Hydroxy-naphthalene-1-carboxylic acid (2,3-dimethyl-phenyl)-amide (18) (170 mg, 0.584 mmol) in DMF (2 mL), K$_2$CO$_3$ (161 mg, 1.168 mmol) and 4-Chloromethyl-3,5-dimethyl-isoxazole (4) (0.101 mL, 0.800 mmol) were added and the reaction was stirred at RT for 16 hours. The reaction mixture was diluted with ethyl acetate, washed with water and brine, dried over sodium sulfate and concentrated. The crude was purified by column chromatography (silica, gradient: 20-30% EtOAc in Hexane) to afford the Compound 40 as white solid (70 mg, 29%).

Synthesis of Compound 49 (N-(2,3-Dimethyl-phenyl)-4-(3,5-dimethyl-pyridin-4-ylmethoxy)-benzamide)

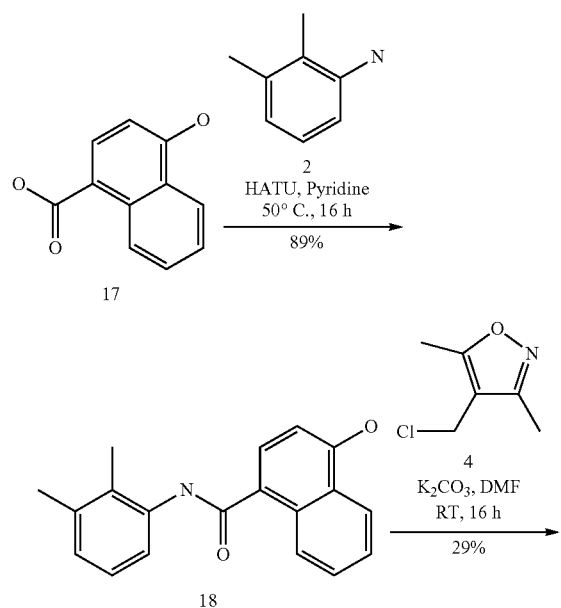

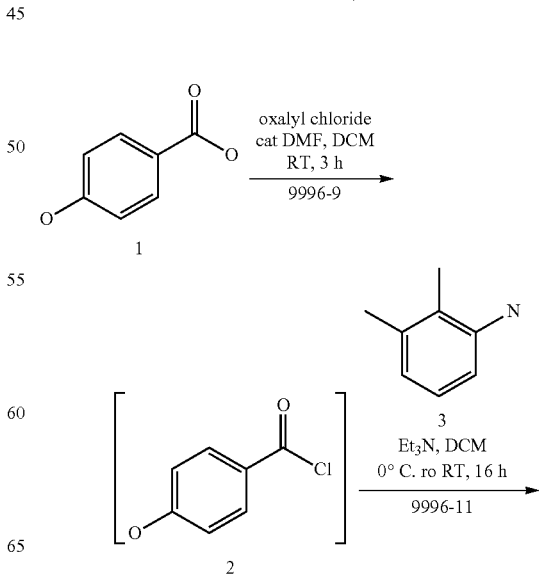

Synthesis of Compound 50 (N-(2,3-Dimethyl-phenyl)-4-(2,4-dimethyl-pyridin-3-ylmethoxy)-benzamide)

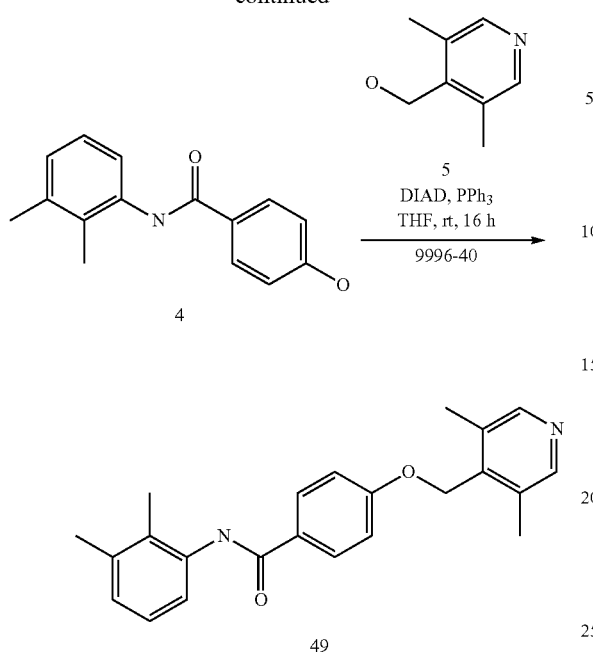

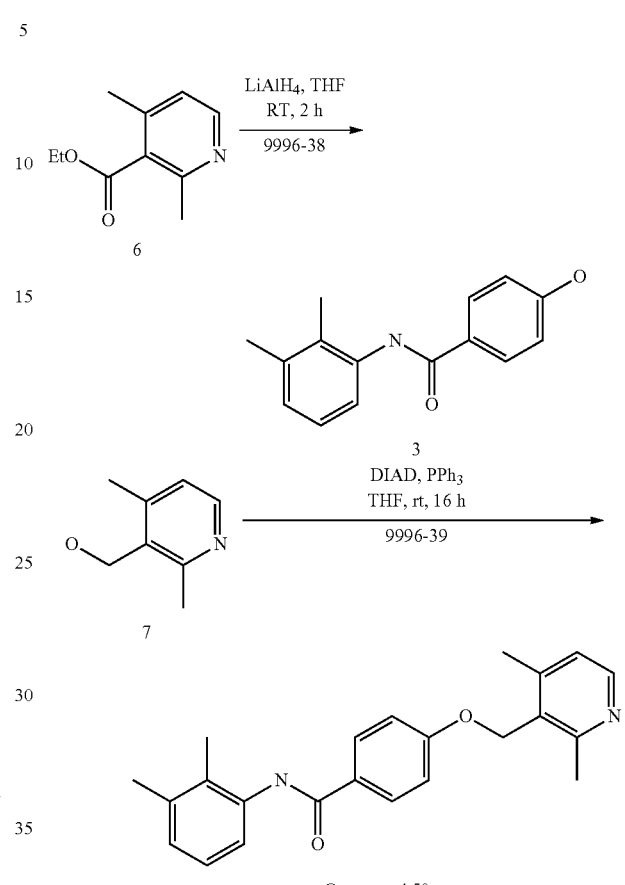

Compound 50

To a stirred suspension of 4-Hydroxy-benzoic acid (1) (5.0 g, 36.179 mmol) in DCM (50 ml), Oxalyl chloride (3.69 ml, 43.415 mmol) was added followed by catalytic DMF at 0° C. The reaction mixture was then stirred at RT for 3 hr. TLC was checked quenching the reaction mixture with MeOH, which showed a spot matching with the authentic 4-Hydroxy-benzoic acid methyl ester (Bellen Chemistry Co.). The reaction mixture was then evaporated under inert atmosphere to afford Intermediate 2 (5.6 g; 100%, crude) as yellow solid.

4-Hydroxy-benzoyl chloride (2) (5.6 g, 36.179 mmol) was dissolved in DCM (20 ml) and was added to a solution of (3,5-Dimethyl-pyridin-4-yl)-methanol (5) (5.28 g, 42.92 mmol) in DCM (30 ml) and DIPEA (13.8 ml, 107.3 mmol). The resultant reaction mixture was then stirred at Rt for 16 h. The reaction mixture was diluted with EtOAc and washed with saturated sodium bicarbonate, water and brine, dried over sodium sulfate and concentrated. The crude was purified by column chromatography (silica, gradient: 0%-40% ethyl acetate/hexane) to afford Intermediate 3 (1.3 g, 15.3%) as brick red solid.

To a stirred solution of Triphenyl phosphine (326 mg, 1.245 mmol) in THF was added DIAD (251 mg, 1.245 mmol) at 0° C. and the reaction mixture was stirred at 0° C. for 15 minutes. Then N-(2,3-Dimethyl-phenyl)-4-hydroxy-benzamide (3) (200 mg, 0.83 mmol) was added to the reaction mixture and stirred for 10 minutes. (3,5-Dimethyl-pyridin-4-yl)-methanol (5) (113 mg, 0.83 mmol) was then added and the reaction mixture was stirred at RT for 16 hours. The reaction mixture was then evaporated to dryness and purified by column chromatography in 100-200 silica using Hexane/EtOAc (5:1) as eluent to afford Compound 49 (47 mg, 15.7%) as white solid.

To a stirred solution of 2,4-Dimethyl-nicotinic acid ethyl ester (6) (500 mg, 2.79 mmol) in THF (10 mL) was cooled to 0° C. and LiAlH4 (424 mg, 11.159 mmol) was added and the resultant reaction was stirred at Rt for 2 hour. The reaction was quenched with 2N NaOH solution and stirred for 10 min. The reaction mixture was then filtered off and washed with ethyl acetate. The filtrate was then further washed with brine, dried over sodium sulfate and concentrated to afford Intermediate 7 (210 mg, 54.8%) as yellow gum.

To a stirred solution of Triphenyl phosphine (326 mg, 1.245 mmol) in THF was added DIAD (251 mg, 1.245 mmol) at 0° C. and the reaction mixture was stirred at 0° C. for 15 minutes. Then N-(2,3-Dimethyl-phenyl)-4-hydroxy-benzamide (3) (200 mg, 0.83 mmol) was added to the reaction mixture and stirred for 10 minutes. (2,4-Dimethyl-pyridin-3-yl)-methanol (7) (113 mg, 0.83 mmol) was then added and the reaction mixture was stirred at RT for 16 hours. The reaction mixture was then evaporated to dryness and purified by column chromatography in 100-200 silica using Hexane/EtOAc (5:1) as eluent followed by Prep HPLC on Waters auto purification instrument. Column name: YMC Prep C18 (100×30 mm, 5µ) is operating at ambient temperature and flow rate of 30.0 ml/min. A=20 mM NH$_4$HCO$_3$ in H$_2$O, B=Acetonitrile. Mobile phase initial from 90% of 20 mM NH4HCO3 in H$_2$O and 10% acetonitrile composition then 60% 20 mM NH$_4$HCO$_3$ in H$_2$O and 40% acetonitrile in 1.00 min, then 30% of 20 mM NH4HCO3 in H2O and 70% acetonitrile in 15.00 min to 5% of 20 mM NH4HCO3 in H2O and 95% acetonitrile in 16.0 min, held in this composition up to 17.0 min, then returned to initial composition in 18.0 min to afford Compound 50 (50 mg, 16.7%) as white solid.

Synthesis of Compound 60 (N-(2,3-Dimethyl-phenyl)-4-(pyridin-4-ylmethoxy)-benzamide)

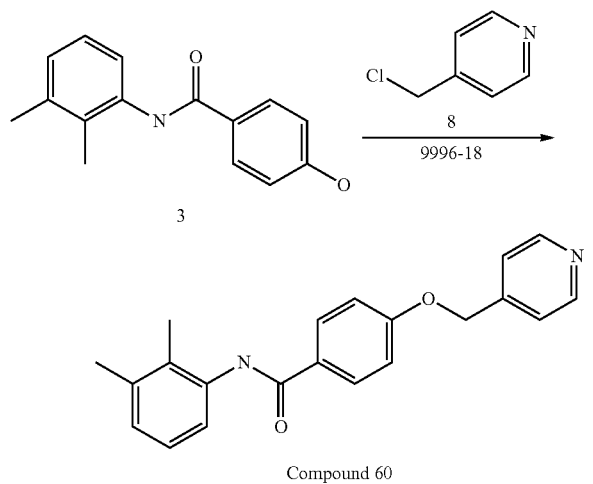

Compound 60

To a stirred solution of N-(2,3-Dimethyl-phenyl)-4-hydroxy-benzamide (3) (200 mg, 0.83 mmol) in DMF (2 ml), K2CO3 (0.345 g, 2.497 mmol) and 4-Chloromethyl-pyridine (8) (0.163 g, 0.999 mmol) were added and the reaction was stirred at RT for 16 hr. The reaction mixture was diluted with ethyl acetate and washed with water and brine, dried over sodium sulfate and concentrated. The crude was purified by column chromatography in 100-200 silica using Hexane/EtOAc (1:1) as eluent to afford Compound 60 (150 mg, 54.2%) as white solid.

Synthesis of Compound 61 (N-(2,3-Dimethyl-phenyl)-4-(pyridin-3-ylmethoxy)-benzamide)

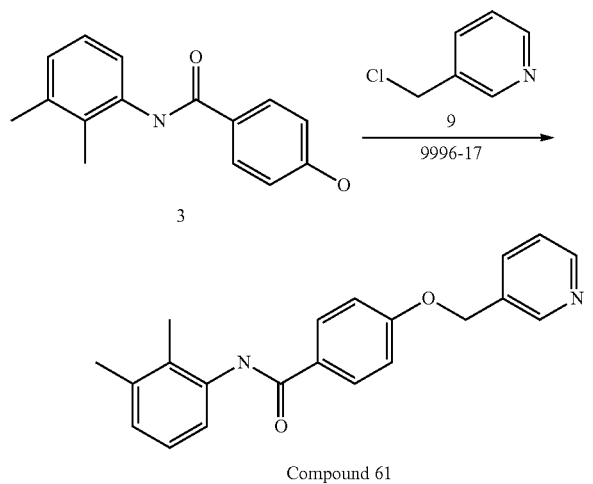

Compound 61

To a stirred solution of N-(2,3-Dimethyl-phenyl)-4-hydroxy-benzamide (3) (200 mg, 0.83 mmol) in DMF (2 ml), K2CO3 (0.345 g, 2.497 mmol) and 3-Chloromethyl-pyridine (9) (0.163 g, 0.999 mmol) were added and the reaction was stirred at RT for 16 hr. The reaction mixture was diluted with ethyl acetate and washed with water and brine, dried over sodium sulfate and concentrated. The crude was purified by column chromatography in 100-200 silica using Hexane/EtOAc (1:1) as eluent to afford Compound 61 (150 mg, 54.2%) as white solid.

Synthesis of Compound 62 (N-(2,3-Dimethyl-phenyl)-4-(pyridin-3-ylmethoxy)-benzamide)

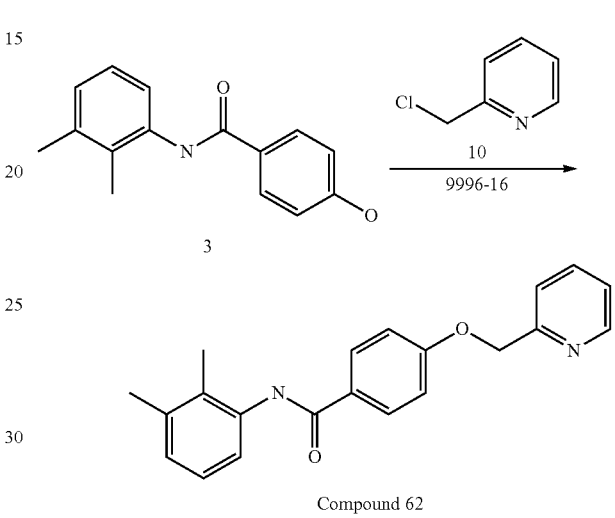

Compound 62

To a stirred solution of N-(2,3-Dimethyl-phenyl)-4-hydroxy-benzamide (3) (200 mg, 0.83 mmol) in DMF (2 ml), K2CO3 (0.345 g, 2.497 mmol) and 2-Chloromethyl-pyridine (9) (0.163 g, 0.999 mmol) were added and the reaction was stirred at RT for 16 hr. The reaction mixture was diluted with ethyl acetate and washed with water and brine, dried over sodium sulfate and concentrated. The crude was purified by column chromatography in 100-200 silica using Hexane/EtOAc (1:1) as eluent to afford Compound 62 (120 mg, 43.3%) as white solid.

Synthesis of Compound 59 (N-(2,3-Dimethyl-phenyl)-4-(pyridazin-4-ylmethoxy)-benzamide)

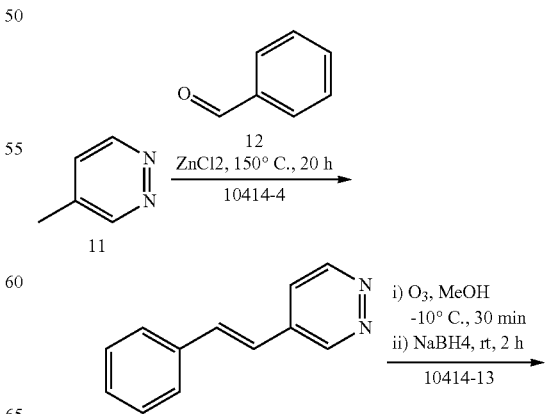

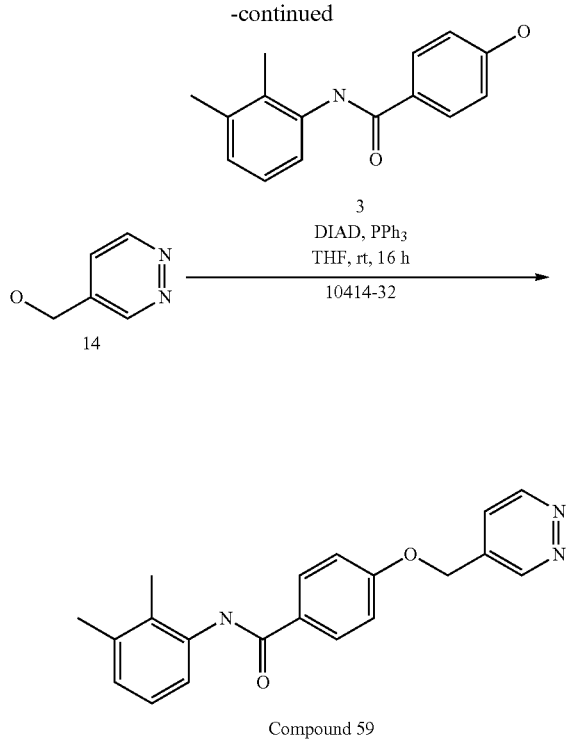

Compound 59

To a stirred mixture of 4-Methyl-pyridazine (11) (0.500 g, 5.312 mmol) and Benzaldehyde (12) (1.1 g, 10.625 mmol) was added zinc chloride (1.44 g, 10.625 mmol) and the resultant reaction mixture was heated at 150° C. for 16 h. The reaction mixture was quenched with 2M NaOH solution and DCM was added. The layers were partitioned and the aqs part was further extracted with DCM (2 times). The combined organic layers were dried over sodium sulfate and concentrated. Portioned between 2M NaOH and DCM and extracted the aqueous layer with DCM. Combined all organic layers and dried over Sodium sulphate. The crude was purified by column chromatography in 100-200 silica using Hexane/EtOAc (4:1) as eluent to afford Intermediate 13 (290 mg, 29.9%) as brown oil.

Ozone gas was bubbled through a stirred solution of 4-((E)-Styryl)-pyridazine (13) (0.400 g, 2.186 mmol) in methanol (15 mL) at −10° C. After 30 minutes the mixture was purged with nitrogen and sodium borohydride (0.0.082 g, 2.186 mmol) was added portion wise and the resulting solution stirred for 2 hours at room temperature. The reaction mixture was acidified with 2M hydrochloric acid, then basified with aqueous ammonia solution and evaporated under reduced pressure. The crude was purified by column chromatography in 100-200 silica using DCM/MeOH (98:2) as eluent to afford Intermediate 14 (100 mg, 41.5%) as yellow gum.

To a stirred solution of Triphenyl phosphine (179 mg, 0.685 mmol) in THF (5 ml) was added DIAD (138 mg, 0.685 mmol) at 0° C. and the reaction mixture was stirred at 0° C. for 15 minutes. Then N-(2,3-Dimethyl-phenyl)-4-hydroxy-benzamide (3) (110 mg, 0.456 mmol) was added to the reaction mixture and stirred for 10 minutes. Pyridazin-4-yl-methanol (14) (50 mg, 0.456 mmol) was then added and the reaction mixture was stirred at RT for 16 hours. The reaction mixture was then evaporated to dryness and purified by column chromatography in 100-200 silica using Hexane/EtOAc (5:1) as eluent to afford Compound 59 (45 mg, 29.5%) as white solid.

Synthesis of Compound 47 (N-(2,3-Dimethyl-phenyl)-4-(isoxazol-4-ylmethoxy)-benzamide)

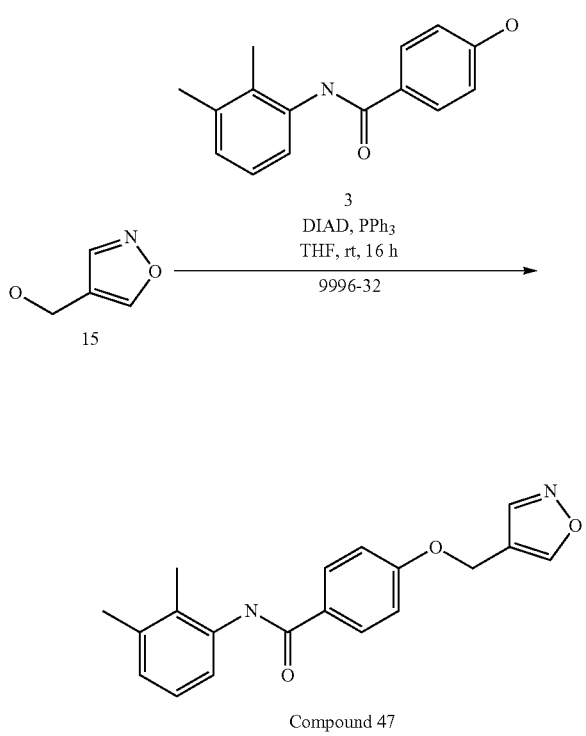

Compound 47

To a stirred solution of Triphenyl phosphine (326 mg, 1.245 mmol) in THF was added DIAD (251 mg, 1.245 mmol) at 0° C. and the reaction mixture was stirred at 0° C. for 15 minutes. Then N-(2,3-Dimethyl-phenyl)-4-hydroxy-benzamide (3) (200 mg, 0.83 mmol) was added to the reaction mixture and stirred for 10 minutes. Isoxazol-4-yl-methanol (15) (82 mg, 0.83 mmol) was then added and the reaction mixture was stirred at RT for 16 hours. The reaction mixture was then evaporated to dryness and purified by column chromatography in 100-200 silica using Hexane/EtOAc (5:1) as eluent to afford Compound 47 (100 mg, 37.8%) as white solid.

Synthesis of Compound 63 (N-(2,3-Dimethyl-phenyl)-4-(2-methyl-pyridin-3-ylmethoxy)-benzamide)

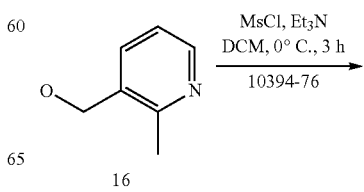

16

-continued

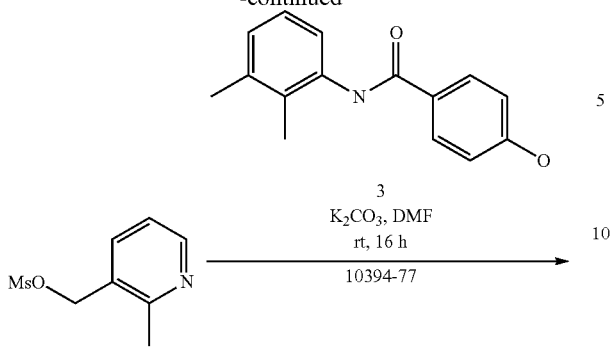

3

K₂CO₃, DMF
rt, 16 h
10394-77

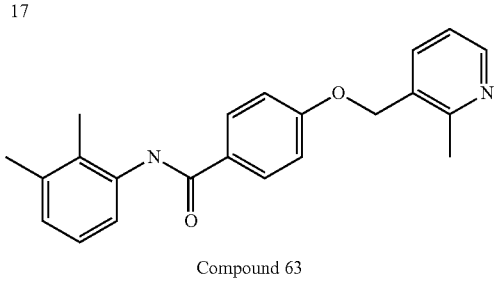

Compound 63

To a stirred solution of (2-Methyl-pyridin-3-yl)-methanol (16) (100 mg, 0.812 mmol) in DCM (5 mL), Et3N (0.226 ml, 1.625 mmol) and Mesyl chloride (0.094 ml, 1.219 mmol) were added at 0° C. and the reaction was stirred at RT for 2 hr. The reaction was diluted with DCM and washed with sat sodium bicarbonate solution, water and brine, dried over sodium sulfate and concentrated to afford Intermediate 17 (150 mg, 91.3%) as yellow oil.

To a stirred solution of N-(2,3-Dimethyl-phenyl)-4-hydroxy-benzamide (3) (75 mg, 0.311 mmol) in DMF (2 ml), K2CO3 (0.085 g, 0.622 mmol) and Methanesulfonic acid 2-methyl-pyridin-3-ylmethyl ester (17) (0.063 g, 0.311 mmol) were added and the reaction was stirred at RT for 16 hr. The reaction mixture was diluted with ethyl acetate and washed with water and brine, dried over sodium sulfate and concentrated. The crude was purified by column chromatography in 100-200 silica using Hexane/EtOAc (4:1) as eluent to afford Compound 63 (55 mg, 51.02%) as off white solid.

Synthesis of Compound 67 (4-(2-Chloro-pyridin-3-ylmethoxy)-N-(2,3-dimethyl-phenyl)-benzamide)

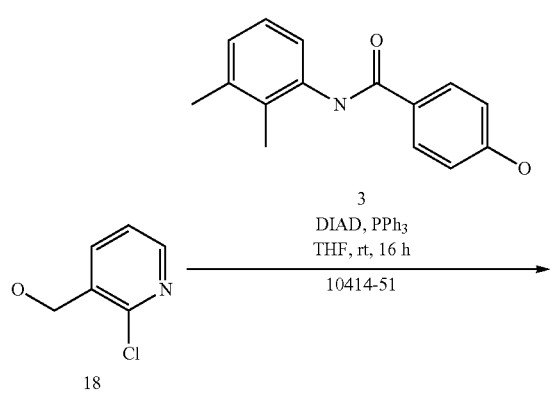

18

3

DIAD, PPh₃
THF, rt, 16 h
10414-51

-continued

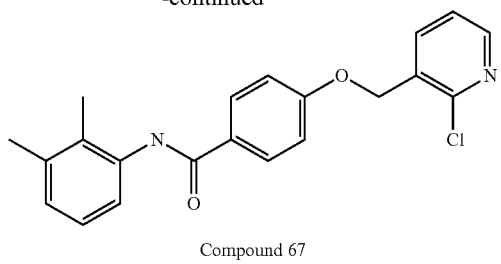

Compound 67

To a stirred solution of Triphenyl phosphine (122 mg, 0.467 mmol) in THF (5 ml) was added DIAD (94 mg, 0.467 mmol) at 0° C. and the reaction mixture was stirred at 0° C. for 15 minutes. Then N-(2,3-Dimethyl-phenyl)-4-hydroxy-benzamide (3) (75 mg, 0.311 mmol) was added to the reaction mixture and stirred for 10 minutes. (2-Chloro-pyridin-3-yl)-methanol (18) (38 mg, 0.311 mmol) was then added and the reaction mixture was stirred at RT for 16 hours. The reaction mixture was then evaporated to dryness and purified by column chromatography in 100-200 silica using Hexane/EtOAc (5:1) as eluent to afford Compound 67 (35 mg, 30.6%) as white solid.

Synthesis of Compound 65 (N-(2,3-Dimethyl-phenyl)-4-(2-methoxy-pyridin-3-ylmethoxy)-benzamide)

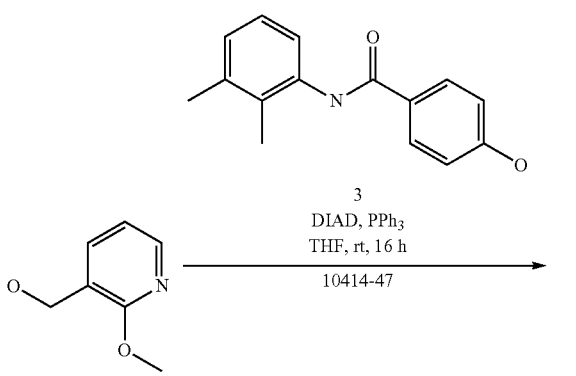

19

3

DIAD, PPh₃
THF, rt, 16 h
10414-47

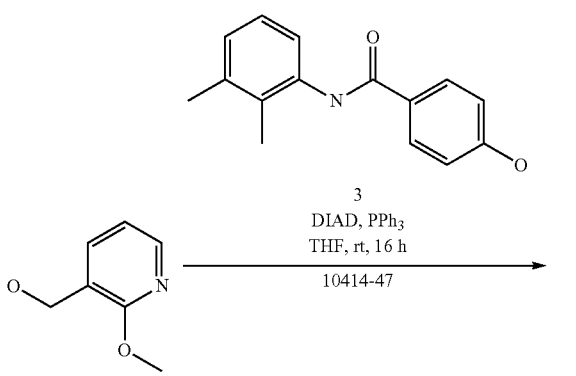

Compound 65

To a stirred solution of Triphenyl phosphine (122 mg, 0.467 mmol) in THF (5 ml) was added DIAD (94 mg, 0.467 mmol) at 0° C. and the reaction mixture was stirred at 0° C.

for 15 minutes. Then N-(2,3-Dimethyl-phenyl)-4-hydroxy-benzamide (3) (75 mg, 0.311 mmol) was added to the reaction mixture and stirred for 10 minutes. (2-Methoxy-pyridin-3-yl)-methanol (19) (43 mg, 0.311 mmol) was then added and the reaction mixture was stirred at RT for 16 hours. The reaction mixture was then evaporated to dryness and purified by column chromatography in 100-200 silica using Hexane/EtOAc (5:1) as eluent to afford compound 65 (25 mg, 22.1%) as white solid.

Synthesis of Compound 64 (N-(2,3-Dimethyl-phenyl)-4-(4-methyl-pyridin-3-ylmethoxy)-benzamide)

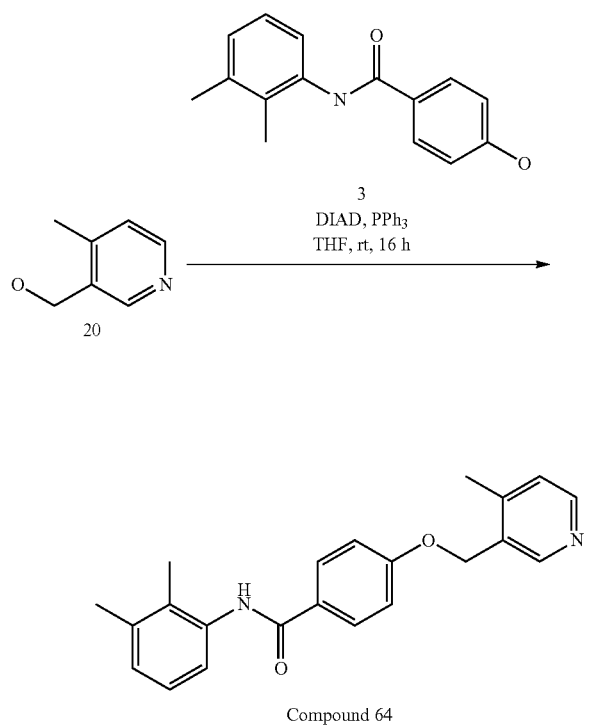

Compound 64

To a stirred solution of Triphenyl phosphine (163 mg, 0.622 mmol) in THF (5 ml) was added DIAD (125 mg, 0.622 mmol) at 0° C. and the reaction mixture was stirred at 0° C. for 15 minutes. Then N-(2,3-Dimethyl-phenyl)-4-hydroxy-benzamide (3) (100 mg, 0.415 mmol) was added to the reaction mixture and stirred for 10 minutes. (4-Methyl-pyridin-3-yl)-methanol (20) (51 mg, 0.415 mmol) was then added and the reaction mixture was stirred at RT for 16 hours. The reaction mixture was then evaporated to dryness and purified by column chromatography in 100-200 silica using Hexane/EtOAc (5:1) as eluent followed by Prep HPLC on Waters auto purification instrument. Column name: YMC Prep C18 (100×30 mm, 5µ) is operating at ambient temperature and flow rate of 30.0 ml/min. A=20 mM NH$_4$HCO$_3$ in H$_2$O, B=Acetonitrile. Mobile phase initial from 90% of 20 mM NH$_4$HCO3 in H$_2$O and 10% acetonitrile composition then 65% 20 mM NH$_4$HCO$_3$ in H$_2$O and 35% acetonitrile in 1.00 min, then 35% of 20 mM NH$_4$HCO$_3$ in H$_2$O and 65% acetonitrile in 15.00 min to 5% of 20 mM NH$_4$HCO$_3$ in H$_2$O and 95% acetonitrile in 16.0 min, held in this composition up to 17.0 min, then returned to initial composition in 18.0 min to afford Compound 64 (40 mg, 27.2%) as white solid.

Synthesis of Compound 66 (4-(4-Chloro-pyridin-3-ylmethoxy)-N-(2,3-dimethyl-phenyl)-benzamide)

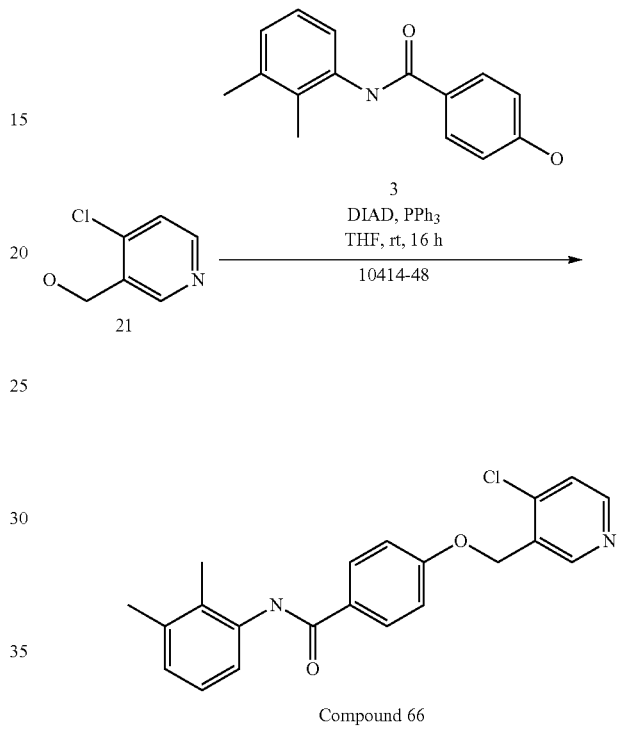

Compound 66

To a stirred solution of Triphenyl phosphine (122 mg, 0.467 mmol) in THF (5 ml) was added DIAD (94 mg, 0.467 mmol) at 0° C. and the reaction mixture was stirred at 0° C. for 15 minutes. Then N-(2,3-Dimethyl-phenyl)-4-hydroxy-benzamide (3) (75 mg, 0.311 mmol) was added to the reaction mixture and stirred for 10 minutes. (2-Methoxy-pyridin-3-yl)-methanol (19) (43 mg, 0.311 mmol) was then added and the reaction mixture was stirred at RT for 16 hours. The reaction mixture was then evaporated to dryness and purified by column chromatography in 100-200 silica using Hexane/EtOAc (5:1) as eluent followed by Prep HPLC on Waters auto purification instrument. Column name: YMC Prep C18 (100×30 mm, 5µ) is operating at ambient temperature and flow rate of 30.0 ml/min. A=20 mM NH$_4$HCO$_3$ in H$_2$O, B=Acetonitrile. Mobile phase initial from 90% of 20 mM NH$_4$HCO3 in H$_2$O and 10% acetonitrile composition then 60% 20 mM NH$_4$HCO$_3$ in H$_2$O and 40% acetonitrile in 1.00 min, then 20% of 20 mM NH$_4$HCO$_3$ in H$_2$O and 80% acetonitrile in 15.00 min to 5% of 20 mM NH$_4$HCO$_3$ in H$_2$O and 95% acetonitrile in 16.0 min, held in this composition up to 17.0 min, then returned to initial composition in 18.0 min to afford Compound 66 (25 mg, 22.9%) as white solid.

153
Synthesis of Compound 89 (3-(3-Azido-propyl)-4-(3,5-dimethyl-isoxazol-4-ylmethoxy)-N-(2,3-dimethyl-phenyl)-benzamide), Compound 87 (3-(3-Amino-propyl)-4-(3,5-dimethyl-isoxazol-4-ylmethoxy)-N-(2,3-dimethyl-phenyl)-benzamide) and HCl salt of Compound 87, and Compound 88 (3-(3-Acetylamino-propyl)-4-(3,5-dimethyl-isoxazol-4-ylmethoxy)-N-(2,3-dimethyl-phenyl)-benzamide)
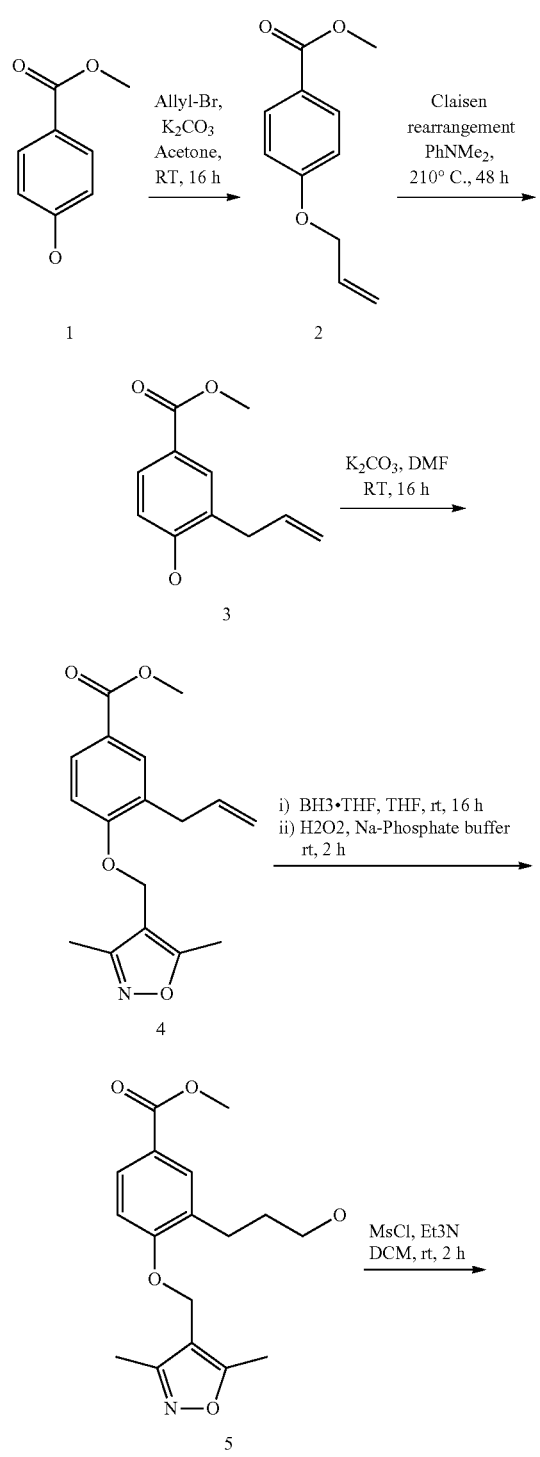
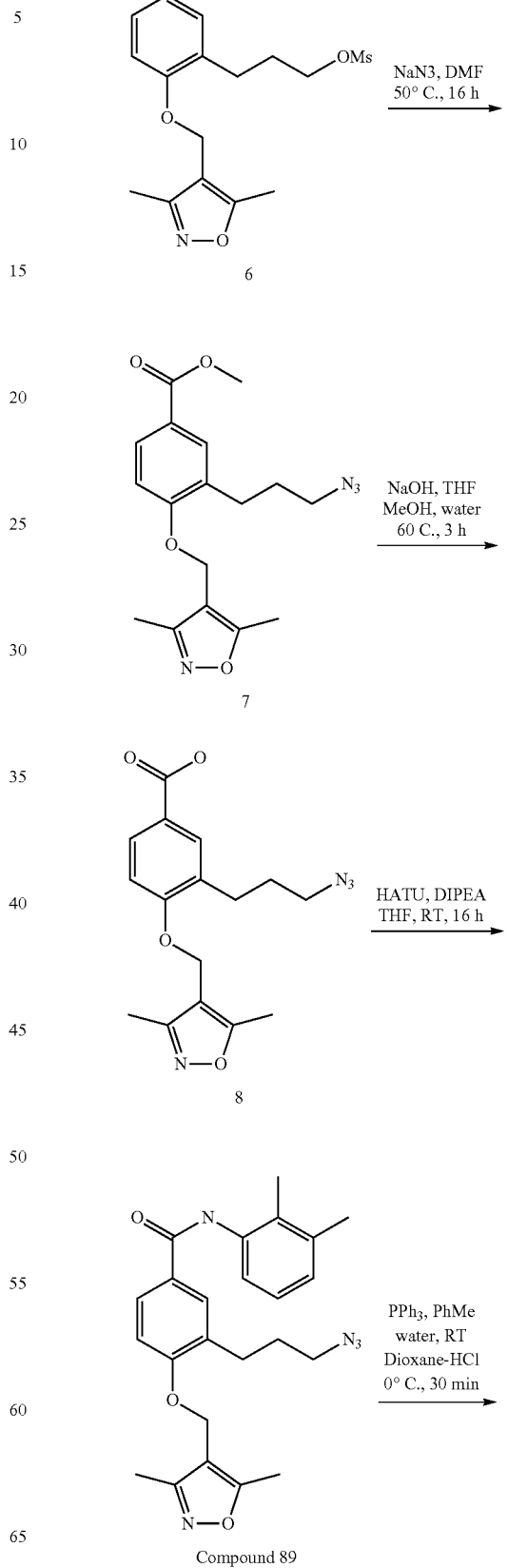

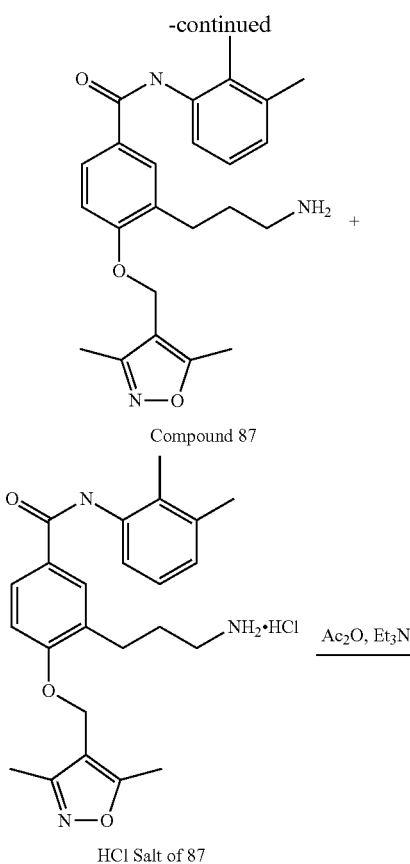

Compound 87

HCl Salt of 87

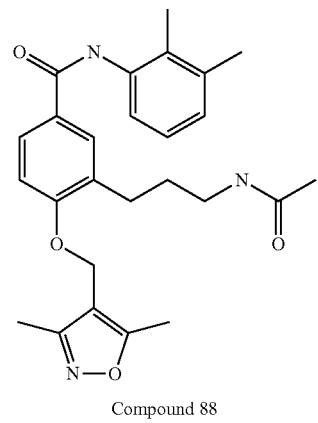

Compound 88

To a stirred solution of 4-Hydroxy-benzoic acid methyl ester (1) (7.5 g, 49.31 mmol) in Acetone (50 mL), K2CO3 (13.6 g, 98.619 mmol) and Allyl bromide (4.68 mL, 54.241 mmol) were added and the reaction mixture was stirred at RT for 16 hours. The reaction mixture was diluted with ethyl acetate, washed with water, brine, dried over sodium sulfate and concentrated. The crude was purified by column chromatography in 100-200 silica using Hexane/EtOAc (5:1) as eluent to afford compound 2 (7.0 g, 73.6%) as colorless oil.

4-Allyloxy-benzoic acid methyl ester (2) (3.0 g, 15.62 mmol) and N,N Dimethyl aniline (10 mL) were taken in a Round bottom flask and heated at 200° C. for 24 hour. TLC was checked which showed formation of a new polar spot along with unreacted SM. The reaction mixture was diluted with EtOAc and washed with water and brine, dried over sodium sulphate and concentrated. The crude was purified by column chromatography in 100-200 silica using Hexane/EtOAc (5:1) as eluent to afford Intermediate 3 (2.0 g, 66.6%) as colorless oil.

To a stirred solution of 3-Allyl-4-hydroxy-benzoic acid methyl ester (3) (2 g, 10.406 mmol) in DMF (15 mL), K2CO3 (2.87 g, 20.812 mmol) and 4-Chloromethyl-3,5-dimethyl-isoxazole (1.30 mL, 10.406 mmol) were added and the reaction mixture was stirred at RT for 16 hours. The reaction mixture was diluted with ethyl acetate, washed with water, brine, dried over sodium sulfate and concentrated. The crude was purified by column chromatography in 100-200 silica using Hexane/EtOAc (4:1) as eluent to afford Intermediate 4 (3.0 g, 95.6%) as off white solid.

Borane-THF complex (1.0 M solution in THF, 15.94 mL, 15.94 mmol) was added to a solution of 3-Allyl-4-(3,5-dimethyl-isoxazol-4-ylmethoxy)-benzoic acid methyl ester (4) (4.0 g; 13.289 mmol) in THF (50 mL) at 0° C. The mixture was stirred at RT for 16 h. The reaction mixture was again cooled to 0° C. And to it a 1.0 M solution of sodium phoshate buffer (pH 7, 25.5 ml) was added, followed by 30% aqueous hydrogen peroxide (4.56 ml). The mixture was allowed to warm to RT, and then water and EtOAc were added. The layers were separated and the organic layer was dried over sodium sulfate and evaporated. The crude was purified by column chromatography in 100-200 silica using Hexane/EtOAc (1:1) as eluent to afford Intermediate 5 (2.3 g, 54.2%) as off white solid.

To a stirred solution of 4-(3,5-Dimethyl-isoxazol-4-yl-methoxy)-3-(3-hydroxy-propyl)-benzoic acid methyl ester (5) (1.3 g; 4.071 mmol) in DCM (20 mL), were added Et3N (0.846 mL; 8.143 mmol) and Mesyl chloride (0.471 mL; 6.107 mmol) at 0° C. and the reaction was stirred at RT for 2 hr. The reaction was diluted with DCM and washed with sat sodium bicarbonate solution, water and brine, dried over sodium sulfate and concentrated to afford Intermediate 6 (1.6 g, 98.8%) as yellow gum.

To a stirred solution of 4-(3,5-Dimethyl-isoxazol-4-yl-methoxy)-3-(3-methanesulfonyloxy-propyl)-benzoic acid methyl ester (6) (1.6 g; 4.02 mmol) in DMF (10 mL) was added NaN3 (0.392 g; 6.03 mmol) and the reaction mixture was heated at 60° C. for 16 hr. The reaction mixture was diluted with ethyl acetate, washed with water (3 times) and brine solution, dried over sodium sulfate and concentrated to afford Intermediate 7 (1.2 g, 86.6%) as off white solid.

To a stirred solution of 3-(3-Azido-propyl)-4-(3,5-dimethyl-isoxazol-4-ylmethoxy)-benzoic acid methyl ester (7) (1.7 g, 4.938 mmol) in THF (16 mL) and Methanol (8 mL), NaOH (0.395 g, 9.875 mmol) dissolved in water (4 ml) was added and the reaction was heated at 60° C. for 4 hr. The reaction mixture was then evaporated to dryness and acidified with 2N HCl solution. The aqs was then extracted with ethyl acetate (3 times) and dried over sodium sulfate and concentrated to afford Intermediate 8 (1.6 g, 98.1%) as off white solid. TLC matched with authentic CR244-10394-6.

To a stirred solution of 3-(3-Azido-propyl)-4-(3,5-dimethyl-isoxazol-4-ylmethoxy)-benzoic acid (8)(1.6 g, 4.848 mmol) and 2,3-Dimethyl-phenylamine (0.593 mL; 4.848 mmol) in THF (20 ml), HATU (2.76 g, 7.273 mmol) and DIPEA (3.35 ml, 19.394 mmol) were added and the reaction was stirred at RT for 16 hr. The reaction mixture was diluted with EtOAc and washed with saturated sodium bicarbonate, water and brine, dried over sodium sulfate and concentrated. The crude was purified by column chromatography in 100-200 silica using Hexane/EtOAc (3:1) as eluent to afford Compound 89 (1.1 g, 52.3%) as off white solid.

To a stirred solution of 3-(3-Azido-propyl)-4-(3,5-dimethyl-isoxazol-4-ylmethoxy)-N-(2,3-dimethyl-phenyl)-benzamide (P9) (0.800 g, 1.848 mmol) in Toluene-THF (1:1, 20 mL) Triphenyl phosphine (0.728 g, 2.771 mmol) and water (catalytic) were added and the reaction was stirred at 80° C. for 16 h. The reaction was then evaporated to dryness and 3M Ether-HCl (10 mL) was added to it at 0° C. and stirred for 30 min. The reaction mixture was again evaporated to dryness and washed with ether, followed by trituration with DCM-Hexane to afford the HCl salt of Compound 87 (600 mg, 79.6%) as yellow solid. 150 mg of the HCl salt of Compound 87 was basified with saturated sodium bicarbonate solution and extracted with Ethyl acetated followed by drying over sodium sulfate and concentration under reduced pressure afforded 100 mg of Compound 87 as free amine.

To a stirred suspension of 3-(3-Amino-propyl)-4-(3,5-dimethyl-isoxazol-4-ylmethoxy)-N-(2,3-dimethyl-phenyl)-benzamide Hydrochloride salt (P11) (0.150 g, 0.369 mmol) in DCM (5 mL), Et3N (0.154 mL, 1.106 mmol) and Acetyl chloride (0.039 mL, 0.553 mmol) were added at 0° C. and the reaction was stirred at RT for 16 hr. The reaction mixture was diluted with ethyl acetate and washed with saturated sodium bicarbonate and water, dried over sodium sulphate and concentrated. The crude was purified by Prep TLC plate in 5% MeOH in DCM to afford Compound 88 (70 mg, 42.2%) as off white solid.

Synthesis of Biotinylated Compound P10 Derivative (4-(3,5-Dimethyl-isoxazol-4-ylmethoxy)-N-(2, 3-dimethyl-phenyl)-3-(3-{6-[5-((3aR,4R,6aS)-2-oxo hexahydro-thieno[3,4-d]imidazol-4-yl)-pentanoylamino]-hexanoylamino}-propyl)-benzamide)

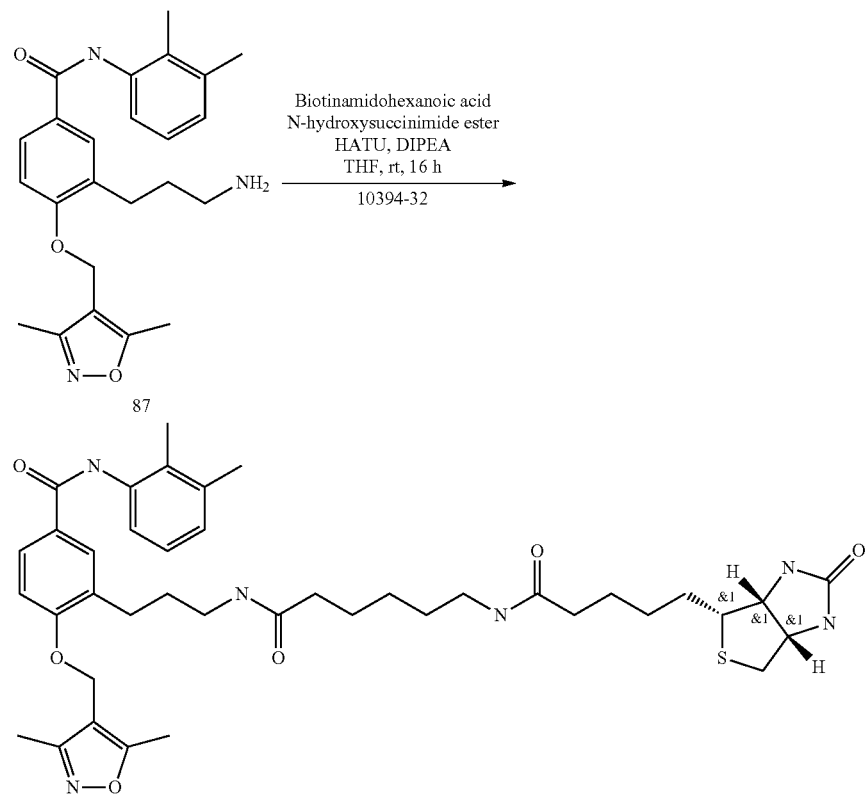

Biotinylated Compound 87 Derivative

To a stirred solution of 3-(3-Amino-propyl)-4-(3,5-dimethyl-isoxazol-4-ylmethoxy)-N-(2,3-dimethyl-phenyl)-benzamide Hydrochloride salt (Compound 87) (0.150 g, 0.369 mmol) and Biotinamidohexanoic acid N-hydroxysuccinimide ester (0.133 mL, 0.369 mmol) in THF (1 mL), Et3N (0.205 mL, 1.474 mmol) and T3P (0.664 mL, 1.106 mmol) were added and the reaction was stirred at RT for 16 hr. The reaction mixture was diluted with ethyl acetate and washed with saturated sodium bicarbonate and water, dried over sodium sulphate and concentrated. The crude was purified by column chromatography in 100-200 silica using DCM/MeOH (100:5) as eluent followed by Prep TLC plate in 7.5% MeOH in DCM to afford a biotinylated derivative of Compound 87 (0.070 g, 25.4%) as yellow solid.

Synthesis of Another Biotinylated Compound P10 Derivative (4-(3,5-Dimethyl-isoxazol-4-ylmethoxy)-N-(2,3-dimethyl-phenyl)-3-{3-[5-((3aS,4S,6aR)-2-oxo-hexahydro-thieno [3,4-d]imidazol-4-yl)-pentanoylamino]-propyl}-benzamide)

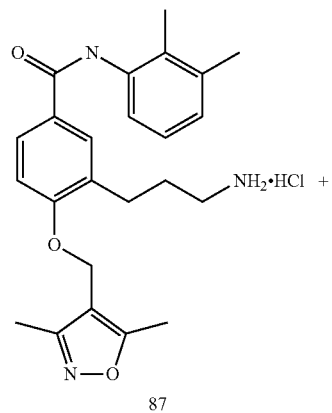

87

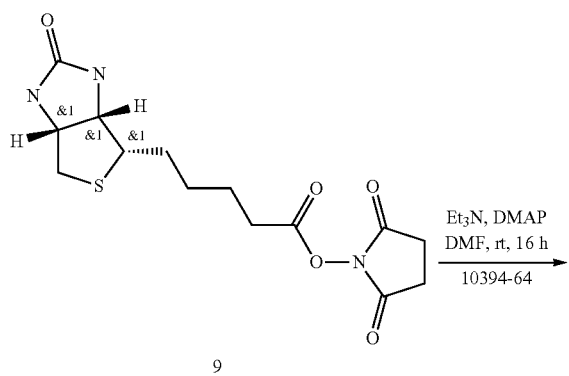

9

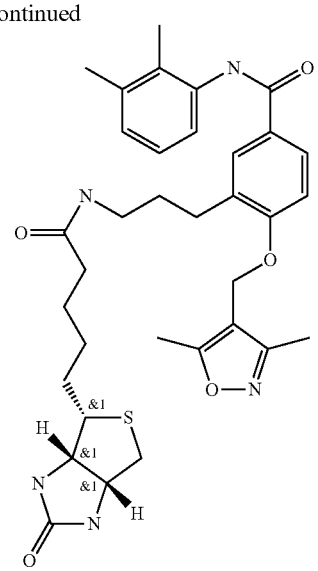

Biotinylated Derivative of Compound 87

To a stirred solution of 3-(3-Amino-propyl)-4-(3,5-dimethyl-isoxazol-4-ylmethoxy)-N-(2,3-dimethyl-phenyl)-benzamide Hydrochloride salt (87) (0.075 g, 0.184 mmol) and 5-((3aS,4S,6aR)-2-Oxo-hexahydro-thieno[3,4-d]imidazol-4-yl)-pentanoic acid 2,5-dioxo-pyrrolidin-1-yl ester (9) (0.062 mg, 0.184 mmol) in DMF (2 mL), Et3N (0.051 mL, 0.368 mmol) was added and the reaction was stirred at RT for 16 hr. The reaction mixture was diluted with ethyl acetate and washed with saturated sodium bicarbonate and water, dried over sodium sulphate and concentrated. The crude was purified Prep TLC plate in 5% MeOH in DCM to afford a biotinylated derivative of Compound 87 (0.055 g, 47.2%) as off white solid.

Example 2: NMR and LC/MS Spectra of Compounds

Nuclear magnetic resonance (NMR) spectra were recorded on a Varian (400 MHz $^1$H) spectrometer. Proton and carbon chemical shifts are reported in ppm ($\delta$) referenced to the NMR solvent (typically CDCl$_3$ unless otherwise specified). Data are reported as follows: chemical shifts, multiplicity (br=broad, s=singlet, d=doublet, t=triplet, q=quartet, m=multiplet; coupling constant(s) in Hz). Table 5 lists the chemical shifts from the NMR measurements and the m/z of the parent peak in the mass spectrum from the LC-MS measurements for various measured compounds.

TABLE 5

| Compound | NMR chemical shifts | LC-MS [M + H]$^+$ |
|---|---|---|
| Compound 1 | $^1$H NMR (400 MHz, CDCl$_3$): $\delta$ 8.81 (s, 1H), 8.31 (d, J = 4.8 Hz, 1H), 8.00 (s, 1H), 7.90 (d, J = 8.8 Hz, 1H), 7.17 (d, J = 4.8 Hz, 1H), 7.01 (d, J = 8.8 Hz, 2H), 4.86 (s, 2H), 2.42 (s, 3H), 2.32 (s, 3H), 2.28 (s, 3H) | 338.15 |

TABLE 5-continued

| Compound | NMR chemical shifts | LC-MS [M + H]+ |
|---|---|---|
| 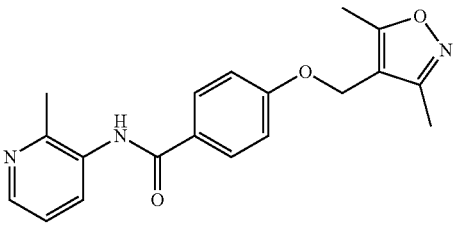<br>Compound 2 | 1H NMR (400 MHz, CDCl3): δ 8.31-8.26 (m, 2H), 7.87 (d, J = 8.8 Hz, 2H), 7.78 (s, 1H), 7.21-7.17 (m, 1H), 7.02 (d, J = 8.8 Hz, 2H), 4.86 (s, 2H), 2.56 (s, 3H), 2.42 (s, 3H), 2.28 (s, 3H) | 338.15 |
| 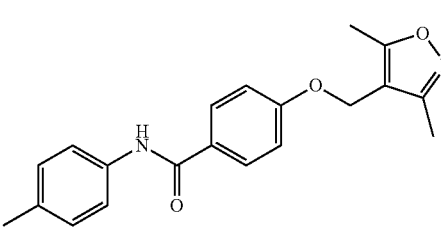<br>Compound 3 | 1H NMR (400 MHz, CDCl3): δ 7.86 (d, J = 8.4 Hz, 2H), 7.67 (s, 1H), 7.50 (d, J = 8.4 Hz, 2H), 7.17 (d, J = 7.6 Hz, 2H), 7.01 (d, J = 8.8 Hz, 2H), 4.86 (s, 2H), 2.43 (s, 3H), 2.34 (s, 3H), 2.30 (s, 3H) | 337.15 |
| 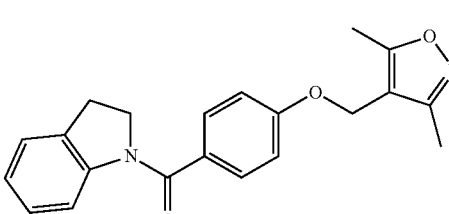<br>Compound 4 | 1H NMR (400 MHz, CDCl3): δ 7.57 (d, J = 8.8 Hz, 2H), 7.21 (d, J = 6.8 Hz, 1H), 7.16-7.13 (m, 1H), 7.04-6.97 (m, 3H), 4.84 (s, 2H), 4.12 (t, J = 8.0 Hz, 2H), 3.12 (t, J = 8.0 Hz, 2H), 2.43 (s, 3H), 2.31 (s, 3H) | 349.15 |
| 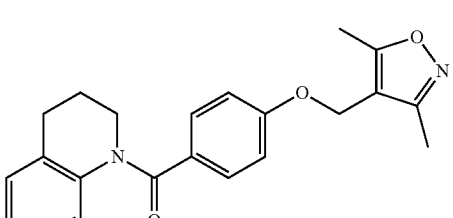<br>Compound 5 | 1H NMR (400 MHz, CDCl3): δ 7.34 (d, J = 8.8 Hz, 2H), 7.15 (d, J = 7.6 Hz, 1H), 7.00 (t, J = 7.2 Hz, 1H), 6.91 (t, J = 8.4 Hz, 1H), 6.80 (d, J = 8.8 Hz, 2H), 6.69 (d, J = 8.0 Hz, 1H), 4.77 (s, 2H), 3.91 (t, J = 6.4 Hz, 2H), 2.84 (t, J = 6.8 Hz, 2H), 2.39 (s, 3H), 2.27 (s, 3H), 2.05 (t, J = 6.8 Hz, 2H) | 363.20 |
| 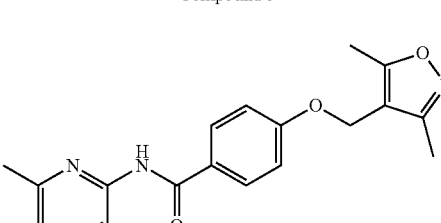<br>Compound 6 | 1H NMR (400 MHz, CDCl3): δ 8.58 (s, 1H), 8.17 (d, J = 8.0 Hz, 1H), 7.93 (d, J = 8.8 Hz, 2H), 7.64 (t, J = 8.0 Hz, 1H), 7.02 (d, J = 8.8 Hz, 2H), 6.92 (d, J = 7.2 Hz, 1H), 4.85 (s, 2H), 2.47 (s, 3H), 2.43 (s, 3H), 2.30 (s, 3H) | 338.10 |
| 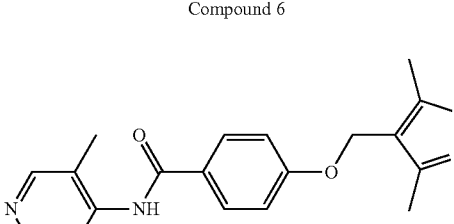<br>Compound 7 | 1H NMR (400 MHz, CDCl3): δ 8.47 (d, J = 5.6 Hz, 1H), 8.43 (s, 1H), 8.31 (d, J = 5.6 Hz, 1H), 7.87 (d, J = 8.8 Hz, 2H), 7.77 (s, 1H), 7.05 (d, J = 8.8 Hz, 2H), 4.88 (s, 2H), 2.44 (s, 3H), 2.34 (s, 3H), 2.30 (s, 3H) | 338.15 |

TABLE 5-continued

| Compound | NMR chemical shifts | LC-MS [M + H]+ |
|---|---|---|
| 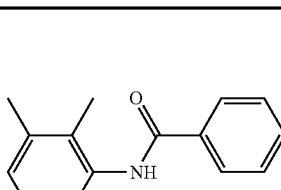<br>Compound 8 | ¹H NMR (400 MHz, CDCl₃): δ 8.47 (d, J = 5.6 Hz, 1H), 8.43 (s, 1H), 8.31 (d, J = 5.6 Hz, 1H), 7.87 (d, J = 8.8 Hz, 2H), 7.77 (s, 1H), 7.05 (d, J = 8.8 Hz, 2H), 4.88 (s, 2H), 2.44 (s, 3H), 2.34 (s, 3H), 2.30 (s, 3H) | 338.15 |
| 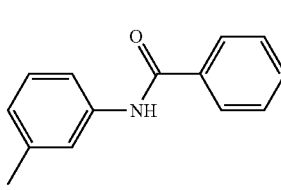<br>Compound 9 | ¹H NMR (400 MHz, CDCl₃): δ 7.85 (d, J = 8.8 Hz, 2H), 7.74 (s, 1H), 7.50 (s, 1H), 7.40 (d, J = 8.4 Hz, 1H), 7.26-7.23 (m, 2H), 7.01 (d, J = 8.4 Hz, 2H), 6.96 (d, J = 6.8 Hz, 1H), 4.85 (s, 2H), 2.42 (s, 3H), 2.37 (s, 3H), 2.30 (s, 3H) | 337.15 |
| 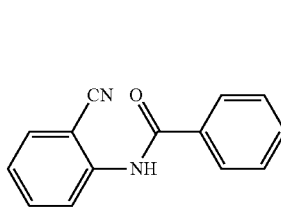<br>Compound 11 | ¹H NMR (400 MHz, CDCl₃): δ 8.61 (d, J = 8.4 Hz, 1H), 8.34 (s, 1H), 7.93 (d, J = 8.8 Hz, 2H), 7.65-7.62 (m, 2H), 7.24-7.20 (m, 1H), 7.06 (d, J = 8.4 Hz, 2H), 4.87 (s, 2H), 2.44 (s, 3H), 2.31 (s, 3H) | 348.15 |
| 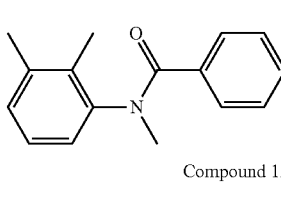<br>Compound 12 | ¹H NMR (400 MHz, CDCl₃): δ 7.22 (d, J = 8.8 Hz, 2H), 7.01 (d, J = 8.8 Hz, 2H), 6.77 (d, J = 7.2 Hz, 1H), 6.60 (d, J = 8.4 Hz, 2H), 4.92 (d, J = 14.8 Hz, 1H), 4.67 (d, J = 14.4 Hz, 1H), 3.70 (s, 3H), 2.13 (s, 3H), 2.04 (s, 3H), 1.95 (s, 3H), 1.79 (s, 3H) | 365.20 |
| 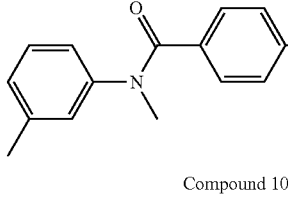<br>Compound 10 | ¹H NMR (400 MHz, CDCl₃): δ 7.28 (t, J = 7.2 Hz, 2H), 7.09 (t, J = 7.6 Hz, 1H), 6.96 (d, J = 7.6 Hz, 1H), 6.90 (s, 1H), 6.79 (d, J = 8.0 Hz, 1H), 6.70 (t, J = 6.4 Hz, 2H), 4.71 (s, 2H), 3.46 (s, 3H), 2.34 (s, 3H), 2.27 (s, 3H), 2.23 (s, 3H) | 351.15 |
| 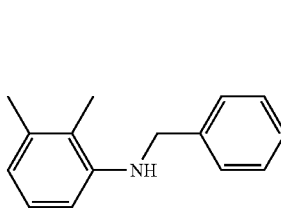<br>Compound 13 | ¹H NMR (400 MHz, CDCl₃): δ 7.33 (d, J = 8.4 Hz, 2H), 7.00 (t, J = 8.0 Hz, 1H), 6.93 (d, J = 8.4 Hz, 2H), 6.61 (d, J = 7.6 Hz, 1H), 6.52 (d, J = 8.0 Hz, 1H), 4.79 (s, 2H), 4.31 (s, 2H), 2.41 (s, 3H), 2.30 (s, 6H), 2.08 (s, 3H) | 337.20 |

Methods and Materials

The results described herein above were carried out using the following methods and materials.

Proinsulin-Luciferase Construct

The proinsulin-luciferase fusion construct was created by Gibson Assembly in the pUC19 vector using two gBlocks (Integrated DNA Technologies) encoding the protein and Gibson Assembly Master Mix (New England Biolabs). The proinsulin-luciferase fusion construct was subsequently PCR-amplified with primers to add attB1 and attB2 sites, inserted by BP Clonase II into the Gateway Entry vector pDONR223 (Invitrogen), and then shuttled by LR Clonase II into the Gateway Destination vector pLX304 (Yang et al., 2011; Addgene plasmid 25890).

Lentiviral Infection

Lentivirus expressing each prohormone-luciferase fusion protein was produced using a second-generation viral packaging system and used to infect rodent beta-cell lines or human islets. Briefly, 2 µg of pLX304 expression plasmid containing the fusion construct, 1.8 µg of psPAX2 packaging plasmid (courtesy of Didier Trono; Addgene plasmid 12260), 200 ng of pMD2.G envelope plasmid (courtesy of Didier Trono; Addgene plasmid 12259) and 12 µL TransIT-LT1 (MirusBio) were used to transfect a 10 cm dish of HEK293T packaging cells (American Type Culture Collection). Virus was pooled from harvests at 48 and 72 hours and passed through 0.2 µm cellulose acetate filters (VWR) prior to use. INS-1E cells and dissociated human islets were plated in their respective growth media with the addition of 8 µg/mL polybrene (Sigma). Virus was then added and the cells were spun at 800×g for 1 hour at 30° C. After 24 hours in the presence of virus, the cells were placed in fresh growth media. Rodent beta-cell lines were treated with 5 µg/mL blasticidin (Invitrogen) for one week to select for infected cells, and then assessed for luciferase localization and secretion. Assays on infected dissociated human islets were performed on unselected cells three days after infection.

Secretion Assays

For standard secretion assays, INS-1E cells were plated in 96-well format, preincubated for 1 hr in Krebs Ringer Buffer (KRB) with 2.8 mM glucose, and then stimulated for 1 hr in fresh KRB containing varying amounts of glucose and compounds. Insulin or C-peptide concentration was determined using an ELISA (Mercodia), following the manufacturer's protocol. Luciferase activity was determined from the same samples by adding the coelenterazine substrate to the supernatant to a final concentration of 10 µM and reading on a standard plate reader (BioTek).

Small Molecule Screens

INS-1E cells were expanded to 80% confluence in their growth medium, washed once in PBS, and preincubated for 1 hr at 37° C. in KRB with 2.8 mM glucose. Cells were then dissociated, spun at 300×g for 2 min, resuspended in fresh KRB without glucose, and filtered through 40 µm mesh (Becton Dickinson). Next, the cells were counted and diluted in KRB to 1×10$^6$ cells per ml, and glucose was added as required for each experiment. Cells were then seeded in 384-well format, 3×10$^4$ cells in 30 µl per well, using a Multidrop Combi device (Thermo Scientific). Compounds were pinned into each well using a Vario robot (CyBio) to a final concentration of 30 µM, and the plates were then incubated for 2 hr at 37° C. For assays involving a transfer step, the plates were then centrifuged at 300×g for 2 min, and 20 µl of supernatant was transferred to a new 384-well plate. Coelenterazine substrate was then added to a final concentration of 10 µM, and luciferase activity was determined using a standard plate reader (BioTek).

CellTiter-Glo (Promega) and the cAMP Dynamic-2 HTRF assay (Cisbio) were used according to the manufacturers' instructions. Luciferase secretion and CellTiter-Glo experiments were performed using a 1 hr incubation with compound, whereas the cAMP assay was performed using a 30 min incubation. Secretion experiments were run in KRB buffer; all other experiments were run in standard INS-1E medium.

Human Islet Cell Culture

Human islets were obtained through the Integrated Islet Distribution Program. Islets were maintained and dissociated in 96-well format as described (Walpita et al., J Biomol Screen 17: 509-518 2012). To test compounds for their effects on insulin secretion, the dissociated islets were washed gently in KRB and preincubated for 1 hr at 37° C. in KRB with 2.8 mM glucose. The cells were then washed twice with zero-glucose KRB and placed in 100 µl of fresh KRB with varied glucose concentrations plus compounds. After a 1 hr incubation at 37° C., the supernatant was removed, and insulin concentration was measured by ELISA (Mercodia) according to the manufacturer's instructions.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

International Application No. PCT/US2012/063982 is incorporated herein by reference for all that it teaches. All patents and publications mentioned in this specification are herein incorporated by reference to the same extent as if each independent patent and publication was specifically and individually indicated to be incorporated by reference.

The invention claimed is:

1. A compound having the structure of Formula I(a):

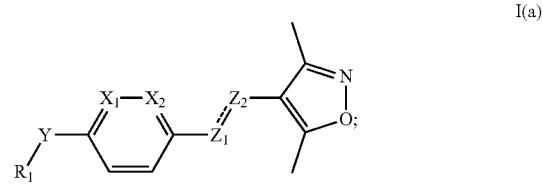

wherein the "dashed" bond is a single or double bond;
X$_1$ and X$_2$ are independently C(R$_2$), wherein two vicinal R$_2$ groups may together form an optionally aromatic five- or six membered fused ring;
Y is selected from —C(O)N(R$_3$)— and —N(R$_3$)C(O)—;
Z$_1$ and Z$_2$ are independently CH$_2$, or O;
R$_1$ is aryl, optionally substituted with one or more substituents independently selected from alkyl, hydroxyalkyl, cyano, and halogen;
R$_2$ is selected from hydrogen, alkyl, —NH$_2$, —(CH$_2$)$_{1-4}$NH$_2$, —(CH$_2$)$_{1-4}$N$_3$, and —(CH$_2$)$_{1-4}$NHC(O)CH$_3$; and
R$_3$ is independently selected at each occurrence from hydrogen and alkyl optionally substituted with one to three groups independently selected from halogen;
or a pharmaceutically acceptable salt, hydrate, solvate, geometric isomer, or stereoisomer thereof;
with the proviso that said compound is not Compound 8 having the structure:

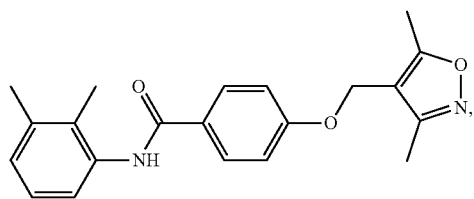 [SMILES: Cc1cccc(NC(=O)c2ccc(OCc3c(C)noc3C)cc2)c1C]

Compound 3 having the structure:

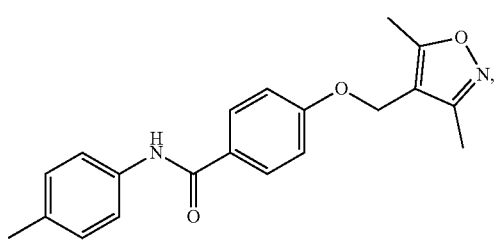 [SMILES: Cc1ccc(NC(=O)c2ccc(OCc3c(C)noc3C)cc2)cc1]

Compound 9 having the structure:

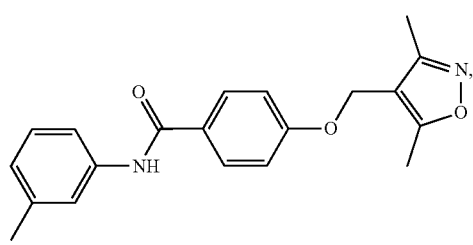 [SMILES: Cc1cccc(NC(=O)c2ccc(OCc3c(C)noc3C)cc2)c1]

Compound 17 having the structure:

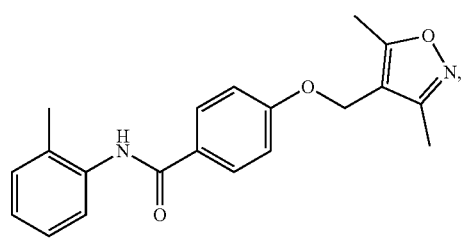 [SMILES: Cc1ccccc1NC(=O)c1ccc(OCc2c(C)noc2C)cc1]

or
Compound 72 having the structure:

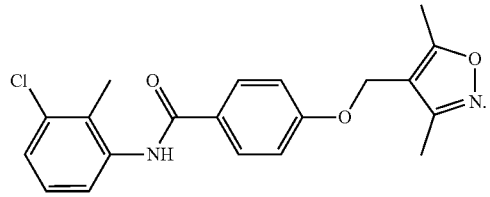 [SMILES: Cc1noc(C)c1COc1ccc(C(=O)Nc2cccc(Cl)c2C)cc1]

2. A compound having the structure of Formula I(d):

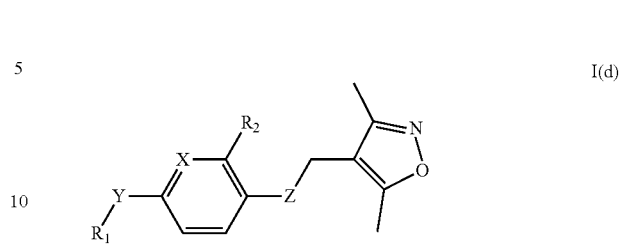

I(d)

wherein X is $CR_2$;

Y is selected from —C(O)$NR_3$— and —$NR_3$C(O)—;

Z is O;

$R_1$ is aryl, optionally substituted with one or more groups selected from alkyl, CN, Cl, F, Br, OH, $NH_2$, wherein if $R_1$ is phenyl, $R_1$ is substituted;

$R_2$ is selected from hydrogen and alkyl; and $R_3$ is independently selected at each occurrence from hydrogen and alkyl;

with the proviso that said compound is not Compound 8 having the structure:

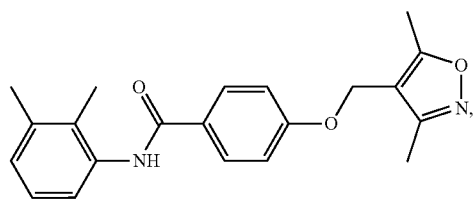 [SMILES: Cc1cccc(NC(=O)c2ccc(OCc3c(C)noc3C)cc2)c1C]

Compound 3 having the structure:

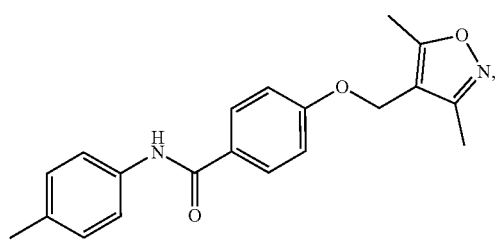 [SMILES: Cc1ccc(NC(=O)c2ccc(OCc3c(C)noc3C)cc2)cc1]

Compound 9 having the structure:

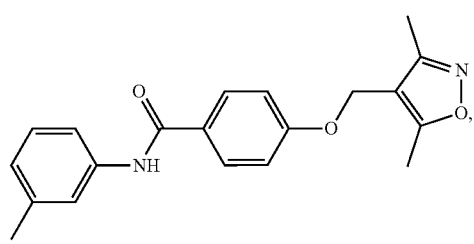 [SMILES: Cc1cccc(NC(=O)c2ccc(OCc3c(C)noc3C)cc2)c1]

Compound 17 having the structure:

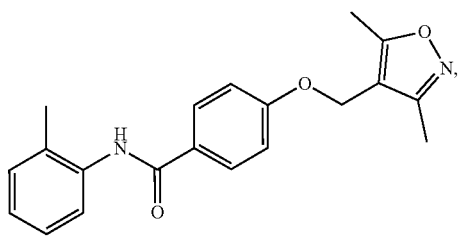 [SMILES: Cc1ccccc1NC(=O)c1ccc(OCc2c(C)noc2C)cc1]

or

Compound 72 having the structure:

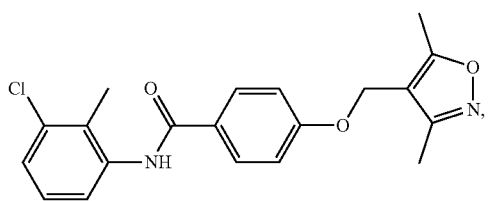 [SMILES: Cc1noc(C)c1COc1ccc(C(=O)Nc2cccc(Cl)c2C)cc1]

or a pharmaceutically acceptable salt, hydrate, solvate, geometric isomer, or stereoisomer thereof.

3. The compound of claim 2, wherein $R_1$ is aryl substituted with one or more substituents selected from alkyl, or cyano.

4. The compound according to claim 1, wherein said compound is

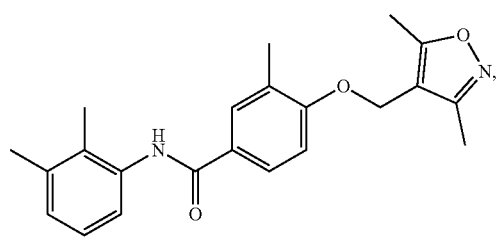

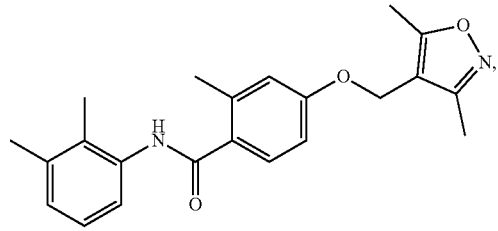

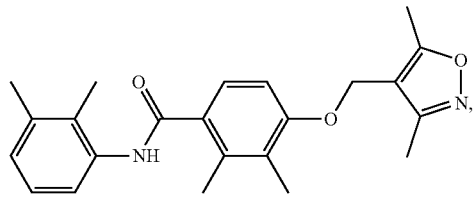

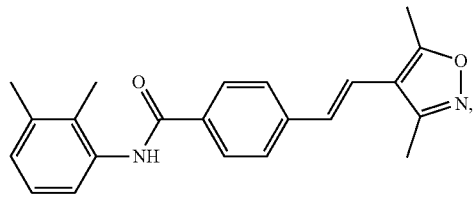

-continued

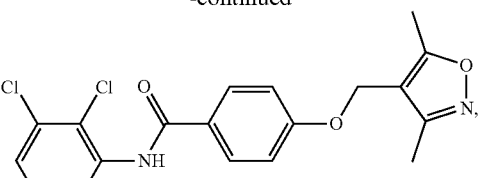

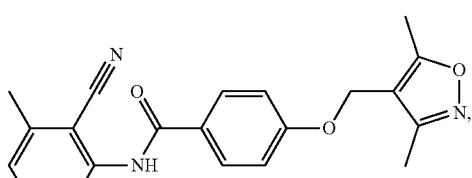

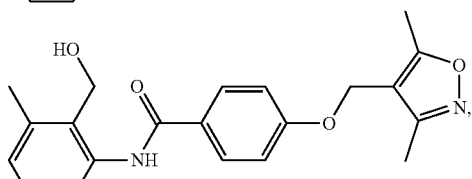

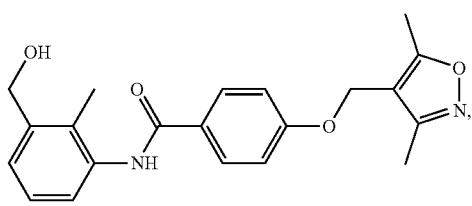

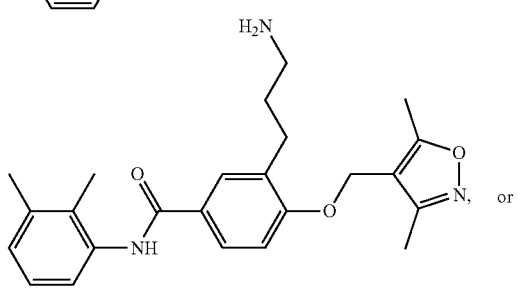

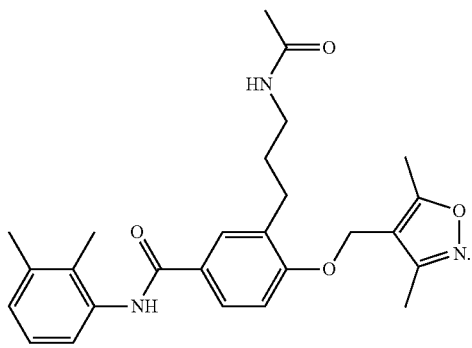

5. A pharmaceutical composition for modulating insulation secretion comprising an effective amount of a compound of claim 1.

6. A pharmaceutical composition for modulating insulin secretion comprising a compound having the structure of Formula I(a):

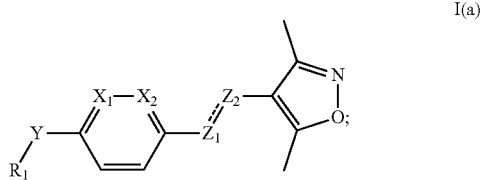

I(a)

wherein the "dashed" bond is a single or double bond;
$X_1$ and $X_2$ are $C(R_2)$, wherein two vicinal $R_2$ groups may together form an optionally aromatic five- or six membered fused ring;
Y is selected from —C(O)N($R_3$)— and —N($R_3$)C(O);
$Z_1$ and $Z_2$ are independently $CH_2$, or O;
$R_1$ is optionally substituted with one or more substituents independently selected from alkyl, hydroxyalkyl, cyano, and halogen;
$R_2$ is selected from hydrogen, alkyl, alkoxy, —CN, —$NH_2$, —$(CH_2)_{1-4}NH_2$, —$(CH_2)_{1-4}N_3$, —$(CH_2)_{1-4}NHC(O)CH_3$; and
$R_3$ is independently selected at each occurrence from hydrogen and alkyl optionally substituted with one to three groups independently selected from halogen;
or a pharmaceutically acceptable salt, hydrate, solvate, geometric isomer, or stereoisomer thereof.

* * * * *